US012678319B2

(12) United States Patent
Price et al.

(10) Patent No.: US 12,678,319 B2
(45) Date of Patent: Jul. 14, 2026

(54) ORTHOPEDIC SPINE BRACE

(71) Applicant: Aspen Medical Products, LLC, Irvine, CA (US)

(72) Inventors: Jane Price, Anaheim, CA (US); Harry Duane Romo, Aliso Viejo, CA (US); Erik Zimmer, Oceanside, CA (US); Jozsef Horvath, Lake Forest, NC (US)

(73) Assignee: Aspen Medical Products, LLC, Irvine, CA (US)

( * ) Notice: Subject to any disclaimer, the term of this patent is extended or adjusted under 35 U.S.C. 154(b) by 279 days.

(21) Appl. No.: 18/224,429

(22) Filed: Jul. 20, 2023

(65) Prior Publication Data

US 2024/0033116 A1 Feb. 1, 2024

Related U.S. Application Data

(60) Provisional application No. 63/391,295, filed on Jul. 21, 2022, provisional application No. 63/401,053, filed on Aug. 25, 2022, provisional application No. 63/410,203, filed on Sep. 26, 2022, provisional application No. 63/426,330, filed on Nov. 17, 2022.

(51) Int. Cl.
*A61F 5/02* (2006.01)

(52) U.S. Cl.
CPC .................................. *A61F 5/022* (2013.01)

(58) Field of Classification Search
CPC ...... A61F 5/01–013; A61F 5/02; A61F 5/022; A61F 5/024; A61F 5/026; A61F 5/028; A61F 5/03
See application file for complete search history.

(56) References Cited

U.S. PATENT DOCUMENTS 3,220,407 A 11/1965 Connelly
2010/0234783 A1 9/2010 Smits

FOREIGN PATENT DOCUMENTS

CN 110101493 A 8/2019
EP 1269942 A1 1/2003
EP 2457544 A1 5/2012
EP 2664307 A1 11/2013
EP 3482726 A1 * 5/2019 ............... A61F 5/03

OTHER PUBLICATIONS

PCT/US2023/028367 filed Jul. 12, 2023 International Search Report and Written Opinion dated Nov. 3, 2023.

* cited by examiner

*Primary Examiner* — Alireza Nia
*Assistant Examiner* — Andrew Jun-Wai Mok
(74) *Attorney, Agent, or Firm* — Rutan & Tucker, LLP

(57) ABSTRACT

According to an embodiment of the disclosure, an orthopedic spine brace is described. The brace features a back panel; a first and second lateral frame assembly; and a chest plate attachment. The first lateral frame assembly includes a first superior frame member and a first hinge coupled to both a first end of the first superior frame member to allow for angular adjustment of the first superior frame member. The second lateral frame assembly includes a second superior frame member and a second hinge coupled to both a first end of the second superior frame member to allow for angular adjustment of the second superior frame member. The chest plate attachment includes (i) a lock attachment member for coupling to a second end of the first superior frame member and (ii) a hinged attachment member for coupling to a second end of the second superior frame member.

24 Claims, 114 Drawing Sheets

100

$160_2$

700

154
152
933
950
932

3020

3000

152

3000

ORTHOPEDIC SPINE BRACE

CROSS-REFERENCE TO RELATED APPLICATION

This application claims the benefit of priority on U.S. Provisional Application No. 63/391,295 filed Jul. 21, 2022, U.S. Provisional Application No. 63/401,053 filed Aug. 25, 2022, U.S. Provisional Application No. 63/410,203 filed Sep. 26, 2022 and U.S. Provisional Application No. 63/426,330 filed Nov. 17, 2022, the entire contents of all of these provisional applications are incorporated by reference herein,

FIELD

Embodiments of the disclosure relate to the field of orthoses. More specifically, one embodiment of the disclosure relates to an orthopedic spine brace that may be used to treat proximal junctional kyphosis (PJK).

GENERAL BACKGROUND

The following description includes information that may be useful in understanding the described invention. It is not an admission that any of the information provided herein is prior art or relevant to the presently claimed invention, or that any publication specifically or implicitly referenced is prior art.

Technical advancements have enabled spinal deformity surgeons to correct severe spinal malalignment. Proximal junctional kyphosis (PJK), or forward curvature of the upper back, is a common complication experienced by adult patients who undergo posterior spinal surgery. After spinal surgery, PJK is often diagnosed by the patient experiencing acute back pain, ambulatory difficulties, and in the most critical cases, neurological deficit.

Currently, a hyperextension orthopedic brace may be provided to a patient suffering from PJK. Conventional hyperextension orthopedic braces operate as a Thoracic Lumbar Sacral Orthosis (TLSO) with tri-planar control and hyperextension of the spine. For example, a conventional hyperextension orthopedic brace includes a rigid anterior frame that extends transversely across the entire pelvic area and non-pivotal, rigid lateral frames that extend upward along a frontal plane. The lateral frames connect at a chest area to receive a chest plate and corresponding padding.

The problems with conventional PJK orthopedic braces are numerous. For example, they are uncomfortable given the rigid construction with limited flexion during occasional forward movement during common activities such as eating. The traverse anterior frame extending across the pelvic area makes the brace uncomfortable for the patient to wear. As a result, removal of the conventional PJK orthopedic braces is difficult as well.

BRIEF DESCRIPTION OF THE DRAWINGS

Embodiments of the invention are illustrated by way of example and not by way of limitation in the figures of the accompanying drawings, in which like references indicate similar elements and in which.

US 12,678,319 B2

3

Figure 5A:
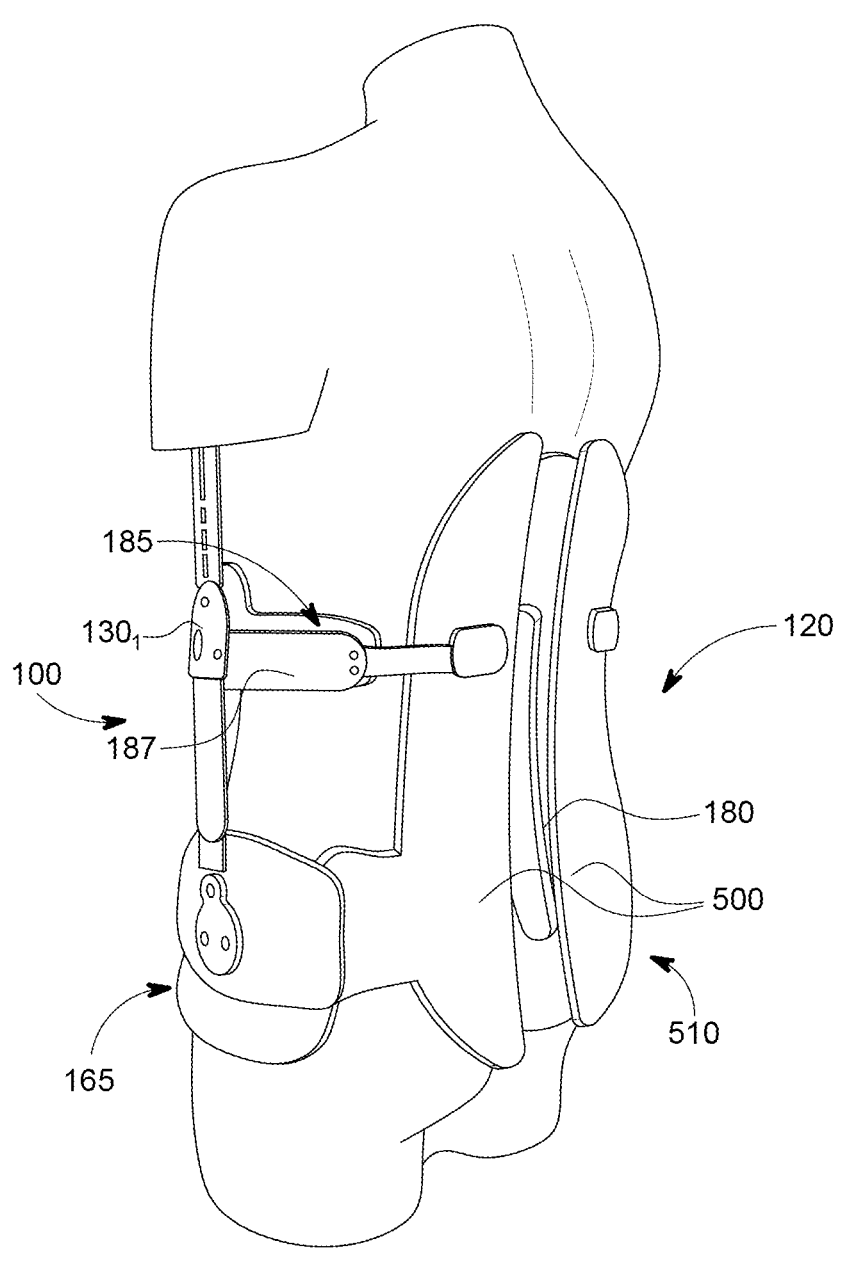
FIG. 5A is a perspective posterior view of the orthopedic spine brace of FIG. 1A.
Figure 5B:
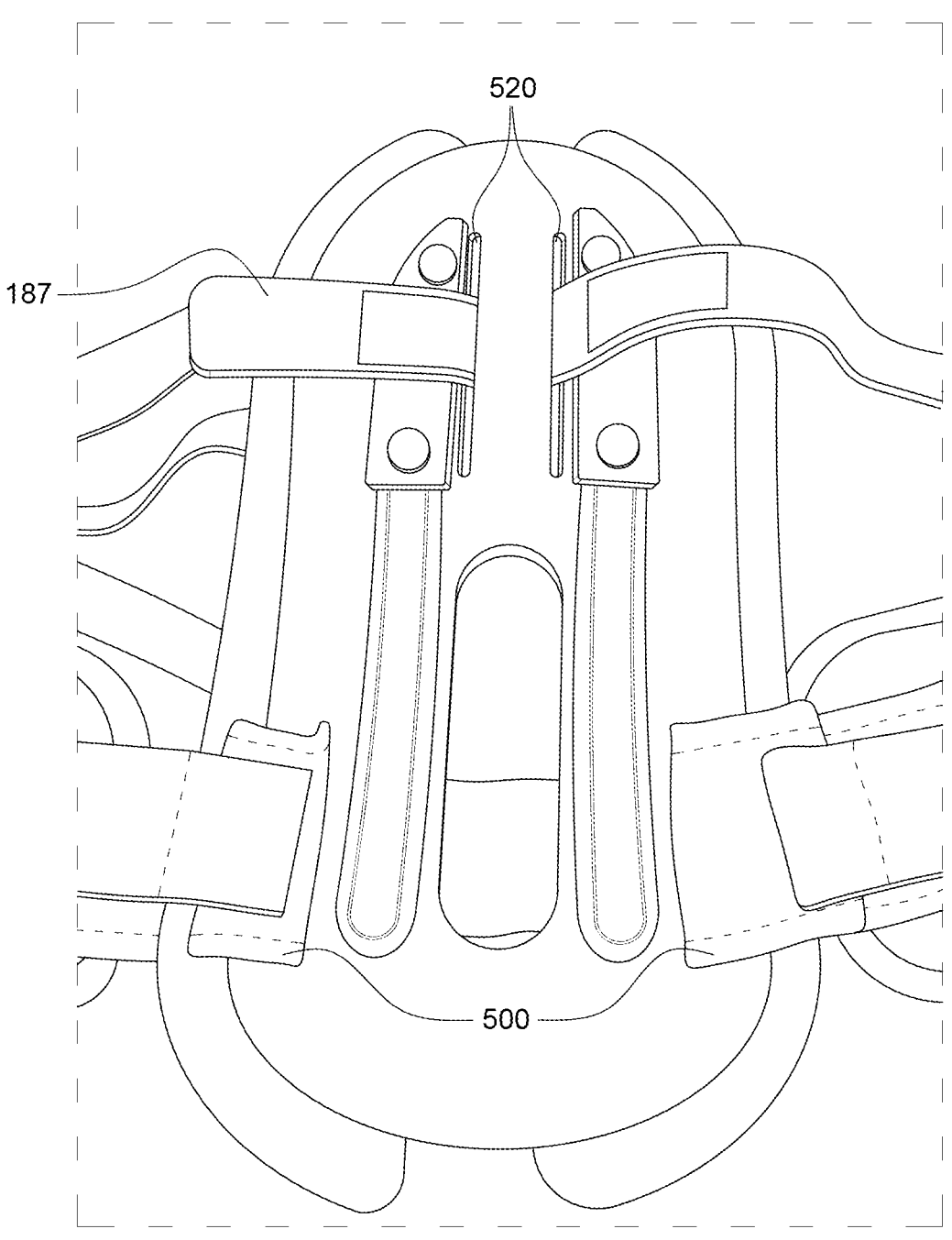
FIG. 5B is an exemplary embodiment of a padded posterior panel and a panel reinforcement member oriented along a traverse plane and coupled to the lateral frame members of the orthopedic spine brace of FIG. 1A.
Figure 5C:
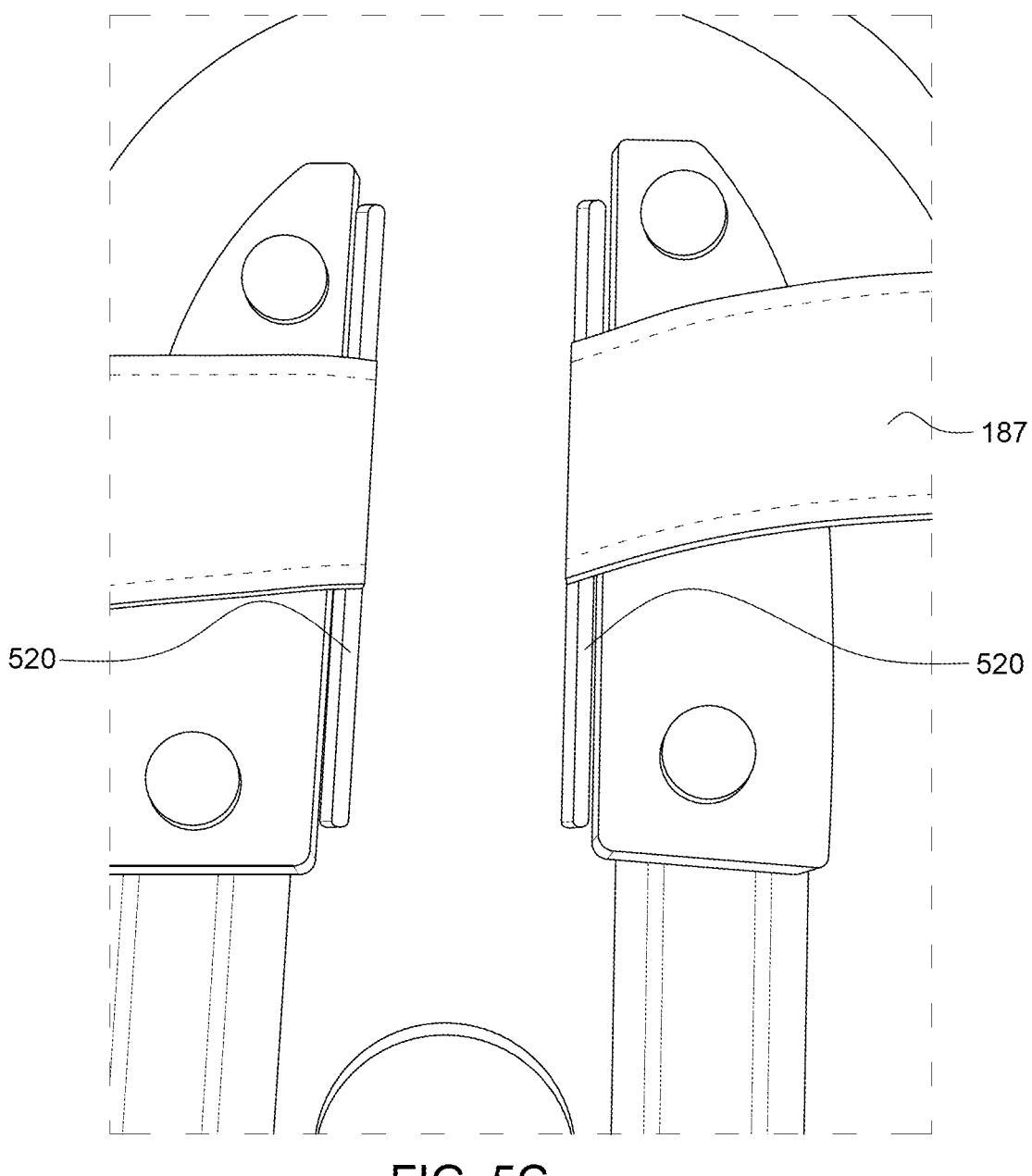
FIG. 5C is an exemplary embodiment of the posterior panel of FIG. 5B.
Figure 5D:
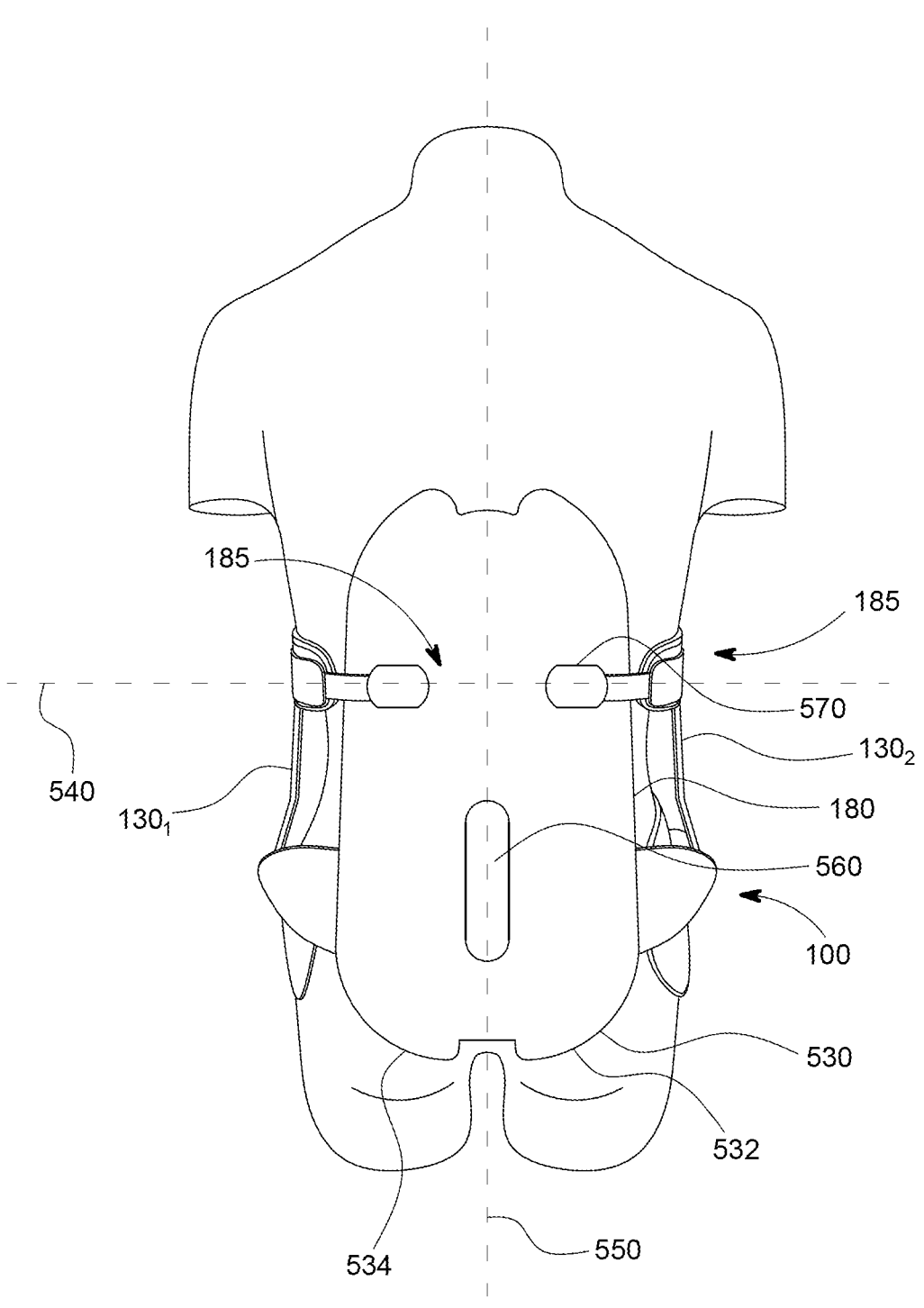
FIG. 5D is an exemplary embodiment of adjustment slots formed within the posterior panel of FIG. 5B.

FIG. 5D is a top-down planar view of an exemplary embodiment of the pulley subsystem operating in a first state.

Figure 1A:
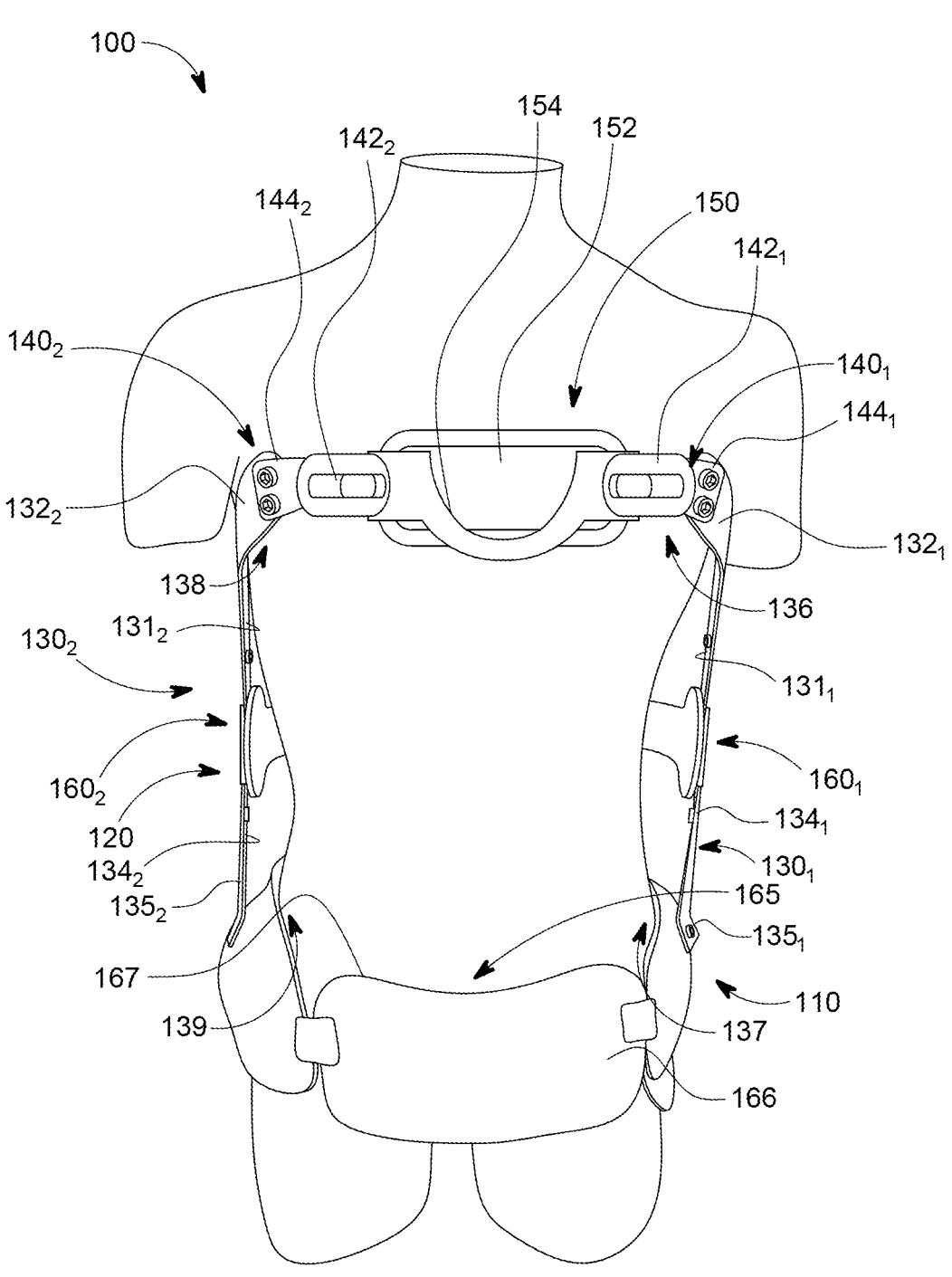
FIG. 1A is a perspective anterior view of an exemplary embodiment of a first embodiment of an orthopedic spine brace.
Figure 6A:
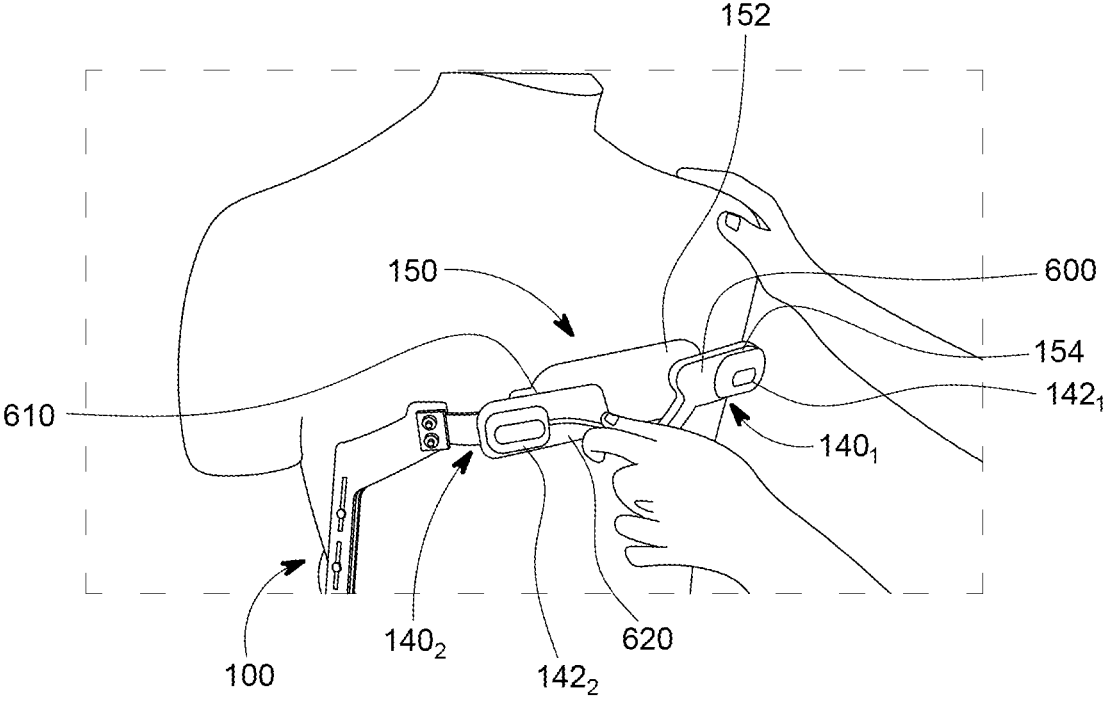

FIG. 6A is an exemplary embodiment of unlocking the chest plate attached to a chest compression member coupled to both lateral frame members of the orthopedic spine brace of FIG. 1A.

Figure 6B:
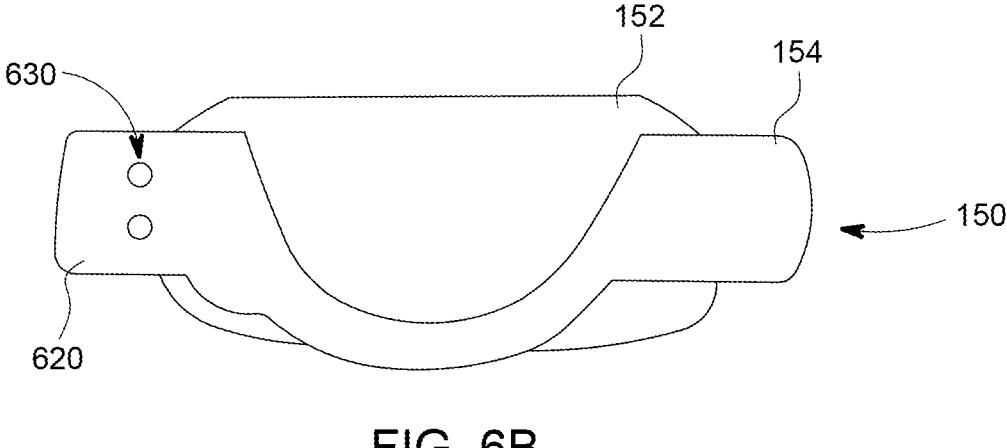

FIG. 6B is an exemplary embodiment of a removal chest plate detached from the orthopedic spine brace of FIG. 1A.

Figure 6C:
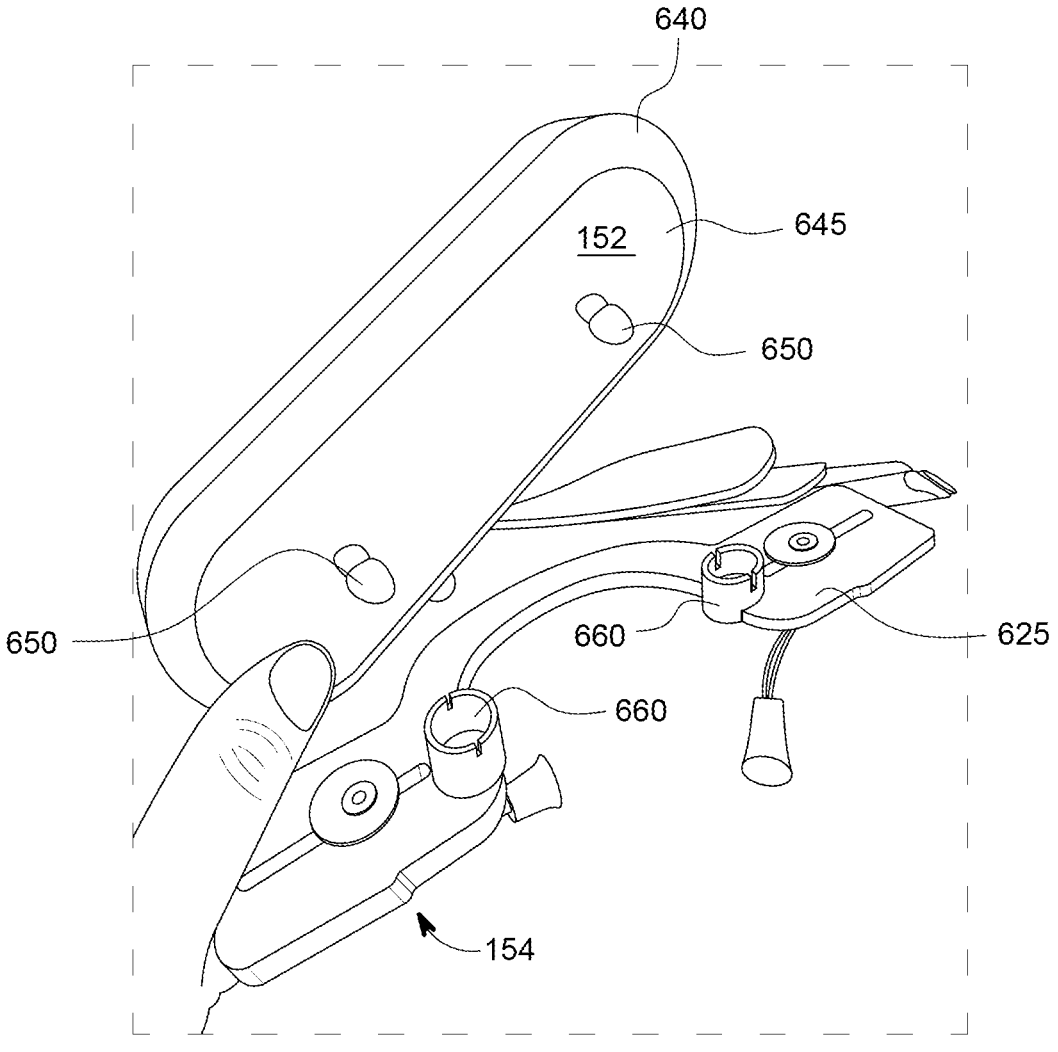

FIG. 6C is an exemplary embodiment of the chest compression member of FIG. 6A.

Figure 6D:
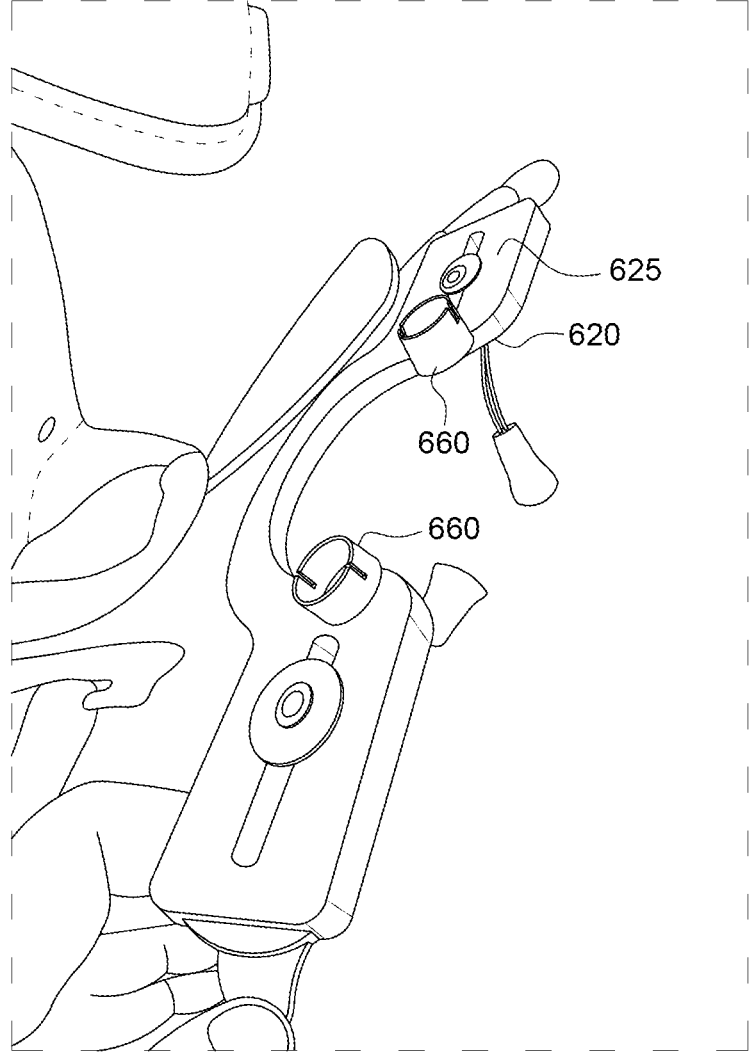

FIG. 6D is an exemplary embodiment of the removal chest plate with a first connector for attachment to a chest compression member featuring a complementary second connector.

Figure 7A:
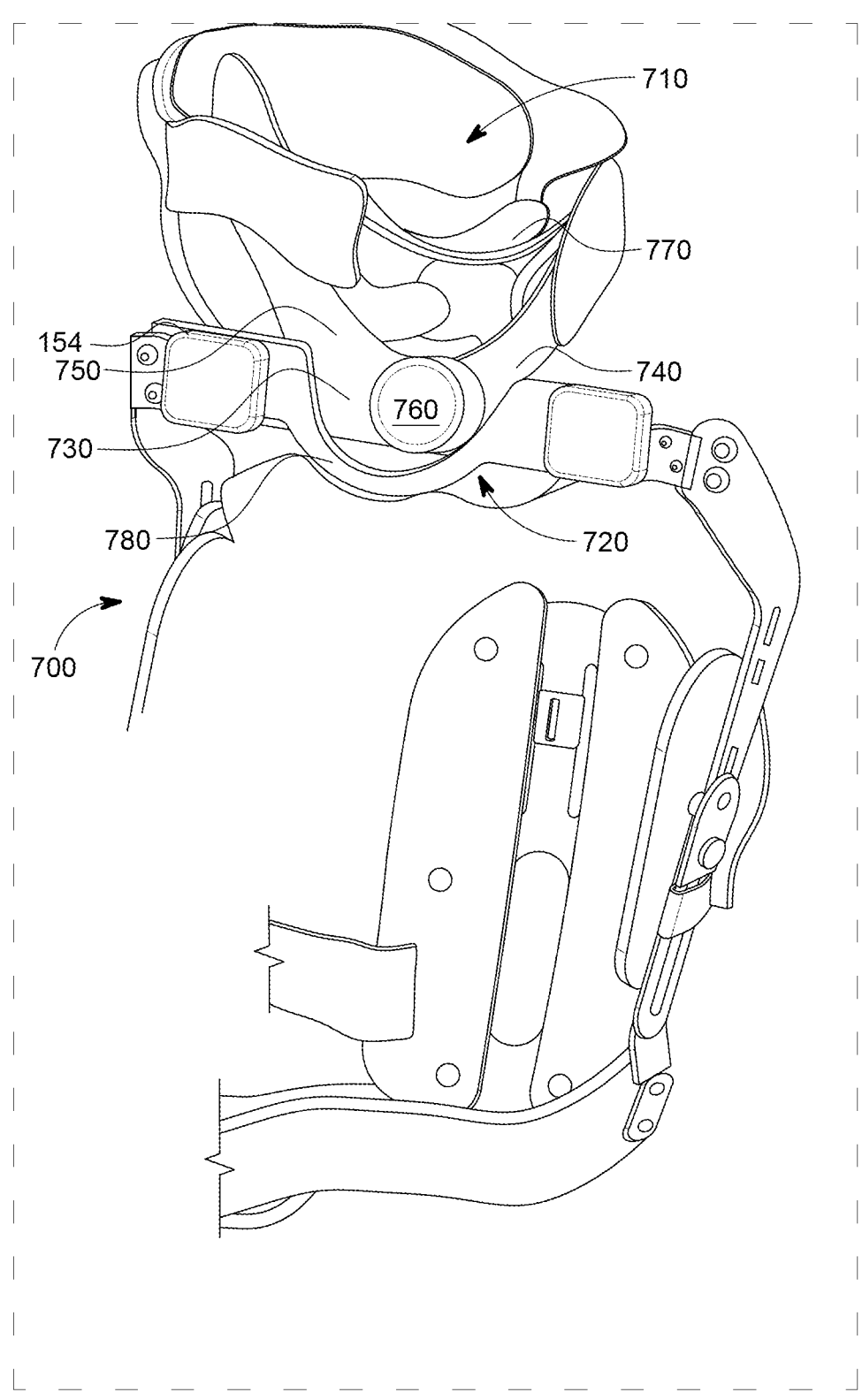

FIG. 7A is a perspective front view of a neck orthosis coupled to the chest compression member of FIG. 6C.

Figure 7B:
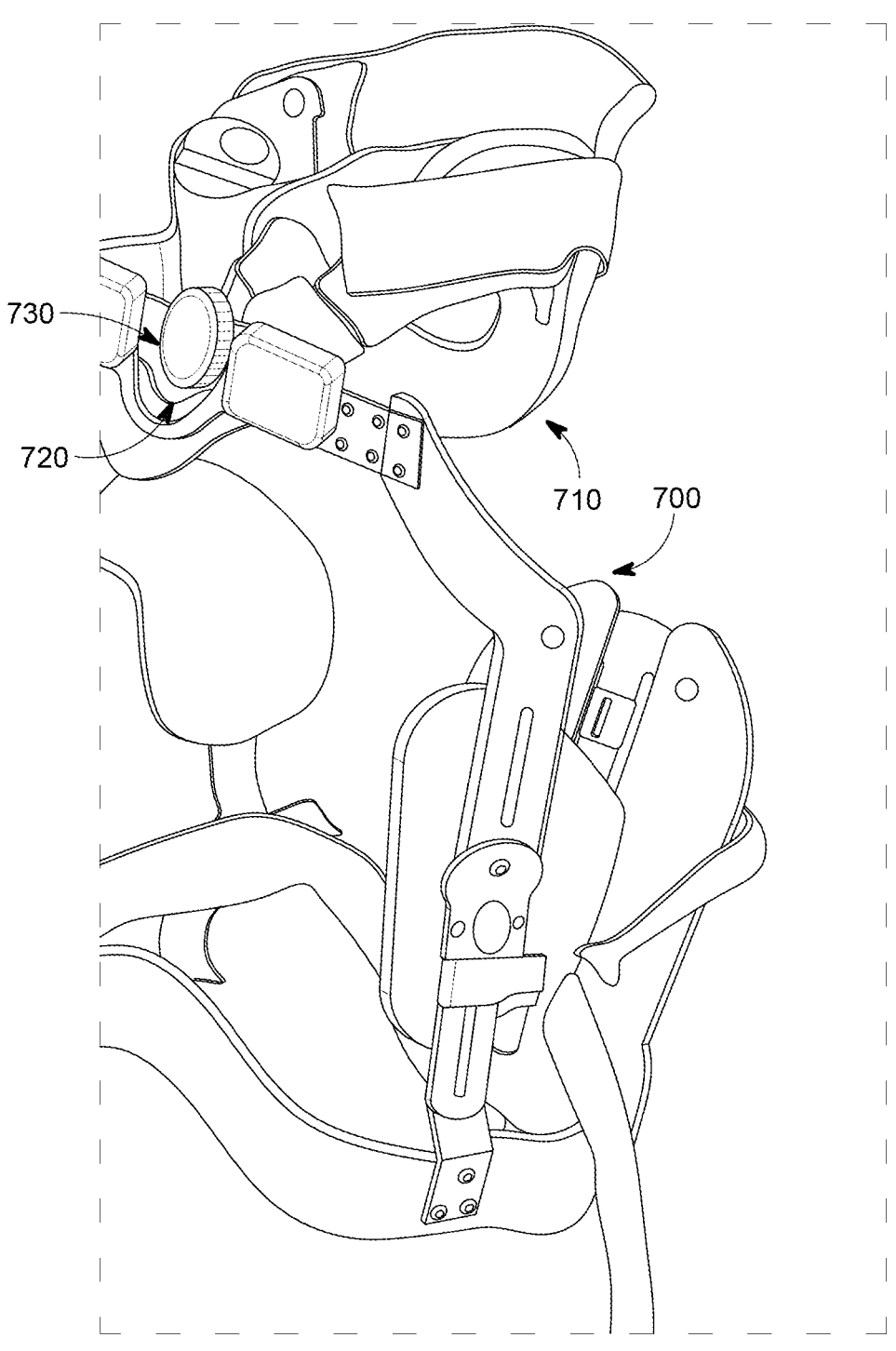

FIG. 7B is a perspective lateral view of the neck orthosis of FIG. 7A coupled to the chest compression member.

Figure 7C:
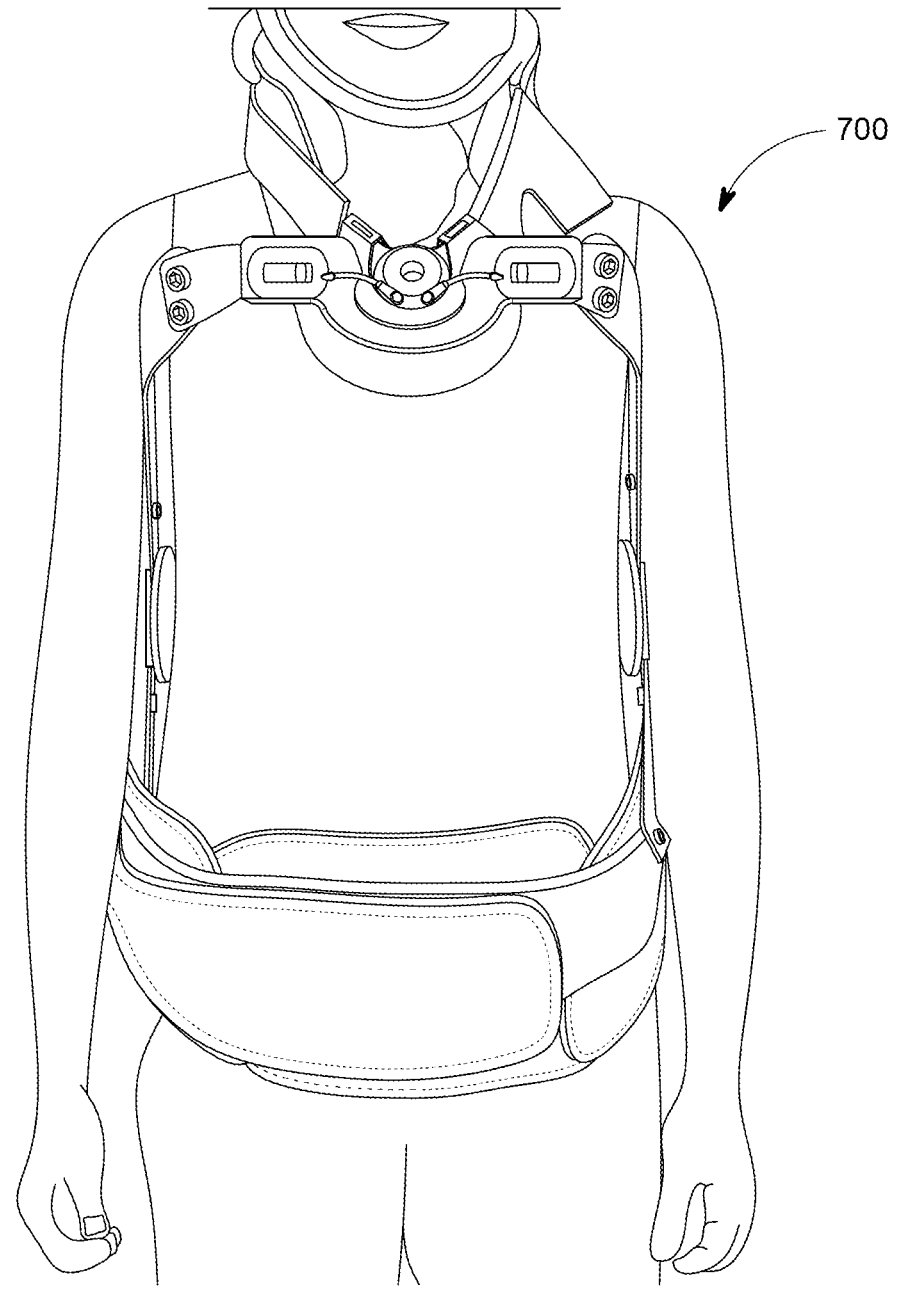

FIG. 7C is a perspective front view of the orthosis spine brace with neck orthosis operating as a version of a cervical thoracic lumbar sacral orthosis (CTLSO) when worn.

Figure 7D:
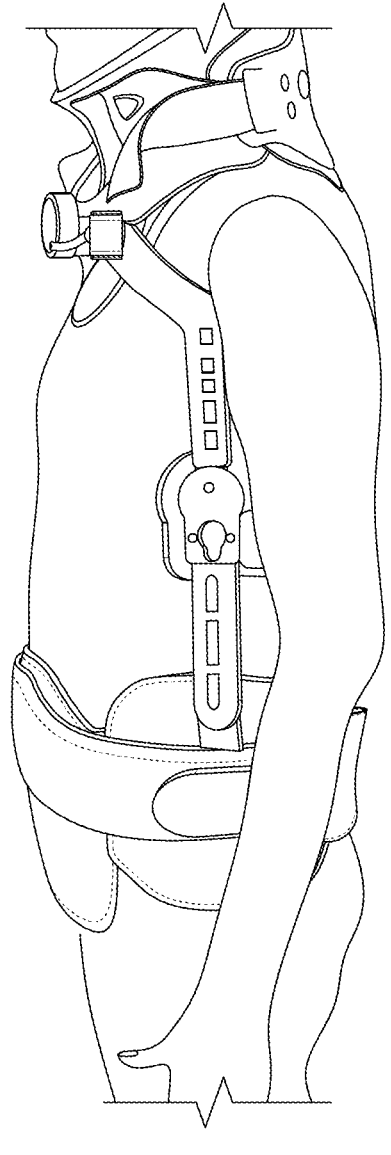

FIG. 7D is a perspective lateral view of the orthosis spine brace with neck orthosis operating as a version of a cervical thoracic lumbar sacral orthosis (CTLSO) when worn.

Figure 7E:
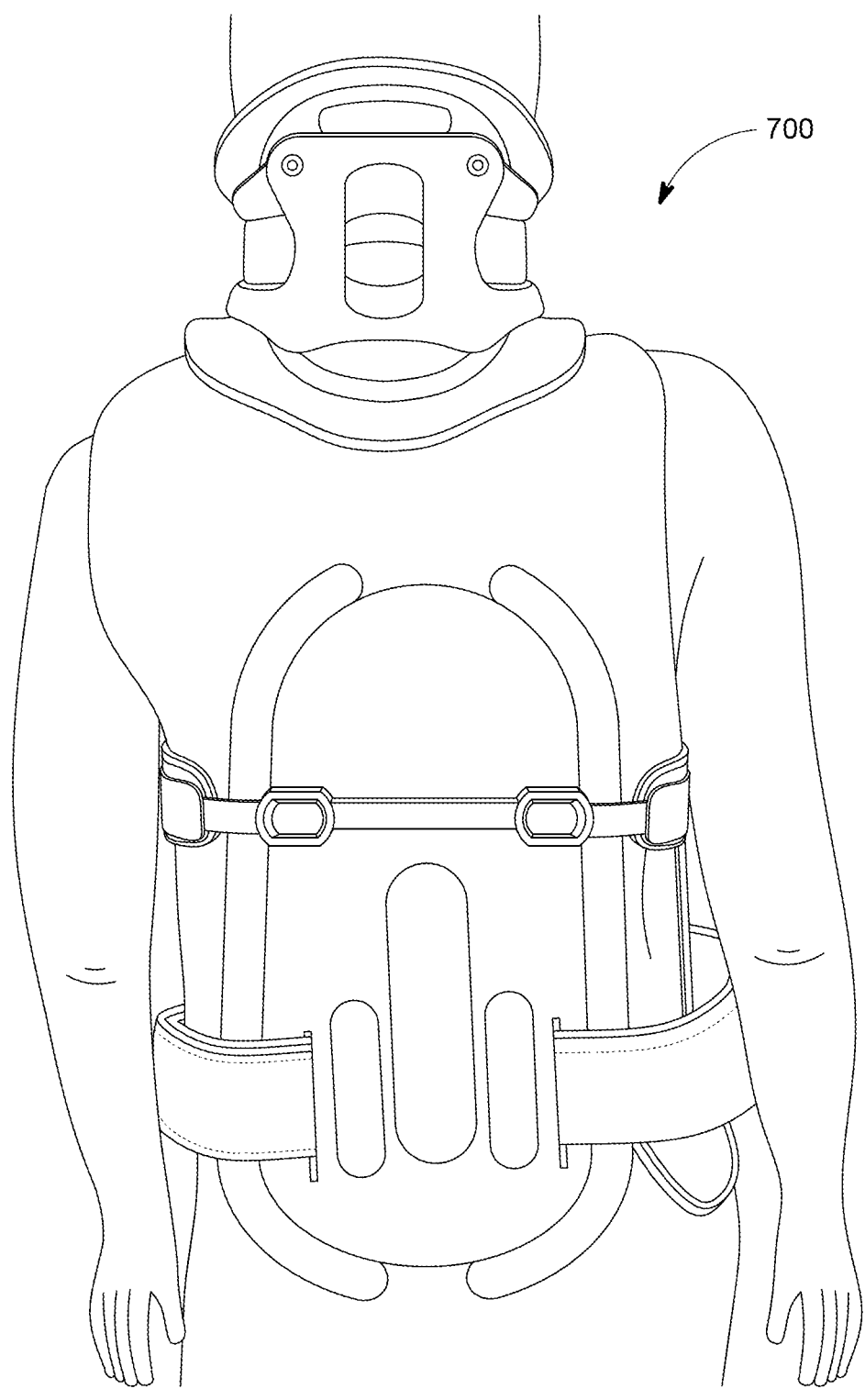

FIG. 7E is a perspective rear view of the orthosis spine brace with neck orthosis operating as a version of a cervical thoracic lumbar sacral orthosis (CTLSO) when worn.

Figure 8:
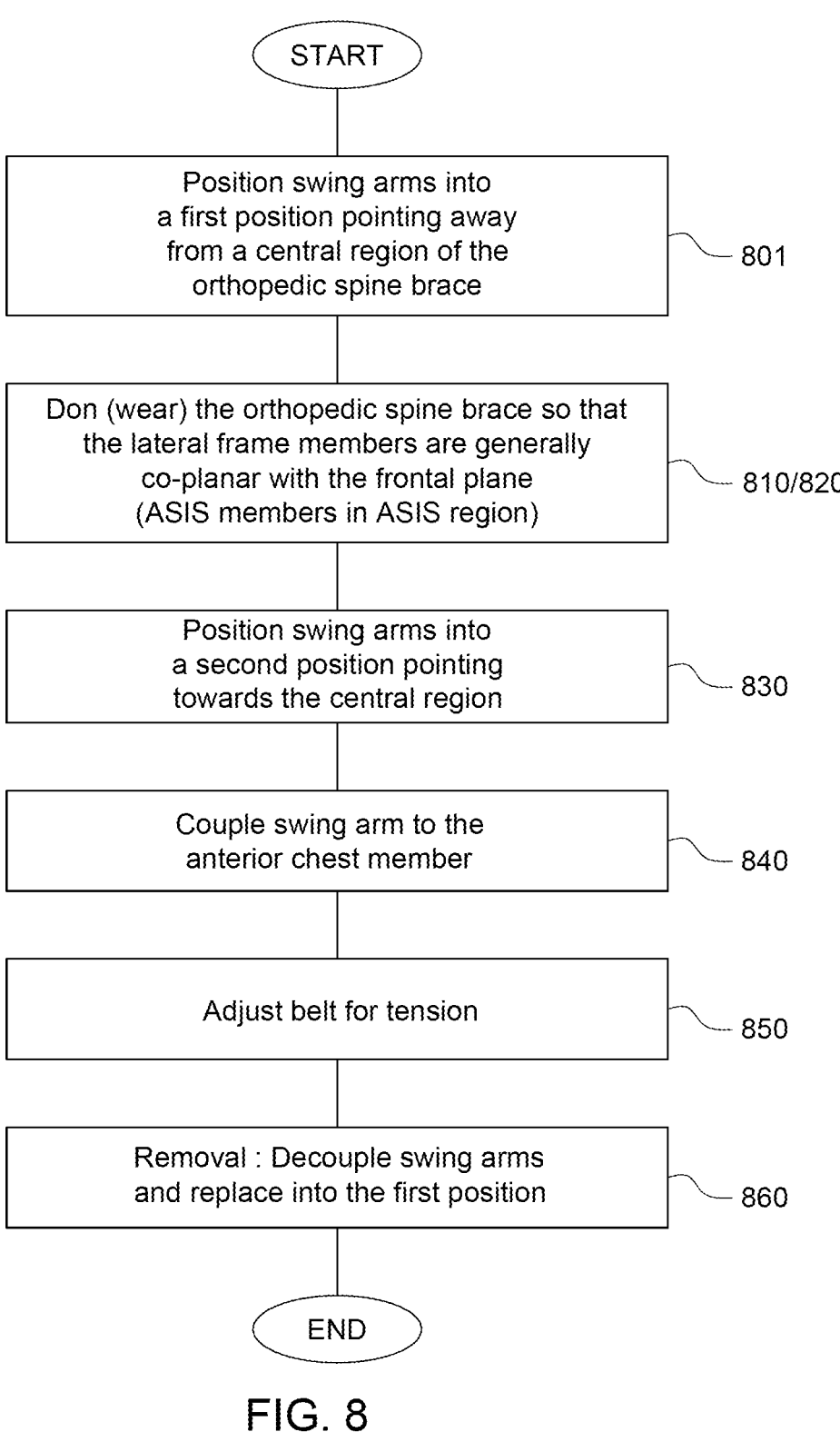

FIG. 8 is a method of donning the orthopedic spine brace of FIGS. 1A-7E.

Figure 9A:
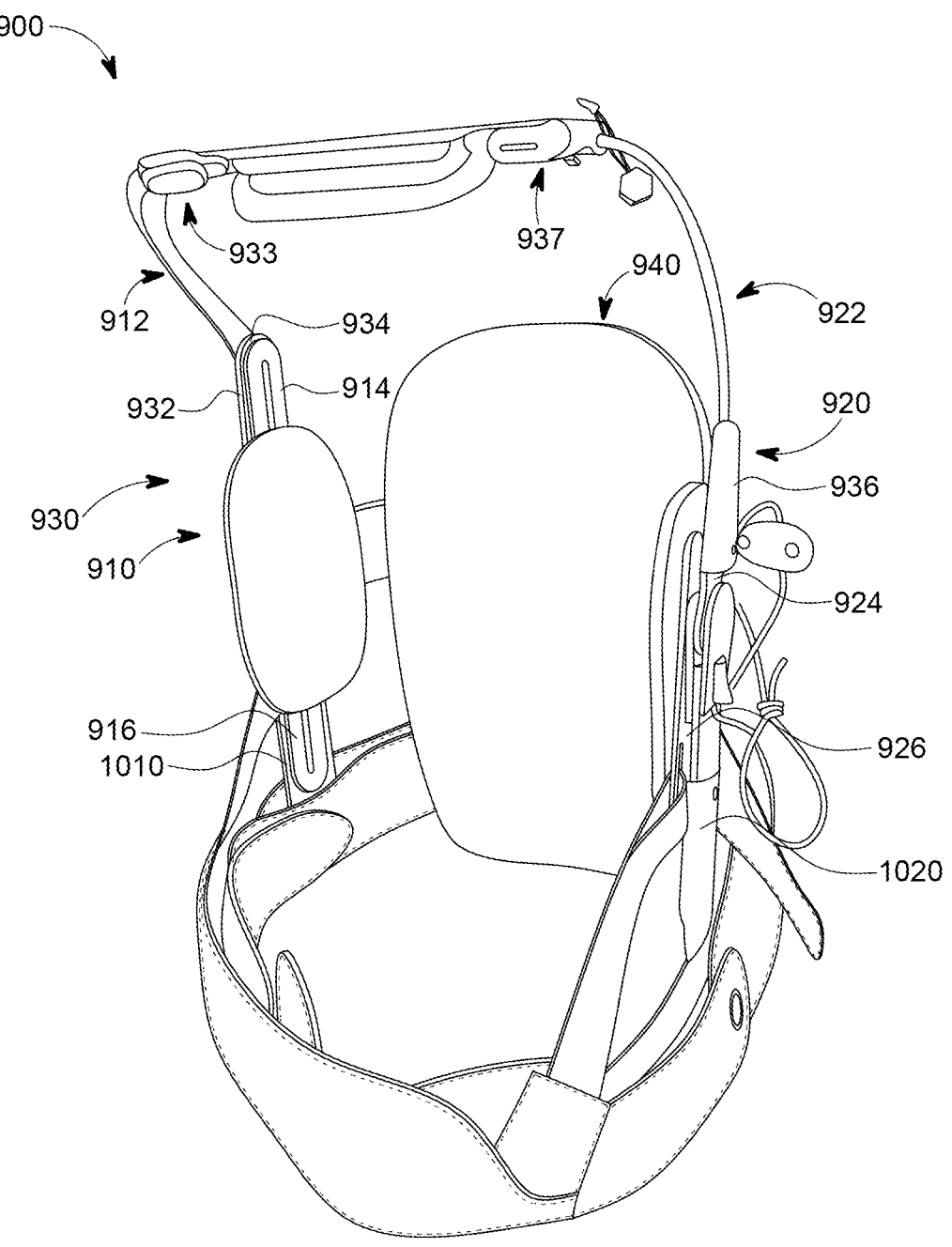

FIG. 9A is a perspective anterior view of an exemplary first embodiment of an orthopedic spine brace.

Figure 9B:
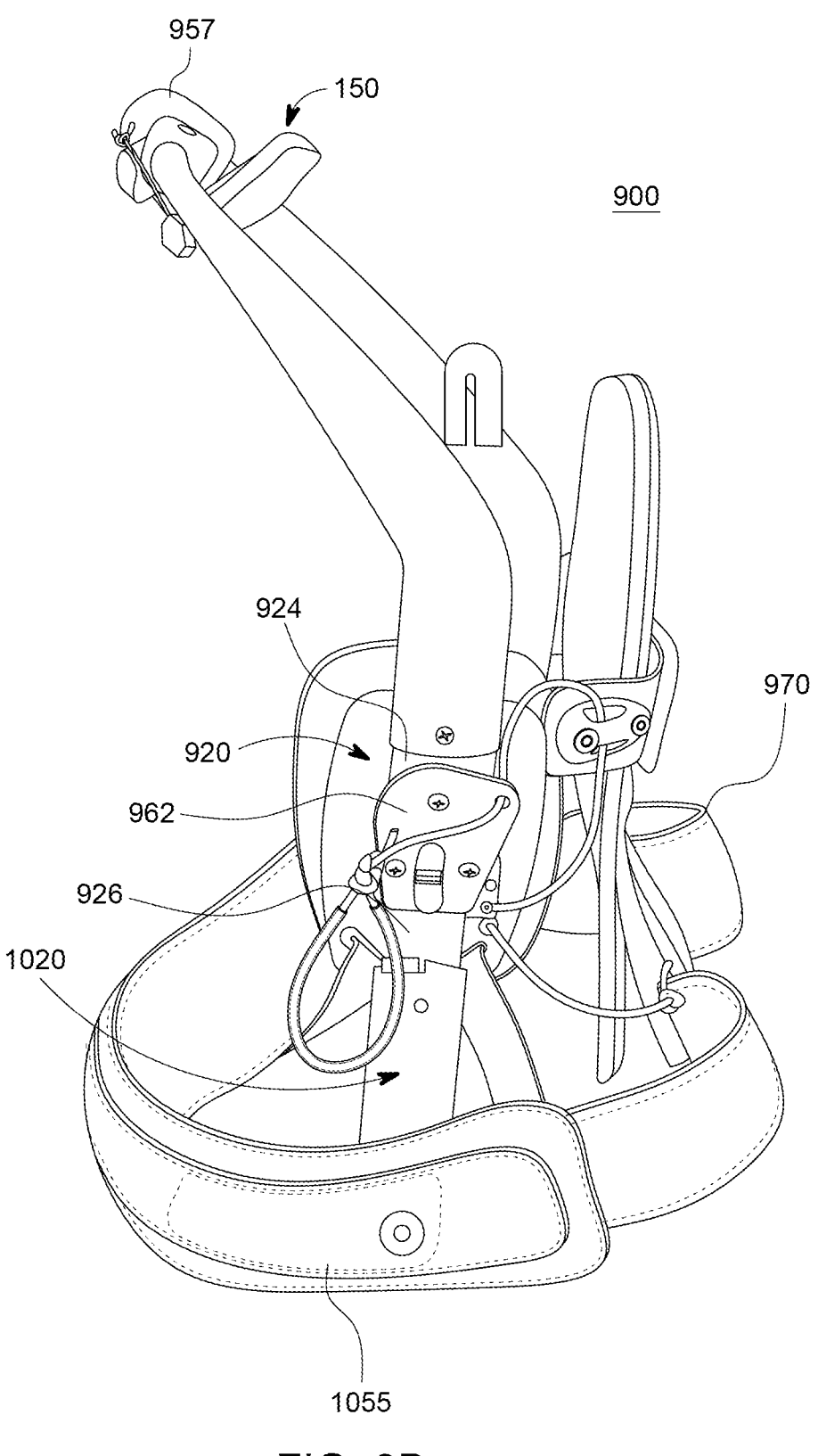

FIG. 9B is a first side-facing perspective view of the orthopedic spine brace of FIG. 9A.

Figure 9C:
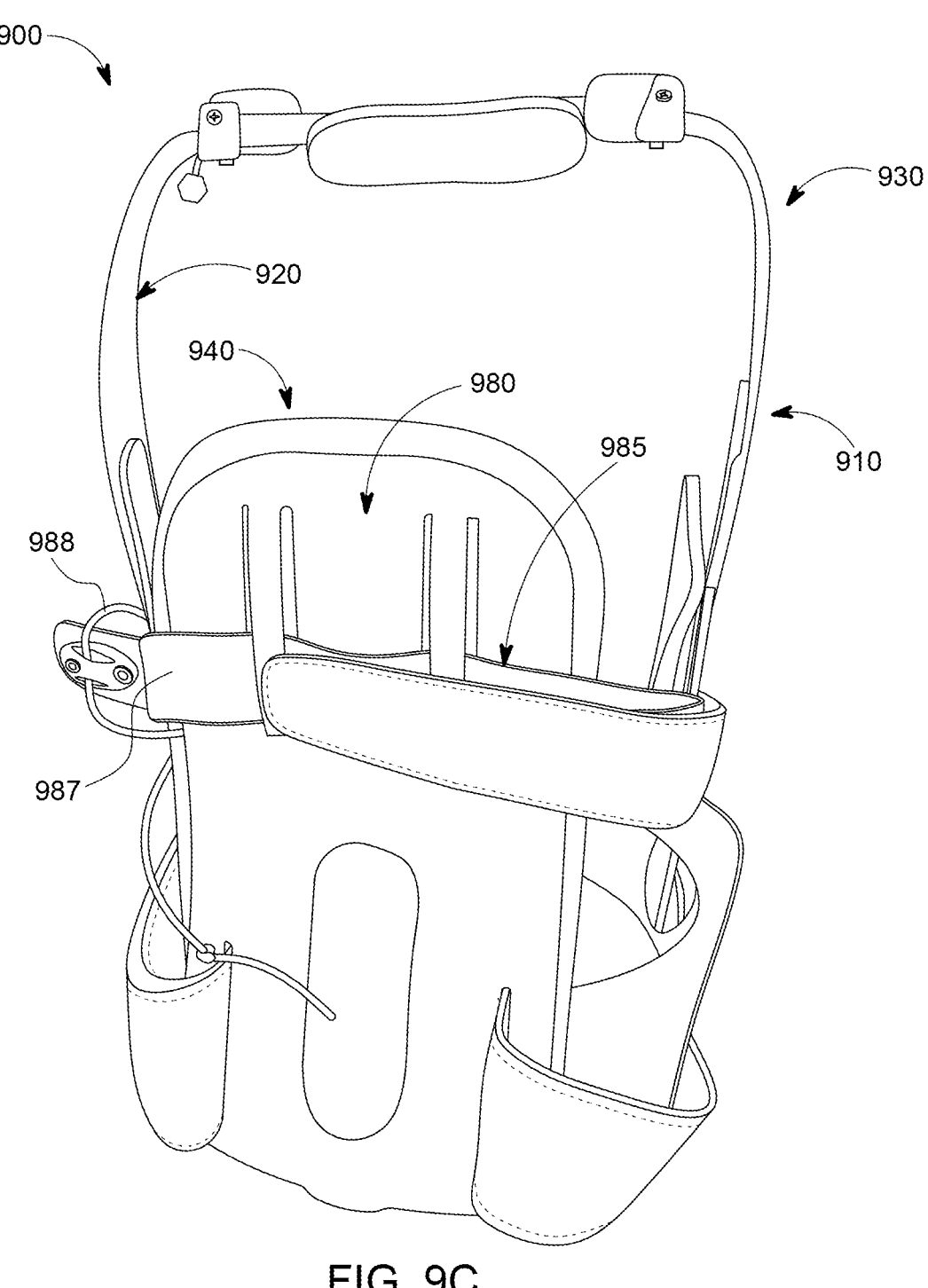

FIG. 9C is a perspective posterior view of the orthopedic spine brace of FIG. 9A.

Figure 9D:
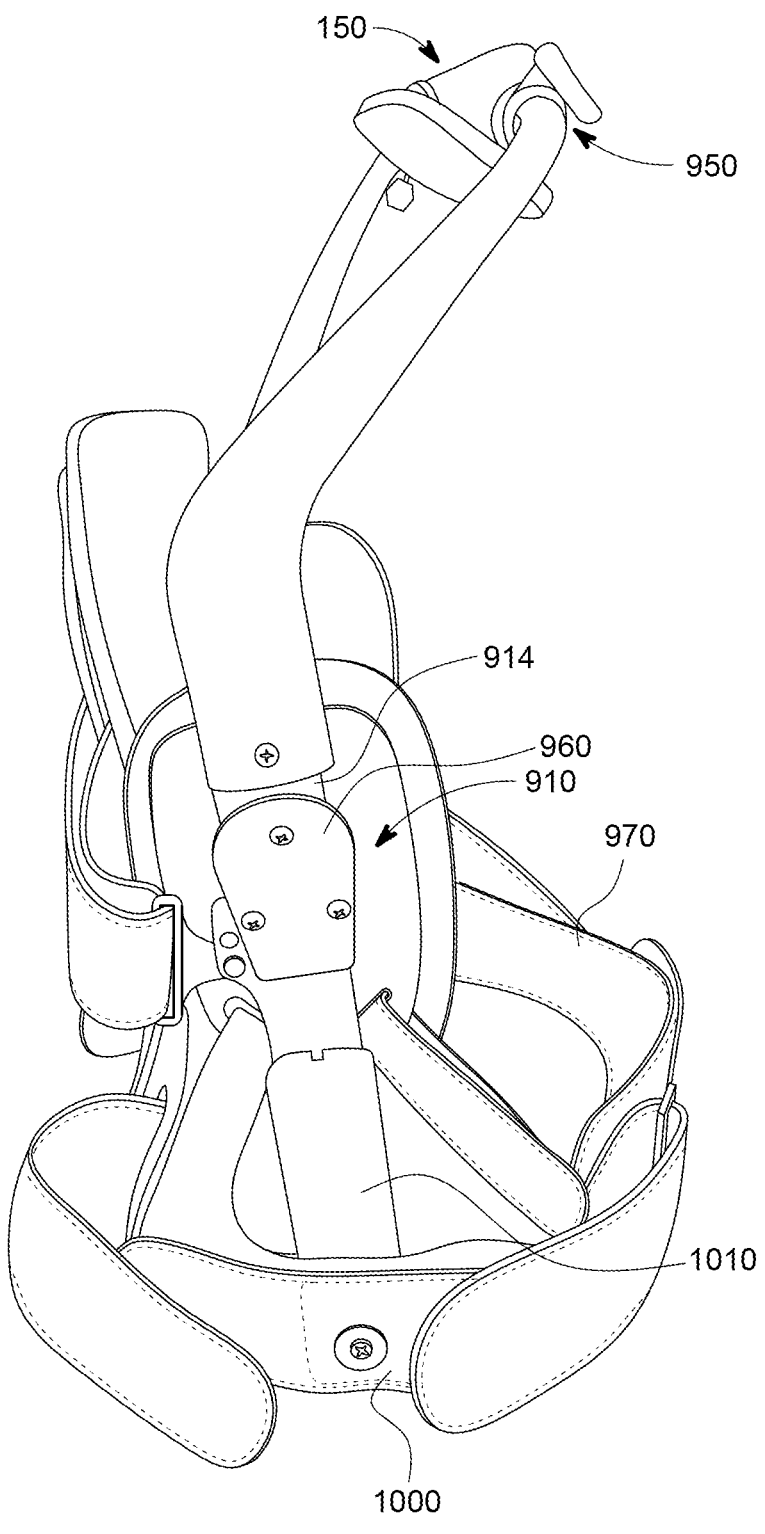

FIG. 9D is a second side-facing perspective view of the orthopedic spine brace of FIG. 9A.

Figure 9E:
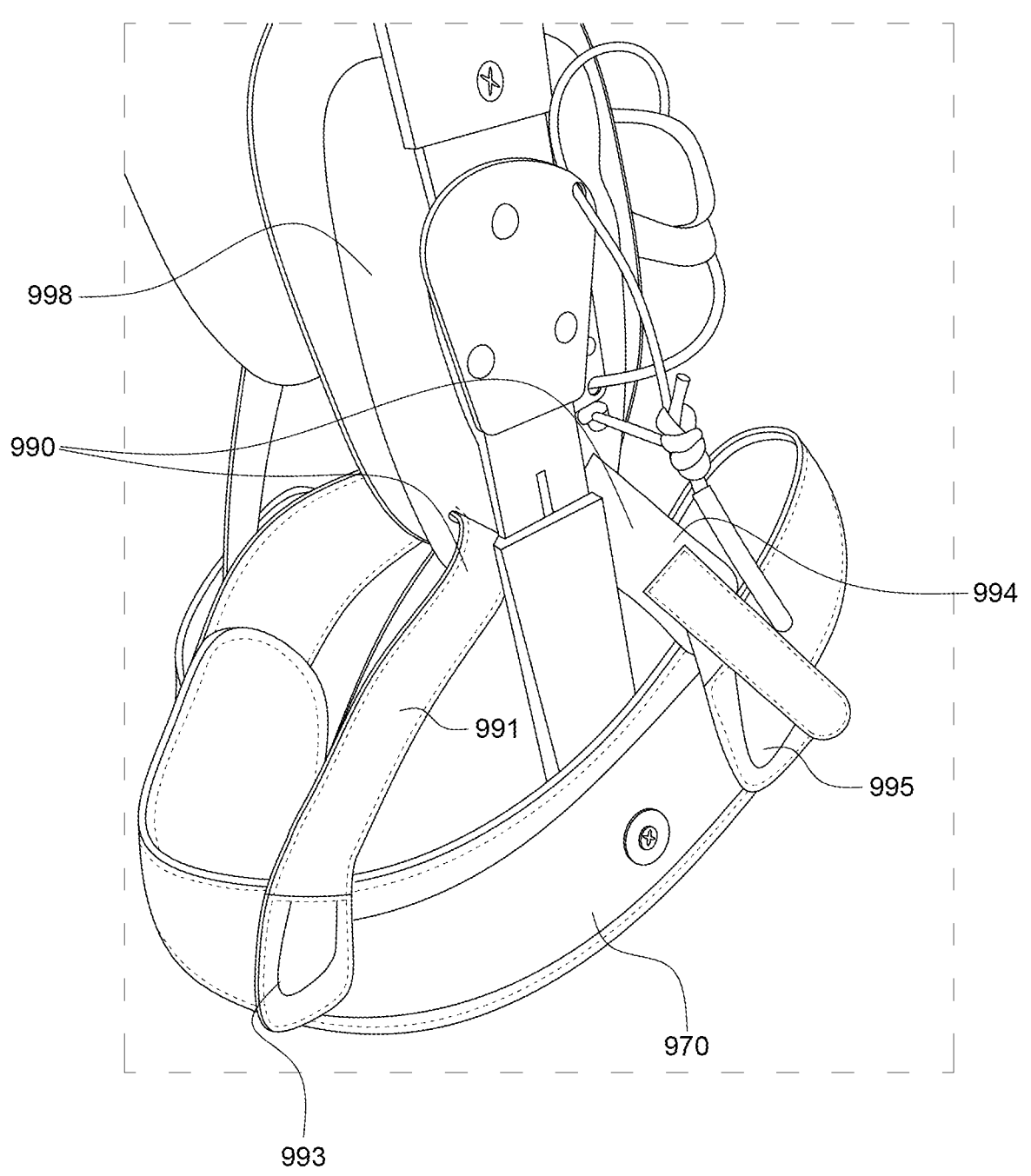
Figure 10A:
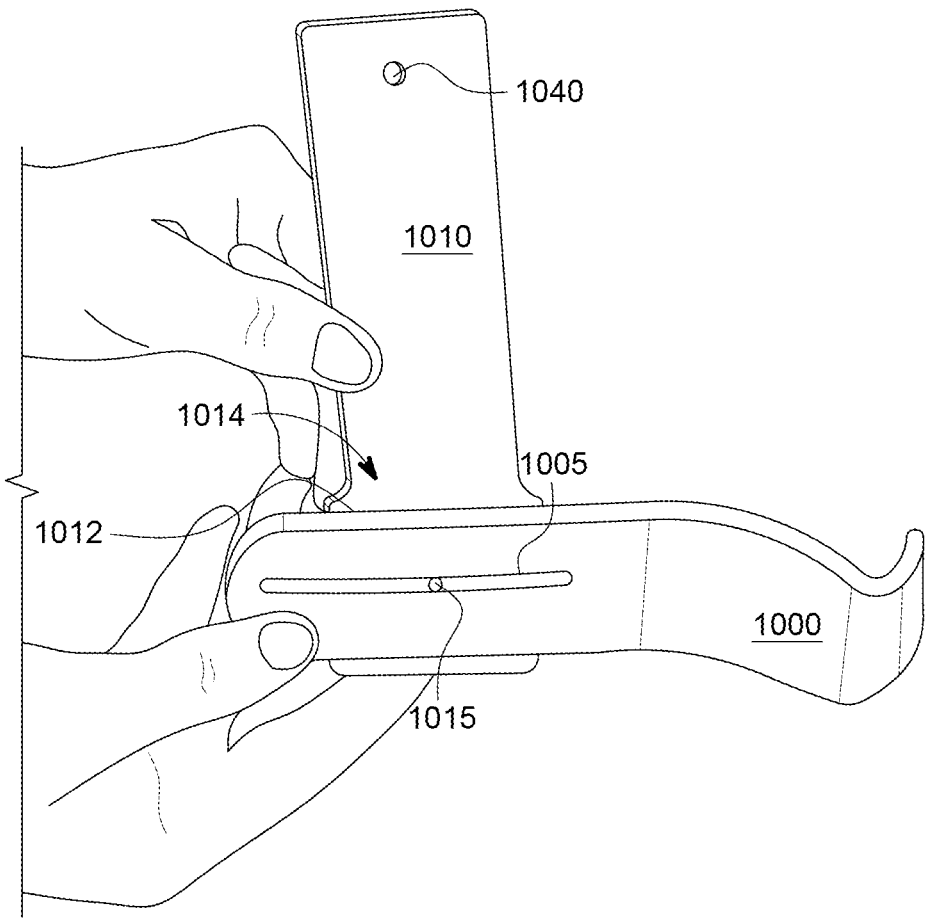

FIG. 9E is a perspective view of the orthopedic spine brace of FIG. 9A focusing on a positioning of tension straps and incorporation of FIG. 10A is a second exemplary embodiment of an anterior superior iliac spine (ASIS) frame member adapted for coupling to the inferior frame of the lateral frame member of the orthopedic spine brace of FIG. 9A.

Figure 10B:
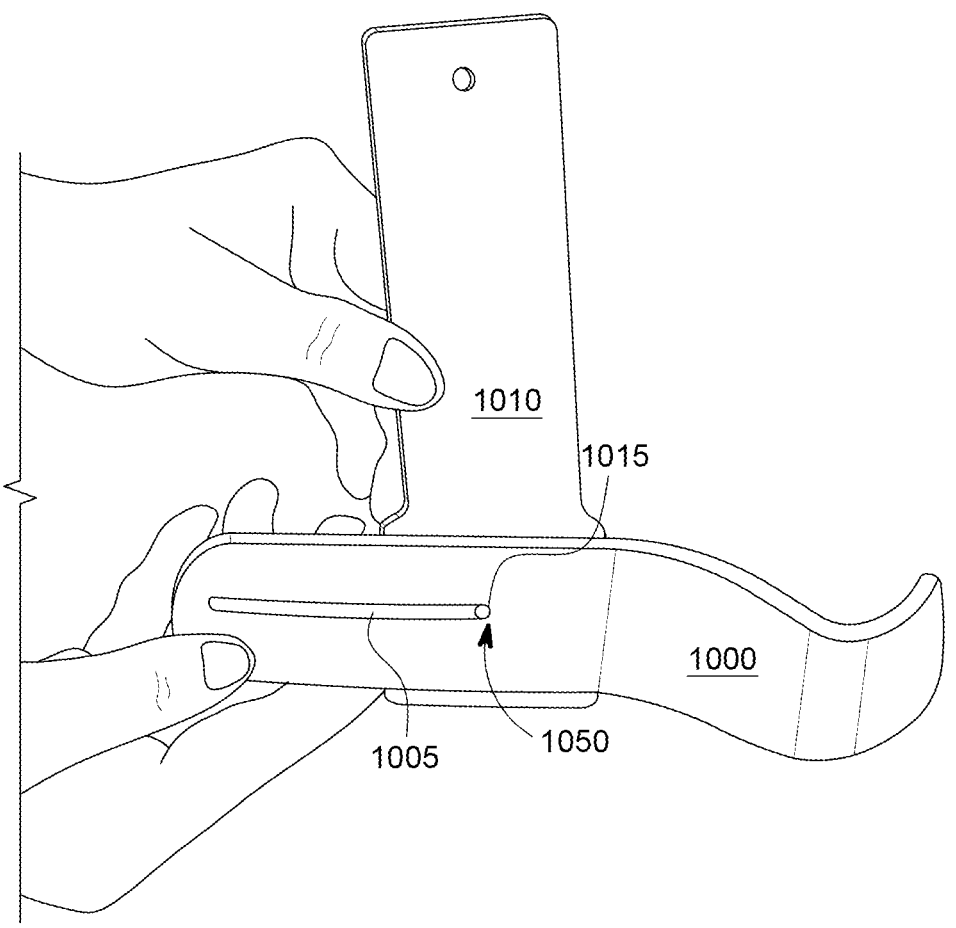

FIG. 10B is a perspective view of the ASIS frame member of FIG. 10A positioned in a minimal extended width state.

Figure 10C:
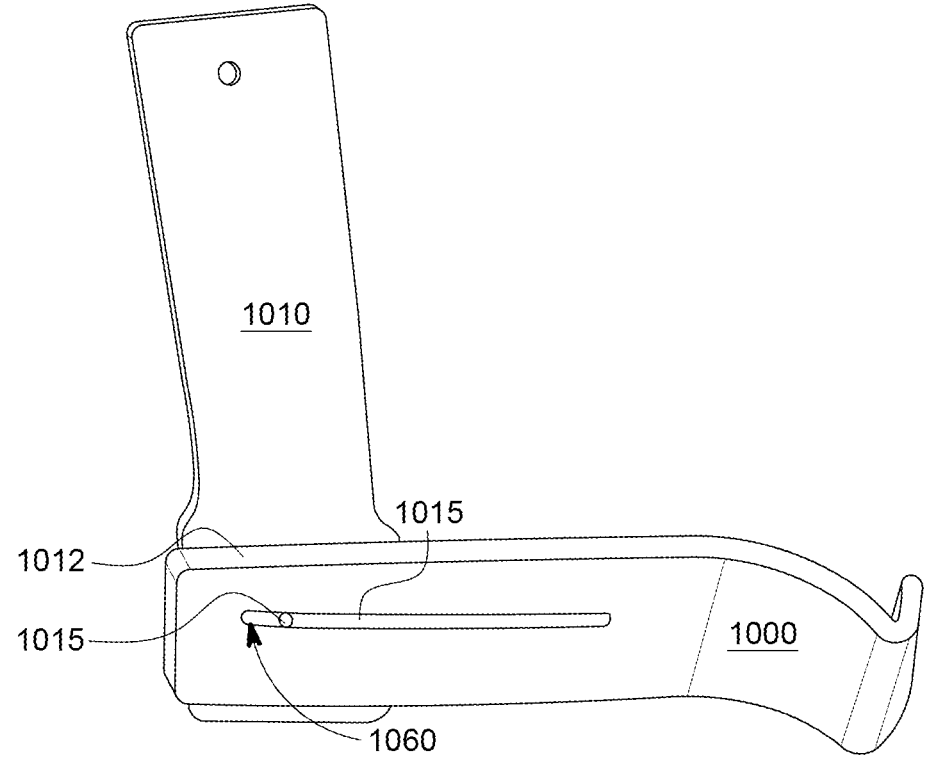

FIG. 10C is a perspective view of the ASIS frame member of FIG. 10A positioned in a maximum extended state.

Figure 10D:
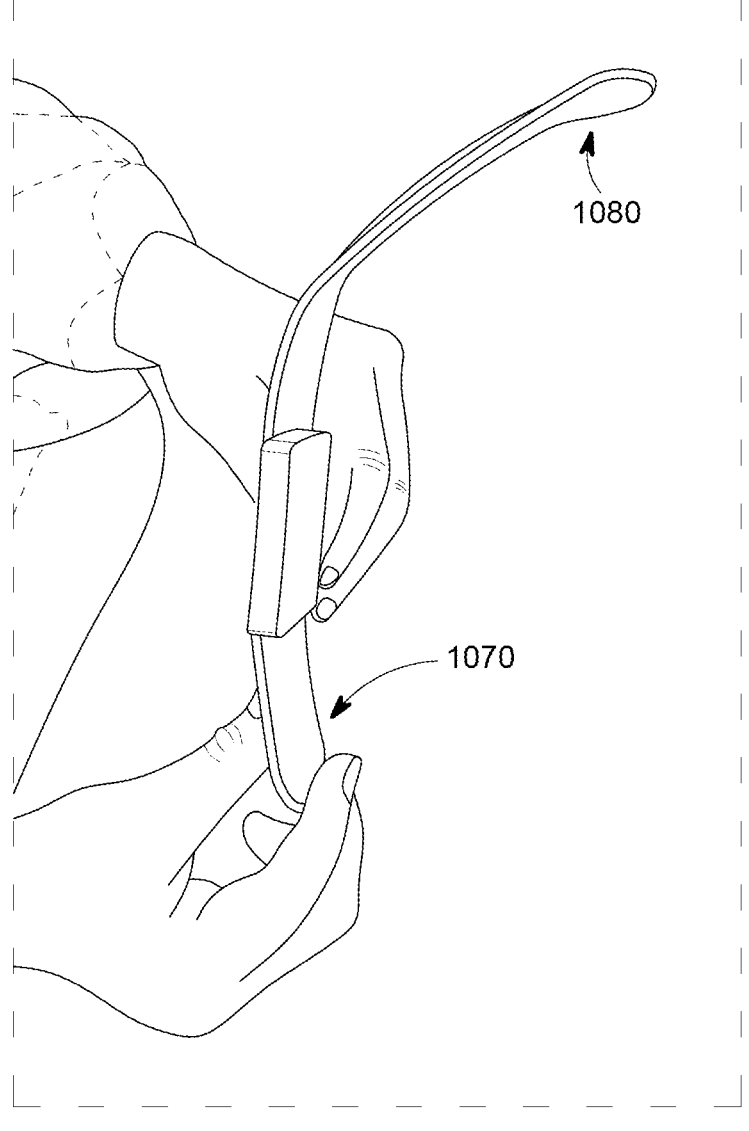

FIG. 10D is a side view of the ASIS frame member of FIG. 10A positioned in a minimal extended state.

Figure 11A:
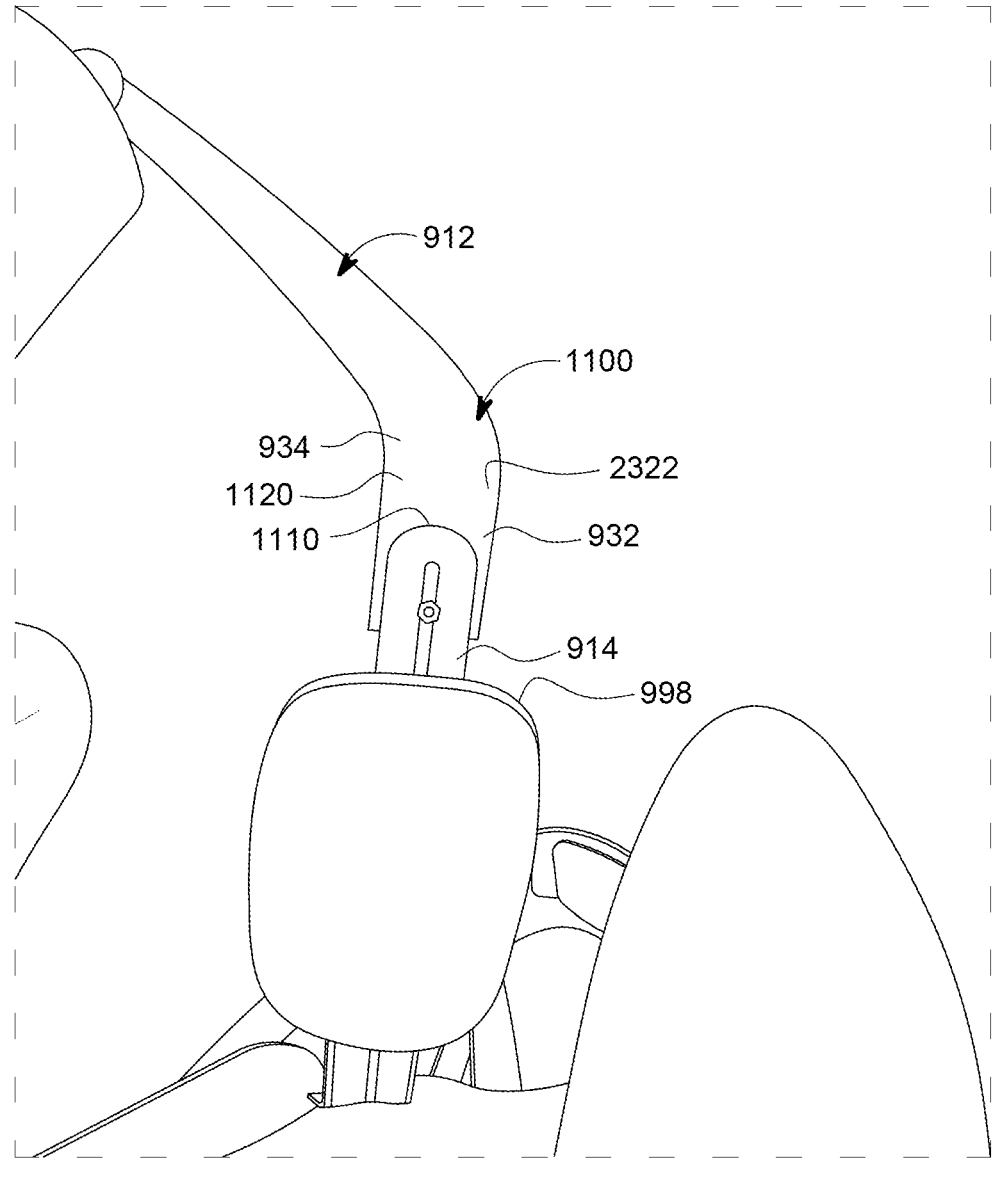

FIG. 11A is a side view of an interior surface of a second embodiment of a proximal (curved) superior frame coupled to a superior strut of the orthopedic brace of FIGS. 9A-9D.

Figure 11B:
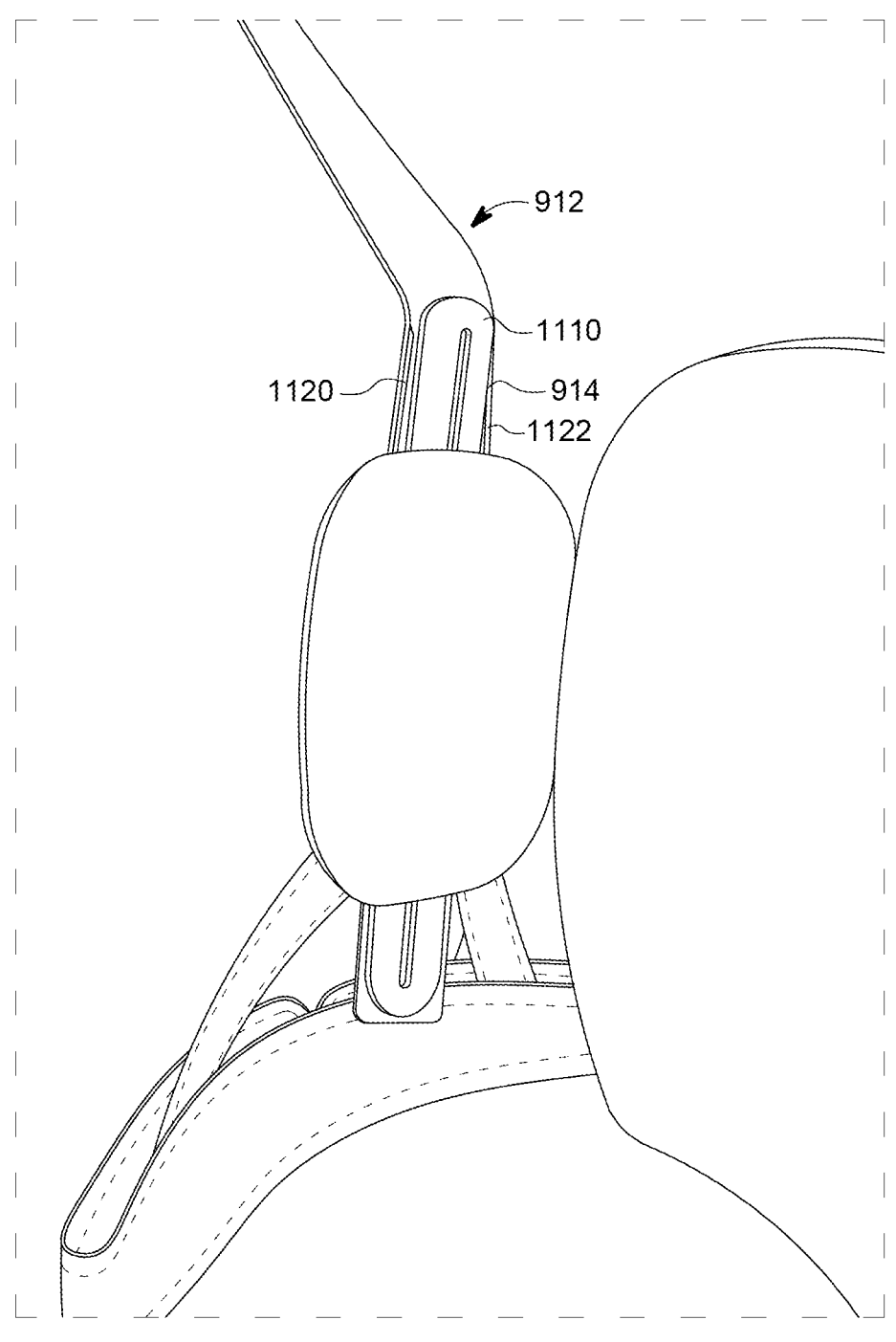

FIG. 11B is a side view of the proximal (curved) superior frame of FIG. 11A coupled to the superior strut of the orthopedic brace positioned within a channel formed in the proximal (curved) superior frame.

Figure 12A:
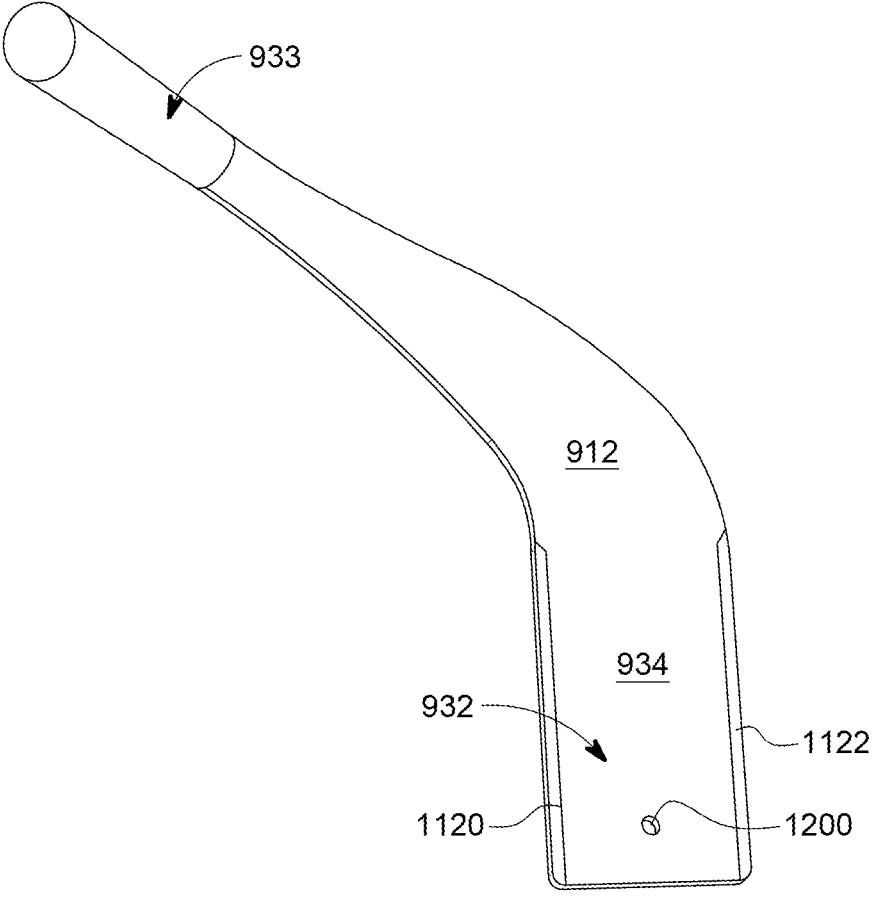

FIG. 12A is a side view of the proximal (curved) superior frame of FIG. 11A.

Figure 12B:

FIG. 12B is a front view of the proximal (curved) superior frame of FIG. 12A.

Figure 13A:
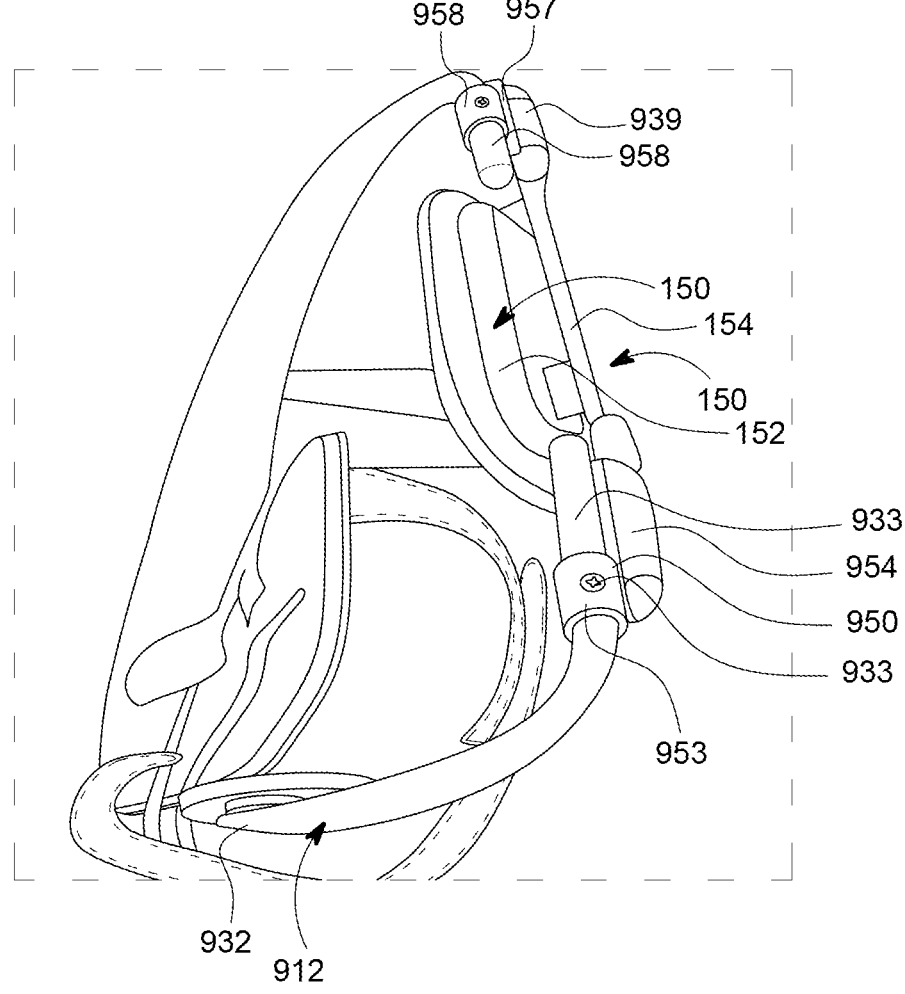

FIG. 13A is an exemplary embodiment of the chest plate of FIG. 6A attached to a chest compression member coupled to fasteners attached to corresponding end portions of the proximal (curved) superior frames.

4

Figure 13B:
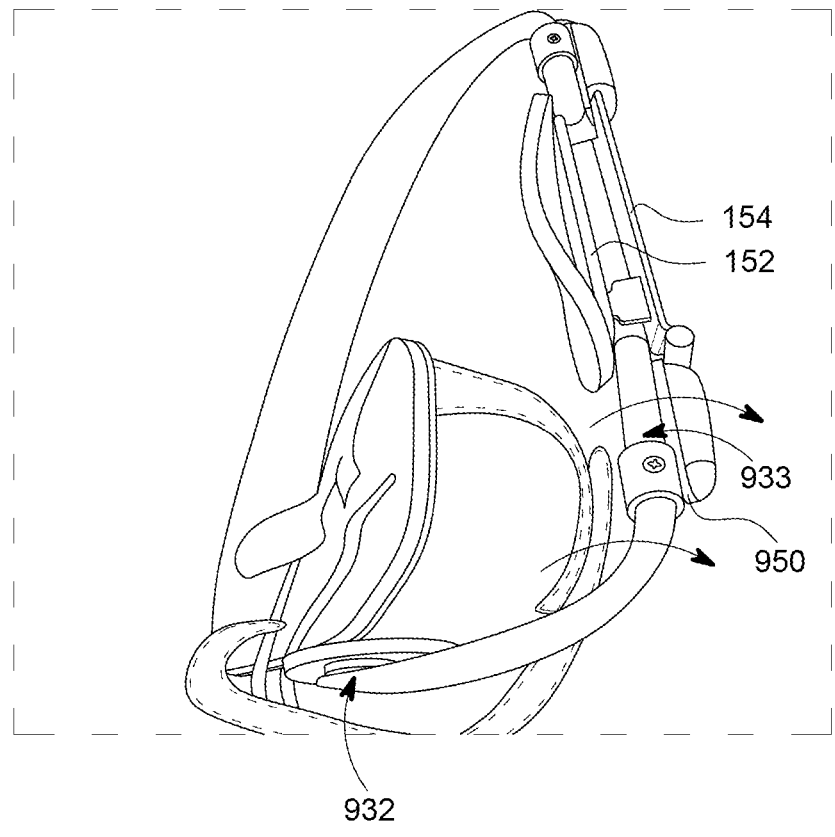

FIG. 13B is an exemplary embodiment of the chest compression member coupled to fasteners that are rotatably attached to the end portions of the proximal (curved) superior frames.

Figure 13C:
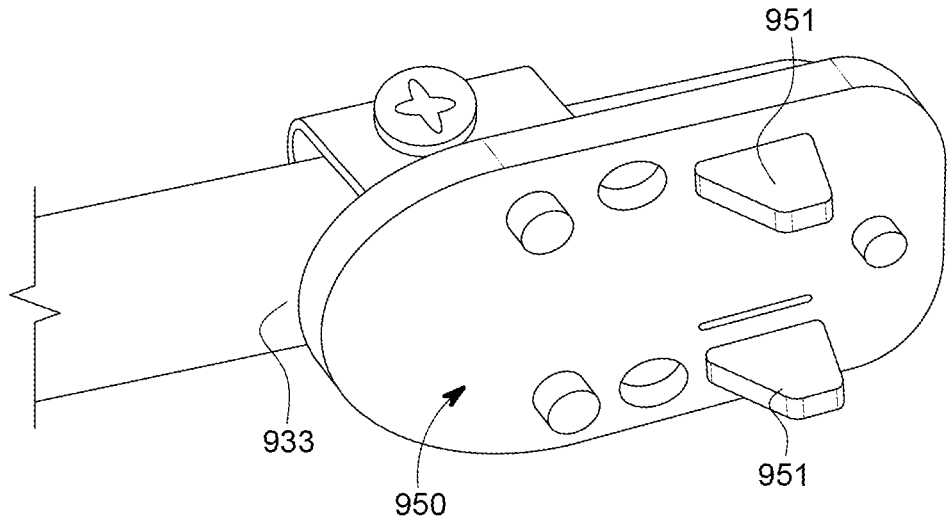

FIG. 13C is an exemplary embodiment of the adjustable chest fastening plate attached to a distal end portion of a superior frame member.

Figure 13D:
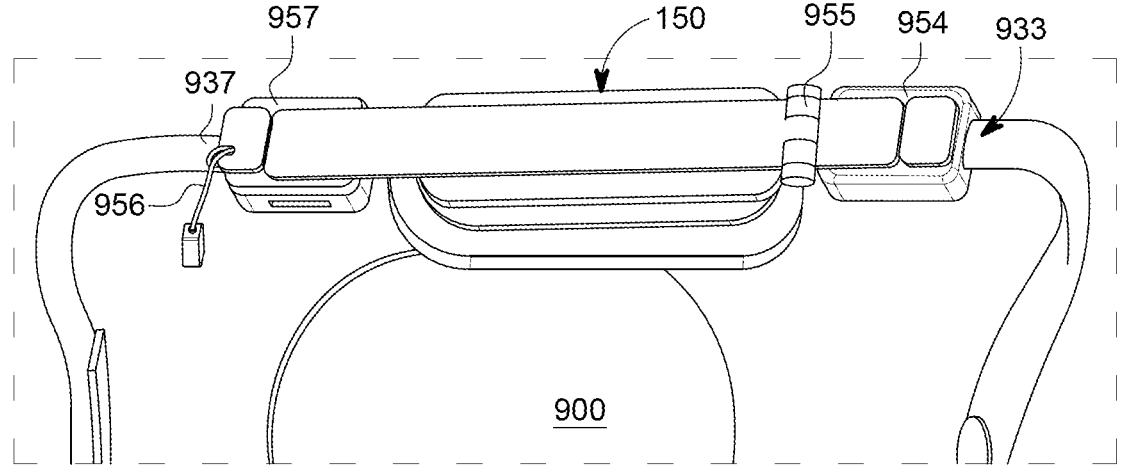

FIG. 13D is an exemplary embodiment of the anterior chest assembly attached to the superior frame members of the orthopedic spine brace.

Figure 13E:
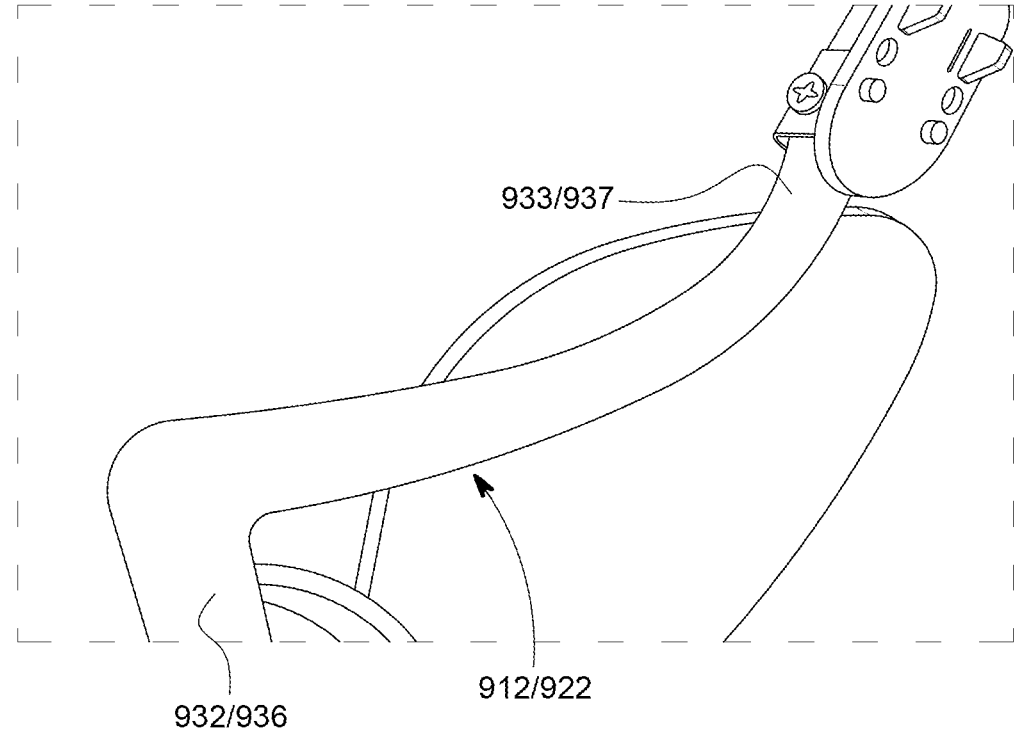

FIG. 13E is an exemplary embodiment of the architectural structure of the superior frame member of FIG. 13C.

Figure 14A:
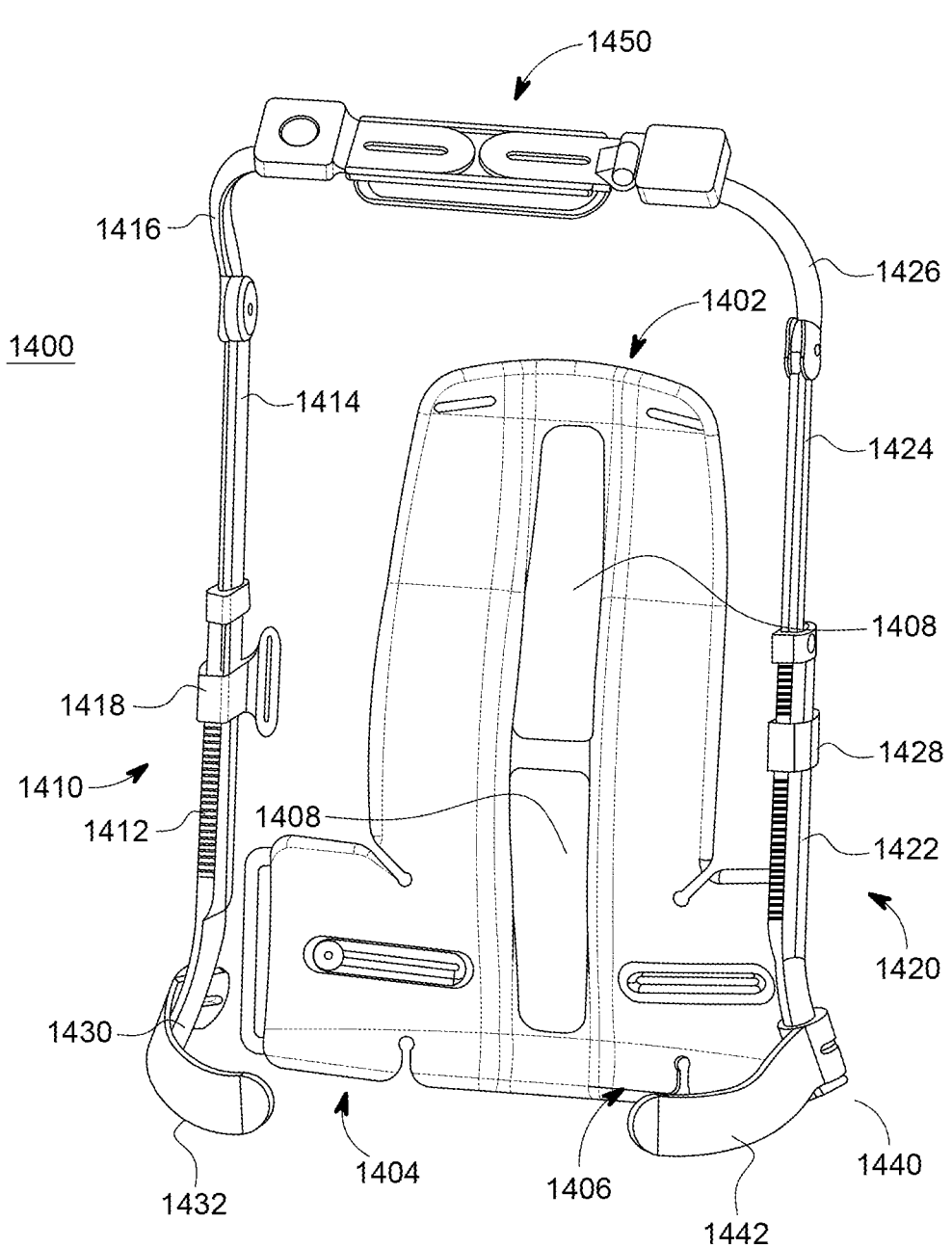

FIG. 14A is a perspective anterior view of a third embodiment of an orthopedic spine brace including a chest plate attachment coupled thereto.

Figure 14B:
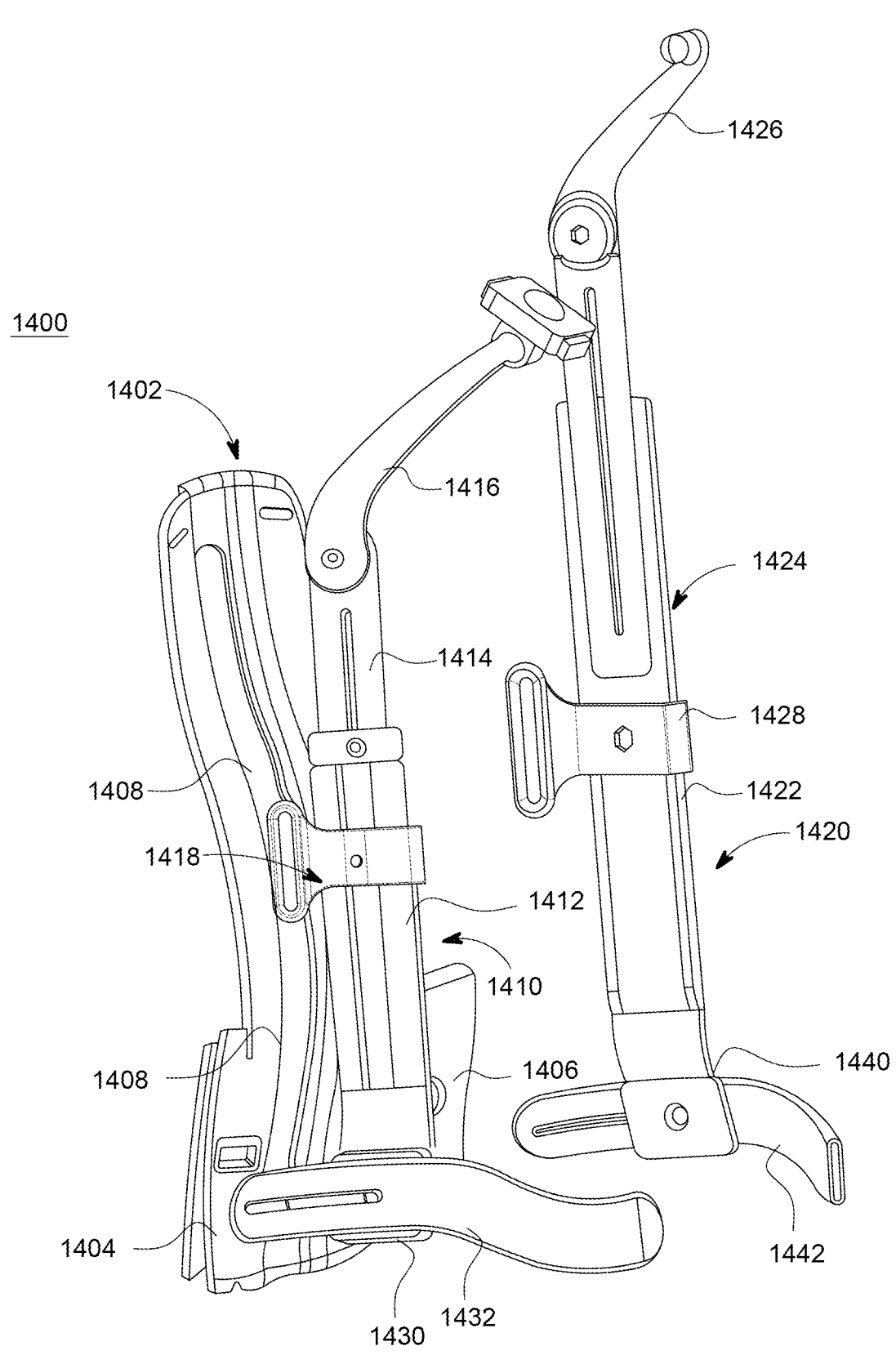

FIG. 14B is a perspective lateral view of the third embodiment of an orthopedic spine brace.

Figures 15A, 15B:
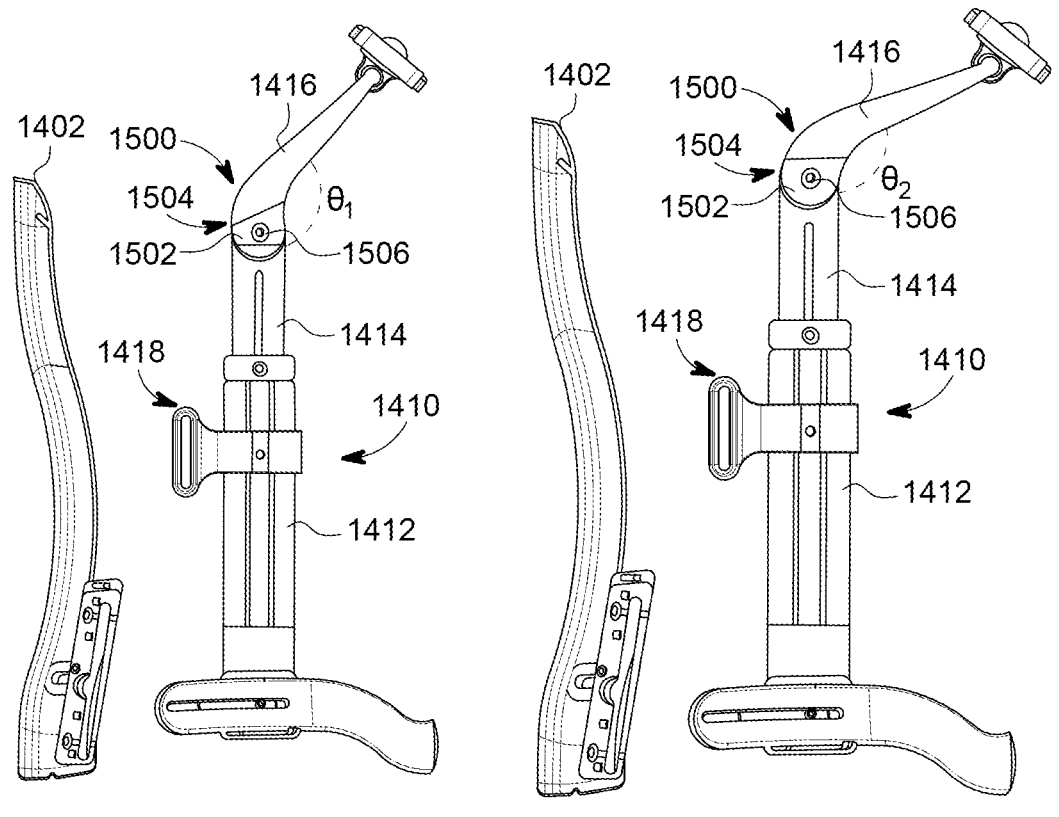

FIGS. 15A-15B illustrate the superior strut of the orthopedic spine brace of FIG. 14A at first and second angles relative to the medial strut.

Figure 15C:
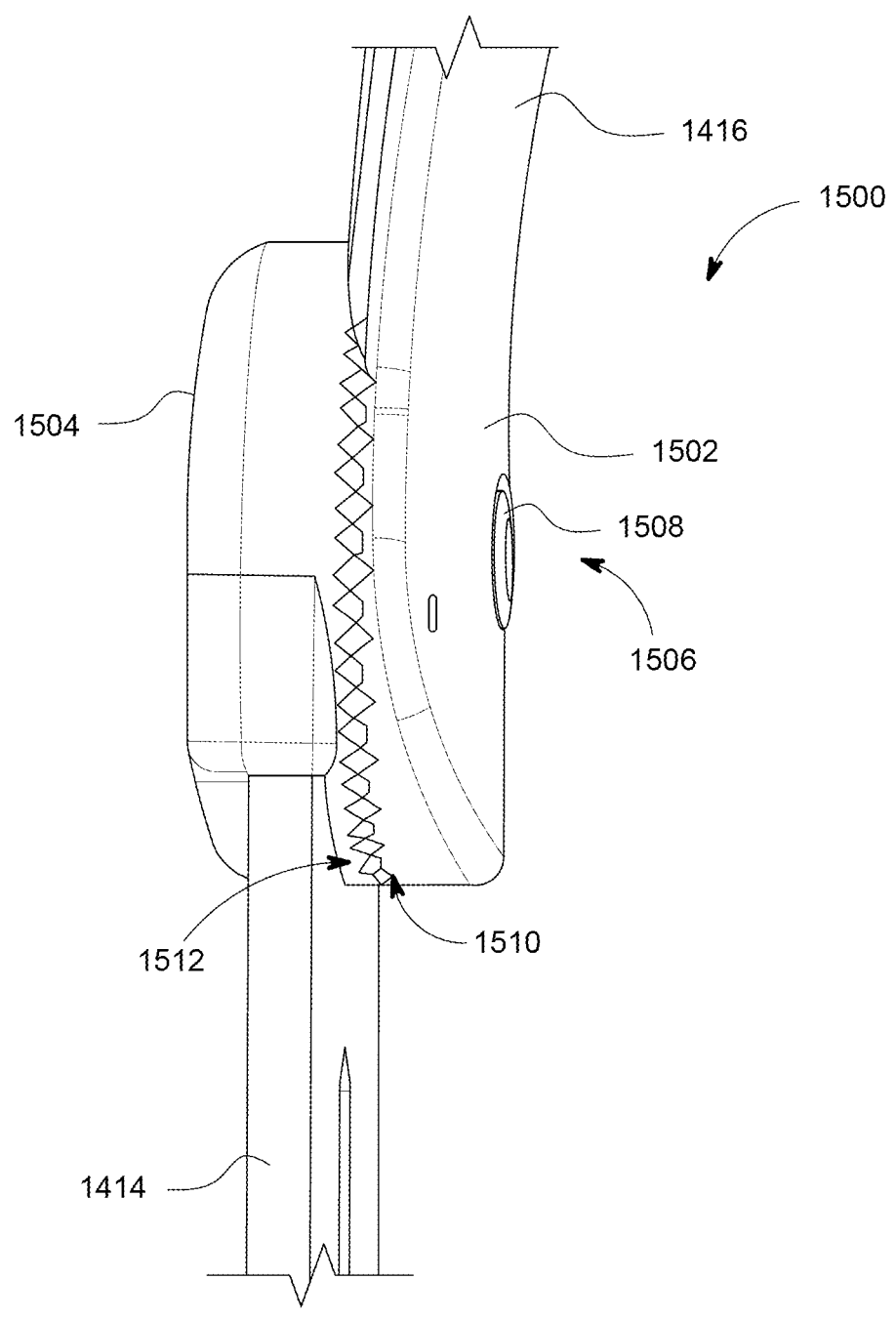

FIG. 15C is a back perspective view of the hinge enabling rotation of the superior strut relative to the medial strut.

Figure 15D:
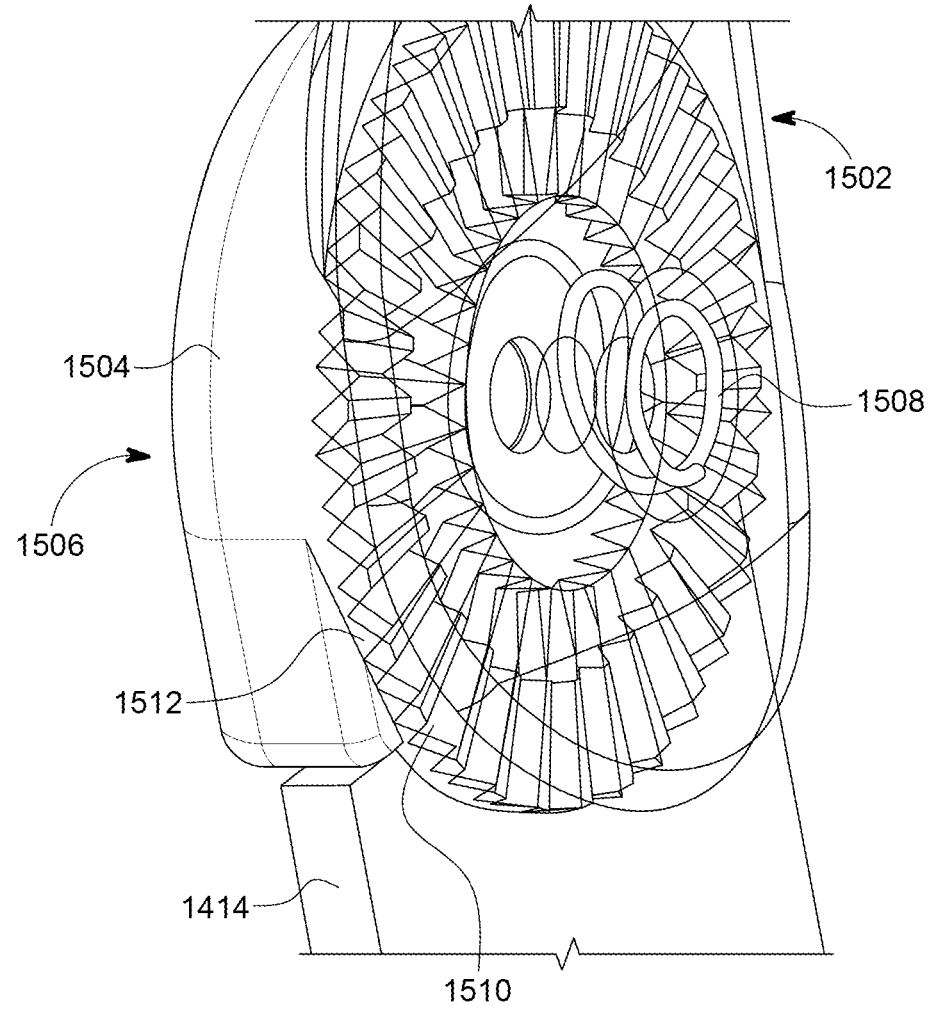

FIG. 15D is a detailed view of the components comprising the hinge of FIGS. 15A-15C.

Figure 15E:
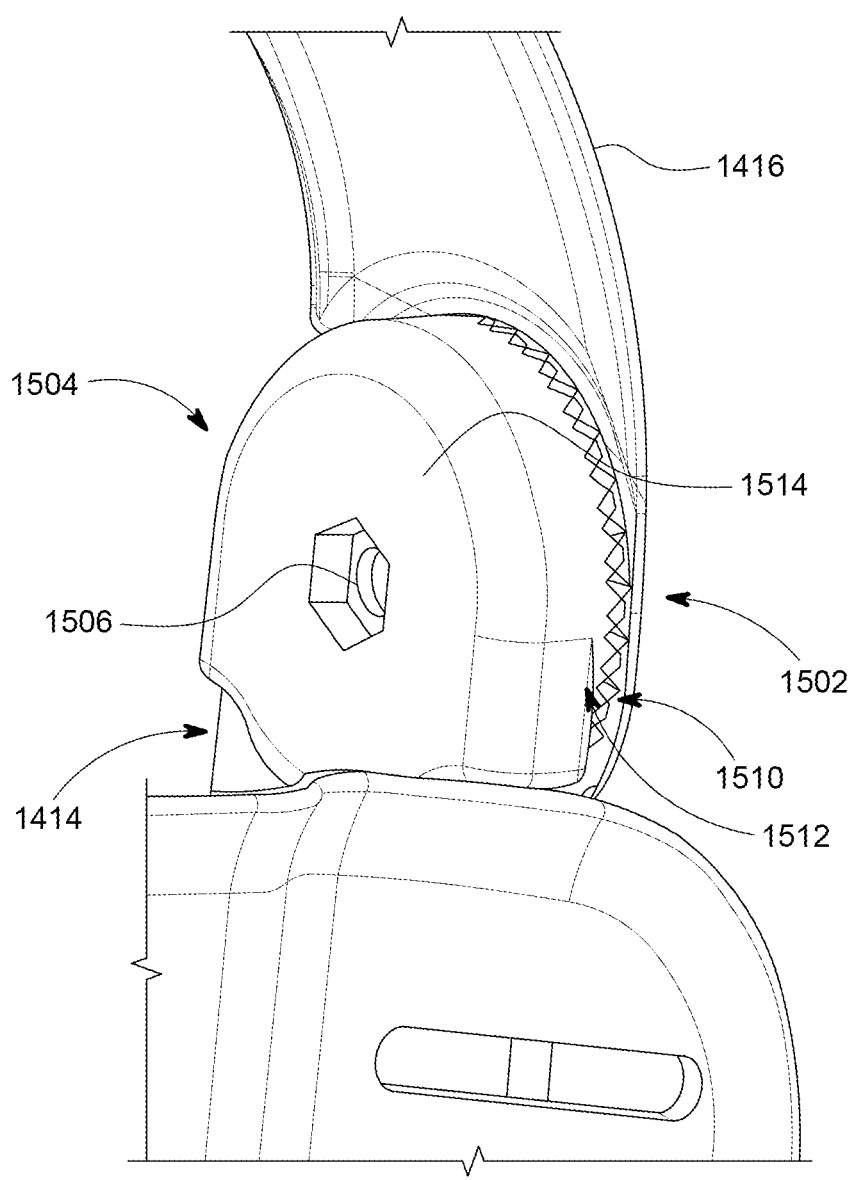

FIG. 15E is a back left perspective view of the hinge of FIGS. 15A-15D.

Figure 15F:
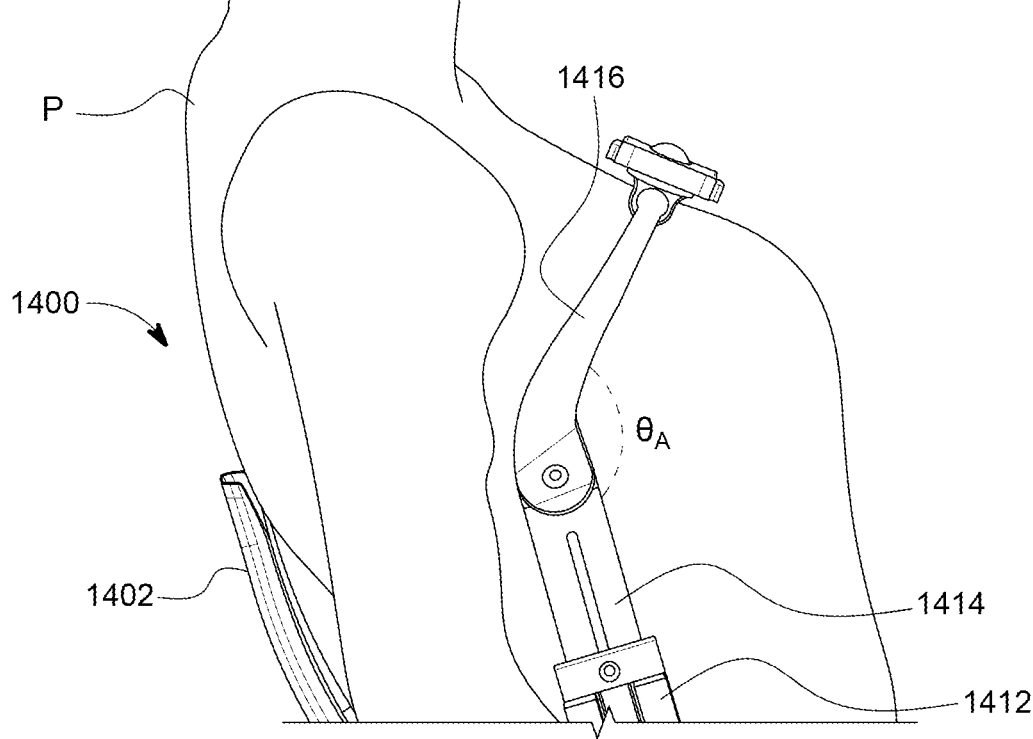

FIG. 15F is an illustration of a patient wearing the orthopedic spine brace of FIG. 14B with the superior struts rotated to an angle 'A' (OA) relative to the medial strut.

Figures 16A, 16B:
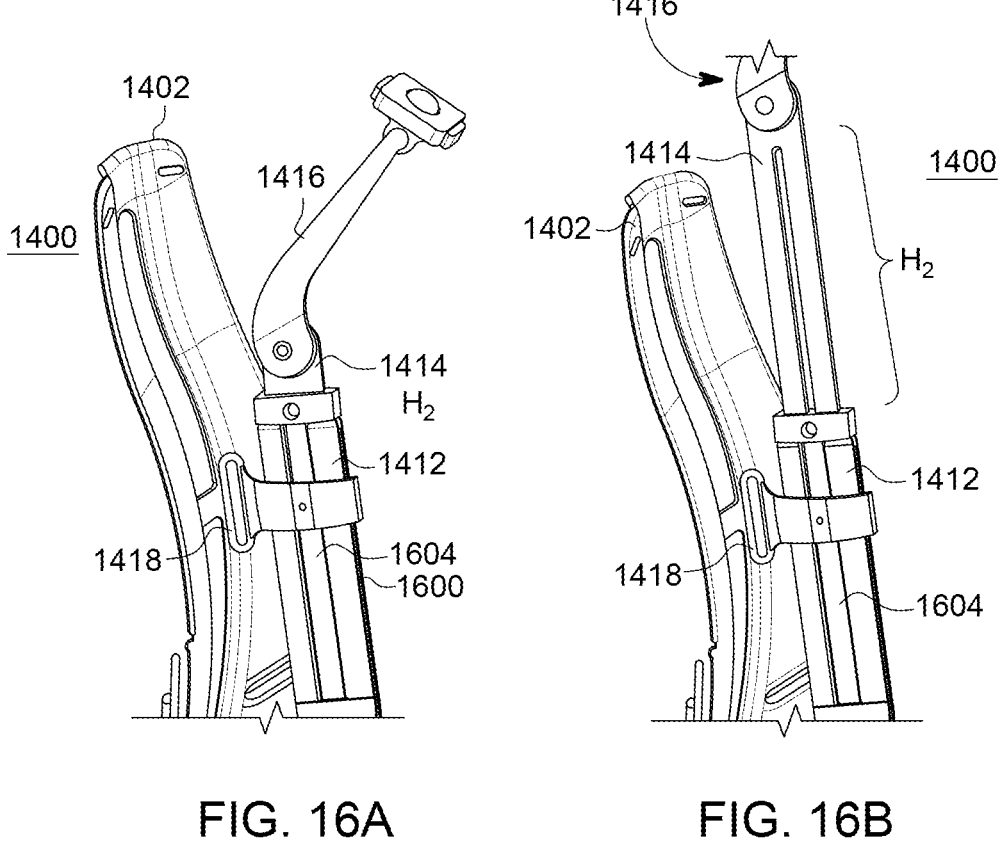

FIGS. 16A-16B illustrate the medial strut adjusted to first and second heights.

Figure 16C:
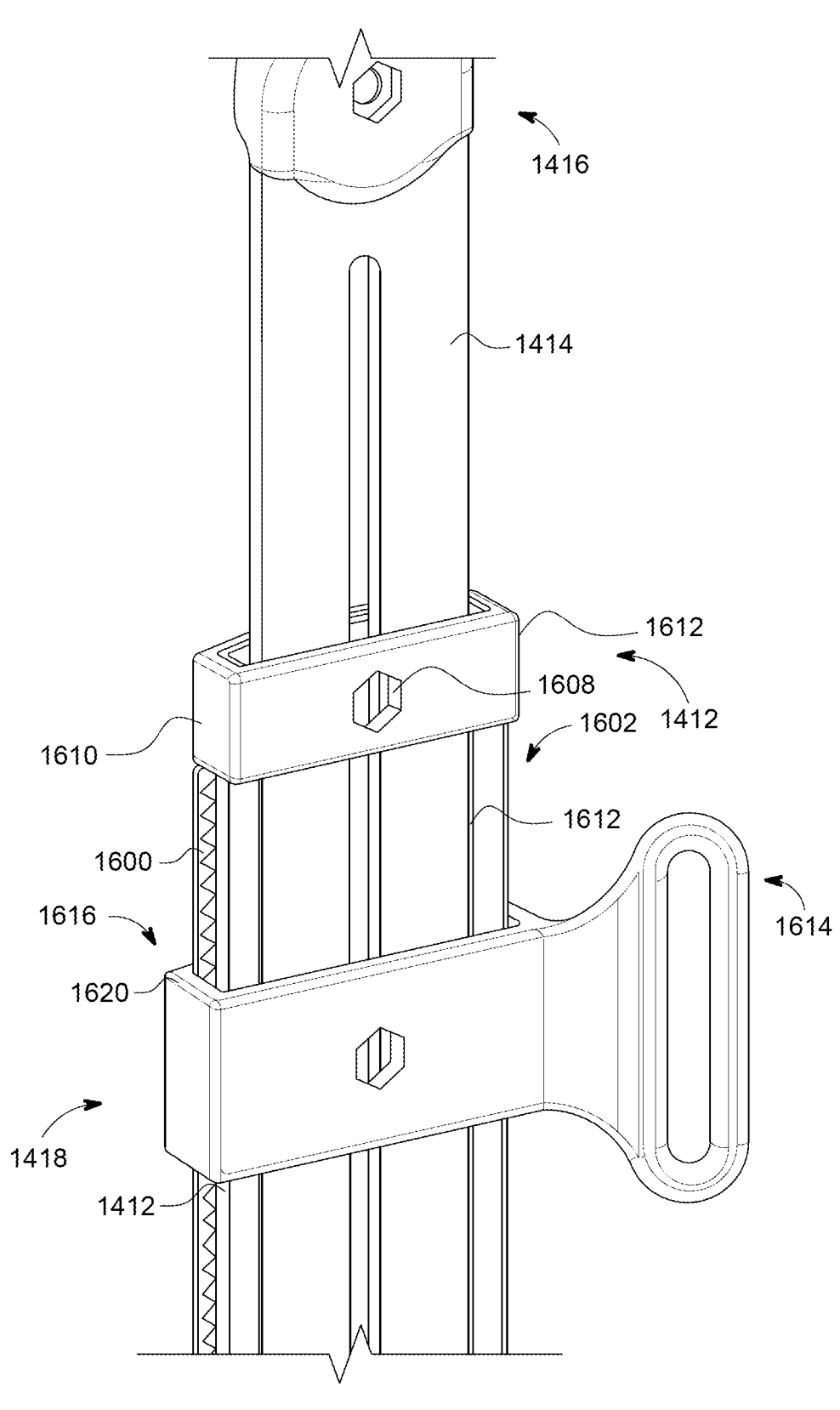

FIG. 16C is a front interior perspective view of first lateral components of the orthopedic spine brace of FIGS. 14A-14B.

Figures 17A, 17B:
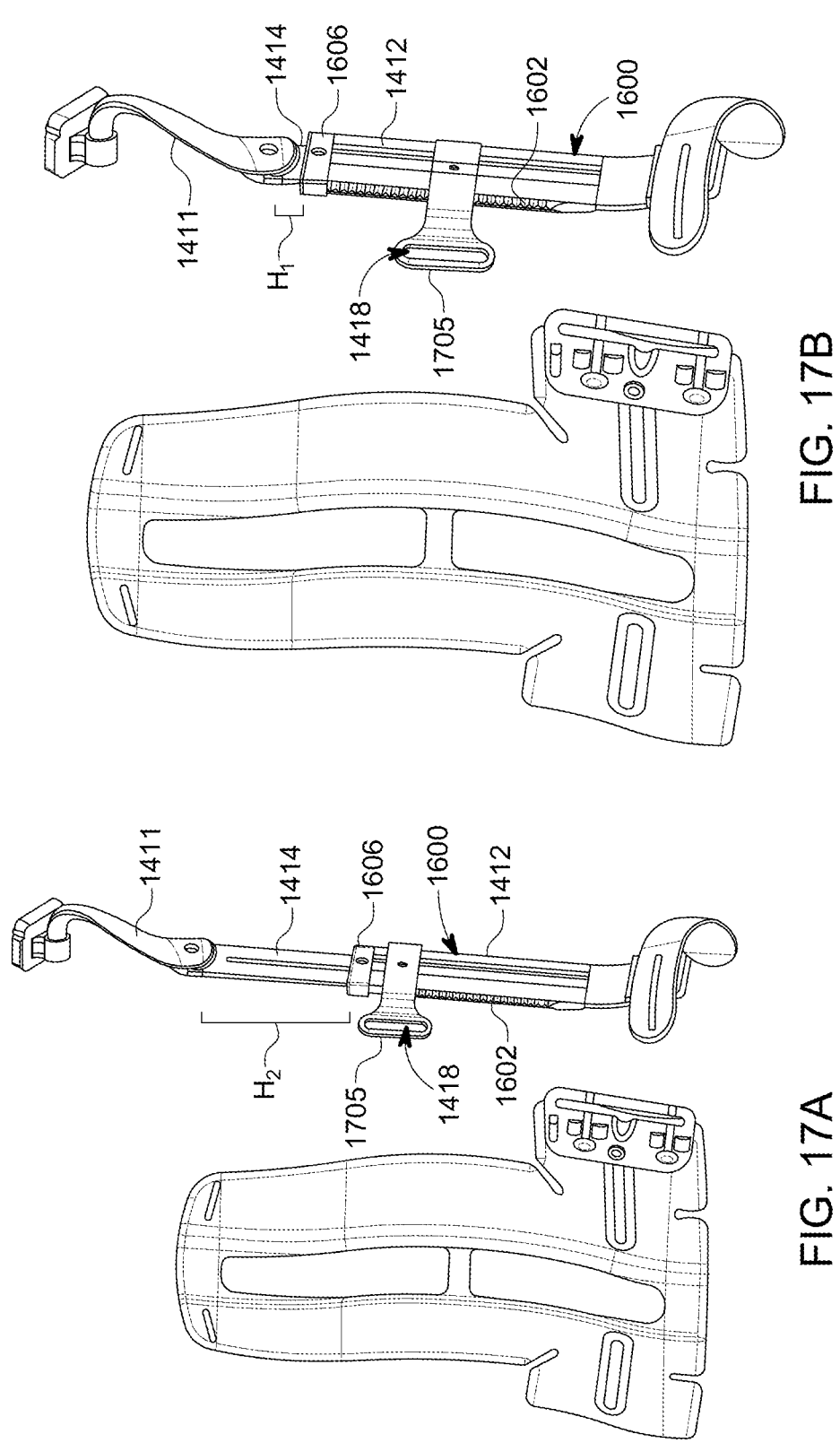

FIGS. 17A-17B illustrate the steering ring fixed at first and second positions along the inferior strut in accordance with the medial strut being extended or retracted to either a first height or a second height.

Figure 17D:
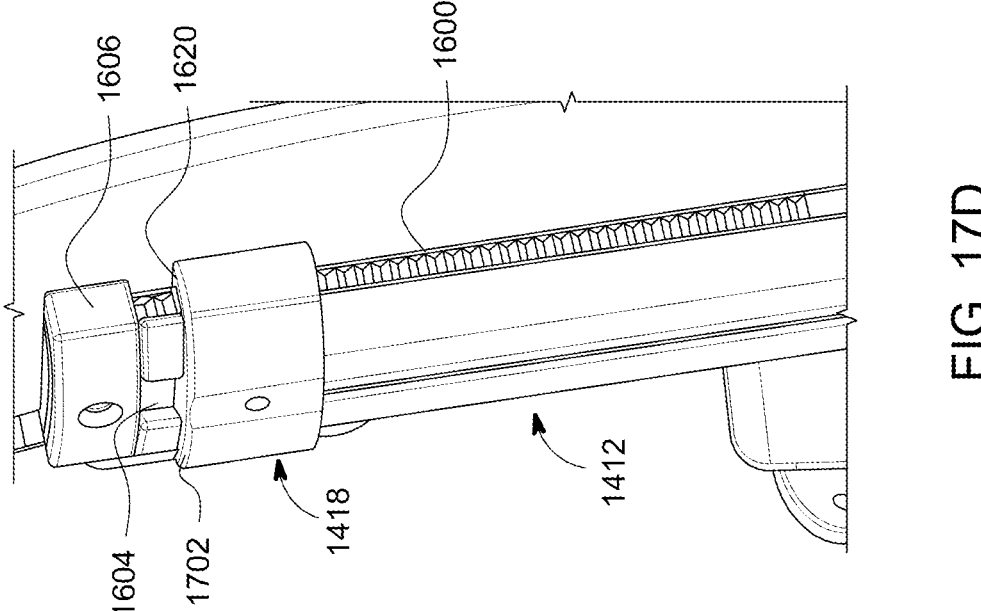
Figure 17C:
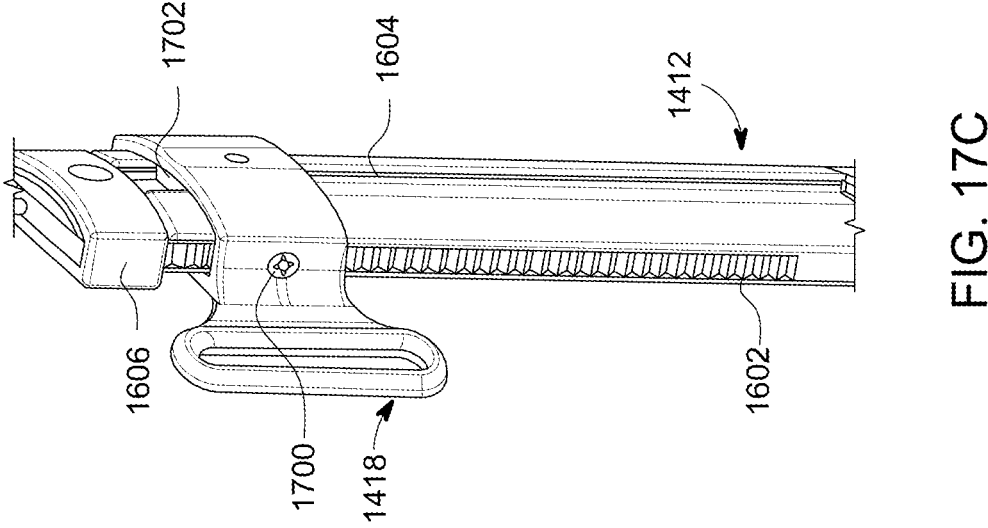

FIG. 17C is a back perspective view of the steering ring fixed at a particular position along the inferior strut.

FIG. 17D is an exterior side perspective view of the steering ring fixed along the inferior strut as seen in FIG. 17C.

Figure 17E:
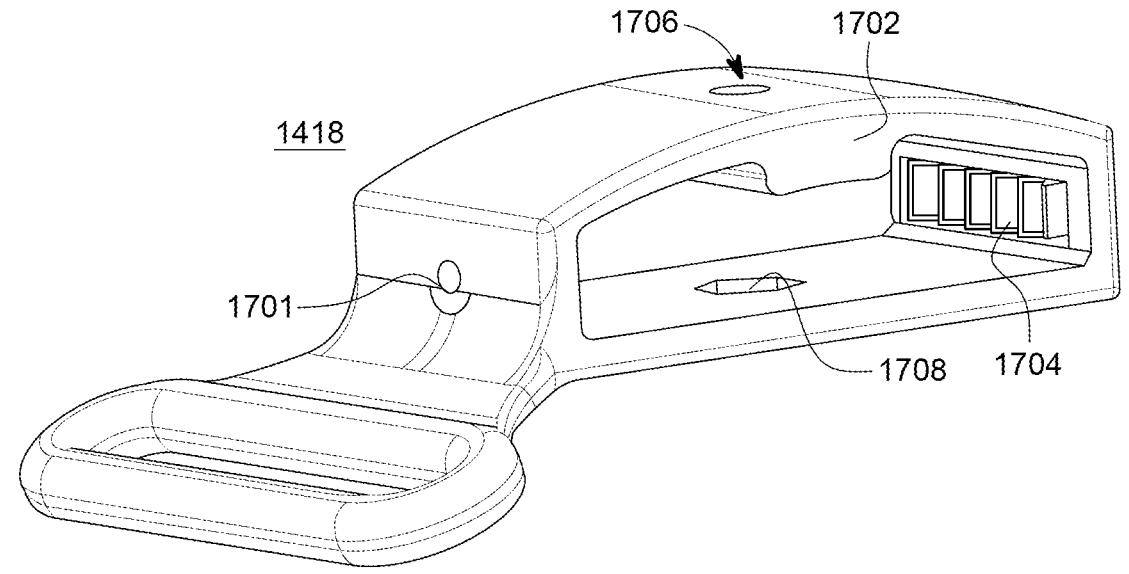

FIG. 17E is a bottom perspective view of the steering ring.

Figure 17F:
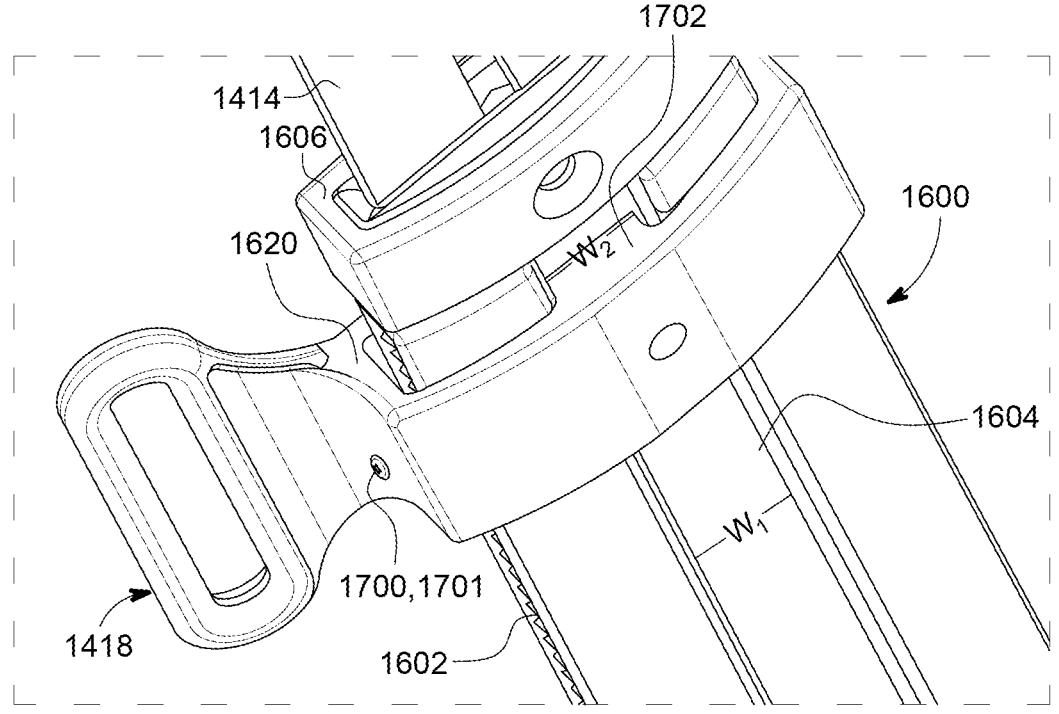

FIG. 17F is a top exterior side perspective of the steering ring positioned along the inferior strut as seen in FIGS. 17C-17D.

Figure 17G:
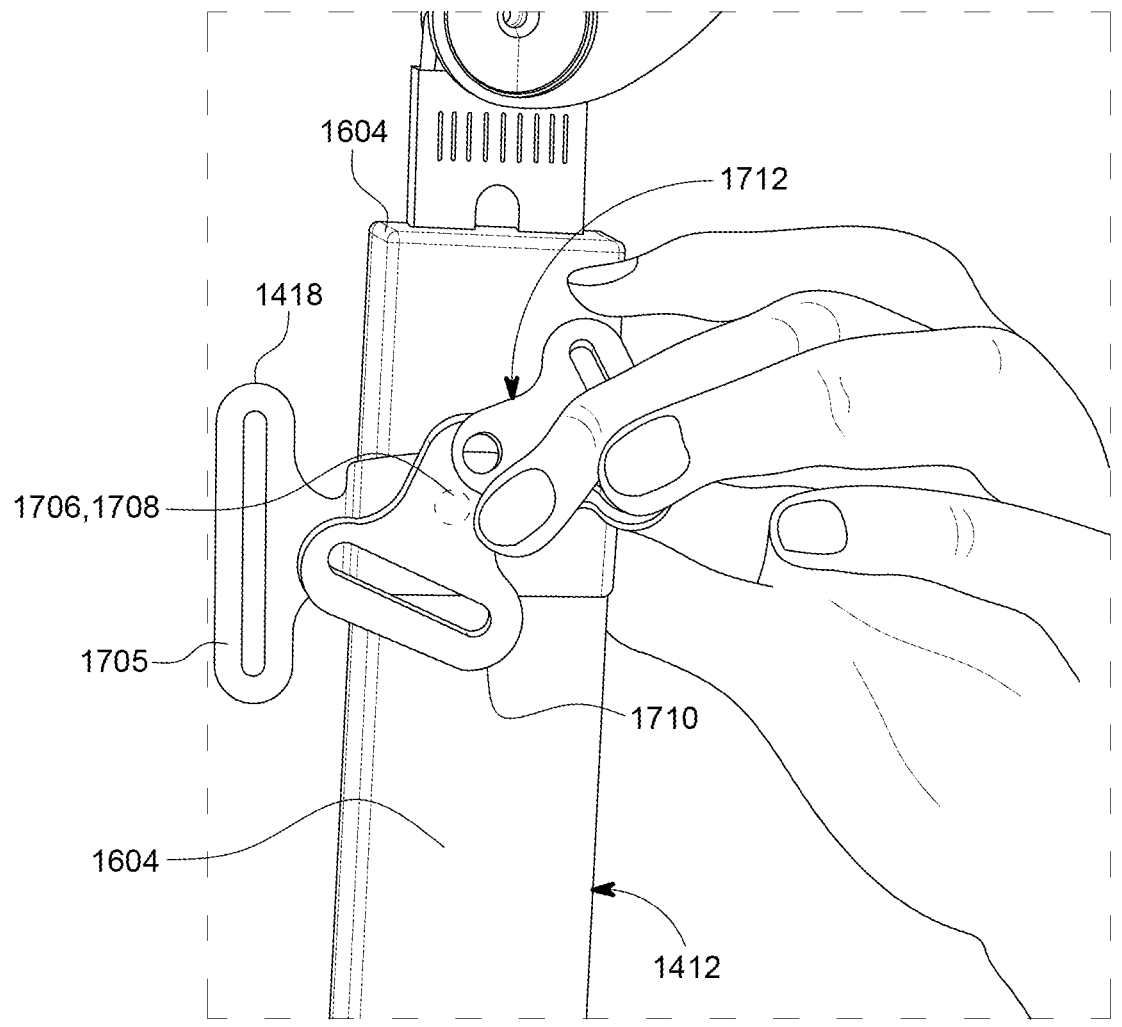

FIG. 17G is a detailed front perspective view of the orthopedic spine brace of FIGS. 14A-14B including the steering ring coupled with buckle accessories.

Figure 18A:
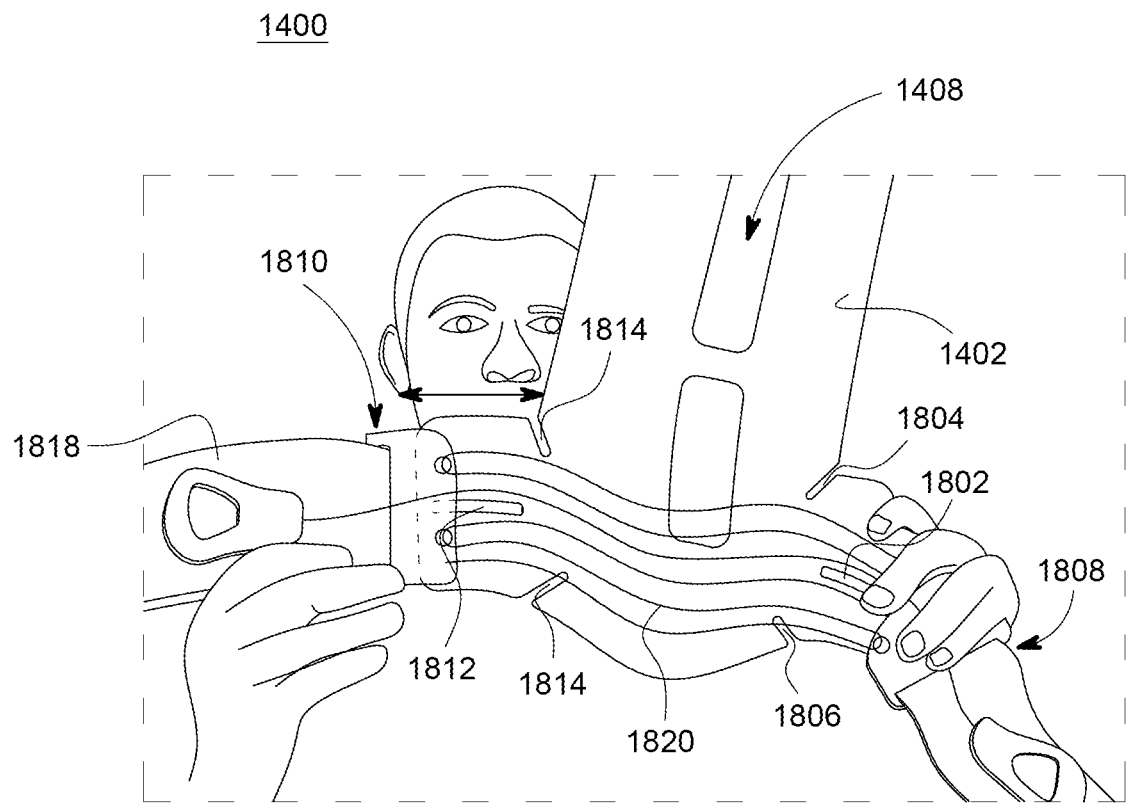

FIG. 18A is a back perspective of a back panel pulley system coupled to the back panel of the orthopedic spine brace.

Figure 18B:
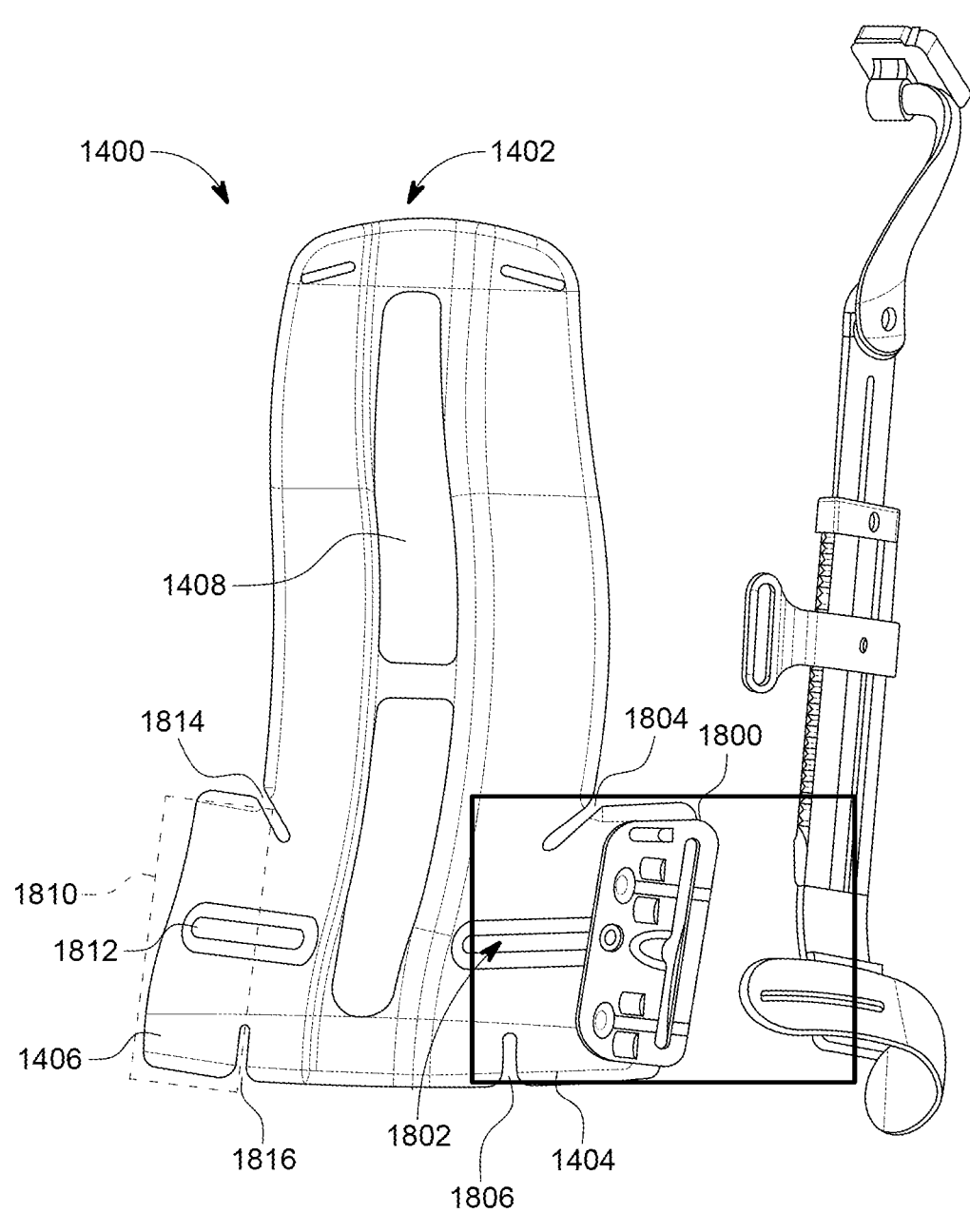

FIG. 18B is a back perspective of the orthopedic spine brace of FIGS. 14A-14B illustrating a first cord attachment plate of the back panel pulley system slidably coupled with a lower wing of the back panel of the orthopedic spine brace.

Figure 19A:
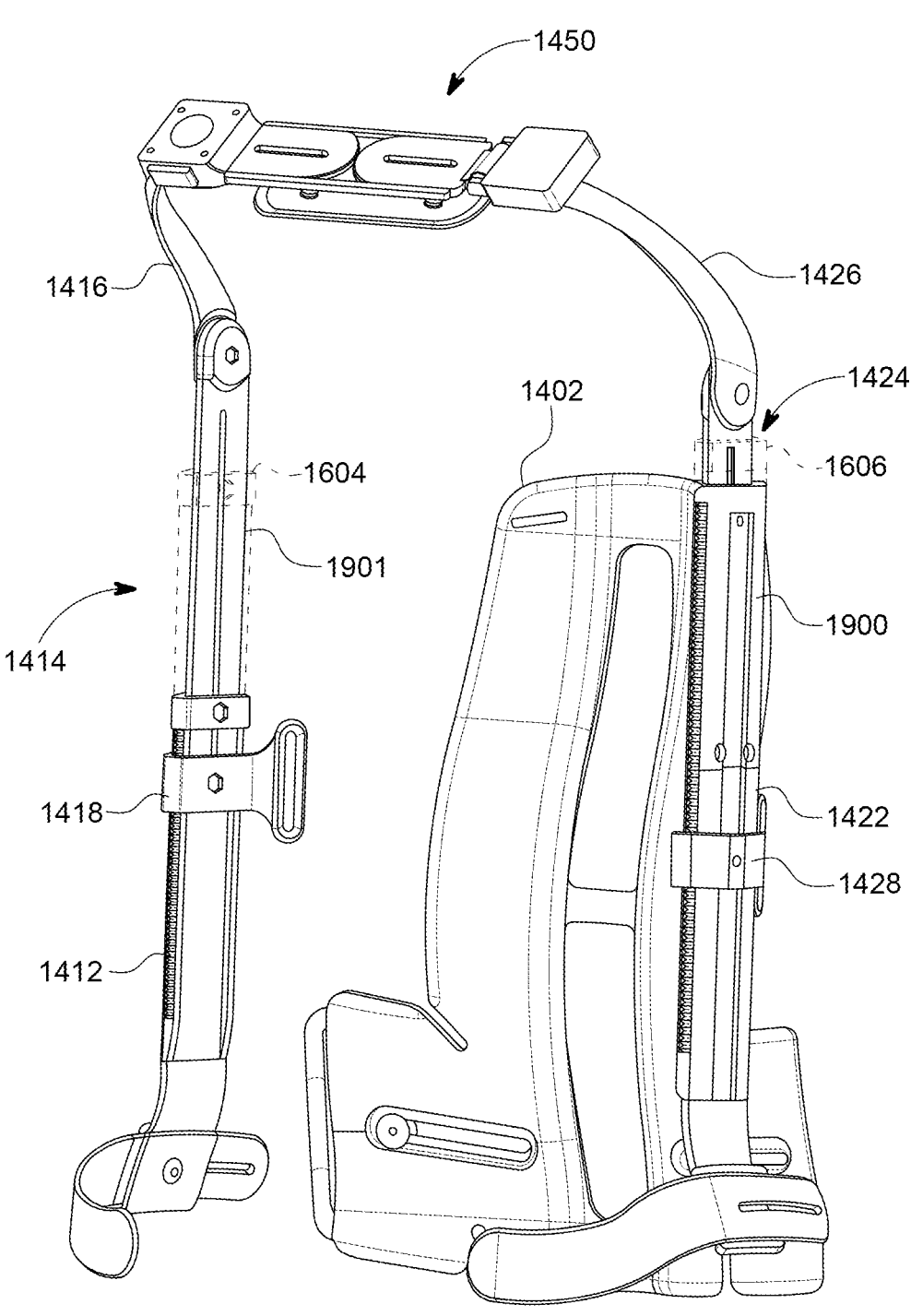

FIG. 19A is a perspective view of the orthopedic spine brace of FIGS. 14A-14B having extension struts installed thereon.

Figure 19B:
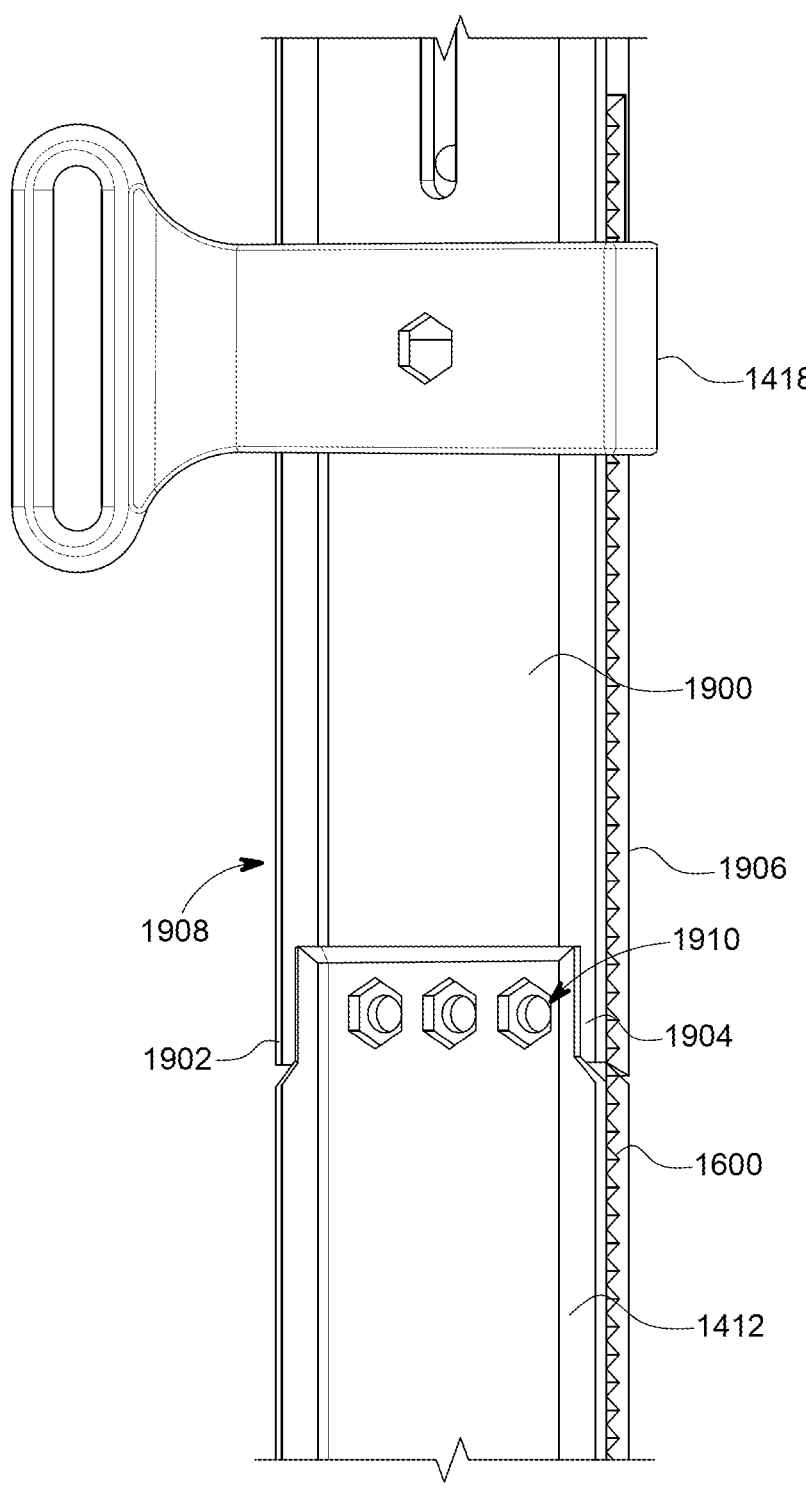

FIG. 19B is a detailed interior perspective view of an extension strut of FIG. 19A coupled with an inferior strut of the orthopedic spine brace.

Figure 19C:
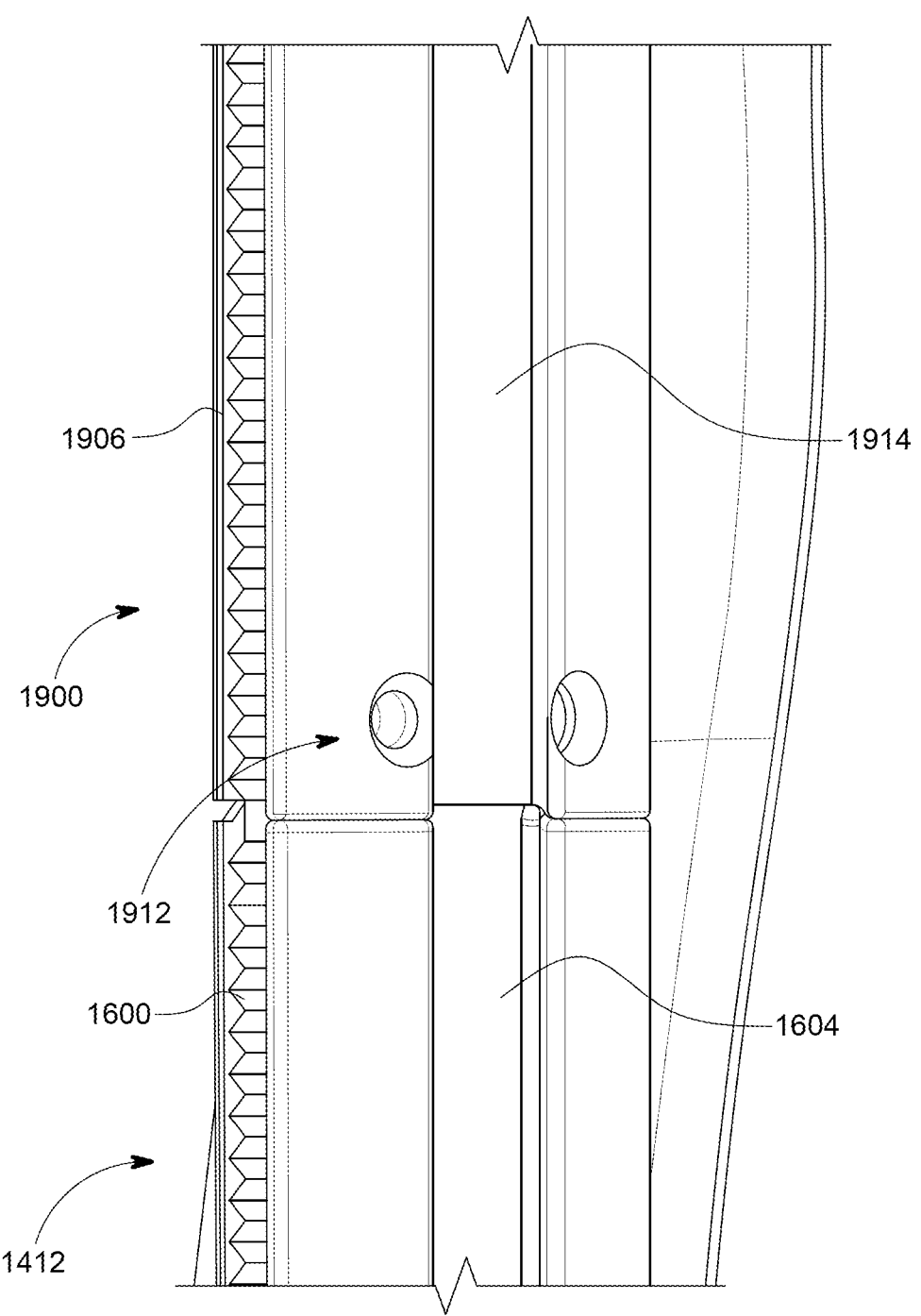

FIG. 19C is a detailed exterior perspective view of the extension strut of FIG. 19A coupled with an inferior strut of the orthopedic spine brace.

Figure 20A:
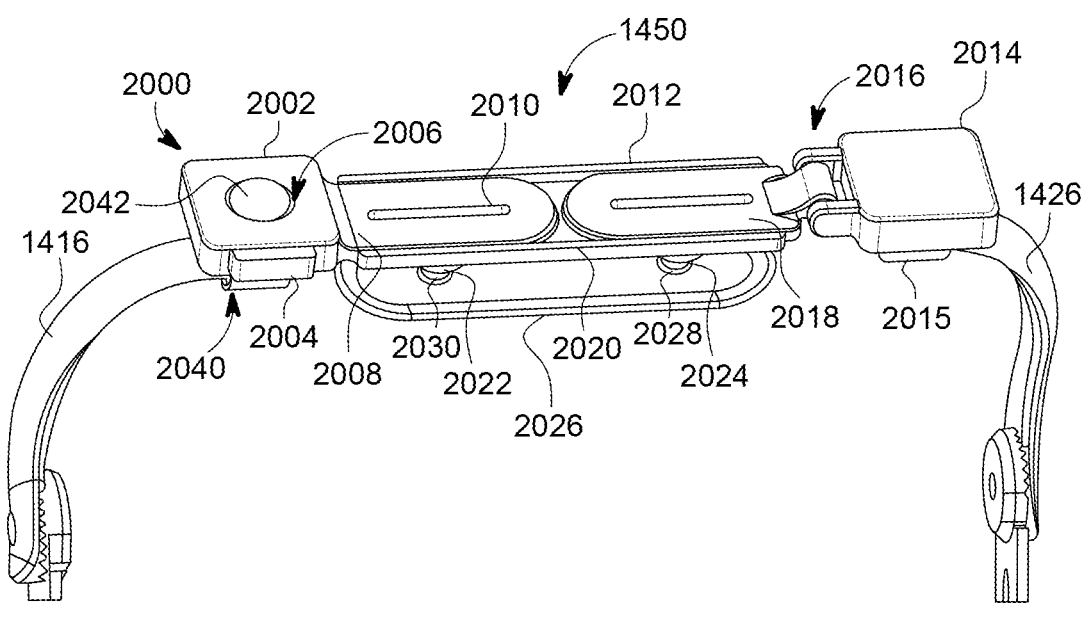

FIG. 20A is a perspective view of the chest plate attachment coupled to the orthopedic spine brace of FIGS. 14A-14B.

Figure 20B:
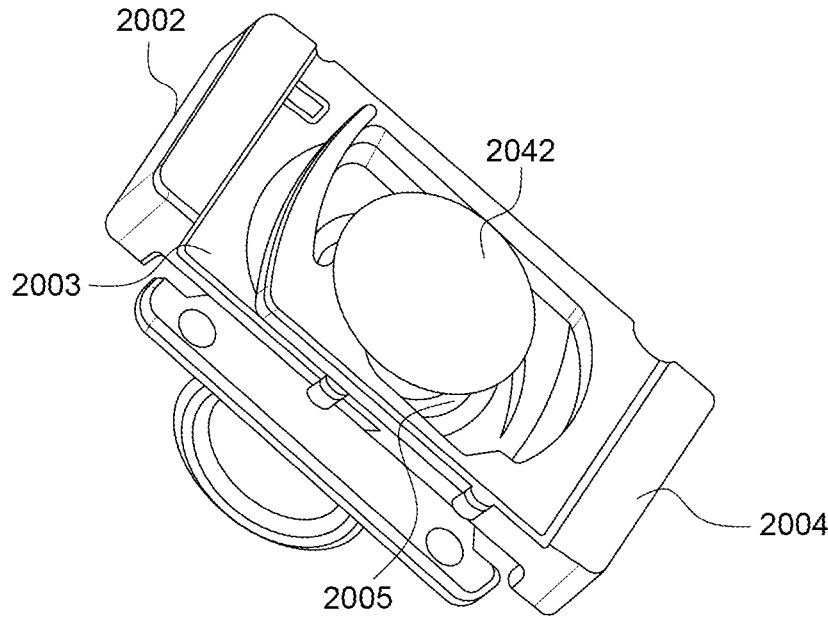

FIG. 20B is a perspective detailed view of internal components of the lock connector of the chest plate attachment coupled to the ball and post assembly of an attachment ring that couples the chest plate attachment to the orthopedic spine brace.

Figure 20C:
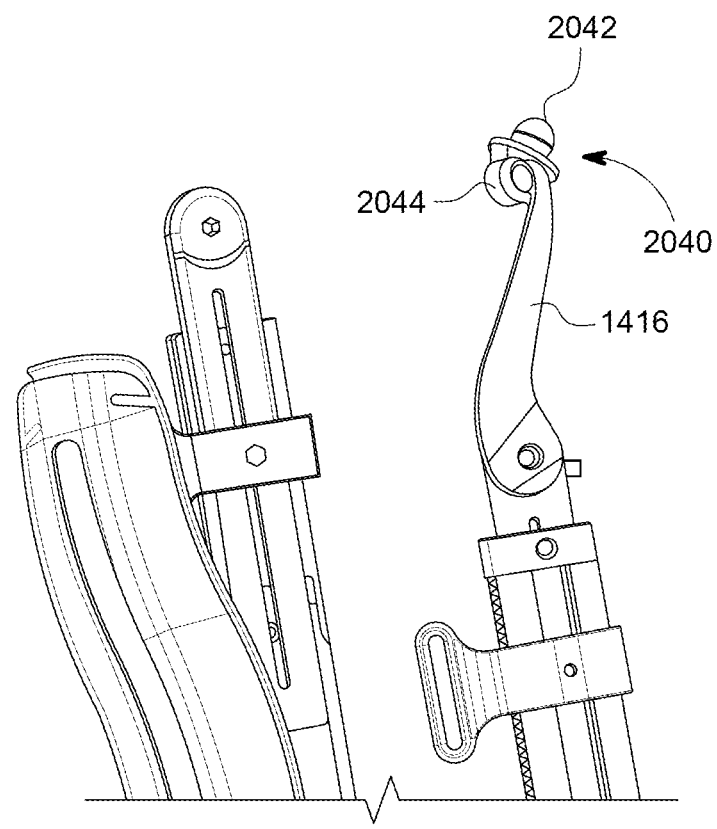

FIG. 20C is a perspective view of the orthopedic spine brace of FIGS. 14A-14B coupled with the attachment ring.

Figure 20D:
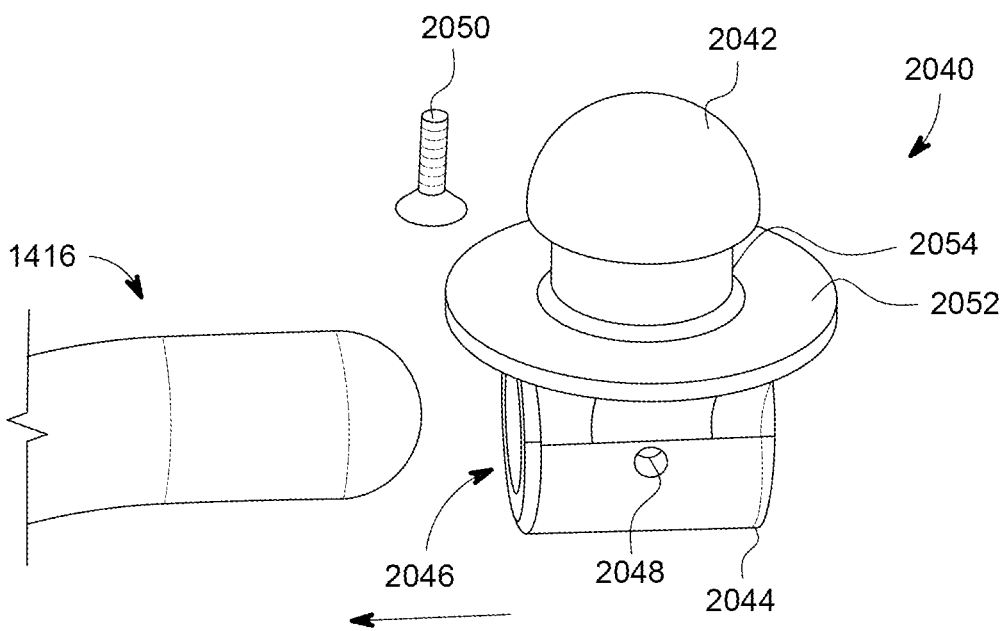

FIG. 20D is a detailed perspective view of the attachment ring.

Figure 21A:
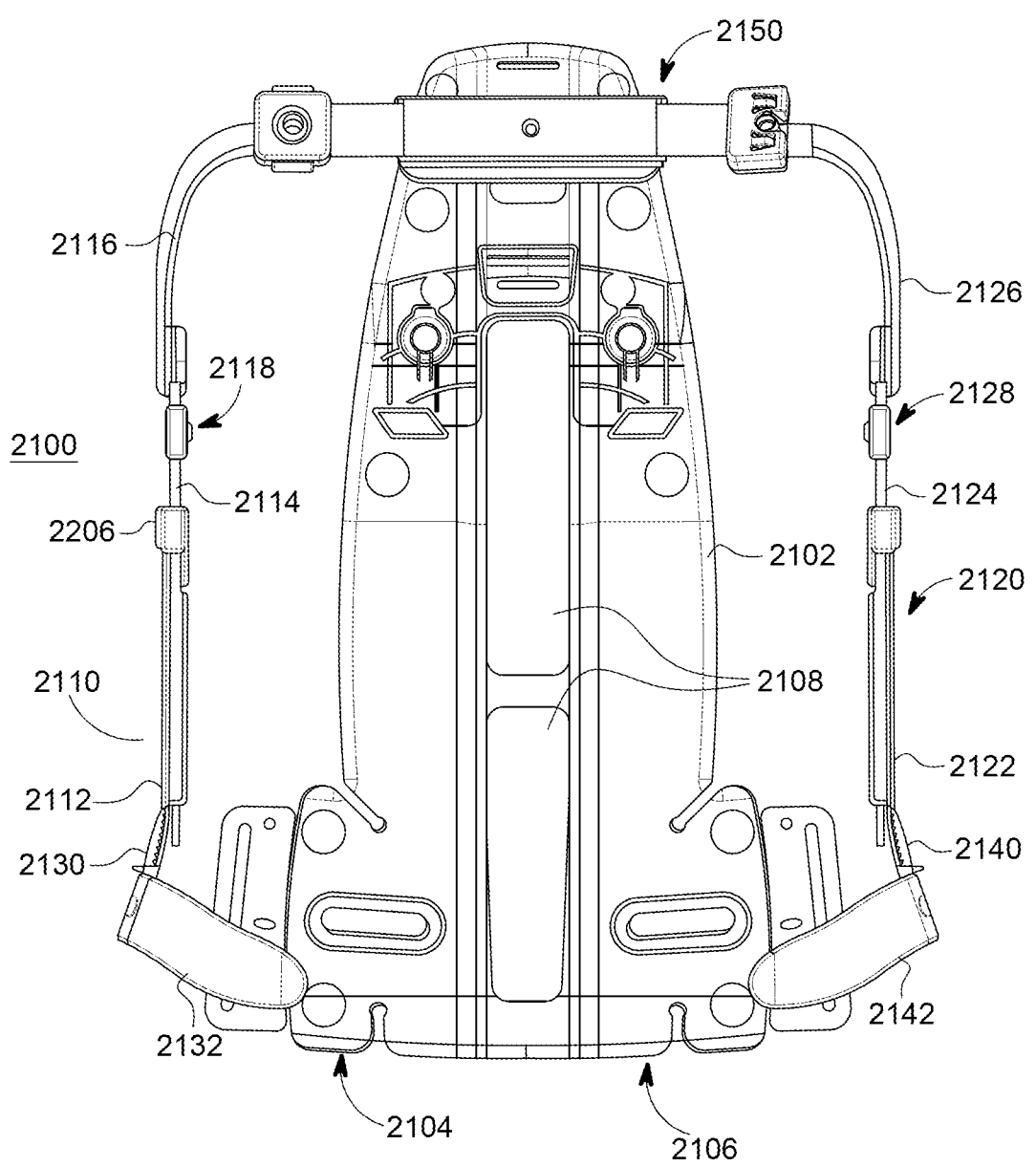

FIG. 21A is a perspective anterior view of a fourth embodiment of an orthopedic spine brace including a chest plate attachment coupled thereto.

Figure 21B:
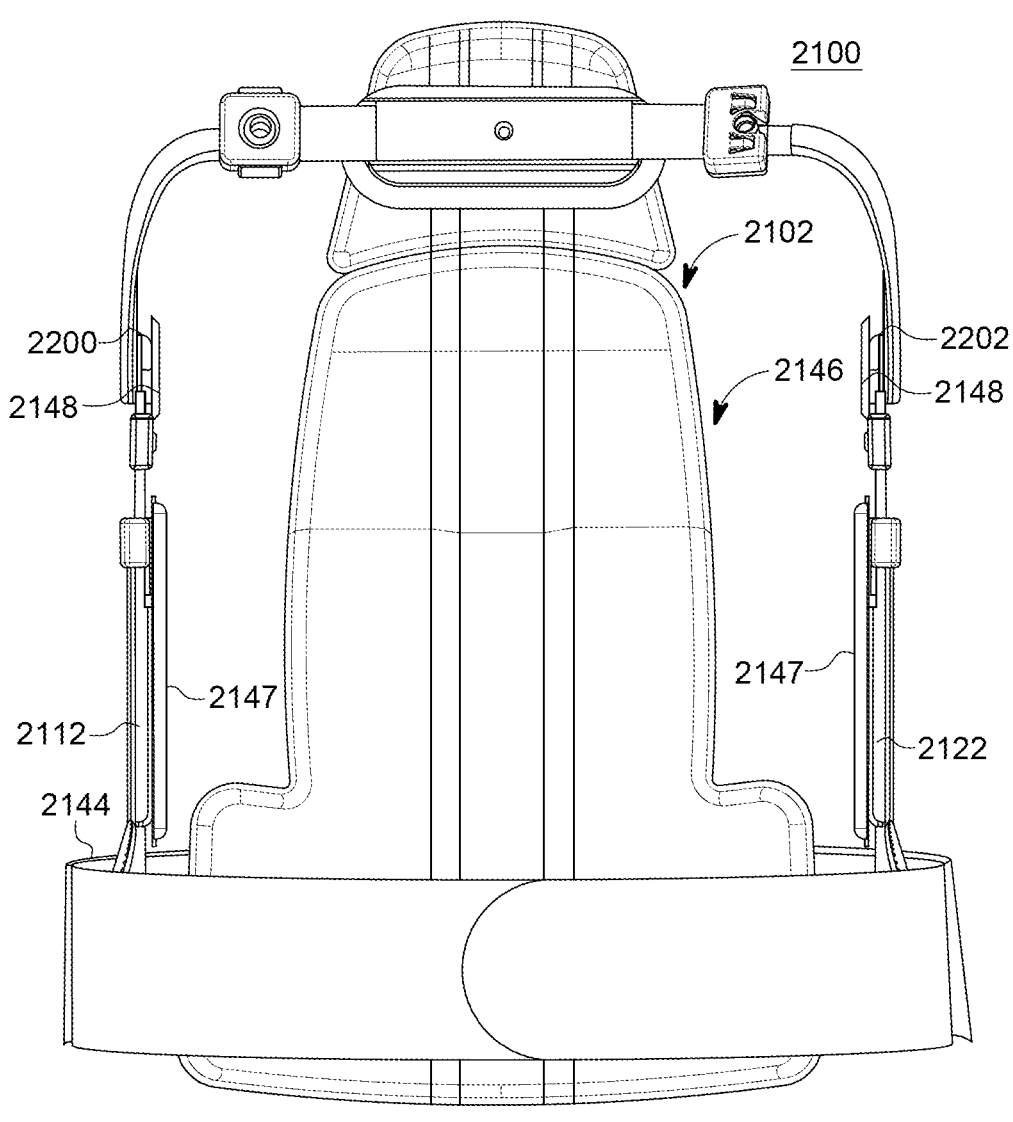

FIG. 21B is a perspective anterior view of the orthopedic spine brace of FIG. 21A including padding coupled thereto.

Figure 21C:
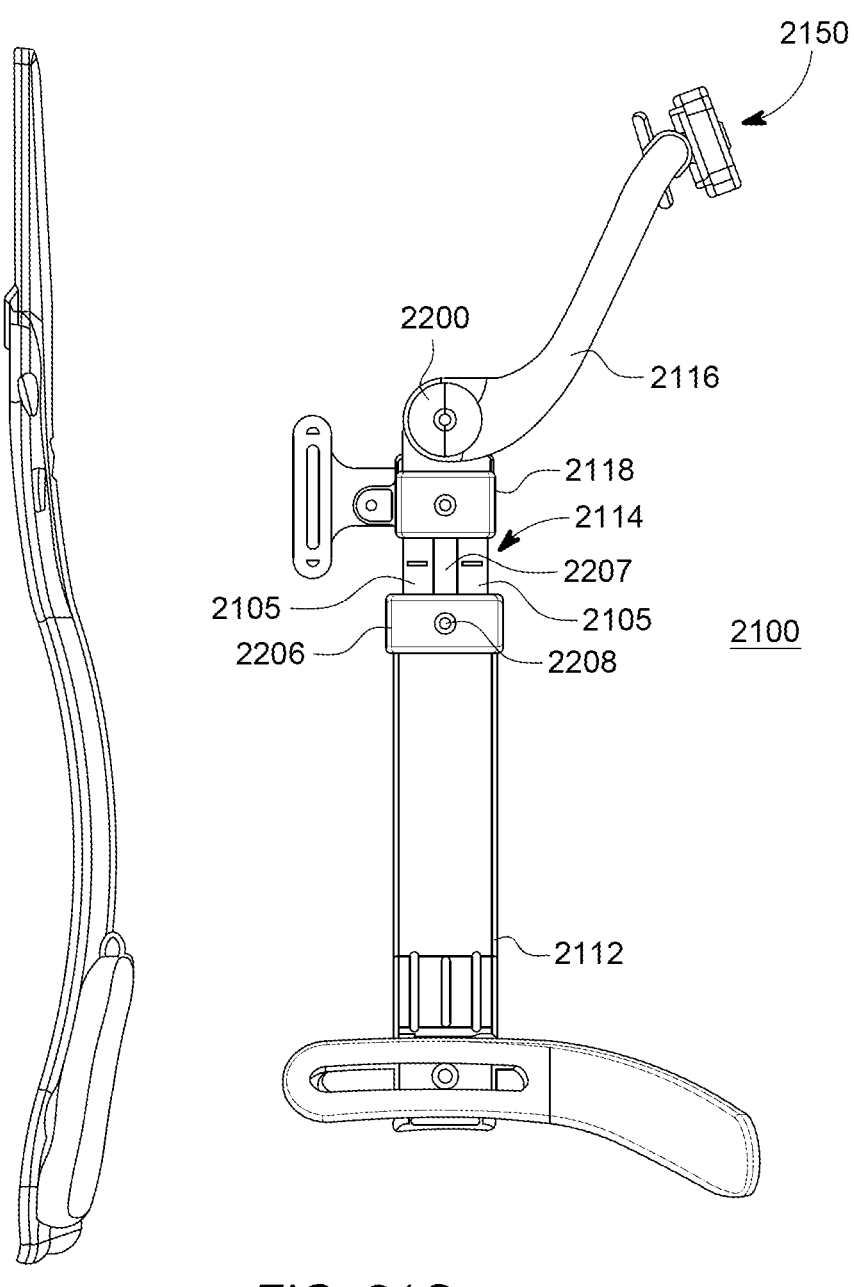

FIG. 21C is a perspective lateral view of the orthopedic spine brace of FIG. 21A.

Figure 21D:
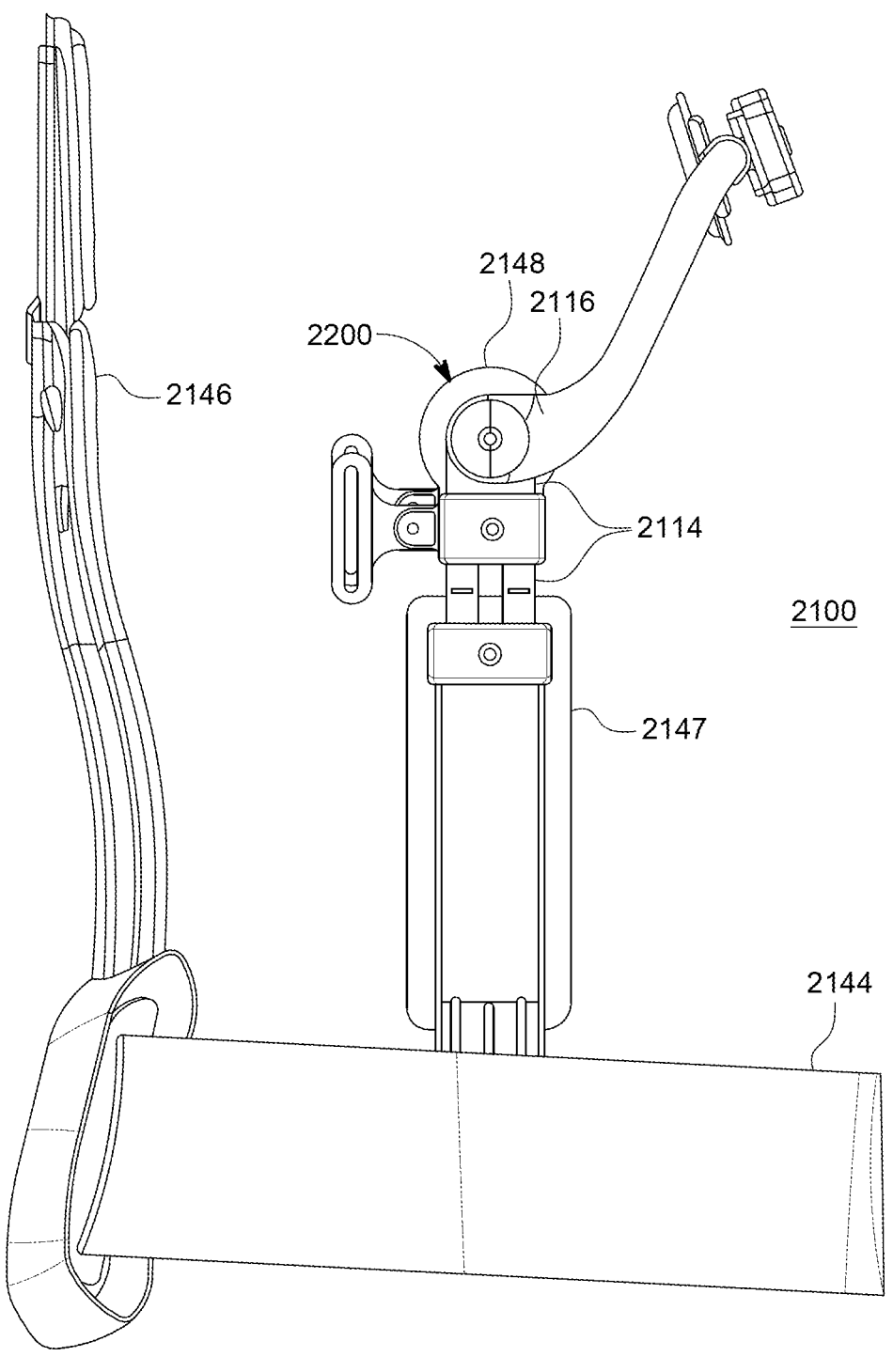

FIG. 21D is a perspective lateral view of the orthopedic spine brace of FIG. 21C including padding coupled thereto.

Figure 22A:
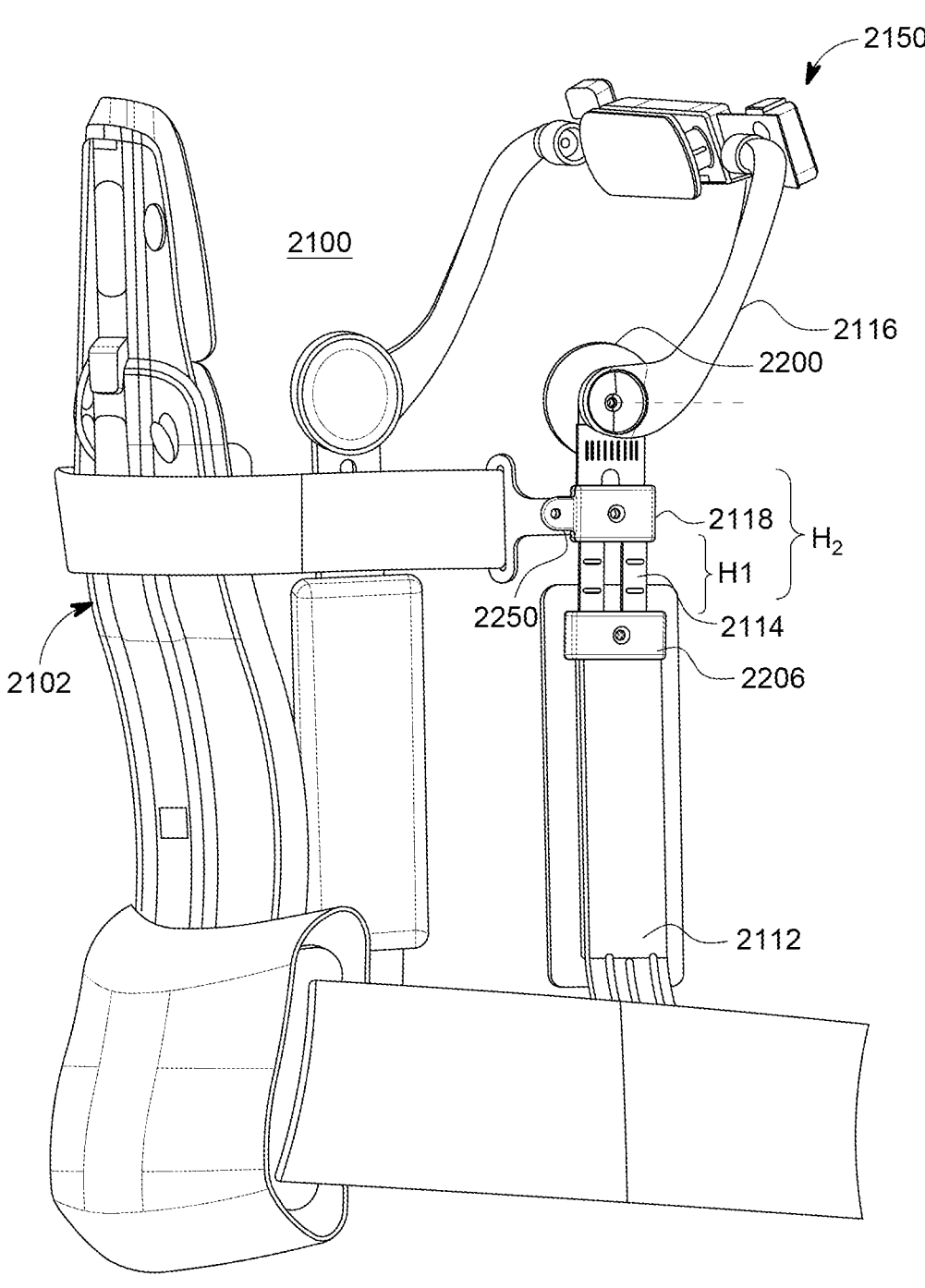

FIG. 22A illustrates the orthopedic spine brace of FIG. 21A that supports angular and linear adjustments of the superior strut, the medial strut, and the strap adjustment member is shown.

Figure 22B:
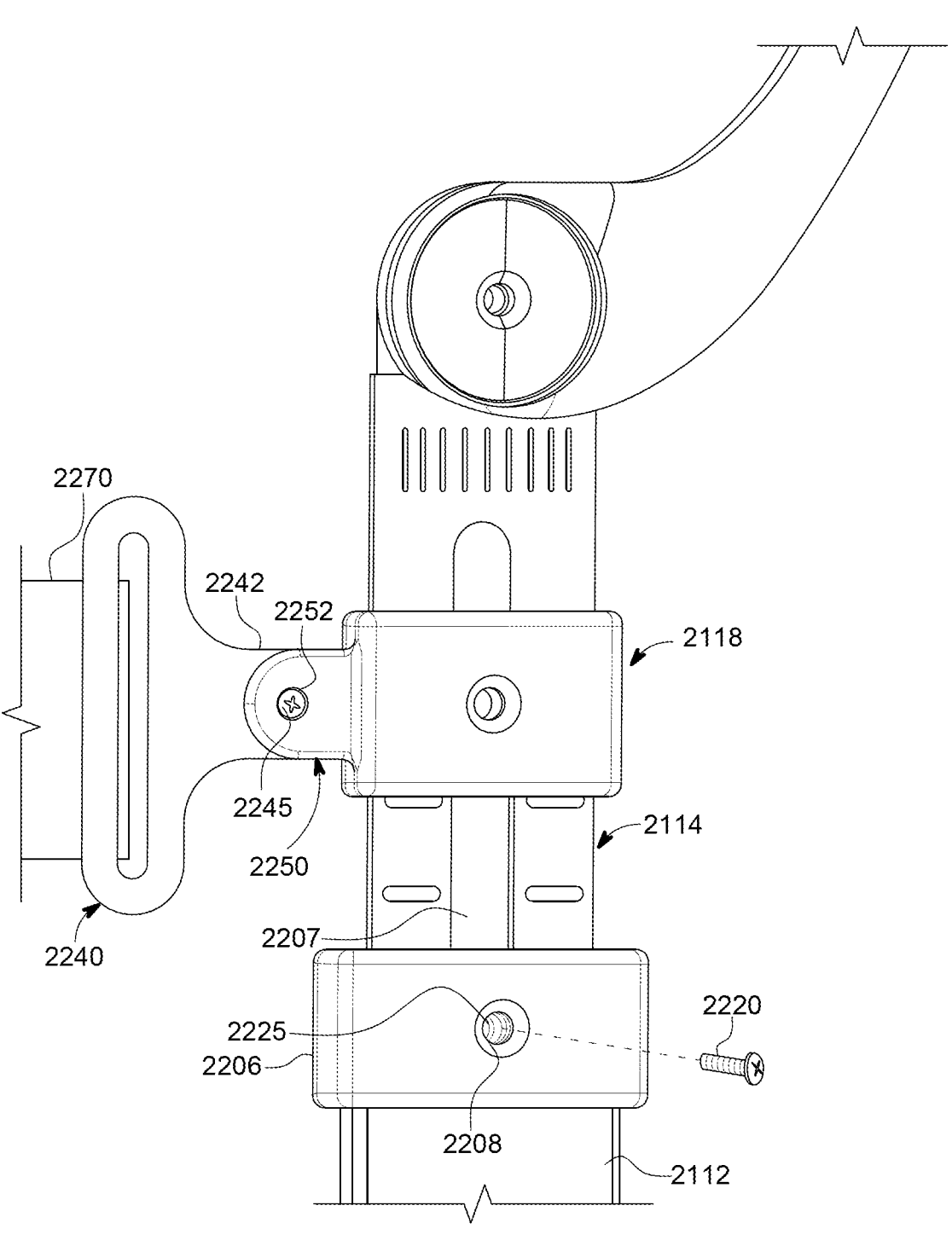

FIG. 22B is a more detailed illustrative view of the second embodiment of the strap adjustment member of FIG. 21A.

Figure 22C:
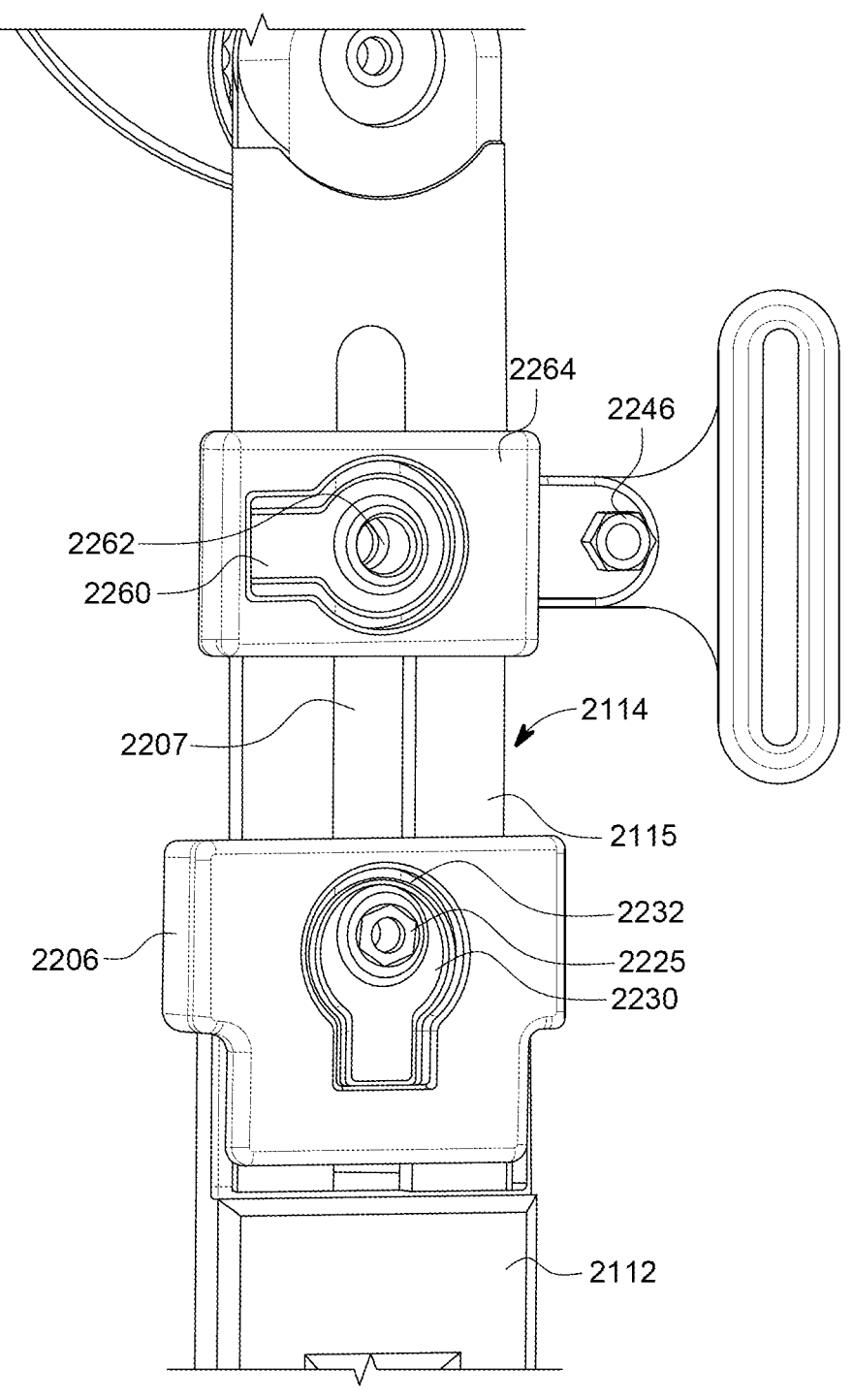
Figure 23A:
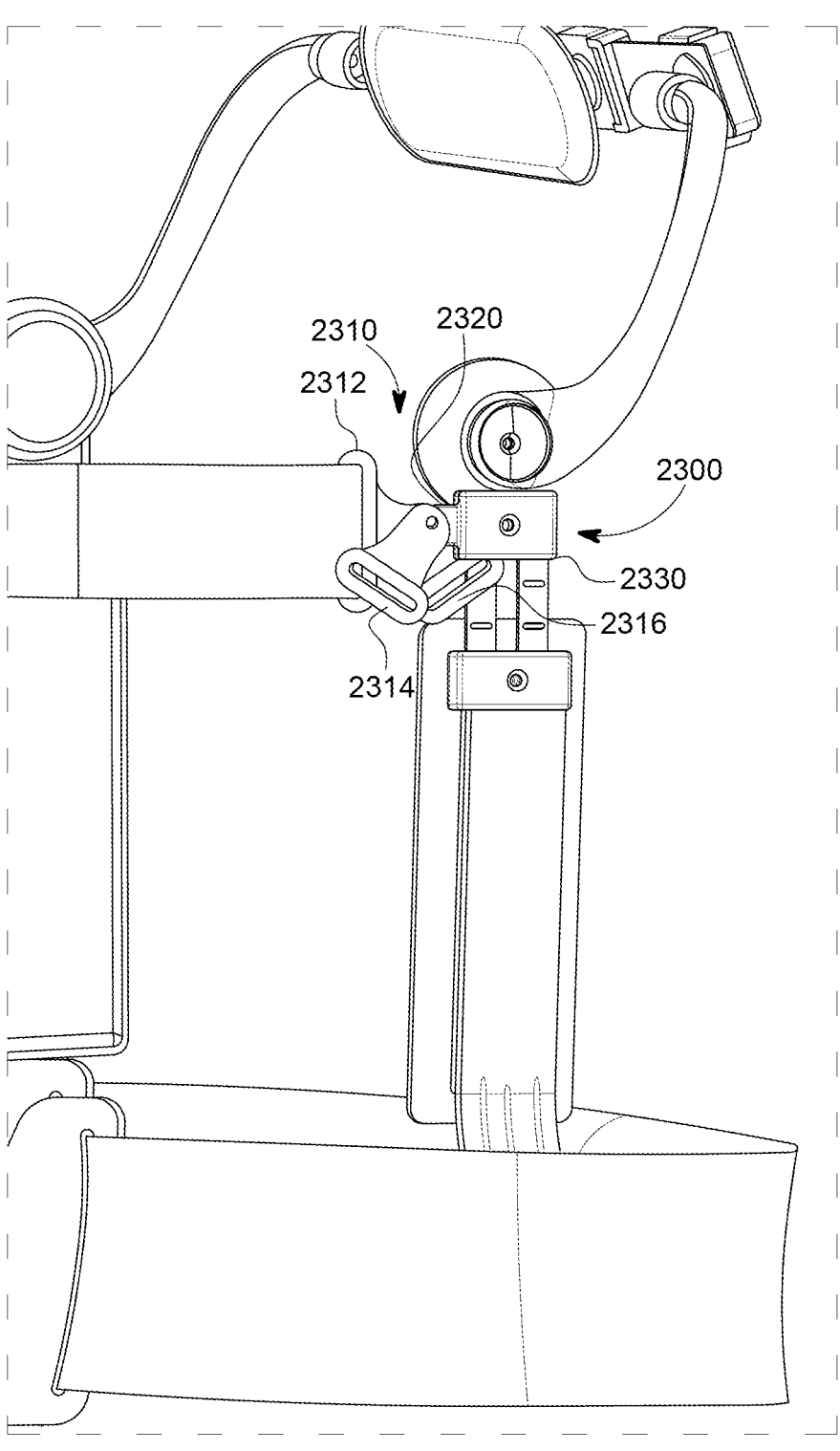
Figure 23B:
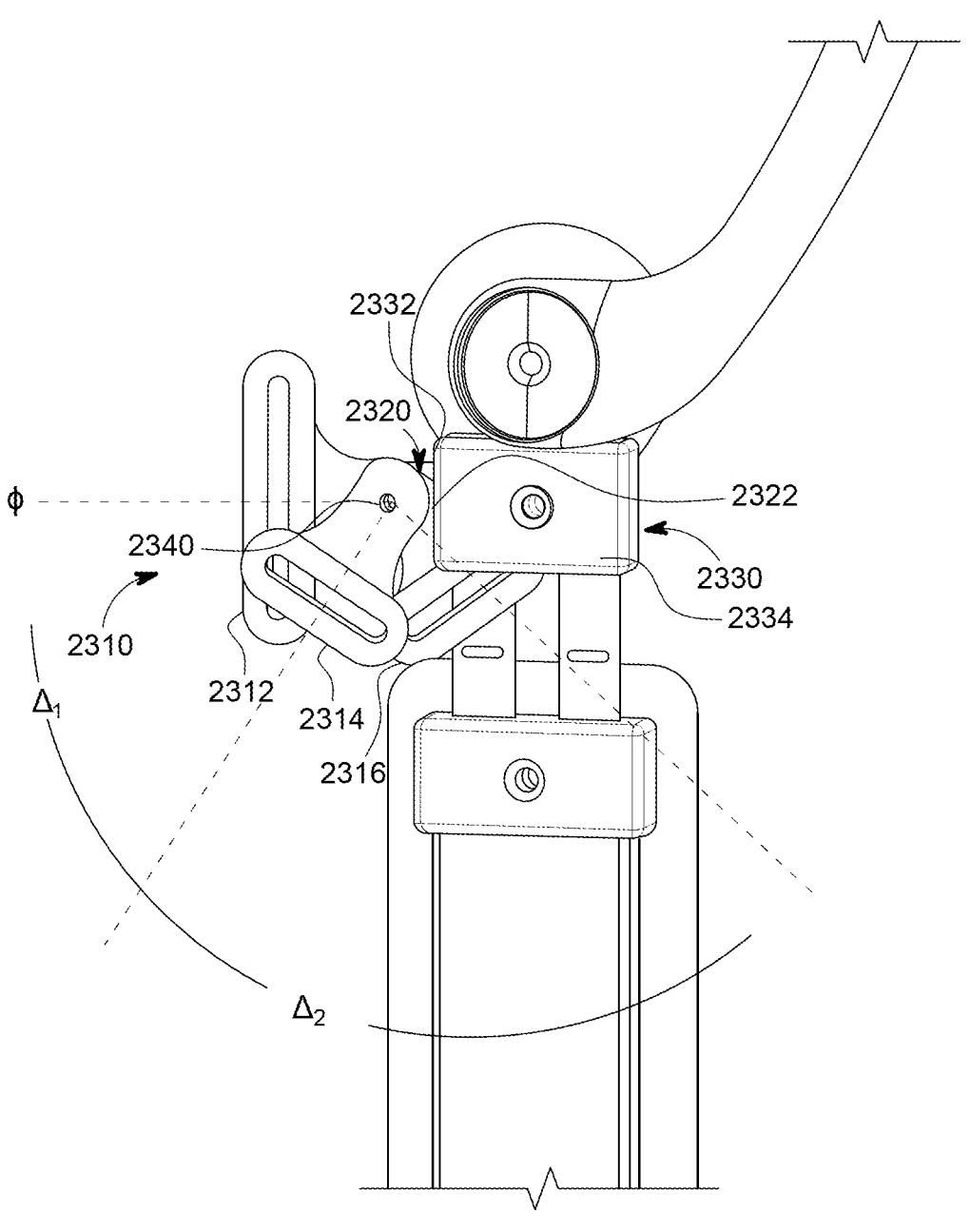

FIG. 22C is a detailed view of the components forming the strap adjustment member of FIGS. 23A-23B.

Figure 22D:
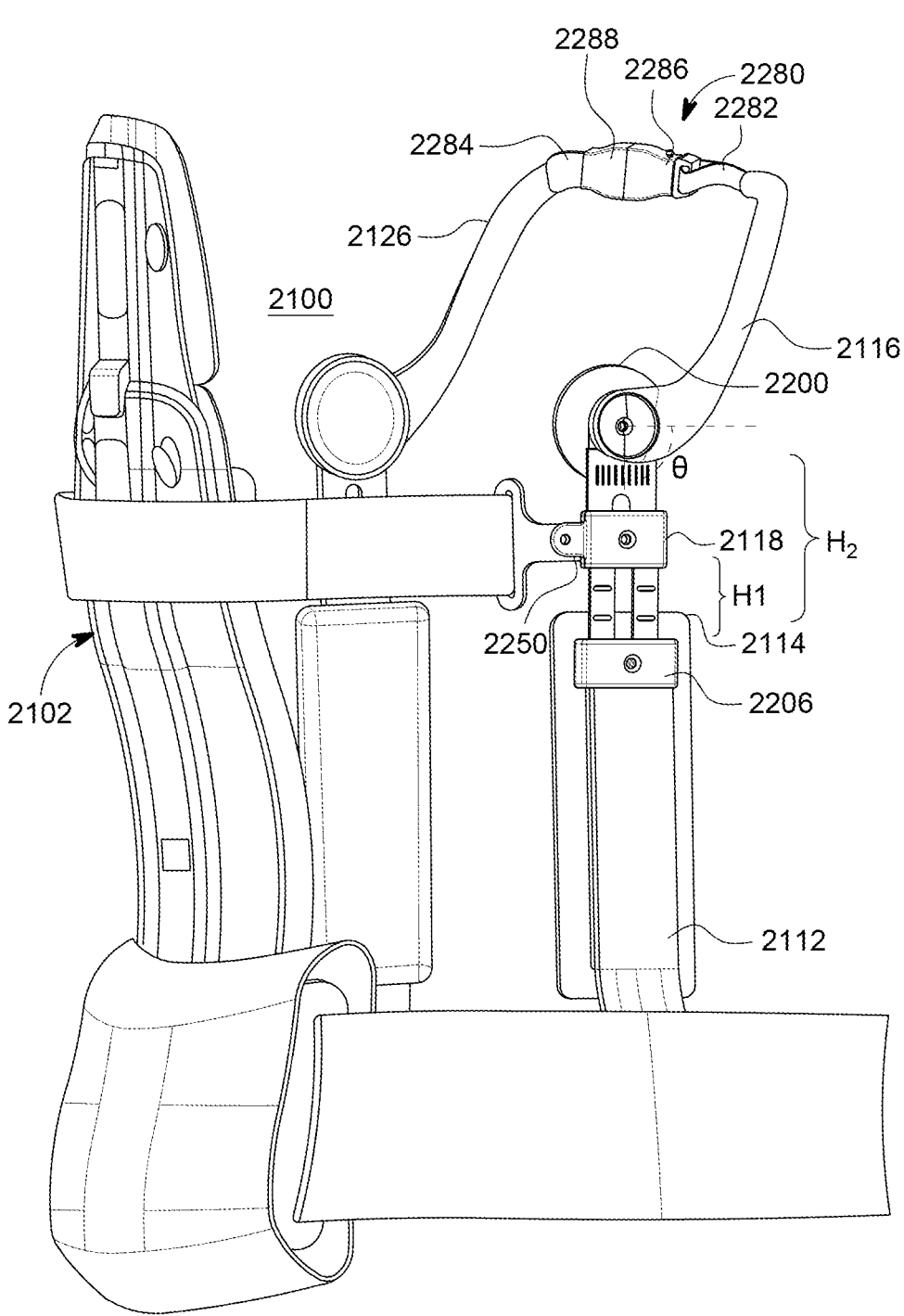
Figure 22E:
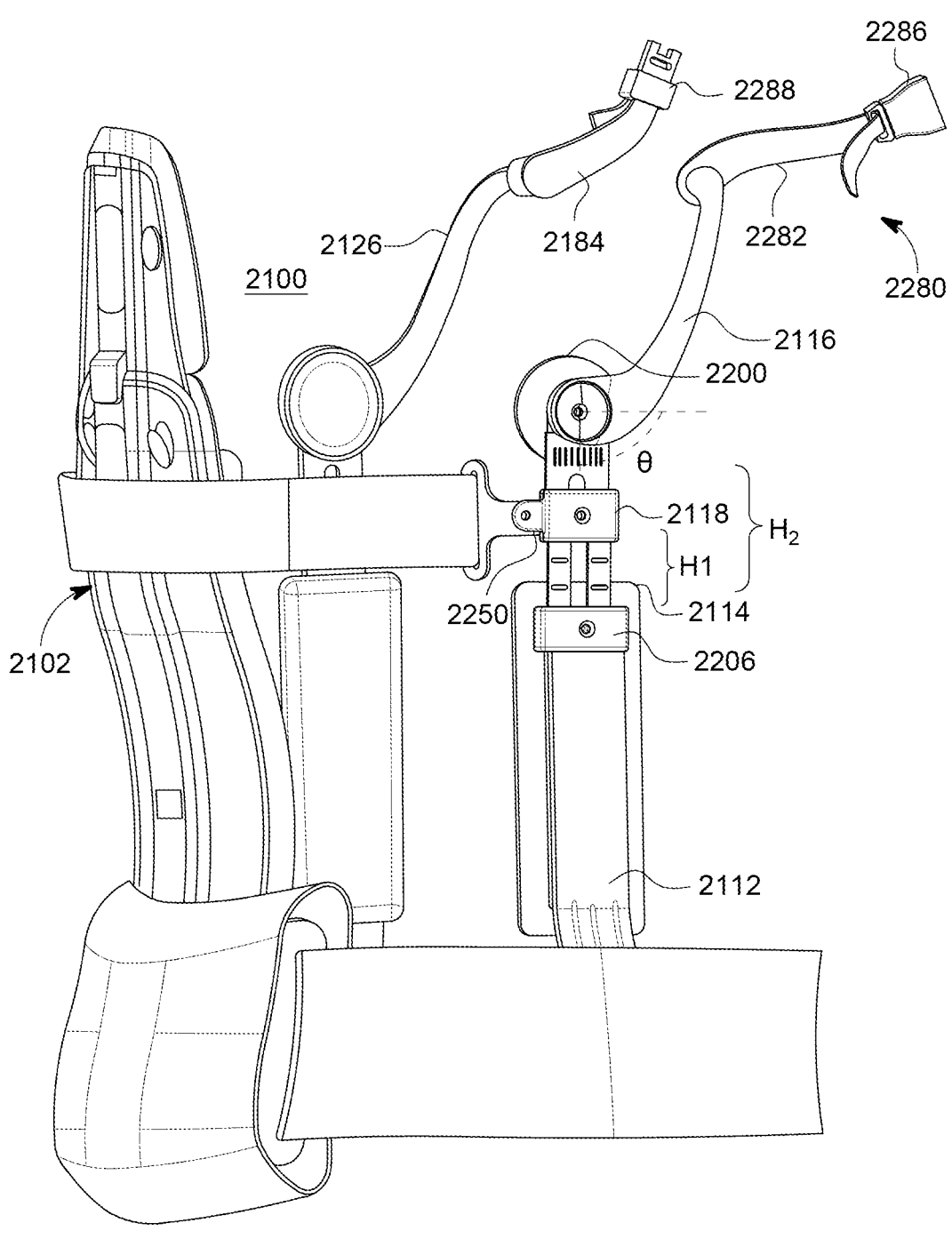

FIGS. 22D-22E illustrate exemplary embodiments of the orthopedic spine brace of FIG. 21A with a different embodiment of the chest plate adjustment of FIG. 21A.

FIG. 23A is a third embodiment of the strap adjustment member featuring multiple, rotational steering rings for strap retention.

FIG. 23B is an illustrative embodiment of the third embodiment of the strap adjustment member of FIG. 23A with rotational steering rings rotated at different angular representations along a common axis.

Figure 23C:
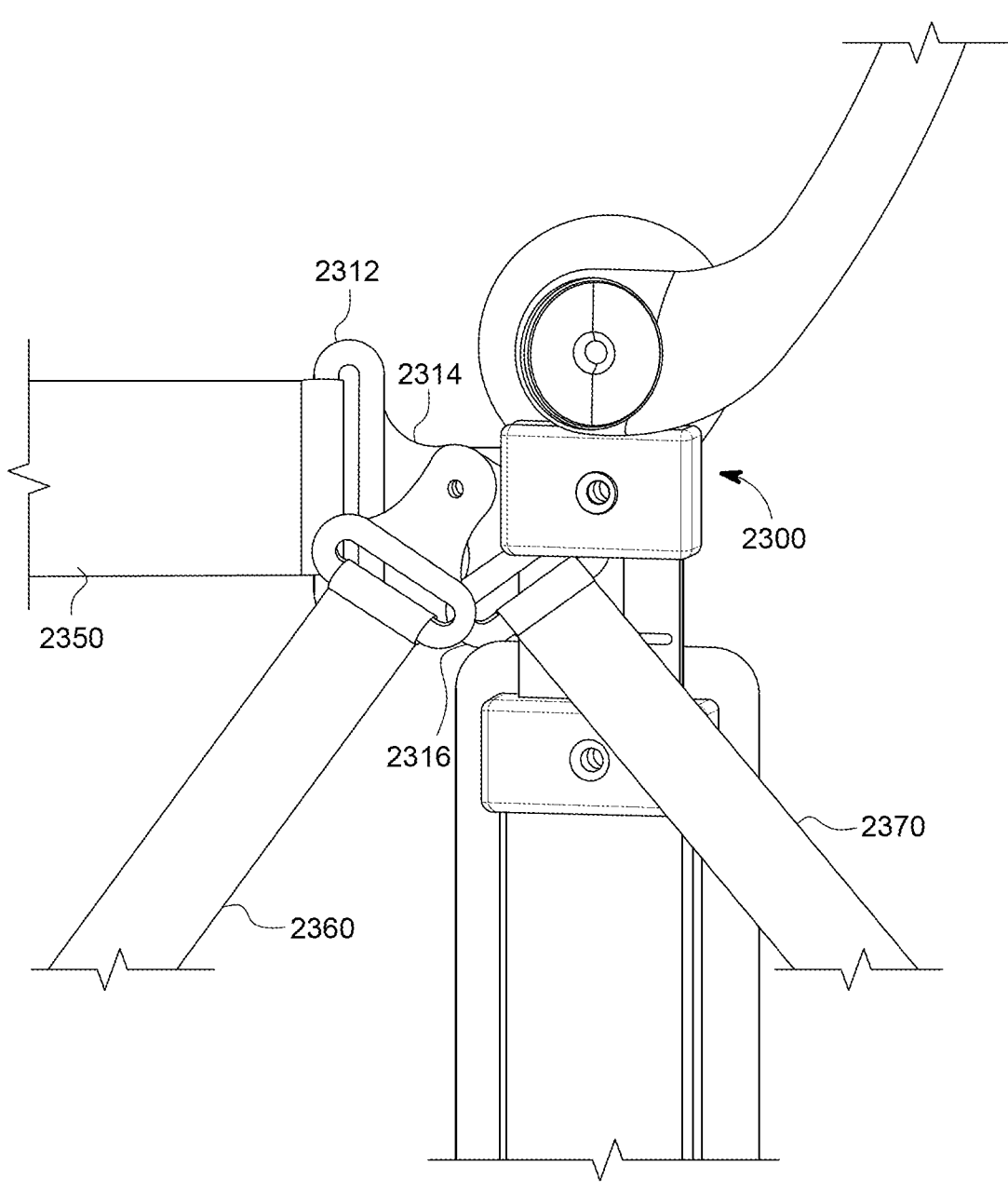
Figure 23E:
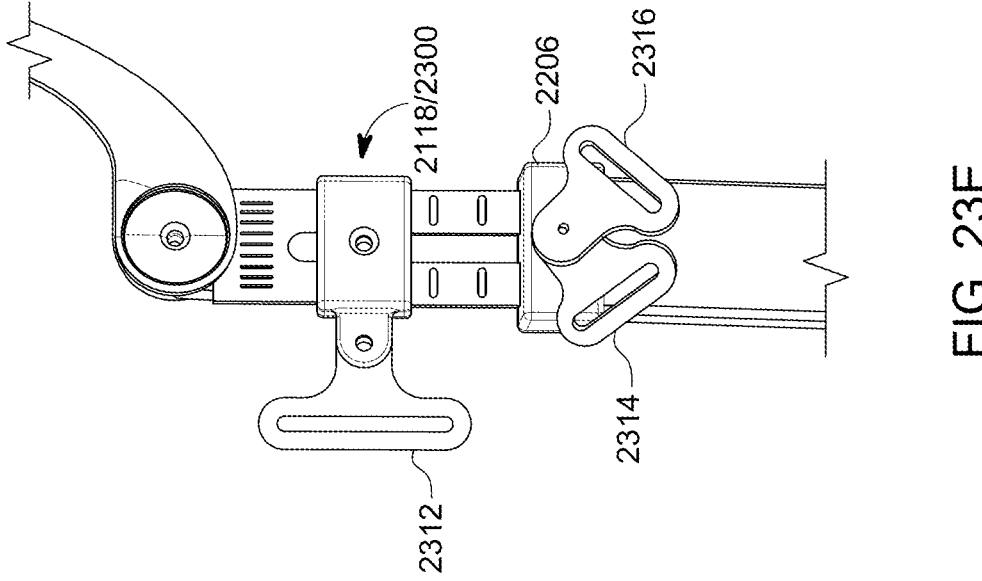
Figure 23D:
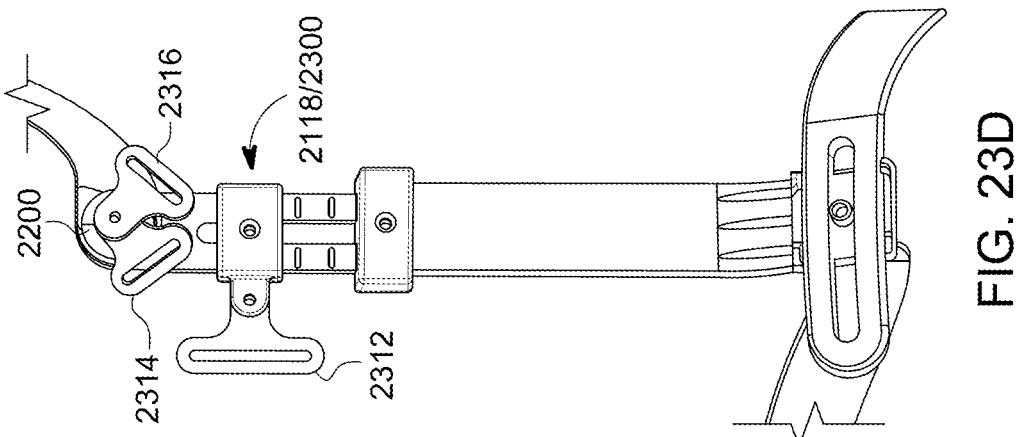

FIGS. 23C-23E are illustrative alterative embodiments of the strap adjustment member of FIG. 23B with multiple rotational steering rings rotated at different angular orientations and coupled to lateral support straps.

Figure 24A:
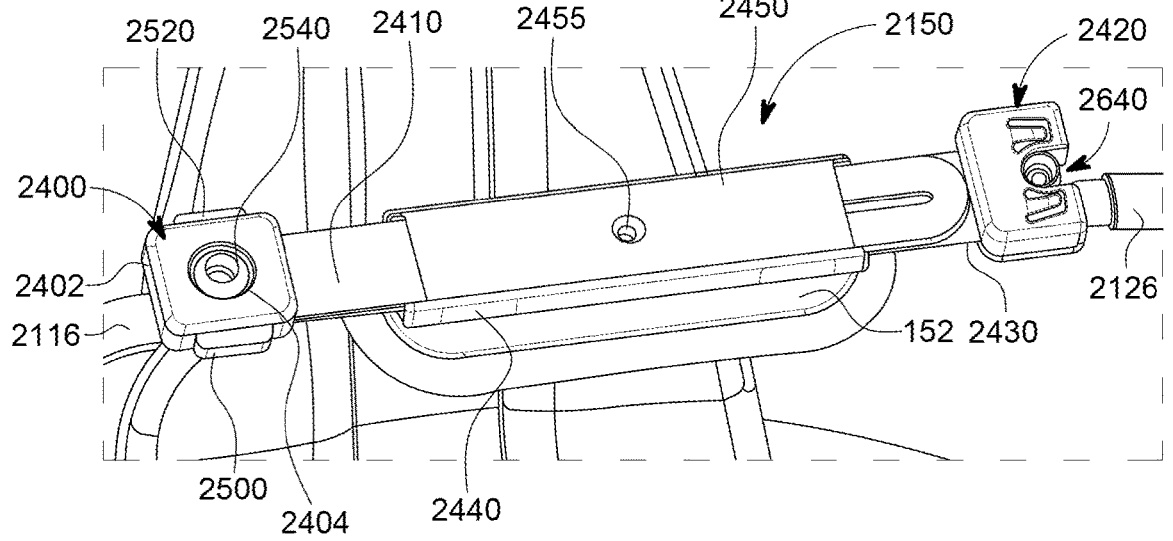

FIG. 24A is a perspective view of a second embodiment of the chest plate attachment of FIGS. 21A-21D.

Figure 24B:
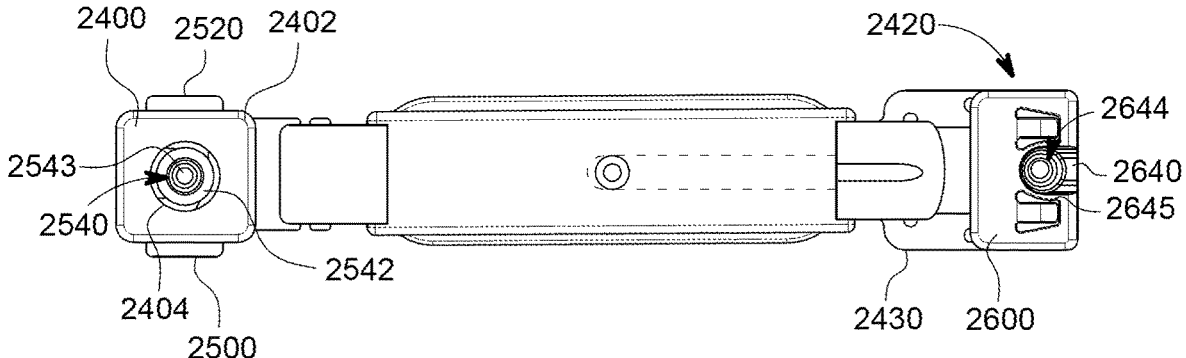

FIG. 24B is a detailed, planar view of internal components of the chest plate attachment of FIG. 24A.

Figure 25A:
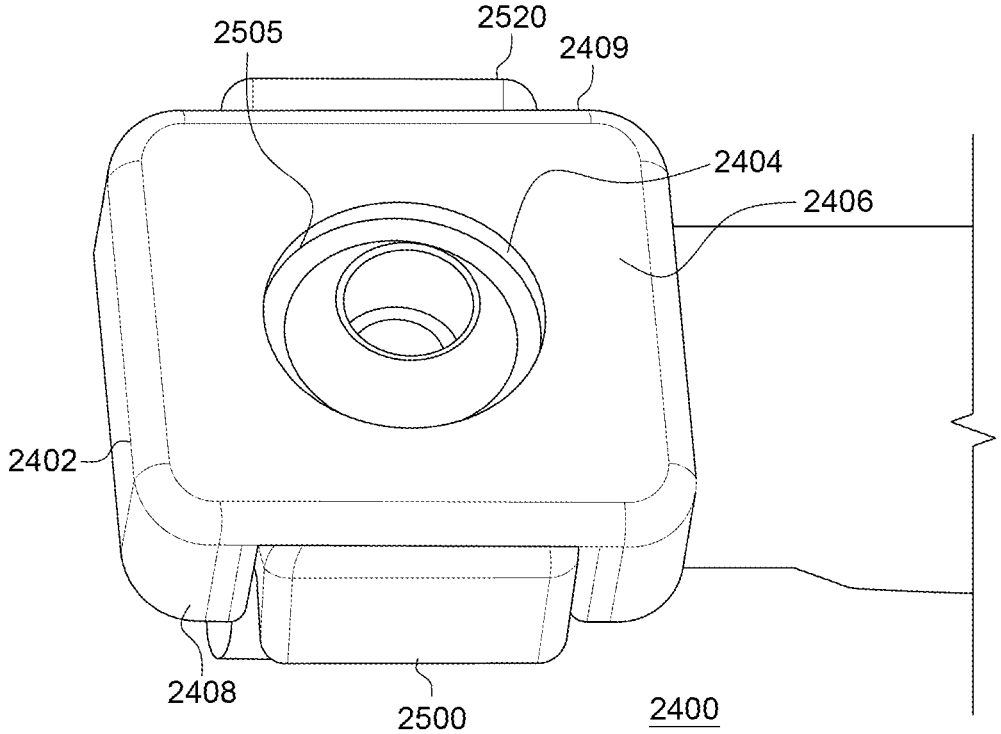

FIG. 25A is a perspective view of a second embodiment of the lock attachment member for the chest plate attachment of FIGS. 24A-24B.

Figure 25B:
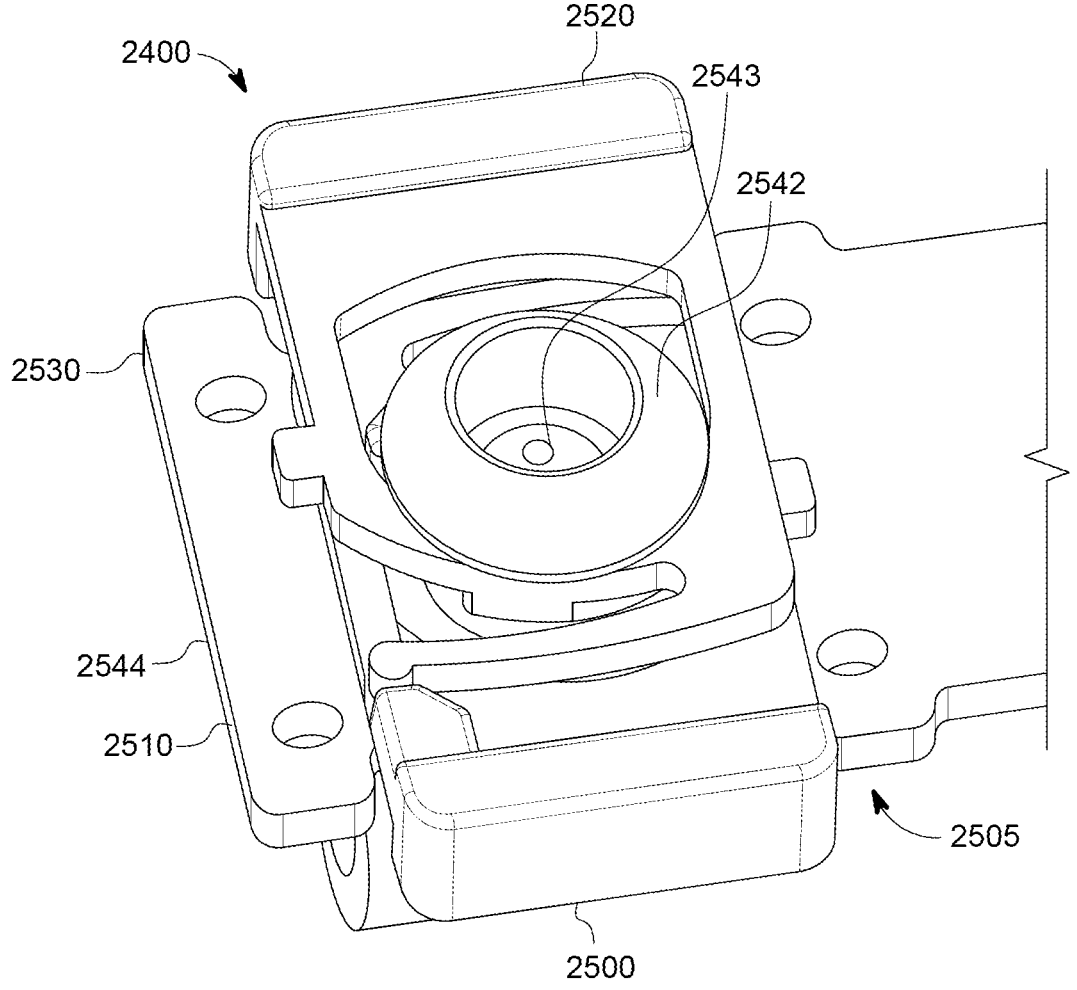

FIG. 25B is a detailed perspective of the lock attachment member of FIG. 25A featuring the first and second spring components also shown in FIG. 20B.

Figure 25C:
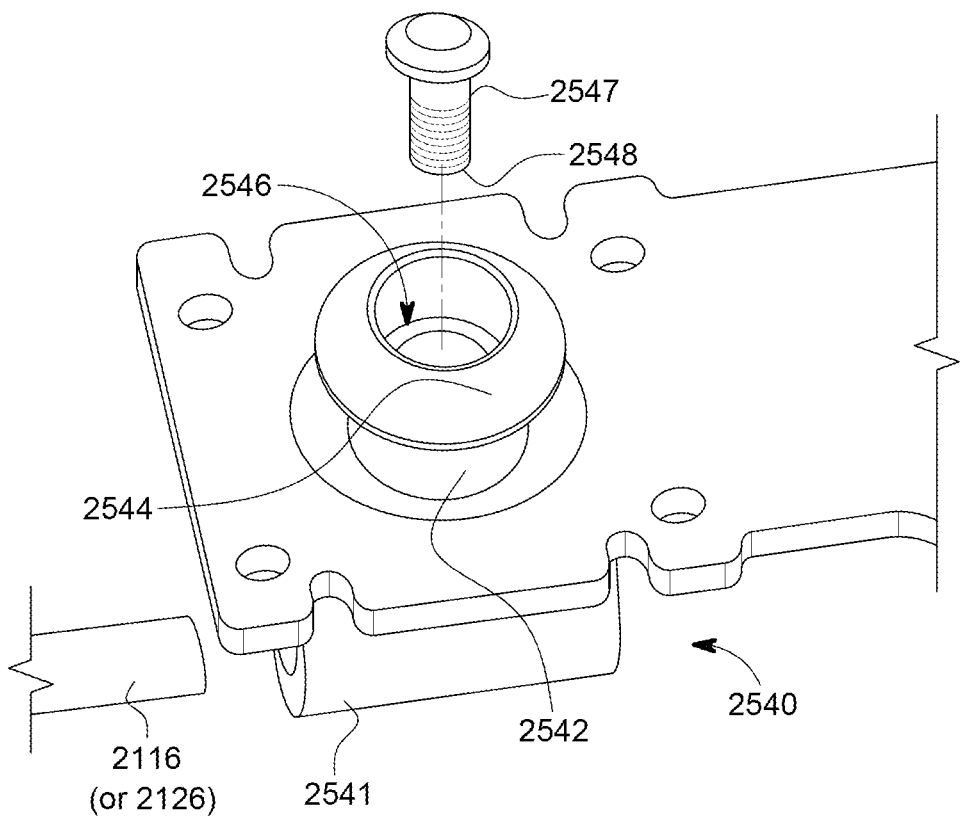

FIG. 25C is a detailed perspective of the lock attachment member of FIG. 25A featuring a first coupling assembly inclusive of a first post member and a ball member configured to receive a superior strut fastener therein.

Figure 26A:
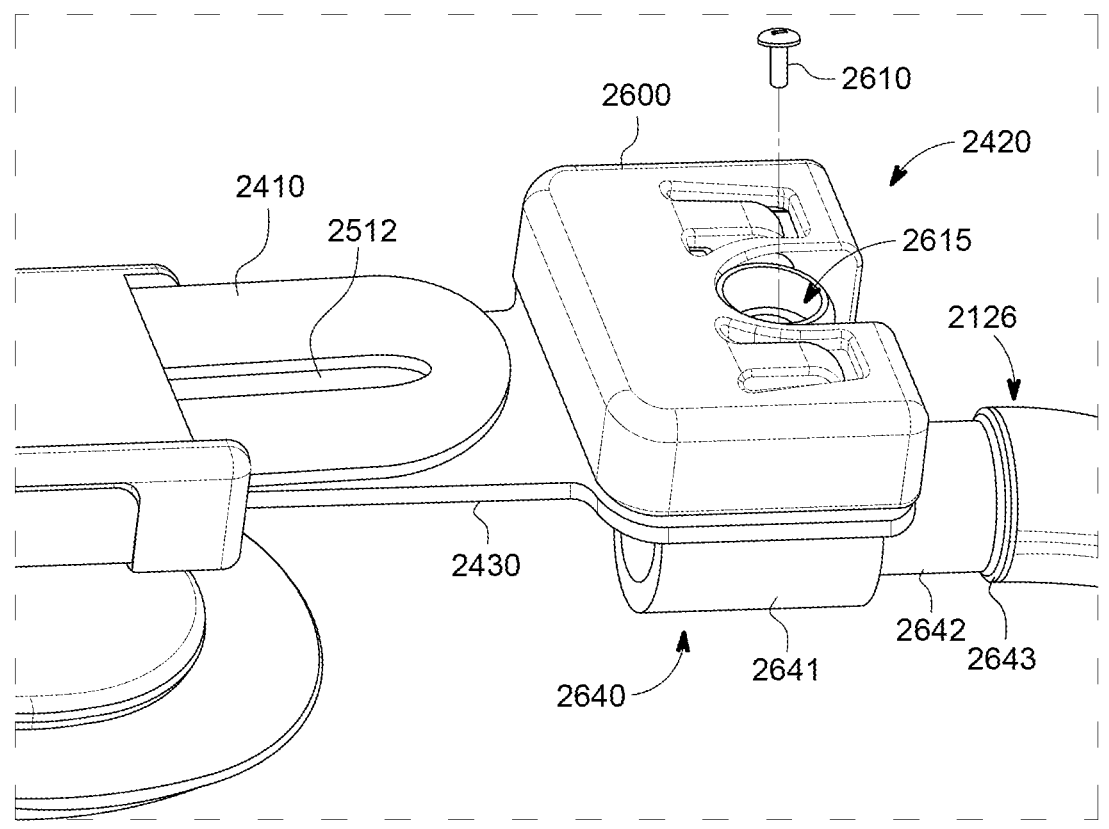

FIG. 26A is a perspective view of a second embodiment of the hinged attachment member for the chest plate attachment of FIGS. 24A-24B.

Figure 26B:
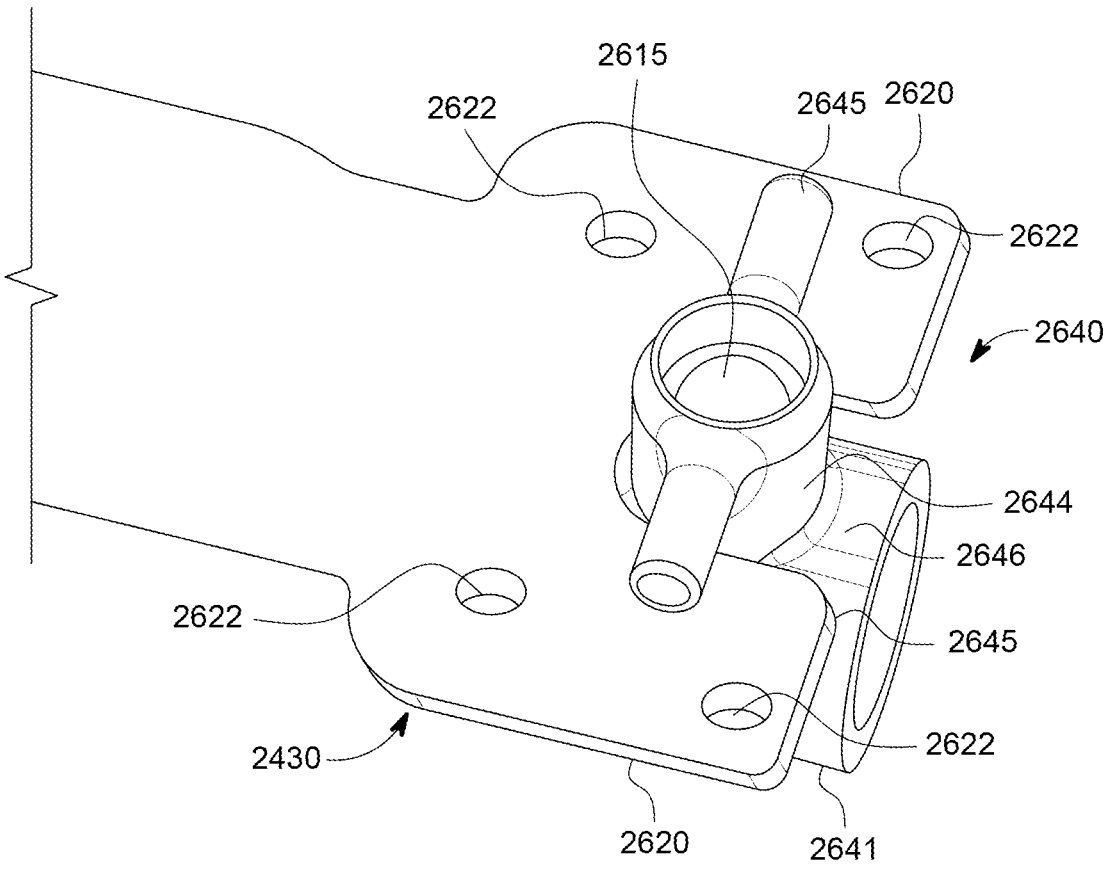

FIG. 26B is an illustrative embodiment of the second post member of FIG. 26A maintaining a chest retention strut member (tongue) in a cantilever arrangement.

Figure 26C:
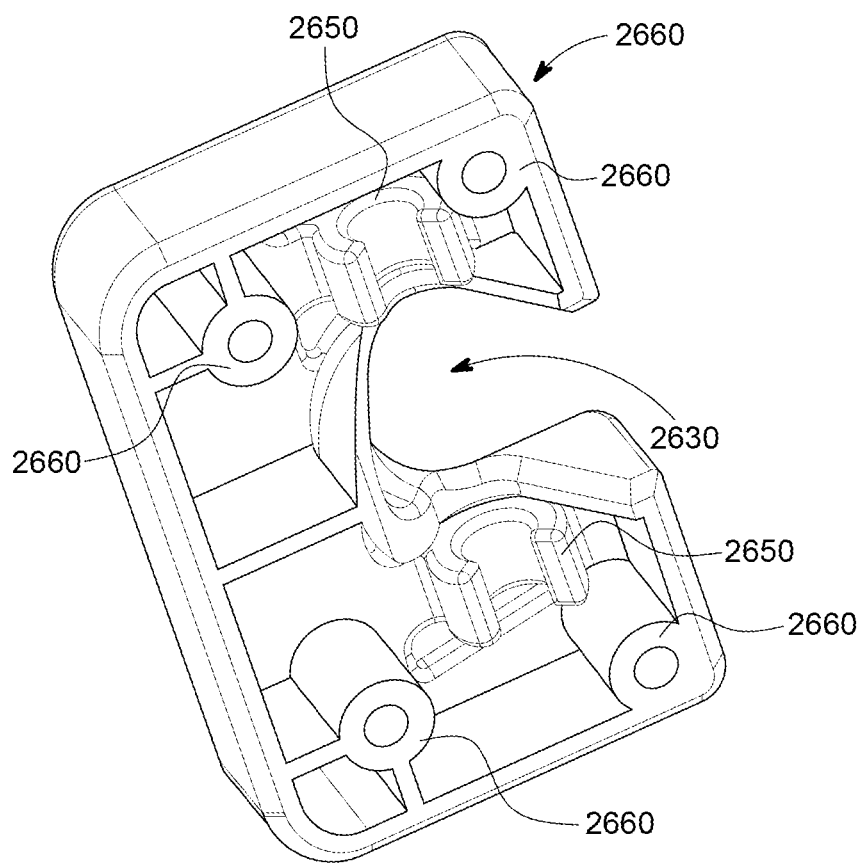

FIG. 26C is an illustrative embodiment of the cantilever hinge of FIG. 26A with an underside featuring C-clamps for retention of lateral arm members extending from the second post member of FIG. 26B.

Figure 26F:
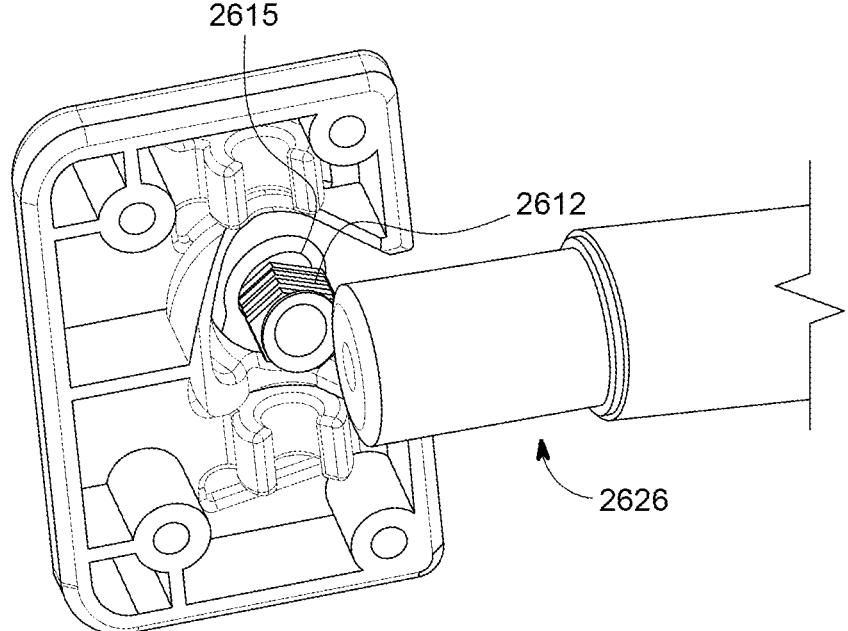
Figure 26D:
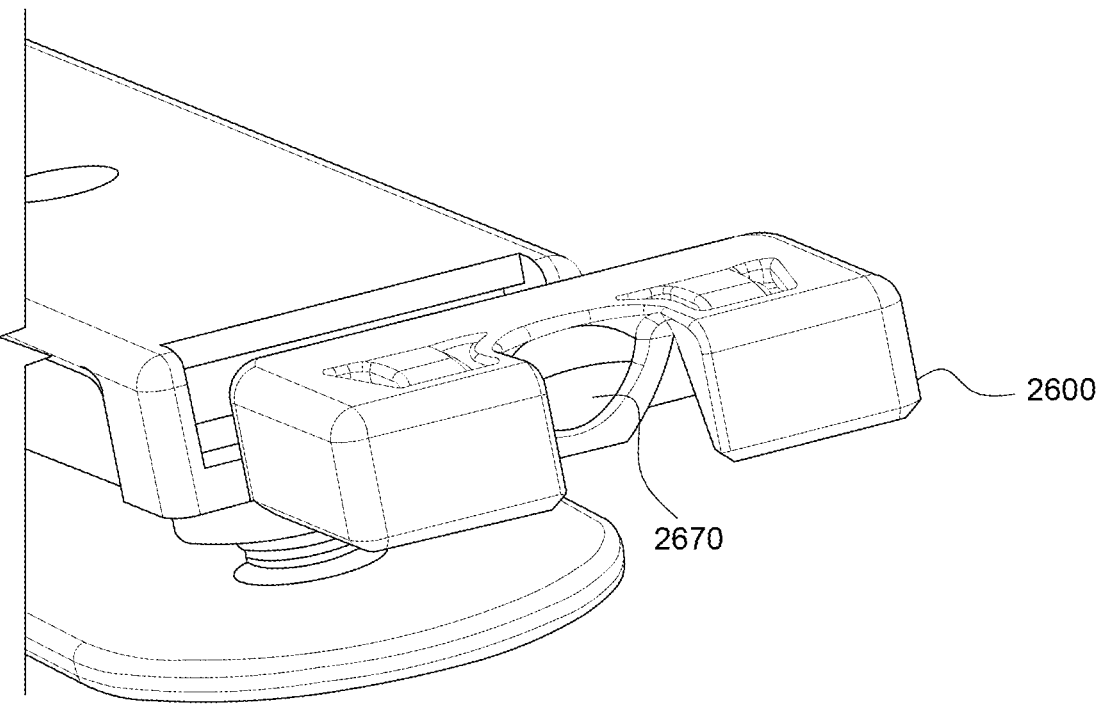

FIG. 26D is an illustrative embodiment of the cantilever hinge of FIG. 26A illustrating a stopper wall to halt rotation of the cantilever hinge and the chest retention strut member upon contact with the second post.

Figure 26E:
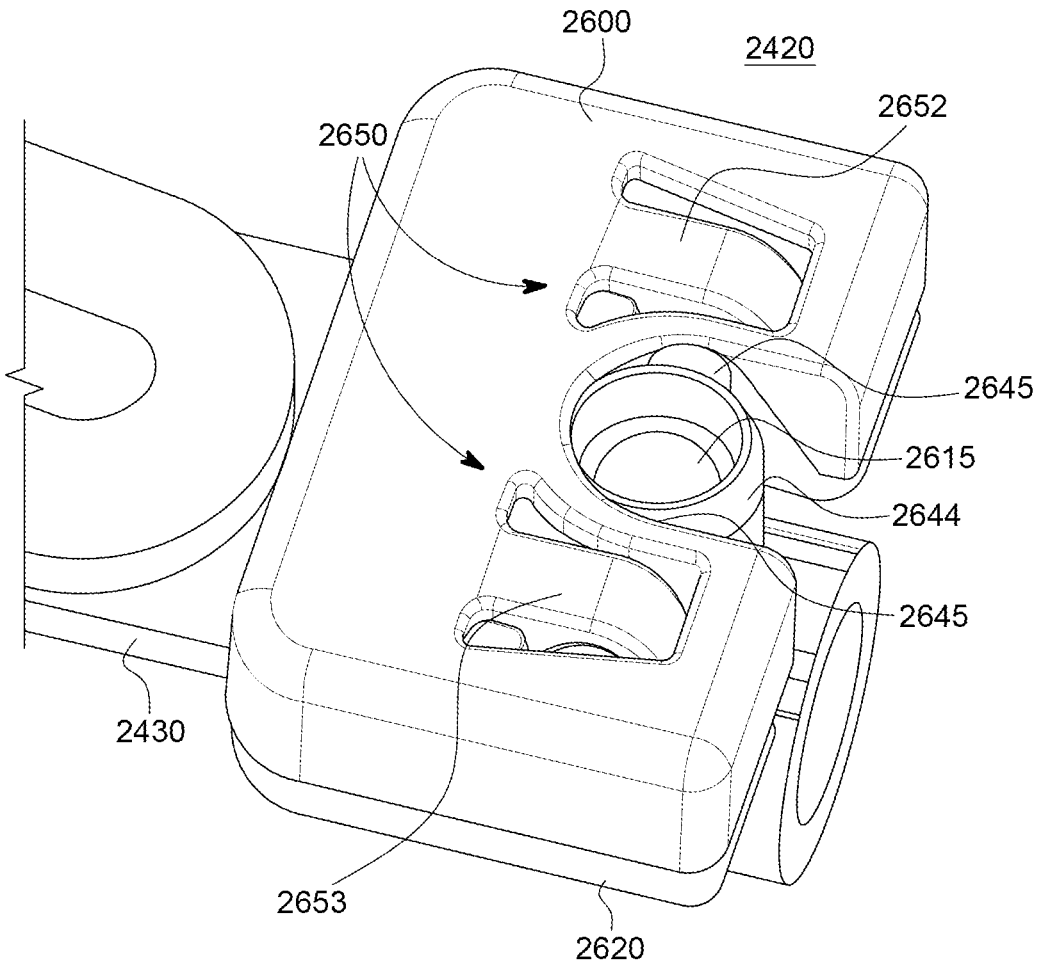

FIG. 26E is an illustrative embodiment of the hinge attachment of FIG. 26A illustrating the cantilever hinge and the second coupling assembly adapted for attachment to a superior strut of the orthopedic spine brace.

FIG. 26F is an illustrative embodiment of the relationship between the cantilever hinge, a complementary fastener placed in the lumen formed within the second post, and the superior strut.

Figure 26G:
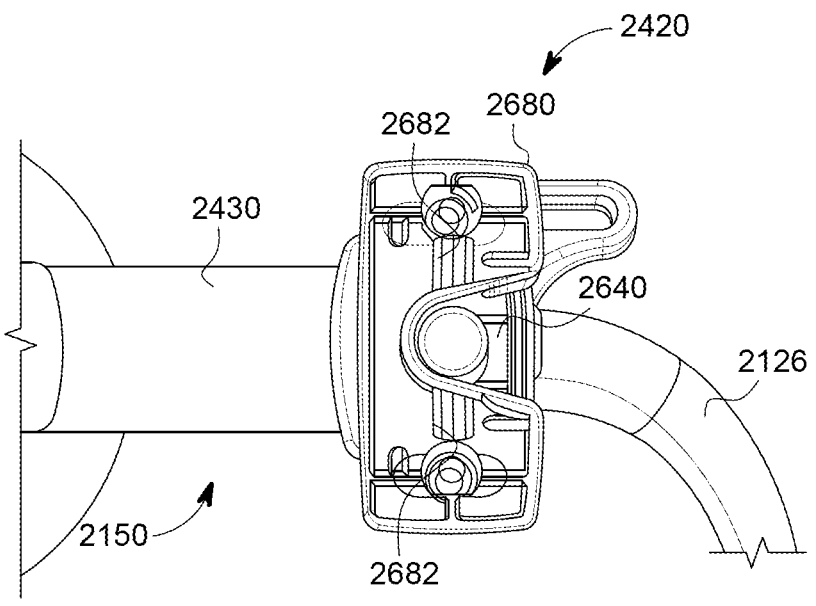

FIG. 26G is a top-down view of an alternative embodiment of the hinged attachment member for the chest plate attachment of FIGS. 24A-24B.

Figure 26H:
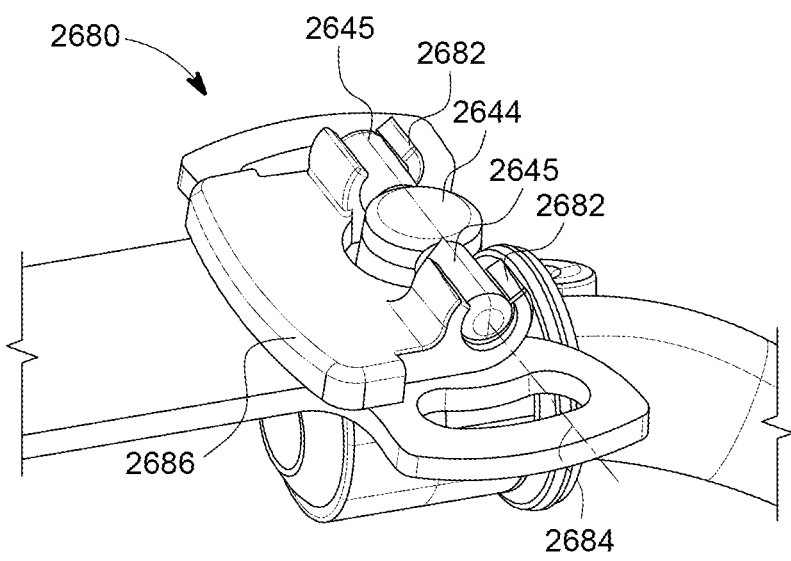

FIG. 26H is a perspective view of the alternative embodiment of the hinged attachment member of FIG. 26G.

Figure 26I:
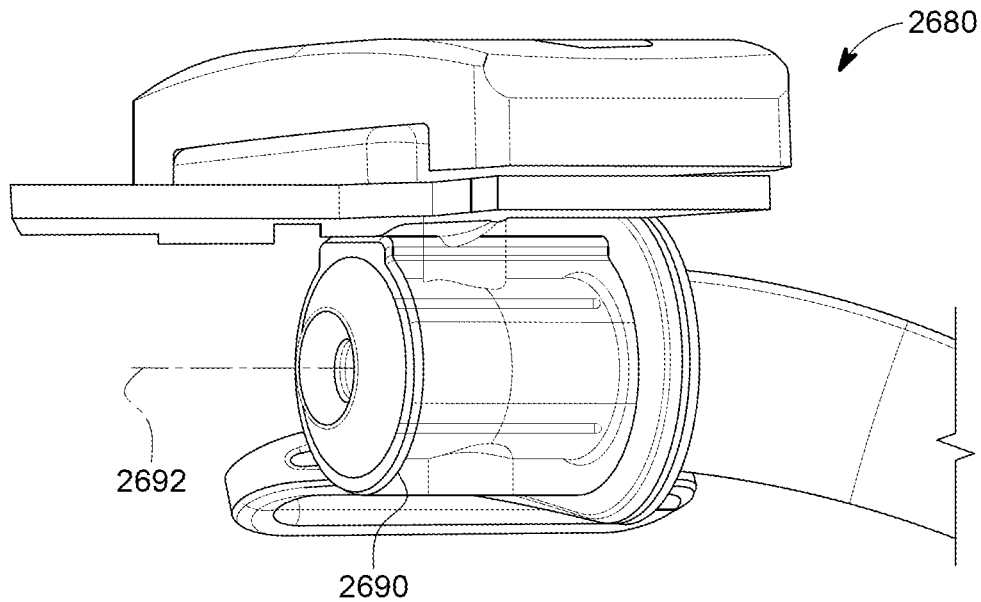

FIG. 26I is a cantilever hinge inclusive of a hinge rotating joint that freely rotates on an end portion of the superior frame member.

Figure 26J:
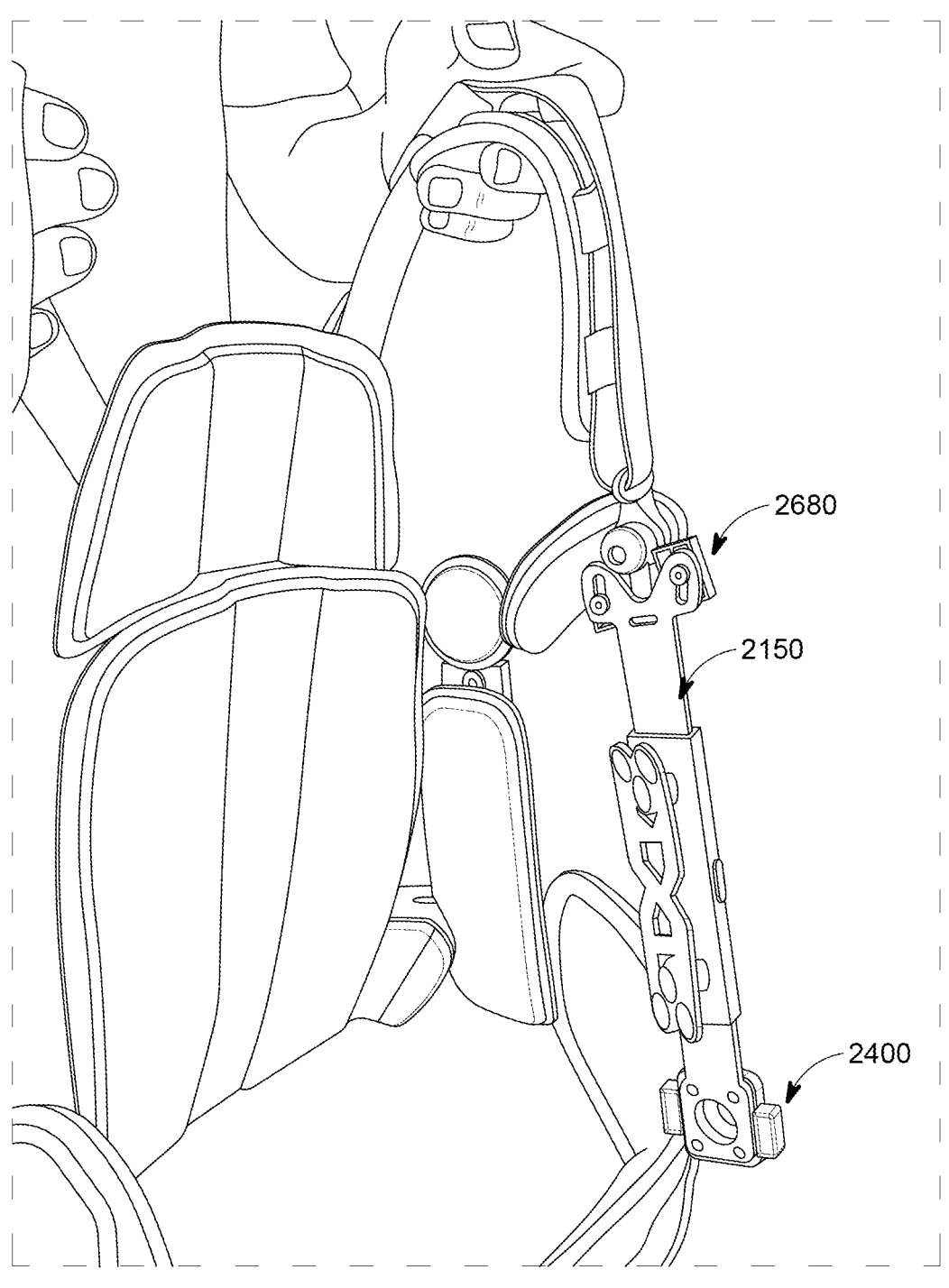

FIG. 26J is a perspective view of the chest plate attachment in a non-connected state in which the cantilever hinge of FIGS. 26G-26I concurrently pivots along two different directional planes.

Figure 27A:
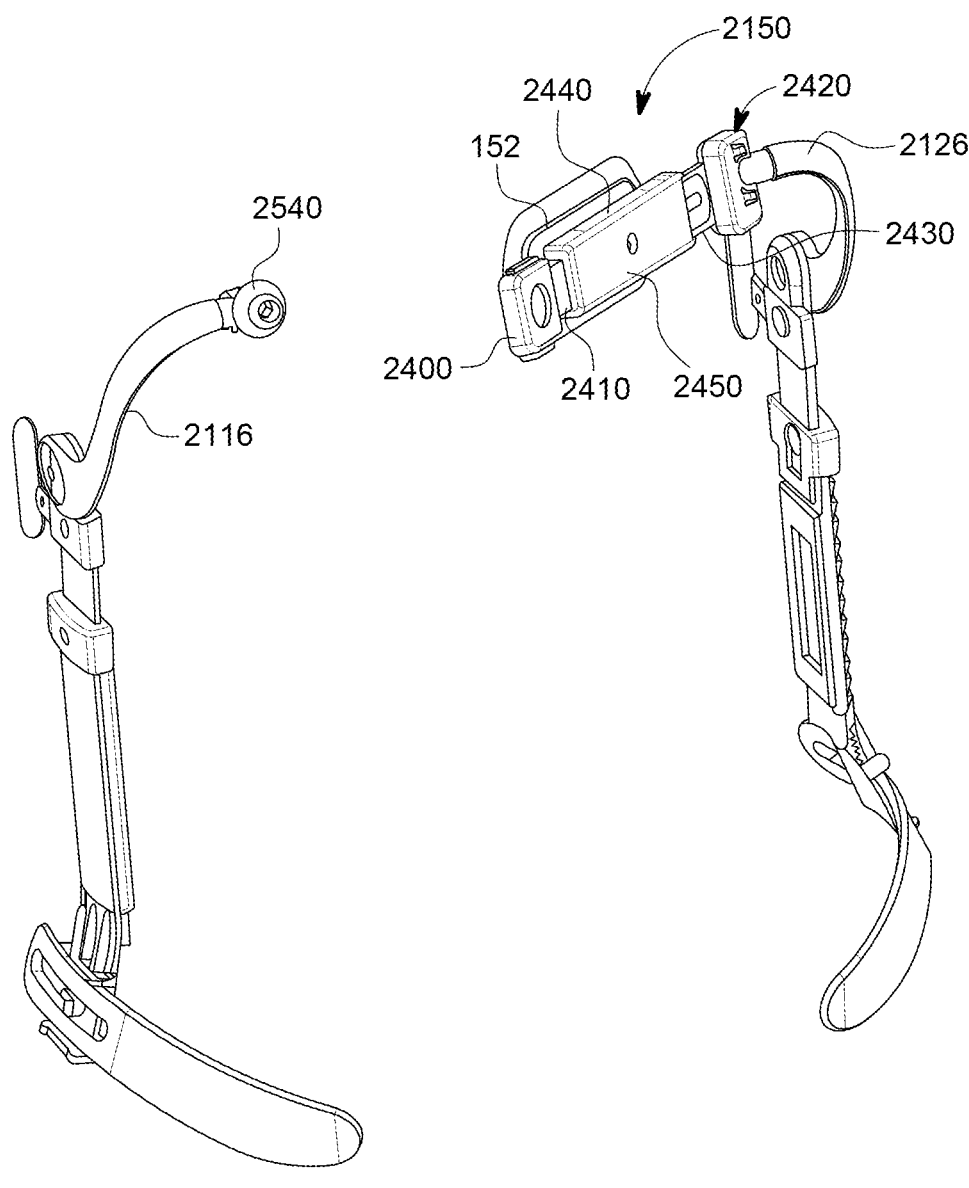

FIG. 27A is a perspective anterior view of the fourth embodiment of the orthopedic spine brace of FIGS. 21A-21D illustrating detachment of the lock attachment member from the coupling attachment attached to the superior strut.

Figure 27B:
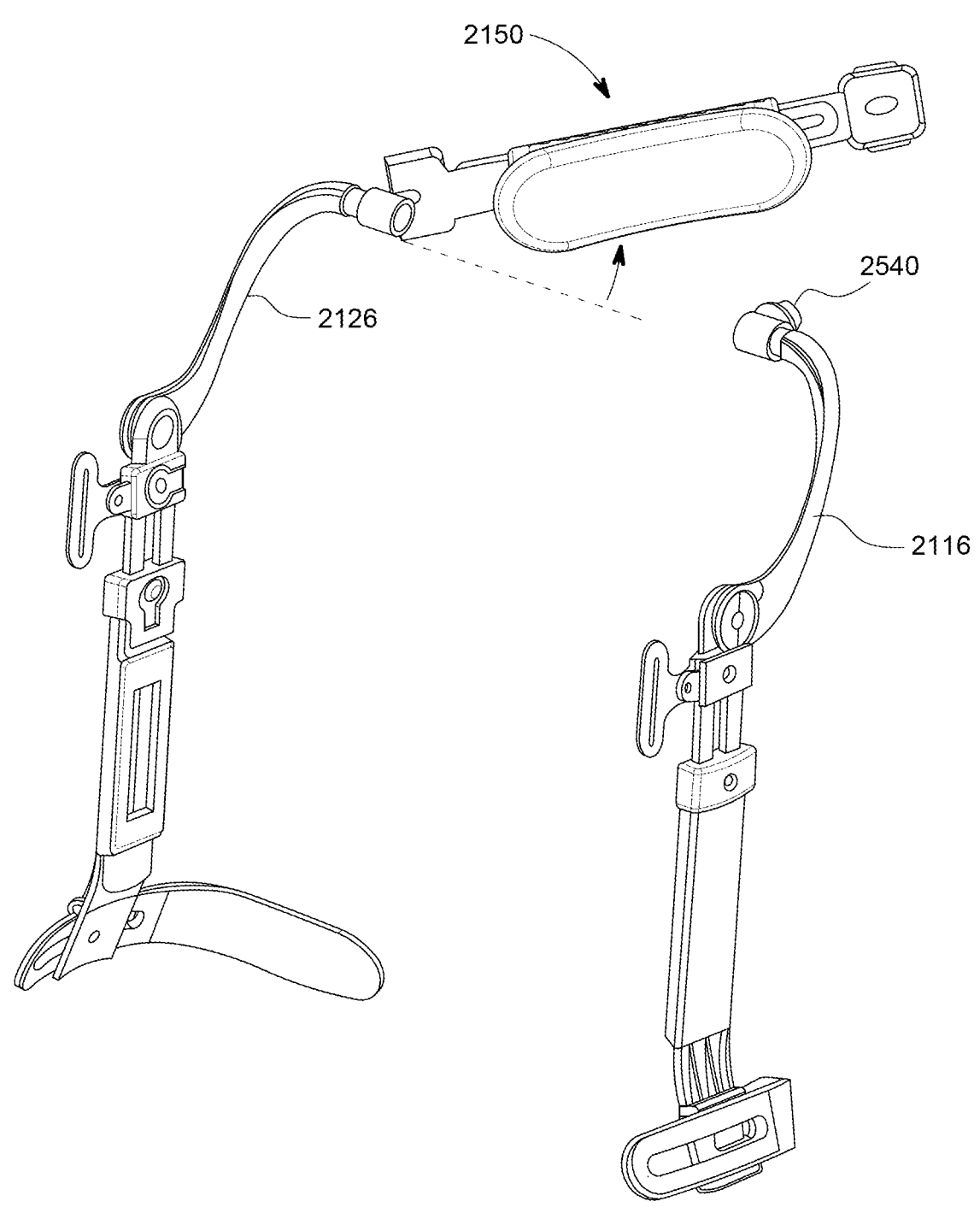

FIG. 27B is a perspective posterior view of the fourth embodiment of the orthopedic spine brace of FIG. 27A illustrating rotation of the chest plate attachment after detachment of the lock attachment member from the coupling attachment.

Figure 28A:
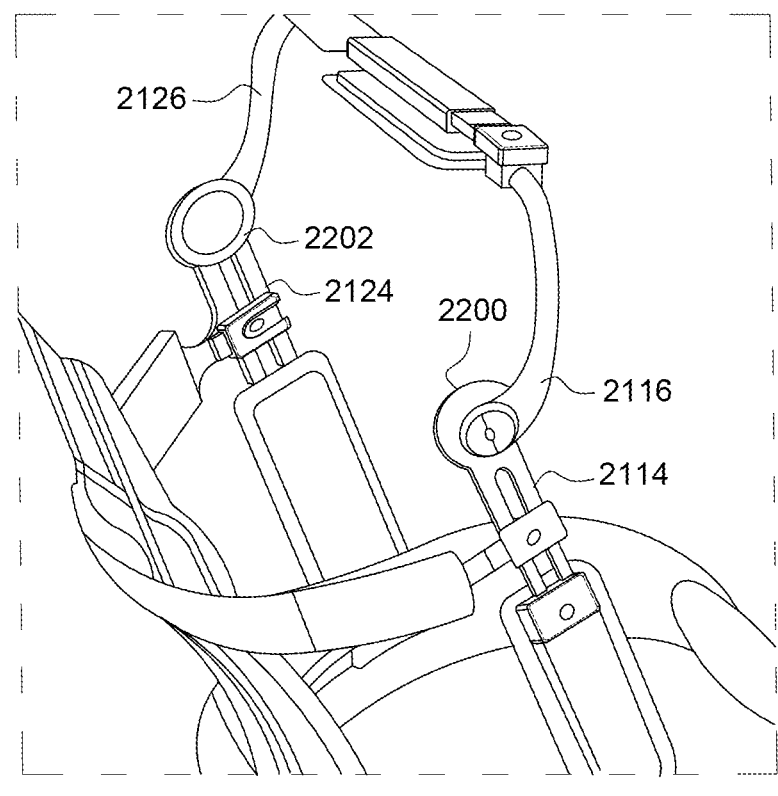

FIG. 28A is a perspective view of a hinge interconnecting the superior strut with the medial strut of FIGS. 21A-21D.

Figure 28B:
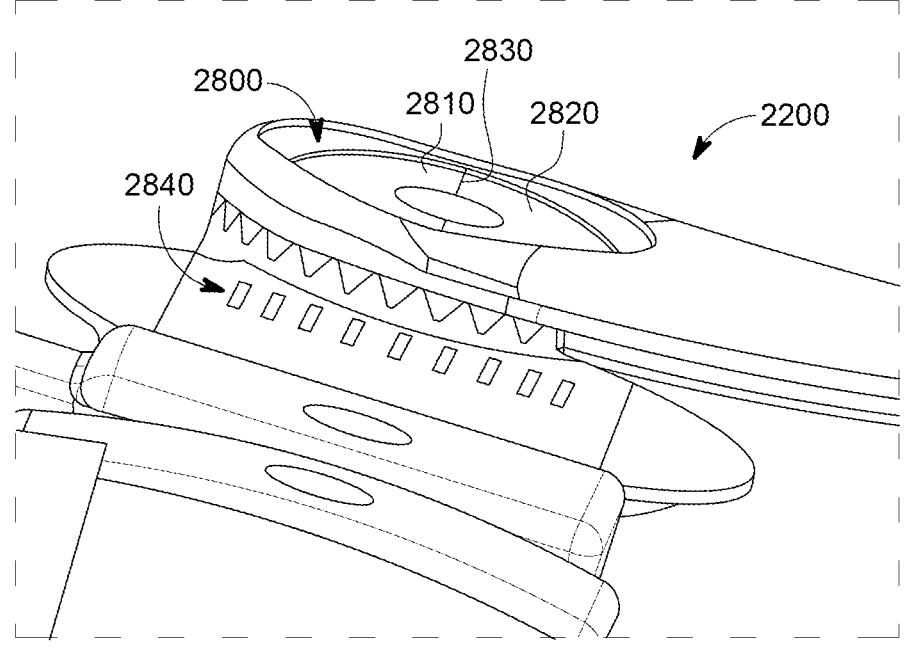

FIG. 28B is lateral view of the hinge of FIG. 28A with concave recesses utilized to provide a size setting.

Figure 28C:
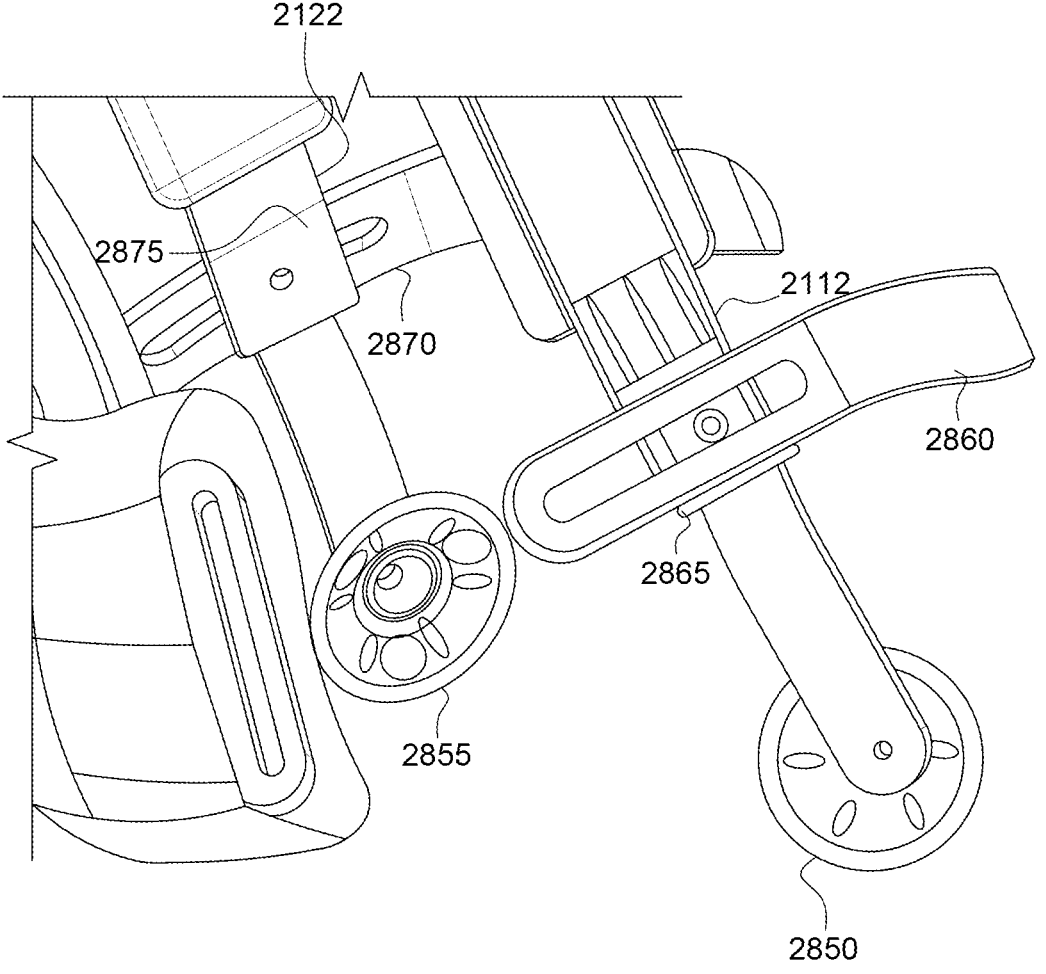

FIG. 28C is a perspective view of an exemplary embodiment of hip support members coupled to the inferior struts of the orthopedic spine brace of FIGS. 21A-21D.

Figure 29A:
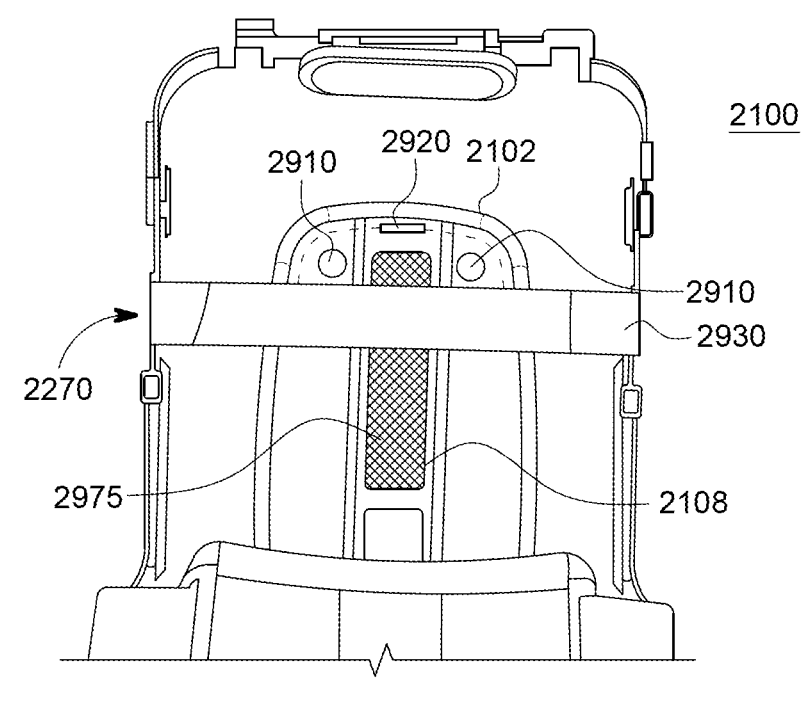

FIG. 29A is a posterior view of the back panel of the fourth embodiment of the orthopedic spine brace of FIGS. 21A-21D.

Figure 29B:
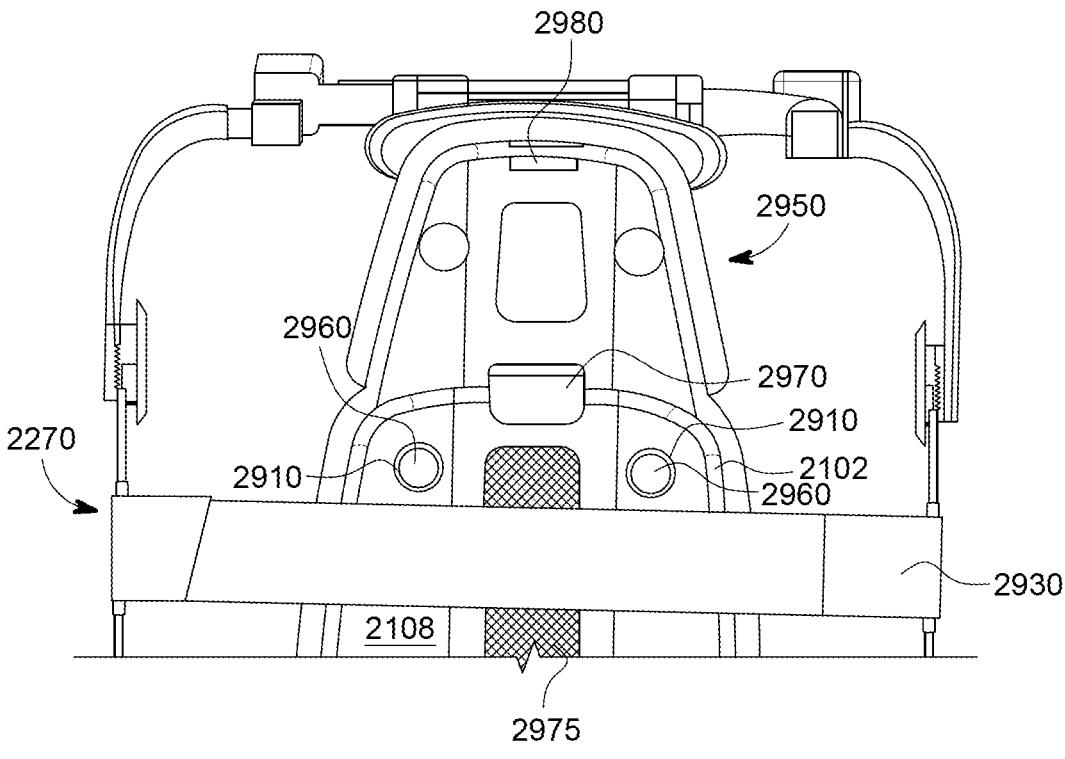

FIG. 29B is a perspective view of an extension panel coupled to the back panel of the fourth embodiment of the orthopedic spine brace of FIGS. 21A-21D.

Figure 30A:
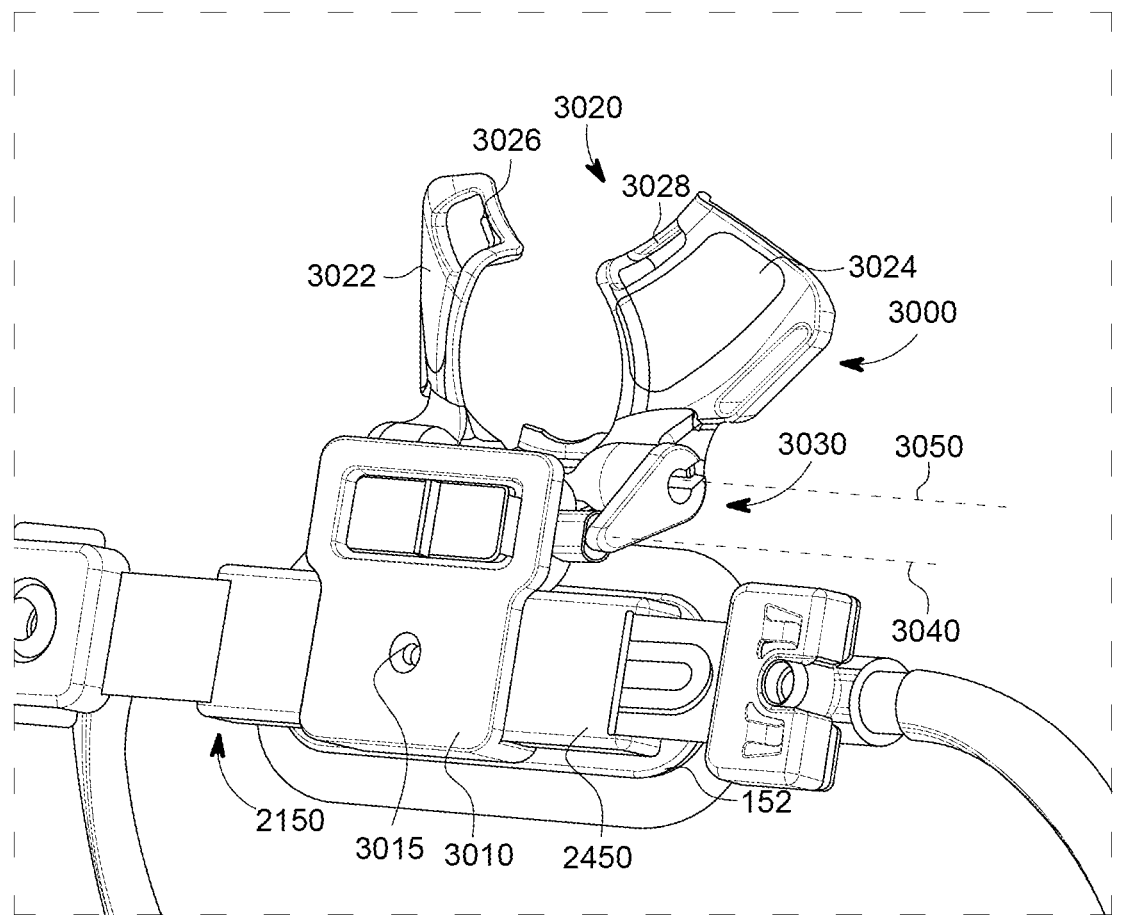

FIG. 30A is a perspective view of a collar attachment member adapted for coupling to the chest plate attachment of FIGS. 24A-24B.

Figure 30B:
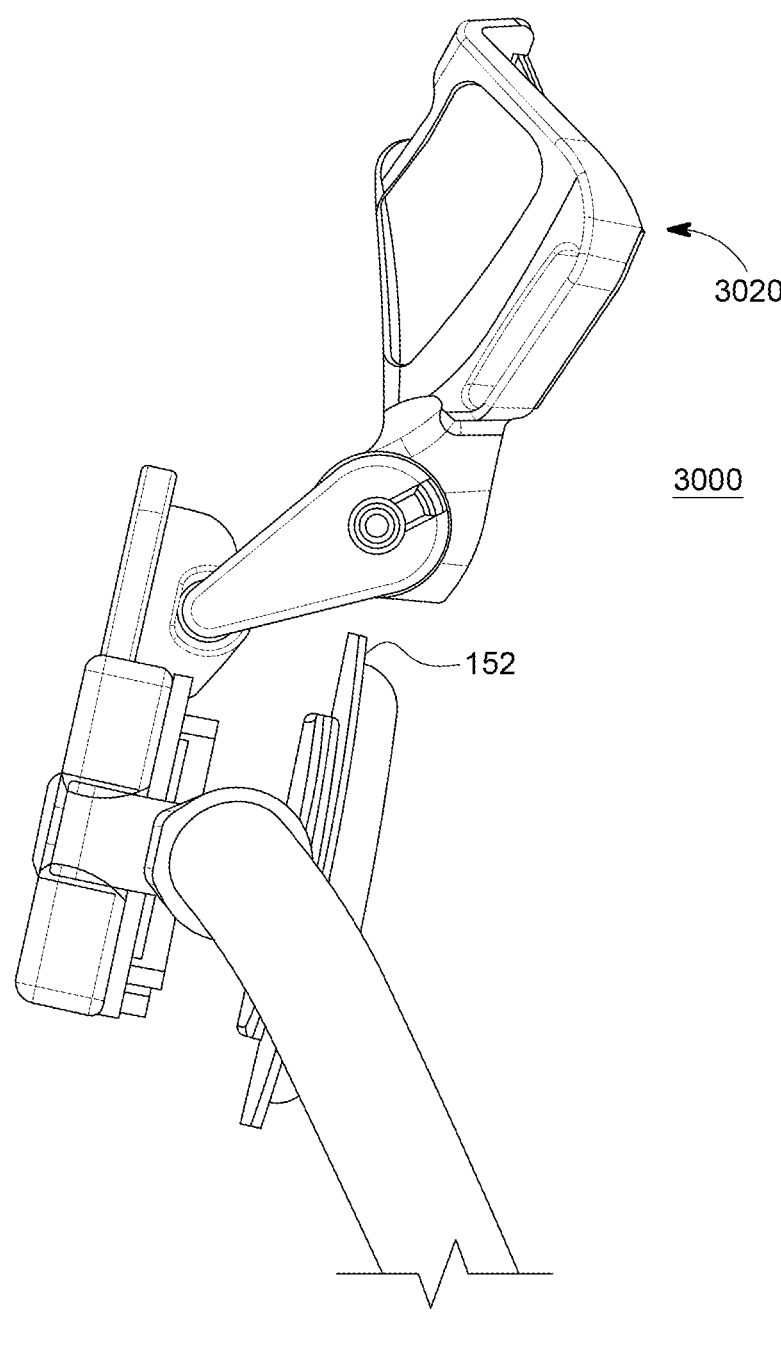

FIG. 30B is a lateral view of the collar attachment member of FIG. 30A positioned within a first orientation.

Figure 30C:
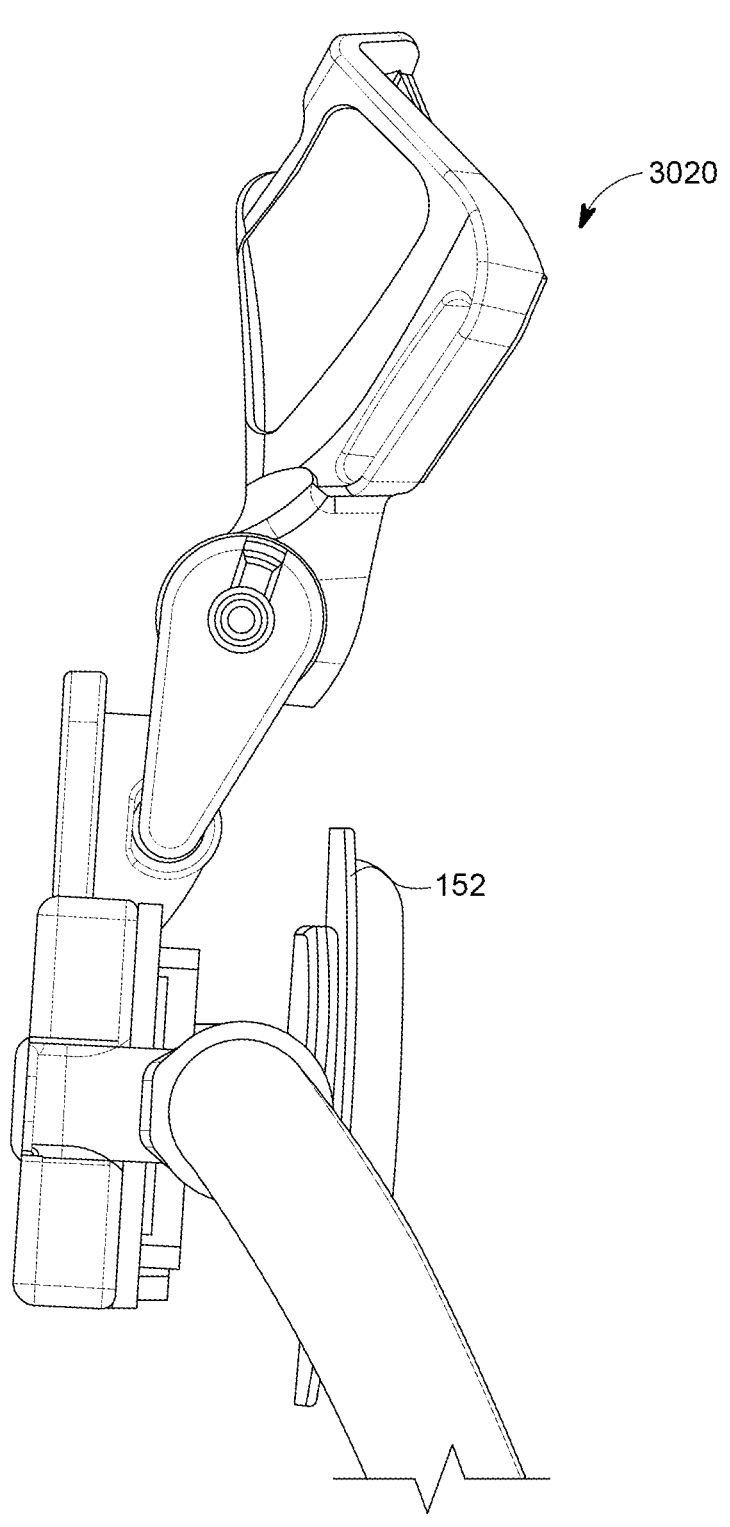

FIG. 30C is a lateral view of the collar attachment member of FIG. 30A positioned within a second orientation.

Figure 30D:
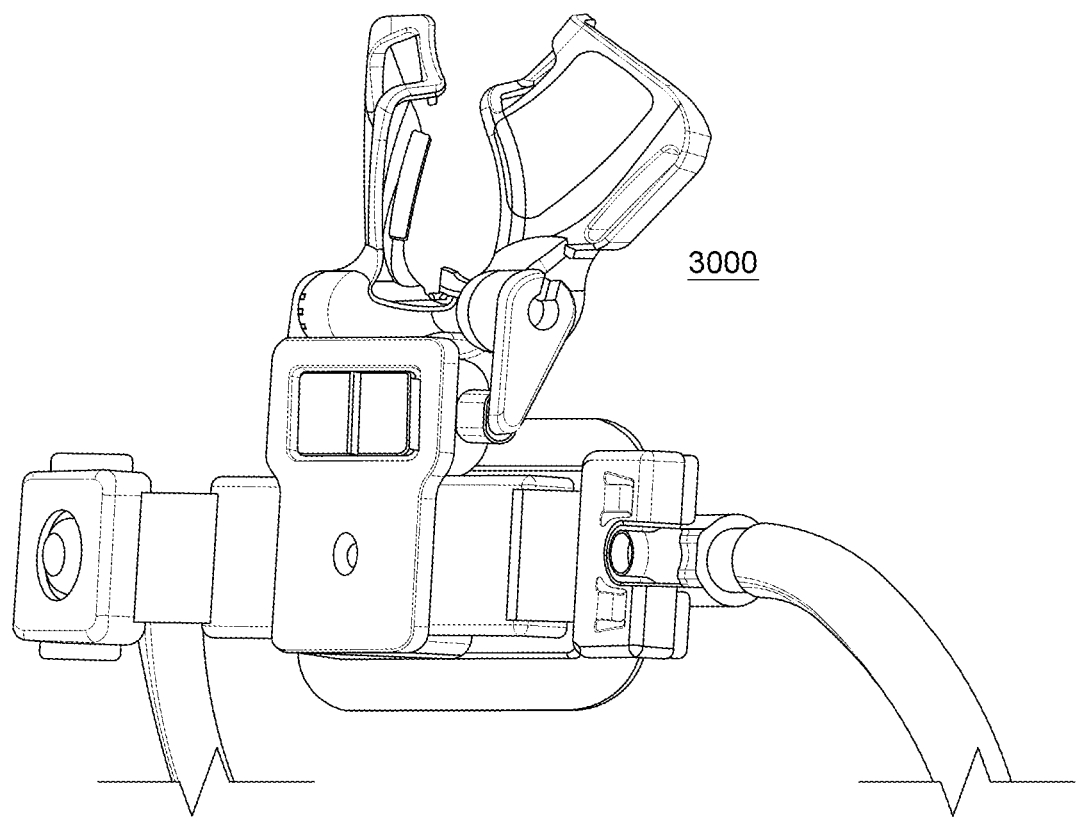

FIG. 30D is a perspective view of the collar attachment member of FIG. 30A positioned in the second orientation and coupling to the chest plate attachment of FIGS. 24A-24B.

Figure 31A:
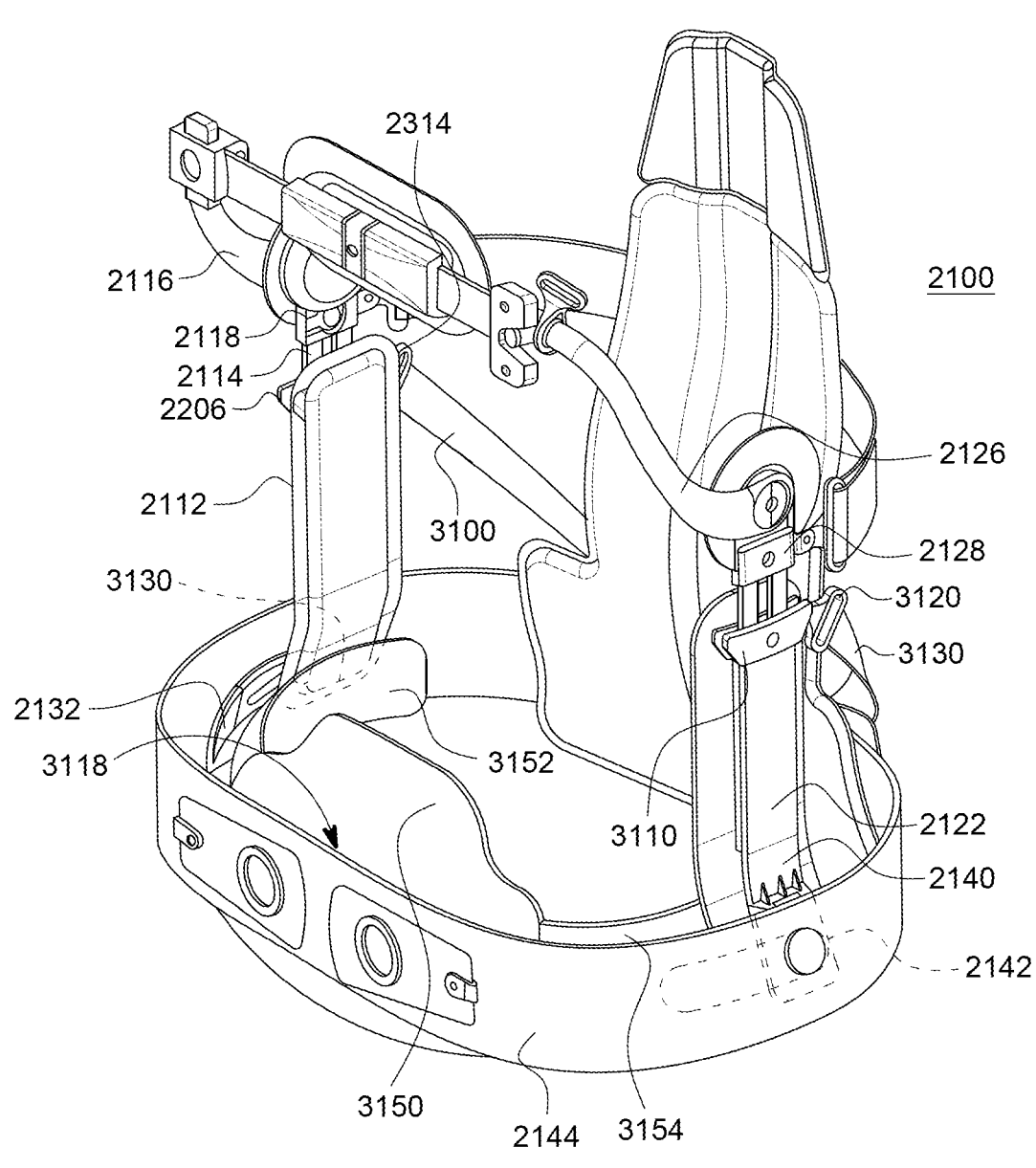

FIG. 31A is a perspective anterior view of the orthopedic spine brace of FIG. 21A including tension straps.

Figure 31B:
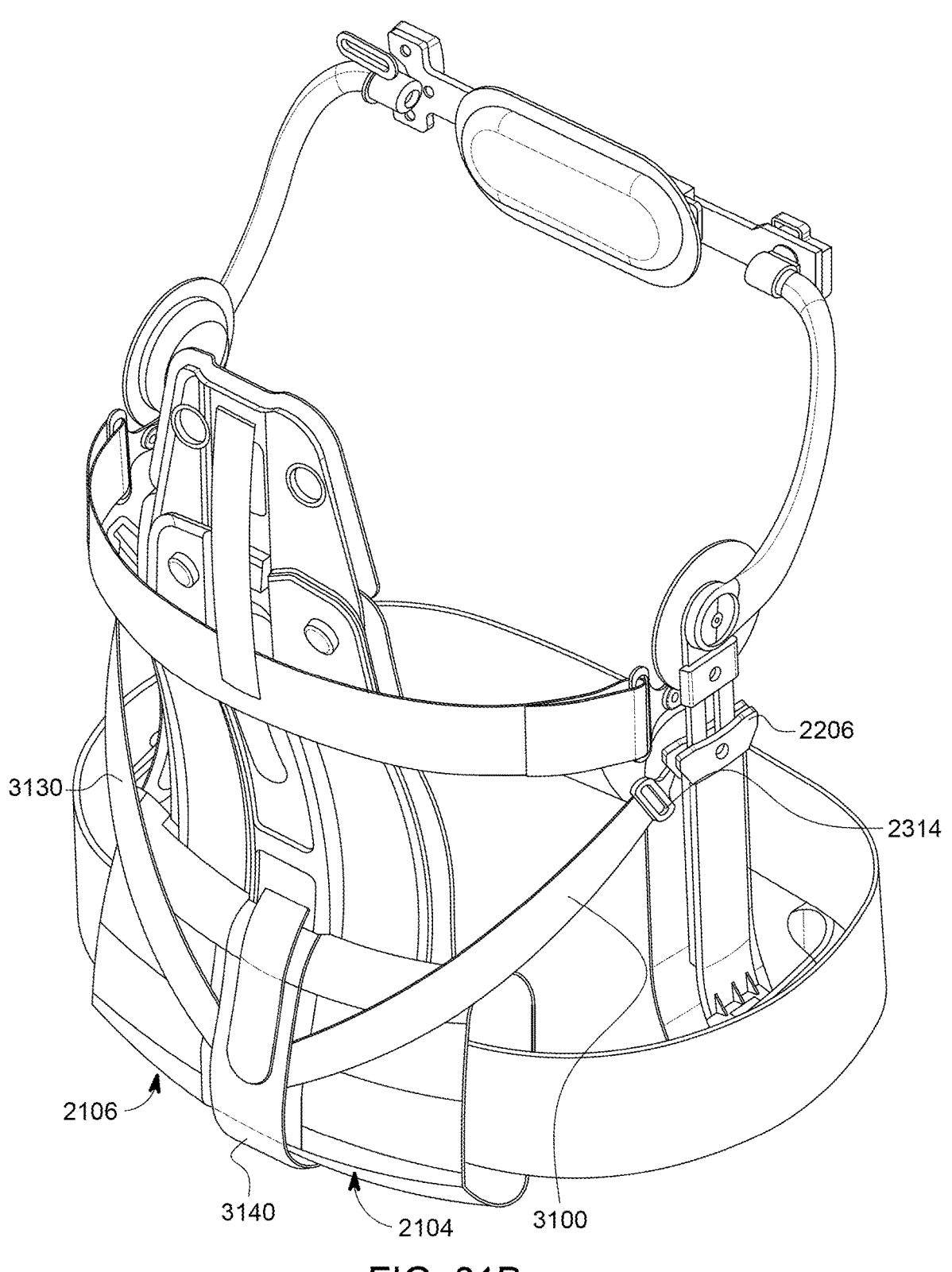

FIG. 31B is a perspective posterior view of the orthopedic spine brace of FIG. 21A including the tension straps coupled to a back panel of the orthopedic spine brace.

Figure 32A:
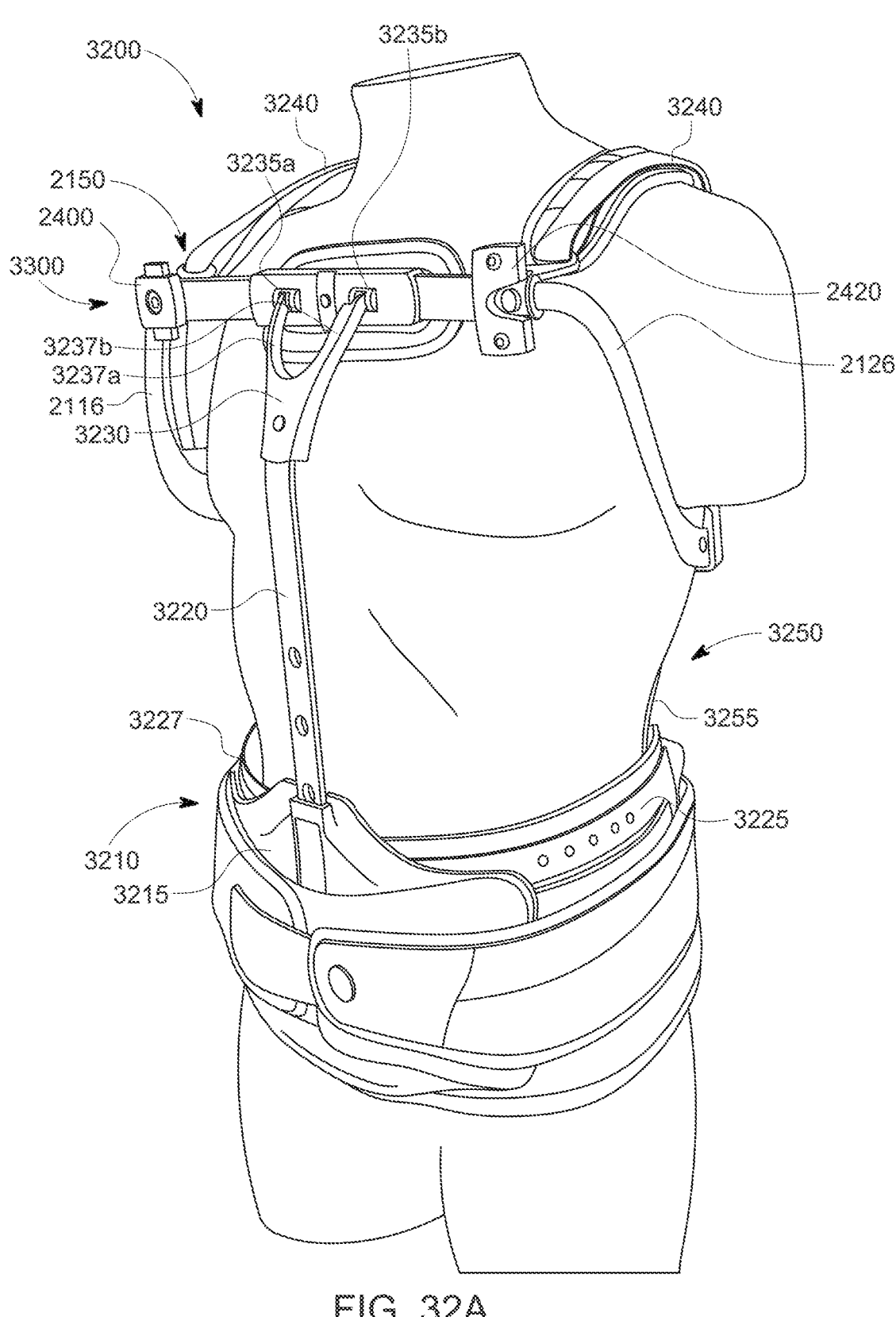

FIG. 32A is a perspective view of another exemplary embodiment of an orthopedic spine brace.

Figure 32B:
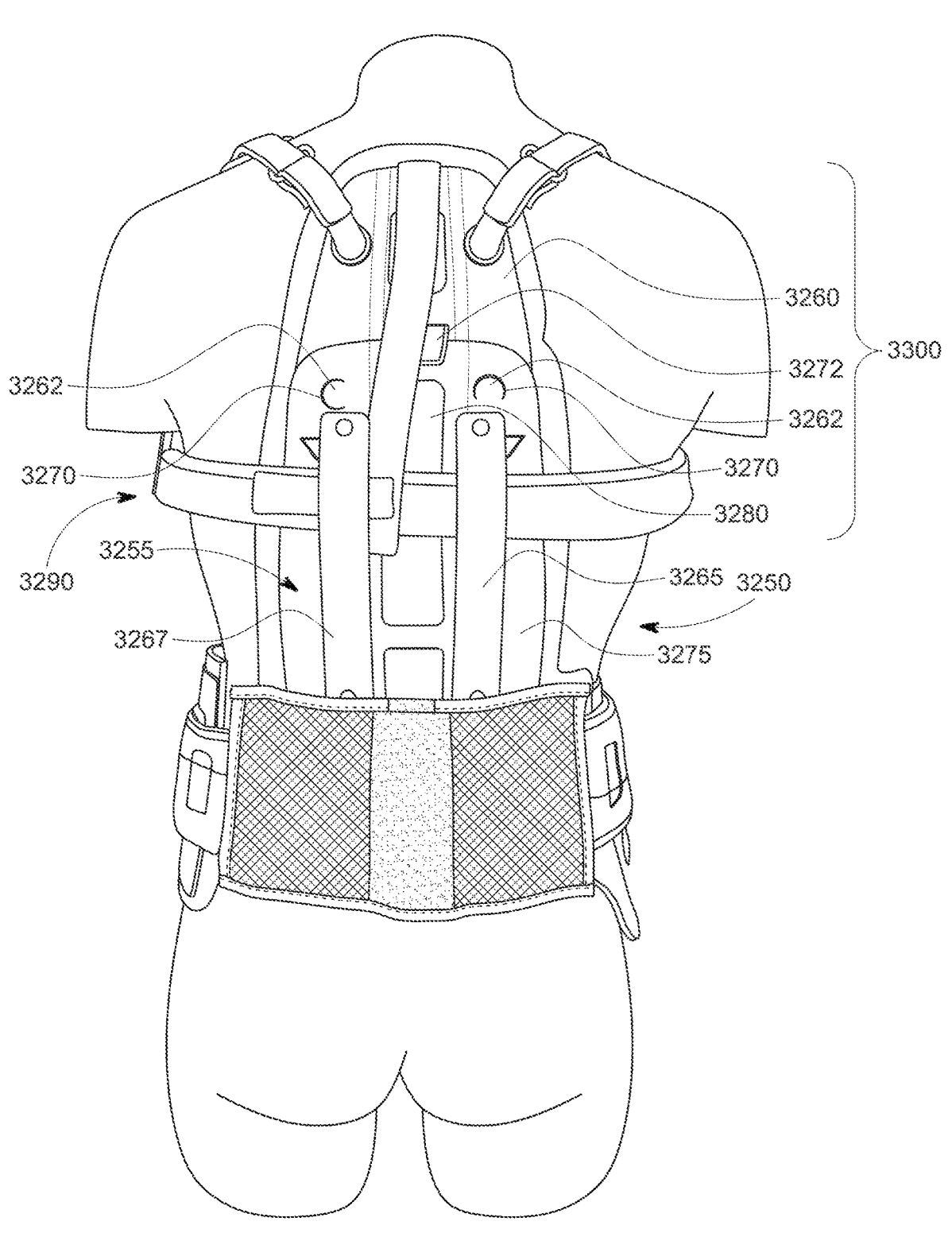

FIG. 32B is an exemplary embodiment of a back-facing view of the posterior bracing system.

Figure 33A:
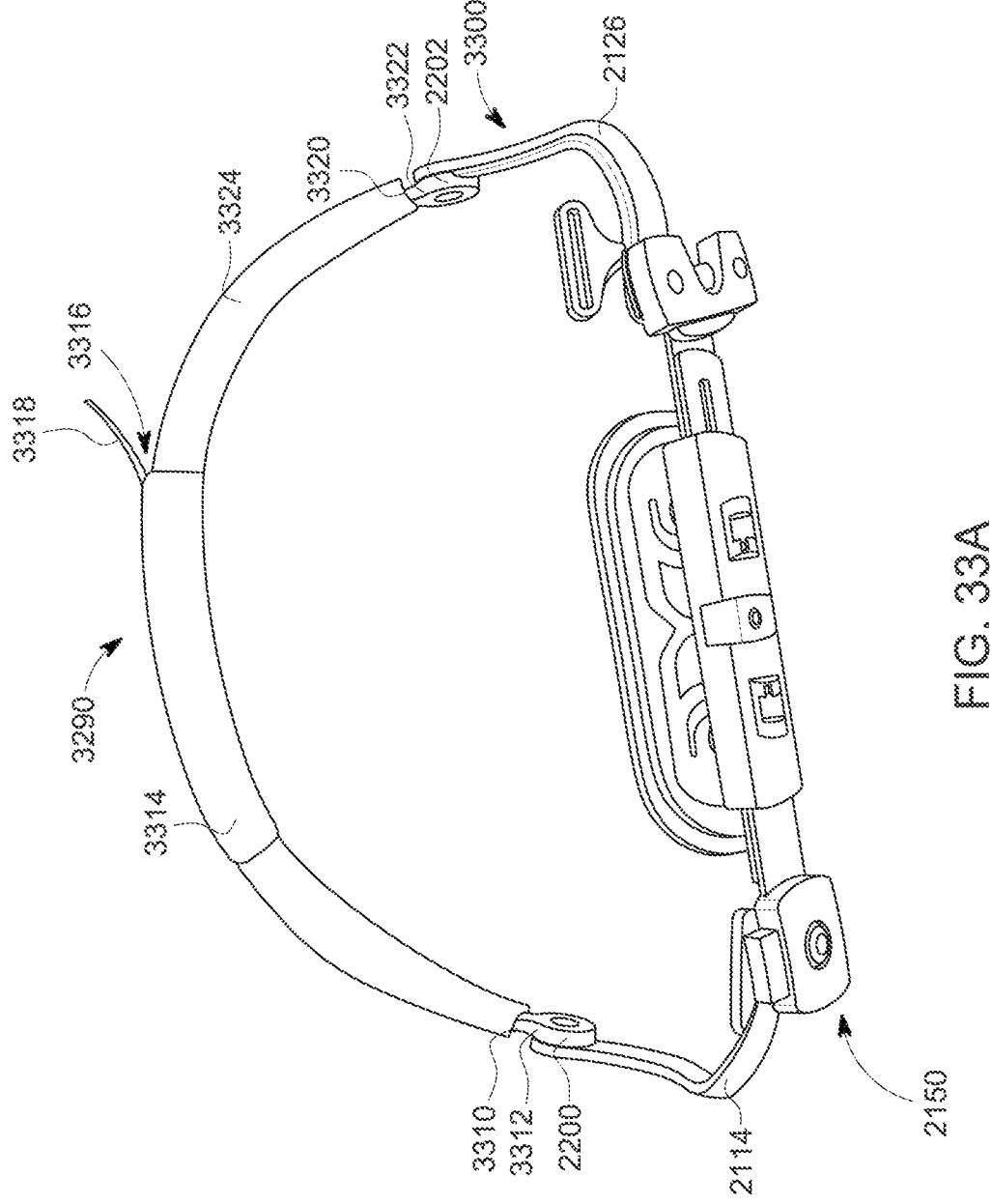

FIG. 33A is an exemplary embodiment of the superior bracing system of FIG. 32A features the chest plate attachment coupled to the pair of superior frame members in a closed state.

Figure 33B:
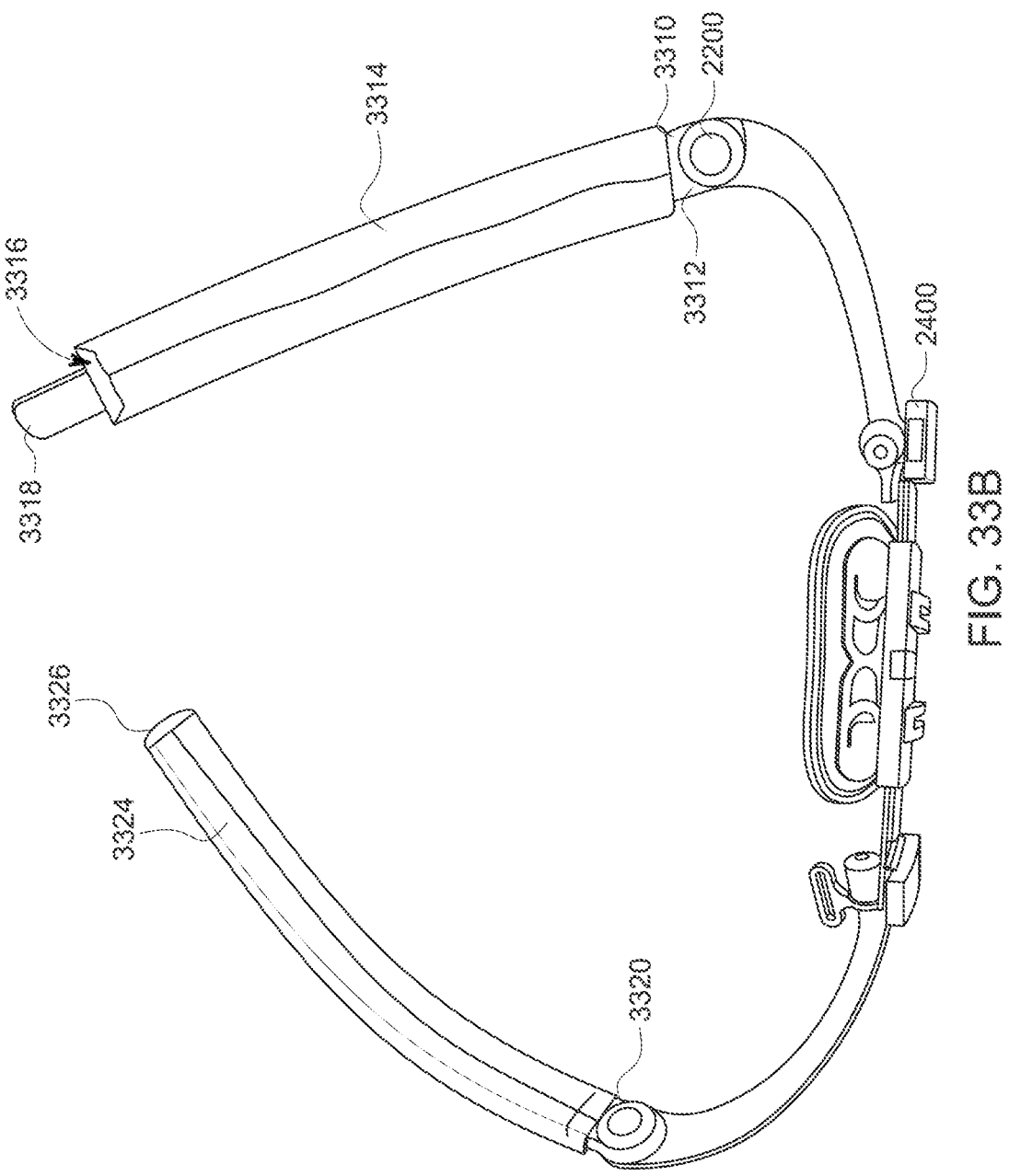

FIG. 33B is an exemplary embodiment of the superior bracing system of FIG. 33A in an opened state.

Figure 33C:
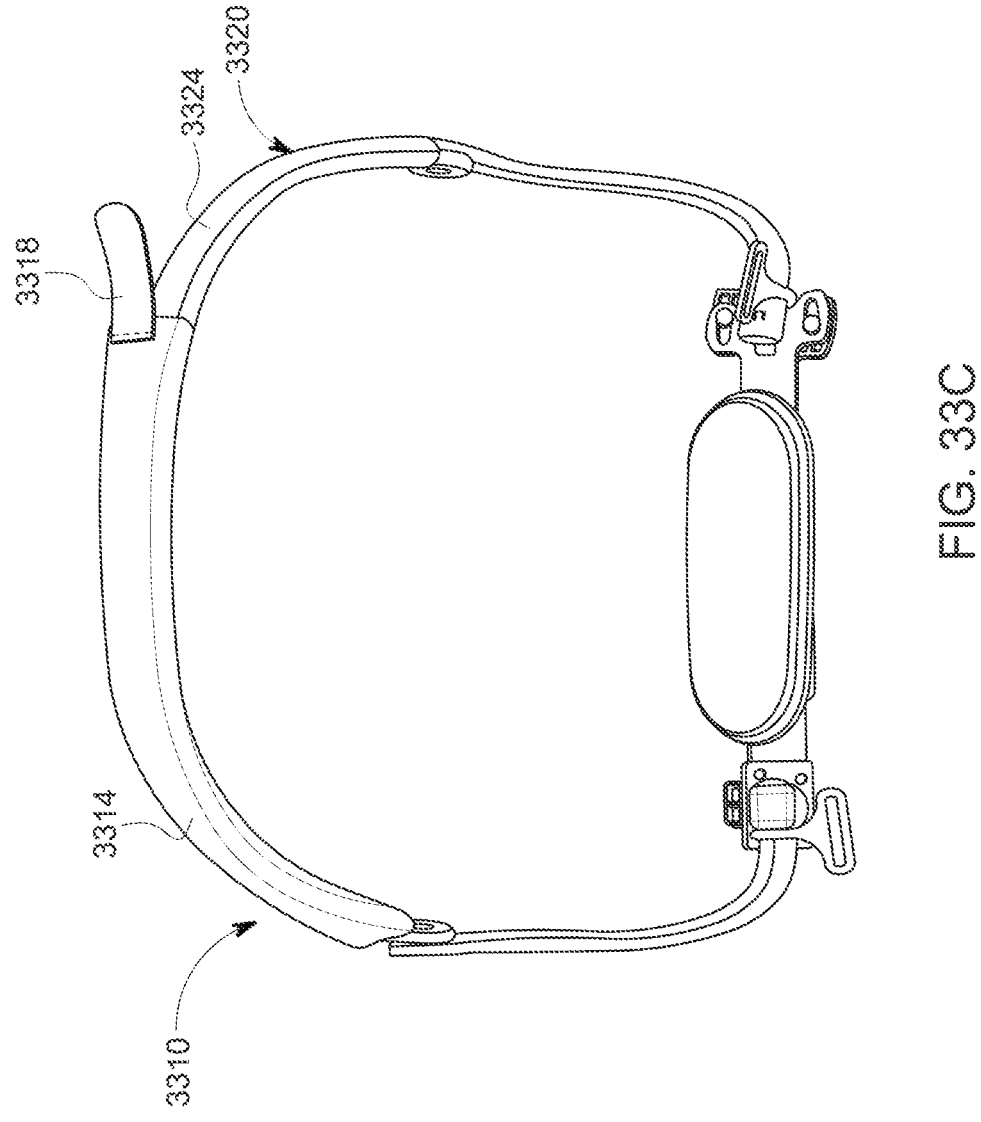

FIG. 33C is an exemplary embodiment of the superior bracing system of FIGS. 33A-33B with the connection straps positioned in an overlapping fashion as the superior bracing system is in the closed state.

Figure 33D:
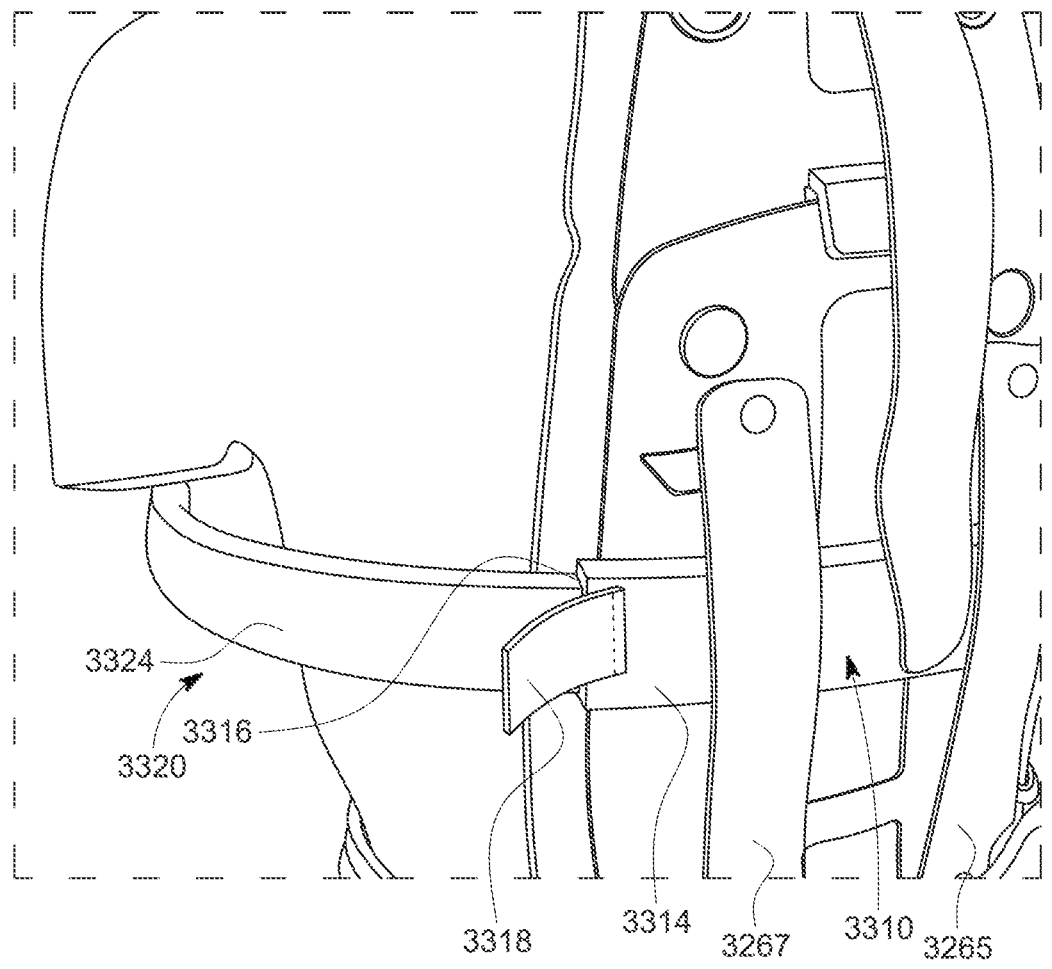

FIG. 33D is an exemplary embodiment of the superior bracing system of FIGS. 33A-33C with the fastening tab being attached to the UBL sleeve of the second connection strap.

While each inventive aspect of the disclosure may be subject to various modifications, equivalents, and alternative forms, specific embodiments thereof have been shown by way of example in the drawings and will now be described in detail. It should be understood that each inventive aspect is not limited to the particular embodiments disclosed, but—on the contrary—the intention is to cover modifications, equivalents, and alternative forms of the inventive aspects within the specific embodiments as each inventive aspect may be implemented into any of these different embodiments.

DETAILED DESCRIPTION

Embodiments of the present disclosure generally relate to an orthopedic spine brace including a posterior bracing system and an anterior bracing system. According to one embodiment of the disclosure, the posterior bracing system features a panel that operates with a panel reinforcement member oriented along a transverse plane and coupled to lateral frame members of an anterior facing system of the orthopedic spine brace. As described herein, the orthopedic spine brace may constitute any type of lumbar sacral orthosis (LSO), including a thoracic LSO (TLSO), or a cervical TLSO (CTLSO) as described below.

When deployed as a TLSO or CTLSO, the orthopedic spine brace may be configured with an anterior bracing system that features lateral frame members including that allow for partial flexion (and return extension) of the superior segments of the lateral frame member. The inferior frames of the lateral frame members include anterior superior iliac spine (ASIS) frame members for placement on the ASIS region of the patient to allow for the pelvic and trunk area to be fastened through soft goods. The superior frames of the lateral frame members include swing arms to be fully opened when removing the orthopedic spine brace and coupled to an anterior chest assembly when the orthopedic spine brace is worn. The anterior chest assembly includes a removable chest plate that may be substituted for a neck orthosis.

I. Terminology

In the following description, certain terminology is used to describe aspects of the invention. For example, the terms "member" may be construed as a component, namely an item with physical structure. In certain situations, a member may include a rigid component of a frame operating as part of the infrastructure for the orthopedic brace. The member may or may not be encased within soft goods (e.g., layers of fabric material connected together).

The term "housing" is a partially enclosed or fully enclosed structure of a component, namely a structure having an enclosed or partially enclosed perimeter configured to secure, maintain, and/or protect inner workings of the component such as a hinge for example. A "hinge" is a type of component that allows angular movement of members coupled thereto while an "assembly" may be construed as a collection of components.

The term "attach" and other tenses of the term (e.g., attached, attaching, etc.) may be construed as an act of physically connecting one member or component to another. The term "coupled" and other tenses of the term (e.g., coupling, couple, etc.) may feature direct or indirect attachment between members or components.

A "fastener" may be construed as any component that is used to attach different members together. An illustrative example of different types of fasteners and fastening techniques may include, but are not limited or restricted to snaps, buttons, clasps, buckles, adhesives, sewing, heat sealing (or melting), gluing, knitting, or other physical coupling techniques such as a hook and loop connection.

The terms "rigid" or "rigidity" with respect to a member or portion of a member may be construed as the member being configured to resist at least partially bending or deformation. According to this definition, different lengths of a given structure and composition can be rigid at a shorter length, and flexible at a longer length. As used herein, the term "rigid" with respect to a member or portion of a member may be construed as permanently deforming or breaking the member if bent or twisted (once or repeatedly) by at least 90°.

Finally, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, functions, steps, or acts are in some way inherently mutually exclusive.

As this invention is susceptible to embodiments of many different forms, it is intended that the present disclosure is to be considered as an example of the principles of the invention and not intended to limit the invention to the specific embodiments shown and described.

II. General Architecture—Orthopedic Spine Brace (1$^{st}$ Embodiment)

Referring to FIG. 1A, a front-facing view of an exemplary embodiment of an orthopedic spine brace 100 is shown. The orthopedic spine brace 100 includes an anterior bracing system 110 and a posterior bracing system 120. The anterior bracing system 110 includes a pair of lateral frame members 130₁ and 130₂, both of which extend superiorly (upwardly) from an anterior superior iliac spine (ASIS) area to a chest area. In particular, according to one embodiment of the disclosure, a first lateral frame member 130₁ includes a superior strut 131₁ coupled to a proximal (curved) superior frame member 132₁ positioned in a first chest area 136. Furthermore, the first lateral frame member 130₁ includes an inferior strut 134₁ coupled to a distal, first inferior frame member 135₁ positioned at a first ASIS area 137. Similarly, a second lateral frame member 130₂ includes a superior strut 131₂ and a proximal (curved) superior frame member 132₂ positioned in a second chest area 138. The second lateral frame member 130₂ further includes an inferior frame (strut) 134₂ coupled to a distal, second inferior frame member 135₂ positioned at a second ASIS area 139.

As further shown in FIG. 1A, corresponding swing arms 140₁ and 140₂ are attached to the superior frame members $132_1$ and $132_2$ of the lateral frame members $130_1$ and $130_2$, respectively. Each swing arm (e.g., swing arm $140_2$) includes a fastener $142_2$ and a (swinging) hinge $144_2$ interposed between the superior frame member $132_2$ of the second lateral frame member $130_2$ and the hinge $144_2$. Although not shown in similar detail due to the perspective view angle, a similar structure may be found in connection with the first lateral frame member $130_1$ in which the hinge $144_1$ is coupled to both the superior frame member $132_1$ of the first lateral frame member $130_1$ and a fastener $142_1$. The fasteners $142_1$ and $142_2$ may operate as quick-release fasteners for attachment to an anterior chest assembly 150.

As further shown in FIG. 1A, the anterior chest assembly 150 maintains the patient in an upright position and provides flexion through hinges $160_1$ and $160_2$, which separate superior struts of the lateral frame members $130_1$ and $130_2$ (including superior frames members $132_1$ and $132_2$) from inferior frames (struts) $134_1$ and $134_2$ of the lateral frame members $130_1$ and $130_2$, respectively. The anterior chest assembly 150 includes a removable chest plate 152 and a chest compression (U-shaped) member 154. The chest compression member 154 is attached to the lateral frame members $130_1$ and $130_2$ via the fasteners $142_1$ and $142_2$ of the swing arms $140_1$ and $140_2$.

Encasing the first inferior frame member $135_1$ and the second interior frame member $135_2$ of the lateral frame members $130_1$ and $130_2$, a belt 165 is arranged to be placed around the waist of the patient and tightened through one or more hook and loop fasteners. As shown, the belt 165 may include a pelvic pad 166 positioned on an inner (posterior) side of the belt 165 and at least a pair of lateral pads 167 and 168 positioned along the inner (lateral) side of the belt 165.

Figure 1B:
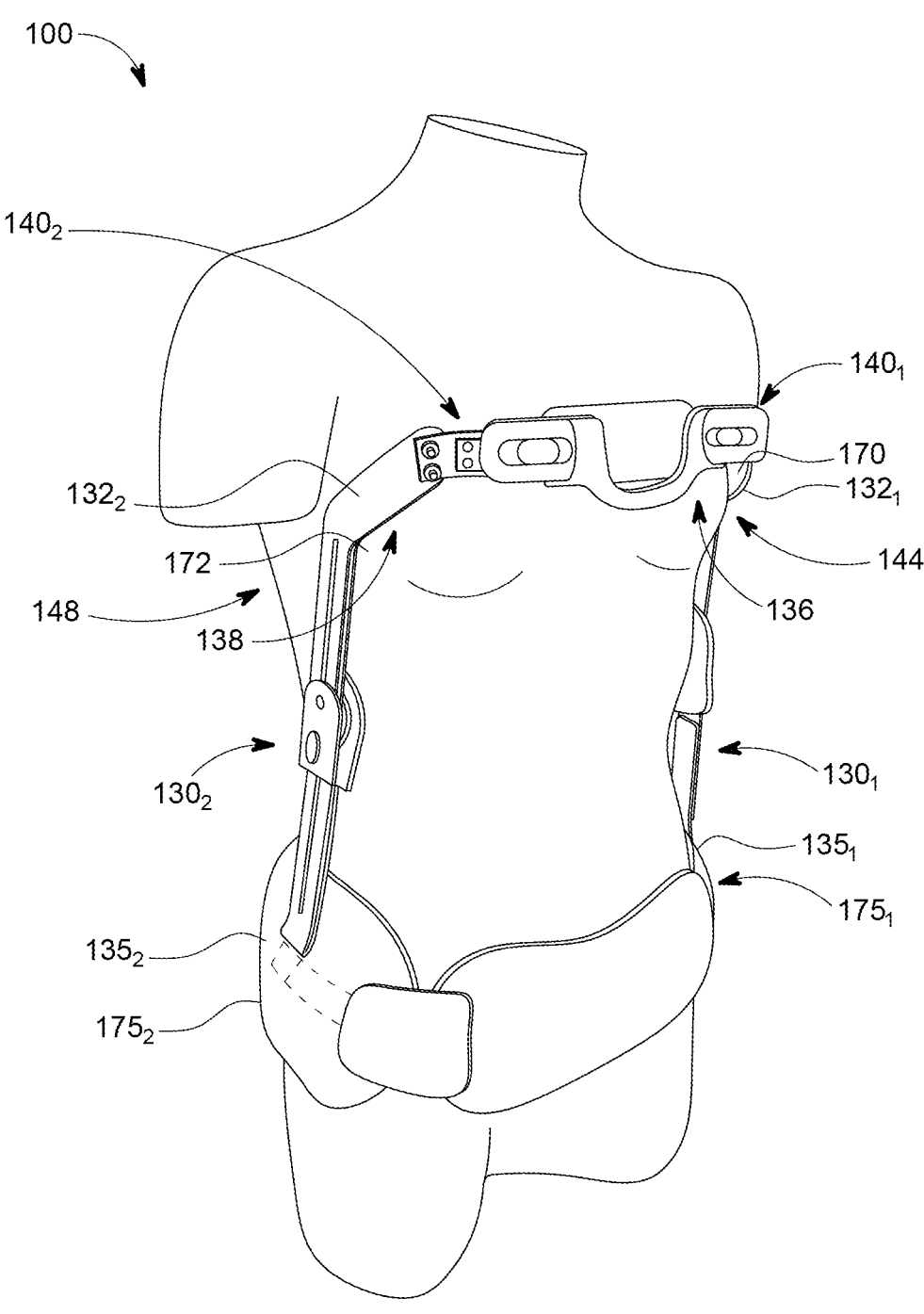
FIG. 1B is a front-facing perspective view of the orthopedic spine brace of FIG. 1A.

Referring now to FIG. 1B, a perspective anterior view of the orthopedic spine brace 100 of FIG. 1A is shown. The orthopedic spine brace 100 features the first lateral frame member $130_1$ including the superior frame member $132_1$ curved inwardly with a first radius of curvature 170 while the second lateral frame member $130_2$ includes the superior frame member $132_2$ curved inwardly with a second radius of curvature 172. The first and second radii of curvature 170 and 172 are selected to provide a comfortable fitting at the chest areas 136/138 and axilla area 146/148 without impeding arm swing by the patient.

Maintained between the inner and outer sewn fabric forming the belt 165, a first anterior superior iliac spine (ASIS) frame member $175_1$ is coupled to the first inferior frame member $135_1$ of the first lateral frame member $130_1$. The first ASIS frame member $175_1$ is configured to fit adjacent to an ASIS of the patient. Hence, the first ASIS frame member $175_1$ is made of a rigid material that is pliable to allow the first ASIS frame member $175_1$ to be contoured (bent) around the (left) ASIS of the patient. Similarly, a second ASIS frame member $175_2$ is coupled to the second inferior frame member $135_2$ of the second lateral frame member $130_2$. The second ASIS frame member $175_2$ is also made of a rigid material that is pliable to allow the second ASIS frame member $175_2$ to be contoured around the (right) ASIS of the patient. As a result, the frame components of the orthopedic spine brace 100 is absent from the pelvic area.

Figure 1C:
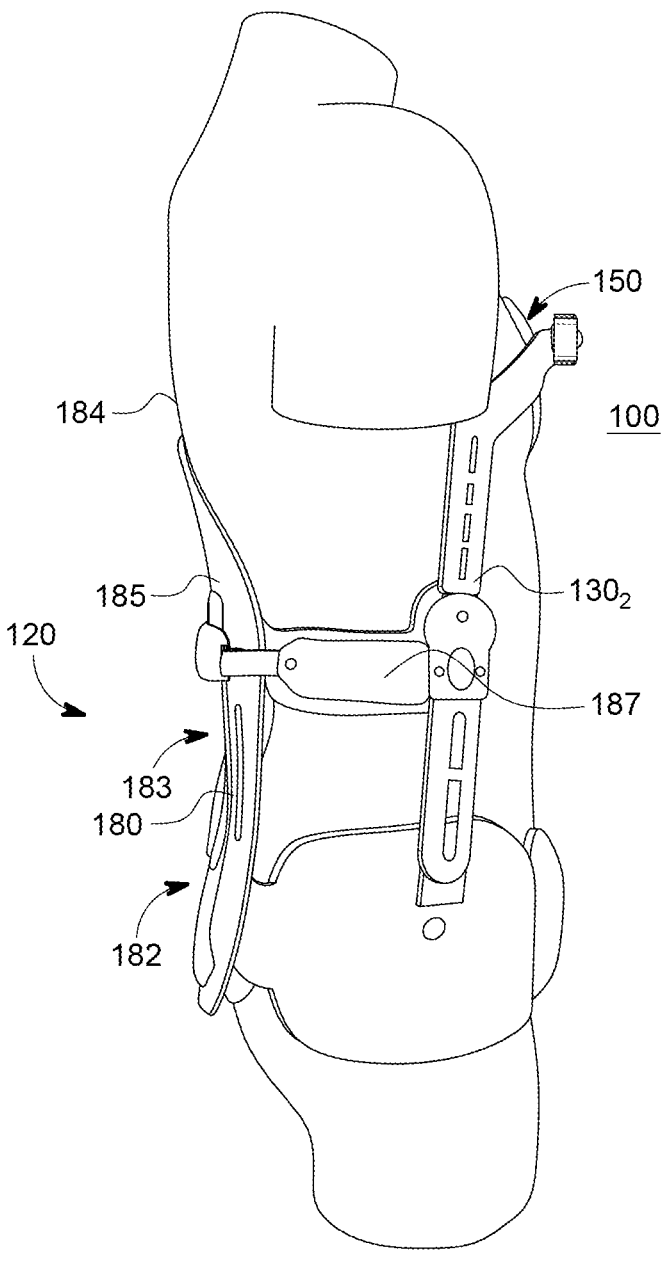
FIG. 1C is a side-facing perspective view of the orthopedic spine brace of FIG. 1A.

Referring to FIG. 1C, a side-facing perspective view of the orthopedic spine brace 100 of FIG. 1A is shown. Herein, the posterior bracing system 120 of the orthopedic spine brace 100 features a posterior panel 180 and a panel reinforcement member 185. The posterior panel 180 is positioned adjacent to sacral and lumbar regions 182-183 of a patient's back 184. The panel reinforcement member 185 is configured for attachment to each of the lateral frame members $130_1$ and $130_2$, and thereafter, a tension may be applied to straps 187 forming a portion of the panel reinforcement member 185. The tension may be applied to tighten the straps 187, and thus, provides a snug fit between the posterior panel 180 to the patient's back 184. Additionally, a force in a posterior direction is being applied from the anterior chest assembly 150. The adjustment in tension may be accomplished through a pull fastener (not shown), which may operate similar to a backpack buckle where tension caused by pulling of the strap 187 (or another interconnect connected to the strap 187) in an anterior direction causes tightening of the posterior bracing system 120.

Figure 1D:
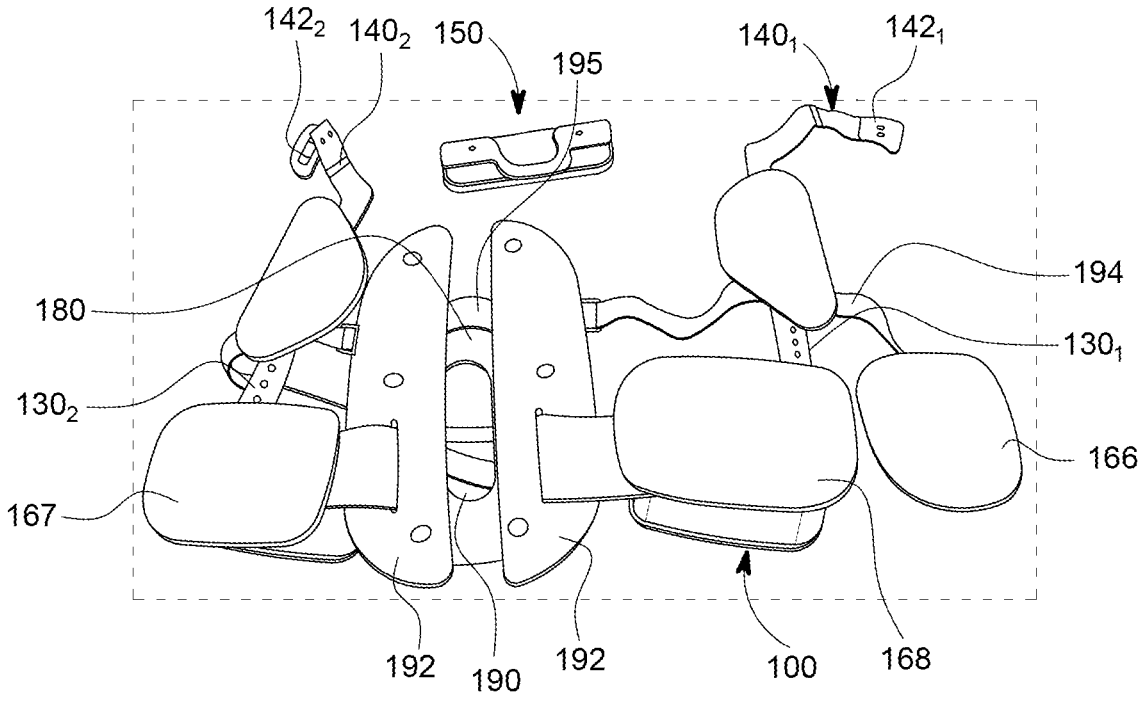
FIG. 1D is a downward view of the orthopedic spine brace of FIG. 1A placed into an open position prior to donning.

Referring now to FIG. 1D, a downward view of the orthopedic spine brace 100 of FIG. 1A is shown, where the orthopedic spine brace 100 is placed into an opened state. According to this embodiment of the disclosure, the posterior panel 180 may include apertures 190 (e.g., slots or windows), which are positioned midline (along a mid-sagittal plane) to create windows to clinicians or caregivers to evaluate or treat spinal incisions and/or wounds as the patient continues to wear the orthopedic spine brace 100. One or more pads 192 may be positioned offset from midline so that pressure applied by the posterior panel 180, during tightening of the posterior bracing system 120, avoids the spinous process by engaging the paraspinal region the patient, not portions of the spine.

As further shown, the lateral pads 167 and 168 are positioned in closer proximity to the posterior panel 180 than the pelvic pad 166. In the open position, at least one of the swing arms $140_1$-$140_2$ of the lateral frame members $130_1$-$130_2$ may be placed into an unlock and opened position. This may be achieved by unlocking the fastener $142_1$-$142_2$ from the chest compression member 154 of the anterior chest assembly 150 and rotating the fasteners $142_1$-$142_2$ in a lateral direction so that they are outwardly facing from the posterior panel 180. As a result, the orthopedic spine brace 100 may be more easily removed or donned. As discussed above, additional pull straps 194 may be attached to the lateral frame members $130_1$-$130_2$ and, more specifically, the pull straps 194 may be attached to corresponding strap termination slots 195 coupled to the posterior panel 180.

Figure 2A:
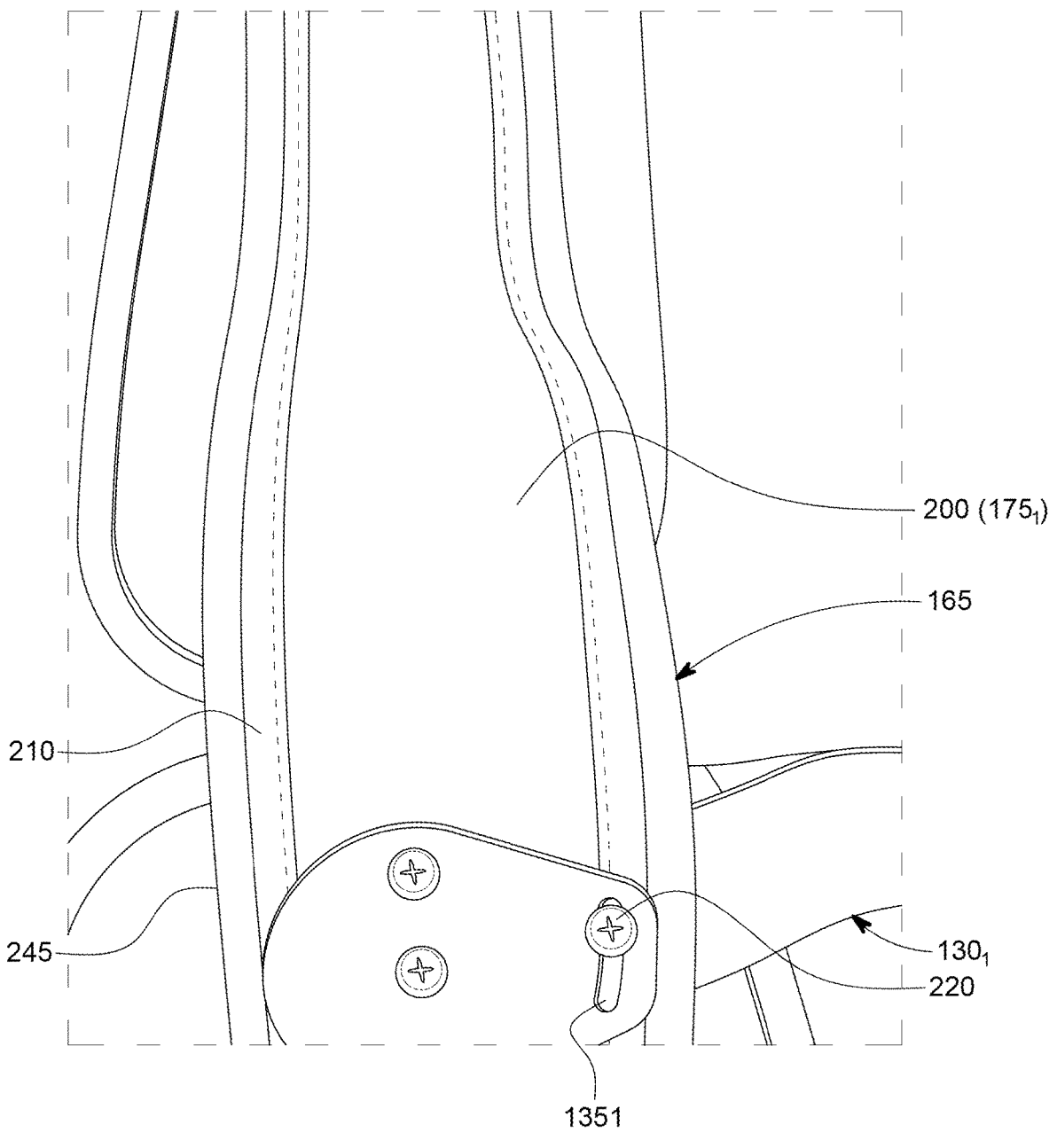
FIG. 2A is an exemplary embodiment of an anterior superior iliac spine (ASIS) frame member positioned within a belt member of the orthopedic spine brace of FIG. 1A
Figure 2B:
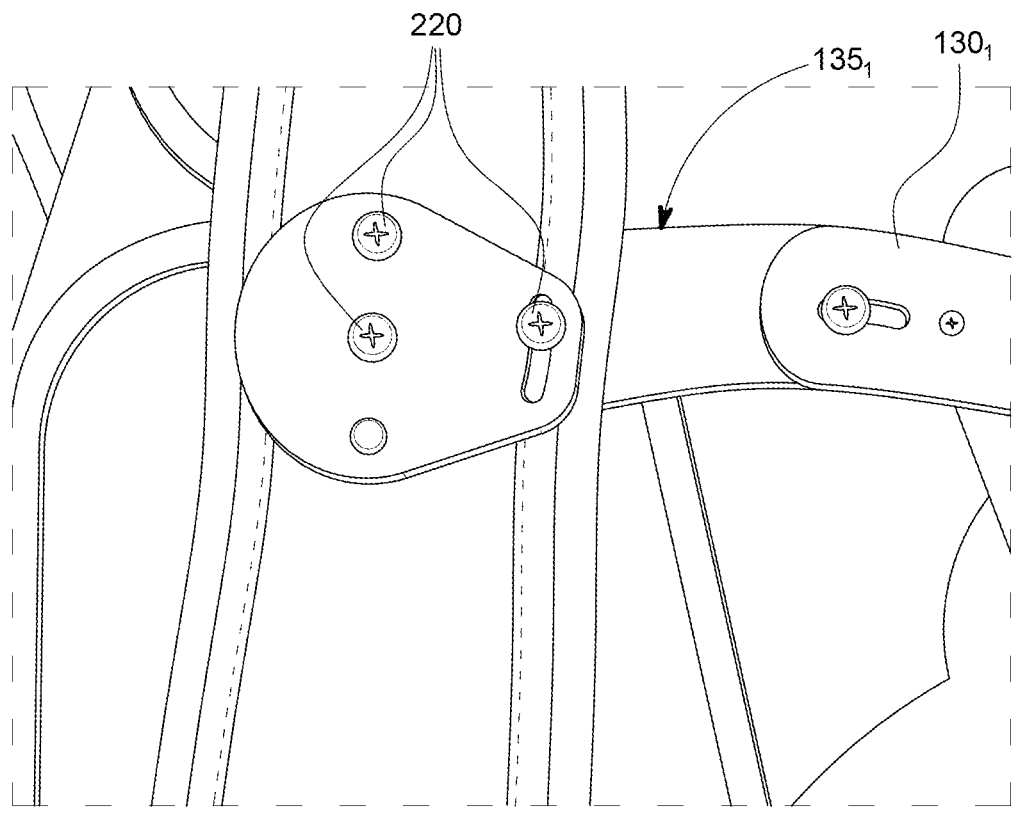
FIG. 2B is a first exemplary embodiment of an inferior frame of a lateral frame member of the orthopedic spine brace of FIG. 1A.

Referring to FIG. 2A, an exemplary embodiment of an anterior superior iliac spine (ASIS) frame member 200, such as first ASIS frame member $175_1$ of FIGS. 1A-1C positioned under a first surface material 210 of the belt 165, is shown. As shown, for this embodiment of the disclosure, the ASIS frame member 200 is attached at the first inferior frame member $135_1$. As shown in FIGS. 2A-2B, this attachment scheme is conducted exterior to the belt 165 where additional padding may be applied at this point of attachment. In particular, one or more fasteners 220 may be used to attach the first inferior frame member $135_1$ of the first lateral frame member $130_1$ to the first ASIS frame member $175_1$, which extends inwardly (medially) from the first inferior frame member $135_1$. This exterior attachment scheme may be deployed to allow clinicians to adjust an angle of the first ASIS frame member $175_1$ by readjustment of the fasteners within different slots or slot locations as shown in FIG. 2C.

Alternatively, the attachment of the first inferior frame member $135_1$ (and at least a proximal end of the first ASIS frame member $175_1$) may be encased between the first surface material 210 and a second surface material 245 of the belt 165. This would hide the point of attachment between first the inferior frame member $135_1$ of the first lateral frame member $130_1$ and the first ASIS frame member $175_1$ from view and protect these components from external environmental conditions.

Figure 2C:
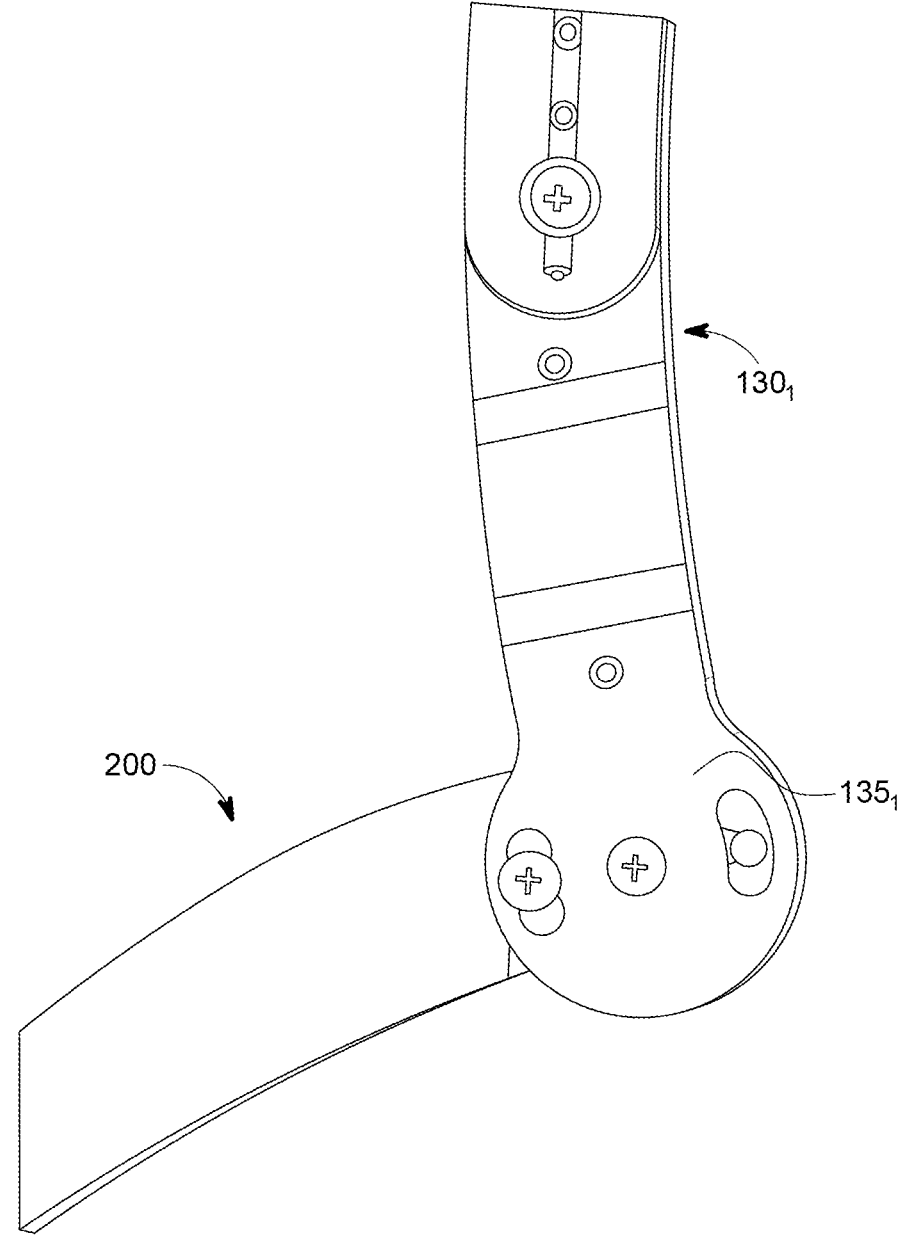
FIG. 2C is an exemplary embodiment of the ASIS frame member of FIG. 2A coupled to the inferior frame of the lateral frame member of the orthopedic spine brace of FIG. 1A.

Referring now to FIG. 2C, a more detailed illustration of the ASIS frame member 200 of FIG. 2A is shown. As in FIGS. 2A-2B, the ASIS frame member 200 is coupled to the first inferior frame member $135_1$ of the first lateral frame member $130_1$. This coupling may be conducted through any type of fastener, including rivets as well as bolts or screws connected through a threaded female connector formed as part of the ASIS frame member 200 or positioned after the bolt/screw is inserted through slots formed within the ASIS frame member 200 and attached by the connector on the posterior side of the ASIS frame member 200. Alternatively, although not shown, the ASIS frame member 200 may be formed as a continuous segment extending from the first inferior frame member $135_1$ of the first lateral frame member $130_1$.

Figure 2D:
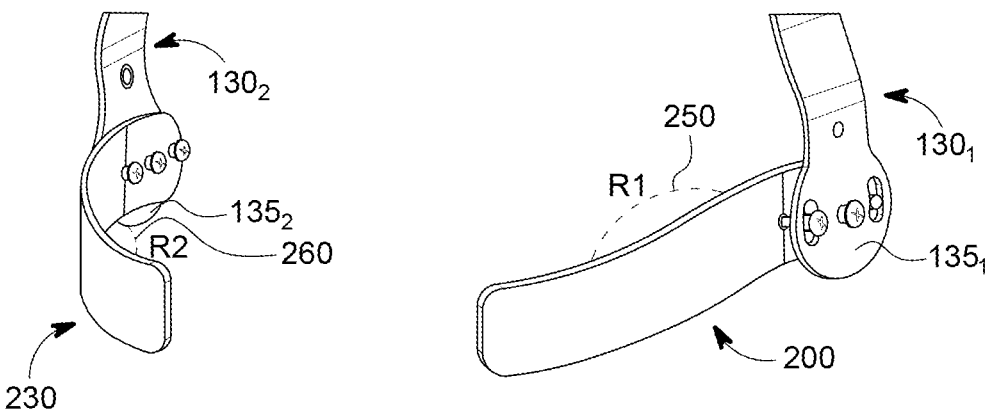
FIG. 2D is an exemplary embodiment of the ASIS frame member of FIG. 2C extending from a proximal end of the ASIS frame member attached to a distal inferior frame of a lateral frame member.
Figure 2E:
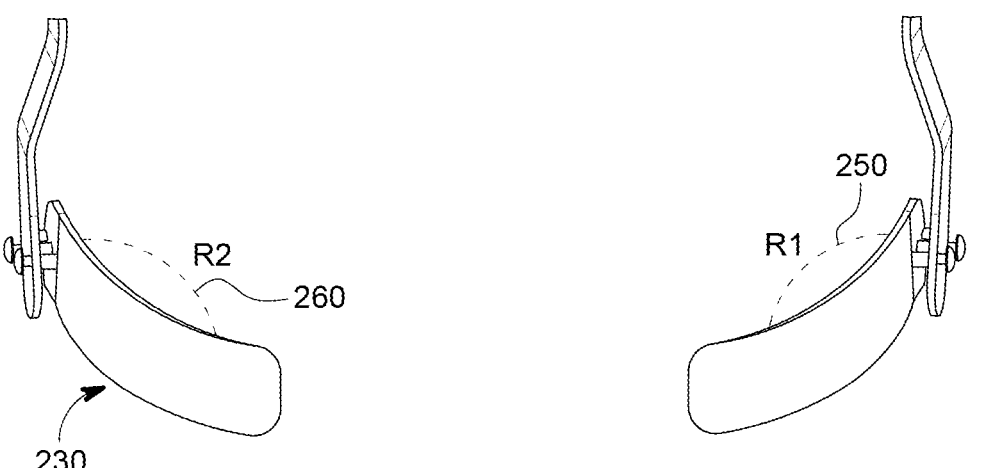
FIG. 2E is an exemplary embodiment of the ASIS frame member of FIG. 2C illustrating an adjustable curved surface extending from the proximal end of the ASIS frame member.

As shown in FIGS. 2D-2E, the ASIS frame member 200, represented as the first ASIS frame member $175_1$ of FIG. 1A, is a concave extension from the first inferior frame member $135_1$ of the first lateral frame member $130_1$ with a radius of curvature (R1) 250. Similarly, a second ASIS frame member 230, which is equivalent to the ASIS frame member $175_2$ of FIG. 1B, is shown. The second ASIS frame member 230 is a concave extension from the second inferior frame member $135_2$ of the second lateral frame member $130_2$ with a radius of curvature (R2) 260. The radii of curvature (R1, R2) 250 and 260 may differ from each other or may be identical (or substantially similar) in degree of curvature Herein, the radii of the curvature 250 and 260 may be substantially consistent with a typical form of an ASIS area of a patient; however, given their malleable nature being made of a material that allows for bending with a first amount of directed force and retains its shape against lesser forces (e.g., aluminum, etc.), each of the ASIS frame members 200 and 230 may be bent and contoured to the ASIS area of the patient. The collective length of the ASIS frame members 200 and 230 is restricted so that the ASIS frame members 200 and 230 reside on the iliac and avoid extending further into the pelvic and trunk area.

Figure 3A:
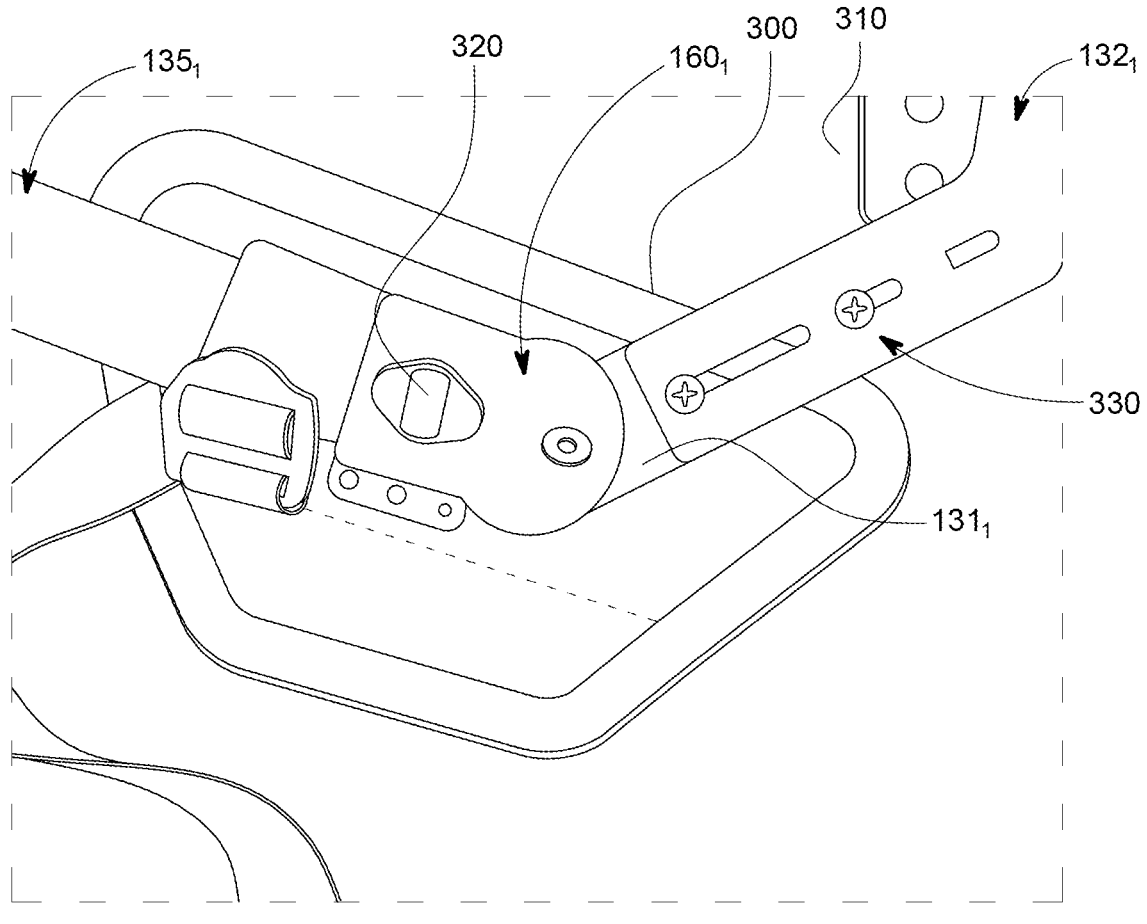
FIG. 3A is a first exemplary embodiment of a perspective view of a locking hinge member that allow for forward flexion while applying rearward forces.

Referring to FIG. 3A, an exemplary embodiment of a perspective view of a hinge $160_1$ or $160_2$ of FIG. 1A is shown, where the hinge (e.g., hinge $160_1$) operates as a locking hinge. When placed into a locked state, the hinge $160_1$ support immobility of the patient's spine by preventing flexion and extension. However, when placed into an unlocked state, the hinge $160_1$ allows flexion 300 (see arrow) during a first movement stage by the patient while concurrently applying rearward forces to the anterior chest assembly 150 in response to extension 310 (see arrow) during a second movement phase by the patient. The hinge $160_1$ is positioned between the inferior strut $134_1$ and the superior strut $131_1$ of the first lateral frame member $130_1$ as shown in FIGS. 1A-1C.

According to one embodiment of the disclosure, the hinge $160_1$ includes a latch 320 that, when actuated, places the hinge $160_1$ into the unlocked state. Hence, this allows anterior rotation of a superior segment 330 (e.g., superior strut $131_1$ and superior frame member $132_1$) of the lateral frame members $130_1$ in response to forward (anterior) flexion by the patient. Stated differently, the latch 320, when placed into an unlocked state, allows the patient to have marginal flexion to bend forward to perform certain events such as eating for example. The hinge $160_1$ is positioned generally at a midpoint between the superior/inferior struts $131_1/134_1$.

Figure 3B:
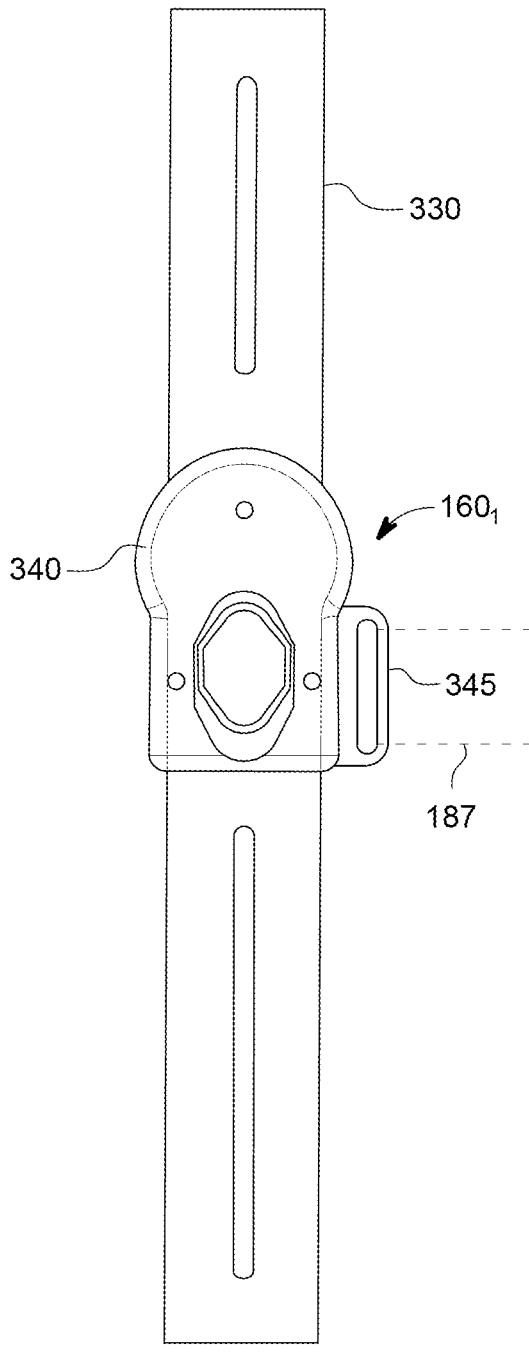
FIG. 3B is an exemplary embodiment of a perspective side view of the locking hinge member of FIG. 3A.

Referring now to FIG. 3B, an exemplary embodiment of a perspective side view of the hinge $160_1$ of FIG. 3A is shown. The hinge $160_1$ includes a casing 340, which operates as a housing that encloses components that control an amount of flexion and extension, if any, permitted by the superior segment 330 of the first lateral frame member $130_1$. The latch 320 controls actuation of the locking operation of the hinge $160_1$ to allow flexion/extension movement. The hinge $160_1$ further includes a connection member 345 (e.g., elongated strap slot), similar in function as the connection member for the hinge $160_1$ of FIG. 3A. The connection member 345 allows the strap 187 associated with the panel reinforcement member 185 to be threaded through the connection member 345 (slot) and tension is to be applied to the strap 187 subsequently. The unlocking of hinges $160_1$ and $160_2$ allows for spring-loaded flexion of up to prescribed angle (e.g., 15-65 degrees such as 45 degrees (45°)) with extension to return to its normal (e.g., 0° degrees) locked position as shown in FIG. 3C.

Figure 3C:
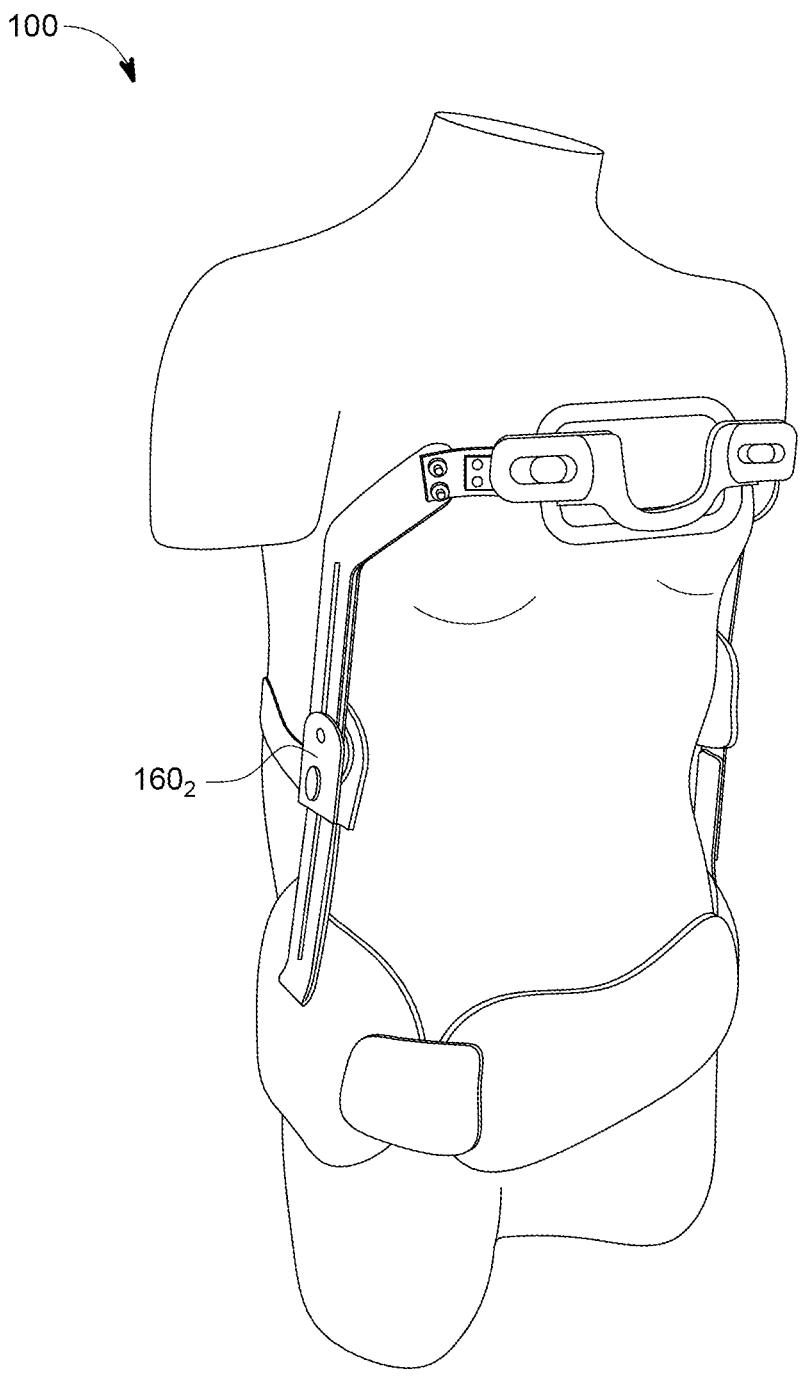
FIG. 3C is an exemplary embodiment of the locking hinge member of FIG. 3A in operation exhibiting forward flexion.
Figure 3D:
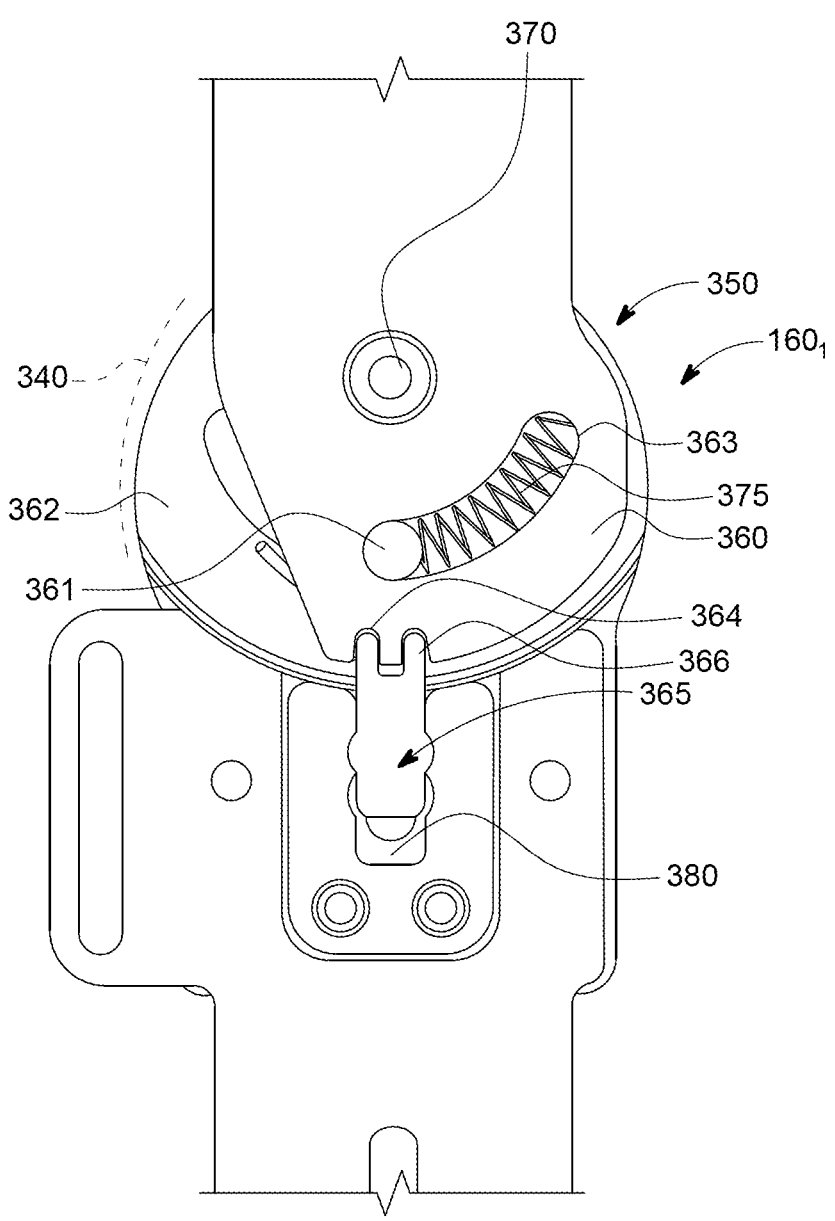
FIG. 3D is a perspective view of an exemplary embodiment of components forming the locking hinge member of FIG. 3C in a locked position.

Referring now to FIG. 3D, a perspective view of an exemplary embodiment of components 350, representing the inner-workings of the hinge $160_1$ that are encapsulated within the casing 340 of the hinge $160_1$, is shown. Herein, the components 350 include a rotatable disc member 360 and a locking actuator 365 that is engages with the disc member 360 based on the setting of the latch 320 of FIG. 3B. The disc member 360 includes (i) a stop 361 extending from a base surface 362, (ii) a rotation slot 363, and (iii) locking inserts 364 situated along an edge of the disc member 360. The locking inserts 364 are sized to engage with locking extensions 366 associated with the locking actuator 365.

The locking actuator 365 is configured with extensions 366 to engage with the locking inserts 364 of the disc member 360 when the hinge $160_1$ is placed into a locked state. The latch 320 is responsible for placement of the hinge $160_1$ into the locked or unlocked state. More specifically, movement of the latch 320 would cause the extensions 366 of the locking actuator 365 to engage with the locking inserts 364 when the rotatable disc member 360 is positioned so that the orthopedic spine brace is at a normal (00 degrees) position. Although not shown, in lieu of a locked and unlocked state, the latch 320 may be configured to allow for different looked states such as a prescribed angle of forward flexion (e.g., 10°, 15°, 20°, etc.).

As further shown in FIG. 3D, according to one embodiment of the disclosure, the rotatable disc member 360 includes the rotation slot 363, which is positioned and sized (in length) provide the degree of rotation allowed for flexion of the lateral frame members $130_1$ of FIG. 3C. As shown, the rotation slot 363 provides for approximately 45° flexion, where extending a length of the slot 363 curved around a pivot point 370 effactually increases the degree of flexion provided by the hinge $160_1$. A spring 375 is deployed within the slot 363 to retain resistance of the anterior chest assembly 150 during flexion and extension, where the anterior chest assembly 150 is coupled to the lateral frame member $130_1$ featuring the hinge $160_1$.

Additionally, as an optional feature, the locking actuator 365 may feature a spring 380 positioned below the locking actuator 365. The spring 380 is biased to automatically alter a state of the locking actuator 365 from an "unlocked" state to a "locked" state when the hinge $160_1$, during extension, returns to its normal position (e.g., 0° spinal positioning). Hence, the latch 320 necessitates manual alteration of the latch 320 to change from a "locked" to an "unlocked" state but returns to the "locked" state is arranged to perform this operation automatically.

Figure 3E:
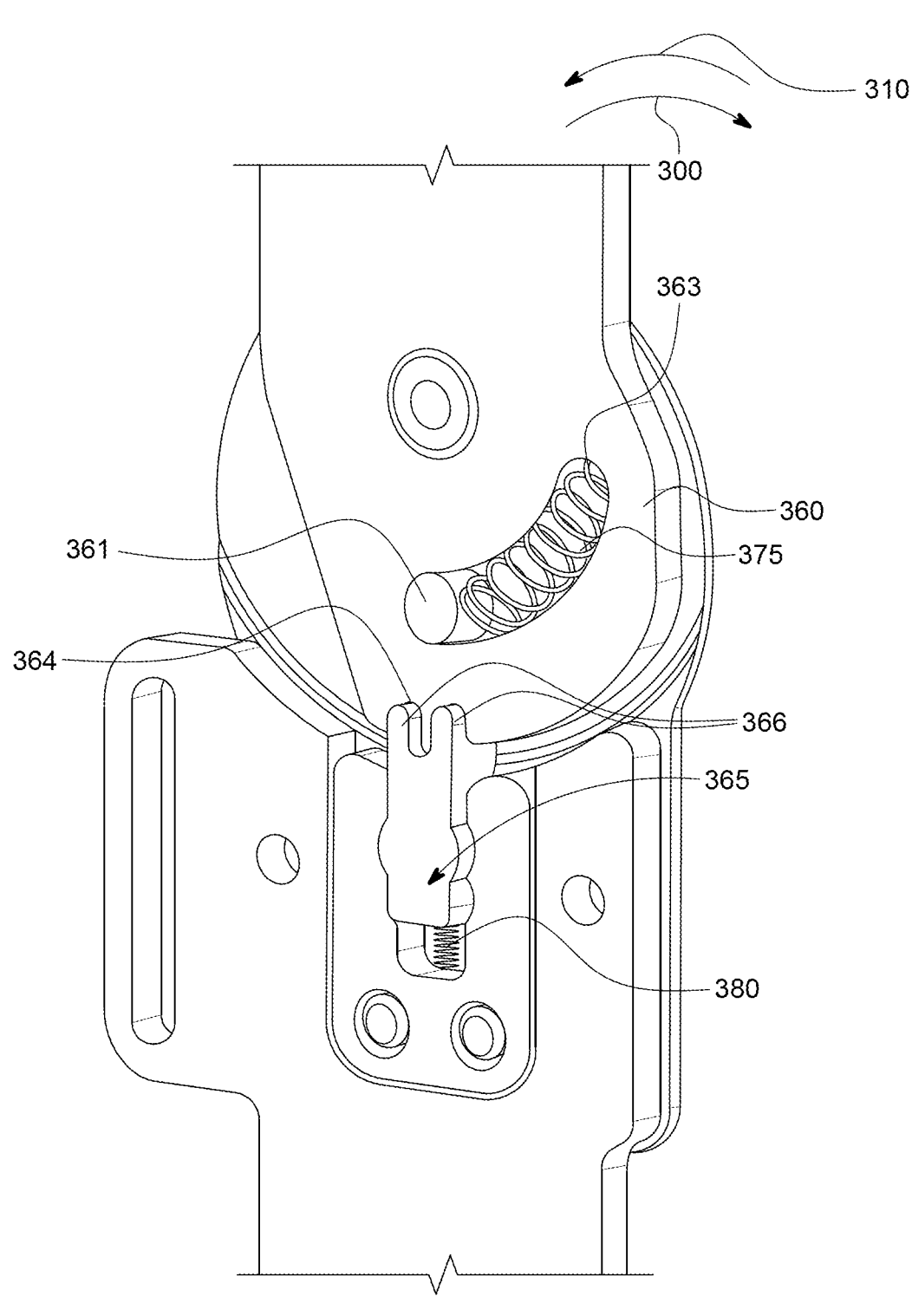
FIG. 3E is a perspective view of an exemplary embodiment of components forming the locking hinge member of FIG. 3C proceeding from a locked position into an unlocked position.
Figure 3F:
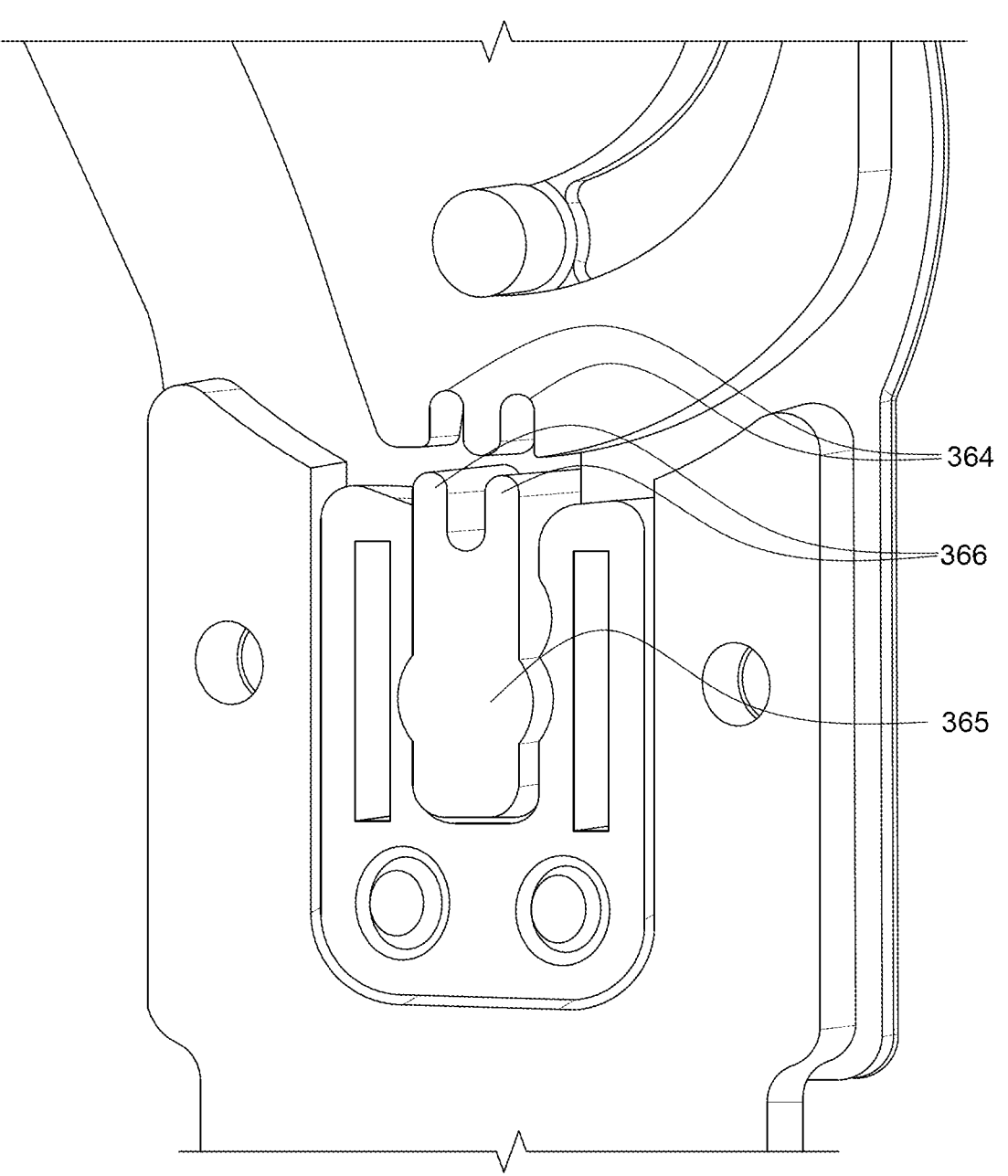
FIG. 3F is a perspective view of an exemplary embodiment of components forming the locking hinge member of FIG. 3C in a locked position.

Referring now to FIG. 3E, a perspective view of an exemplary embodiment of components 350 forming the hinge $160_1$ of FIG. 3C progressing from a "locked" state to an "unlocked" state is shown. Herein, the extensions 366 of the locking actuator 365 becomes disengaged from the locking inserts 364 to allow for rotation of the rotatable disc member 360 as shown in FIG. 3F. Rotation of the disc member 360 during flexion 300 by the patient causes compression of the spring 375 by the stop 361. In response to extension 310 by the patient, the spring 375 decompresses and resulting forces are applied so that the anterior chest assembly (including chest plate) remains in contact with the patient. Upon the extensions 366 of the locking actuator 365 aligning with the locking inserts 364, the second spring 380, if deployed, would cause the extensions 366 of the locking actuator 365 to engage in the locking inserts 364. If solely manual actuation, the latch 320 would need to be manually adjusted (e.g., shifted upward) to place the locking hinge 160₁ into a locked state.

Figure 3G:
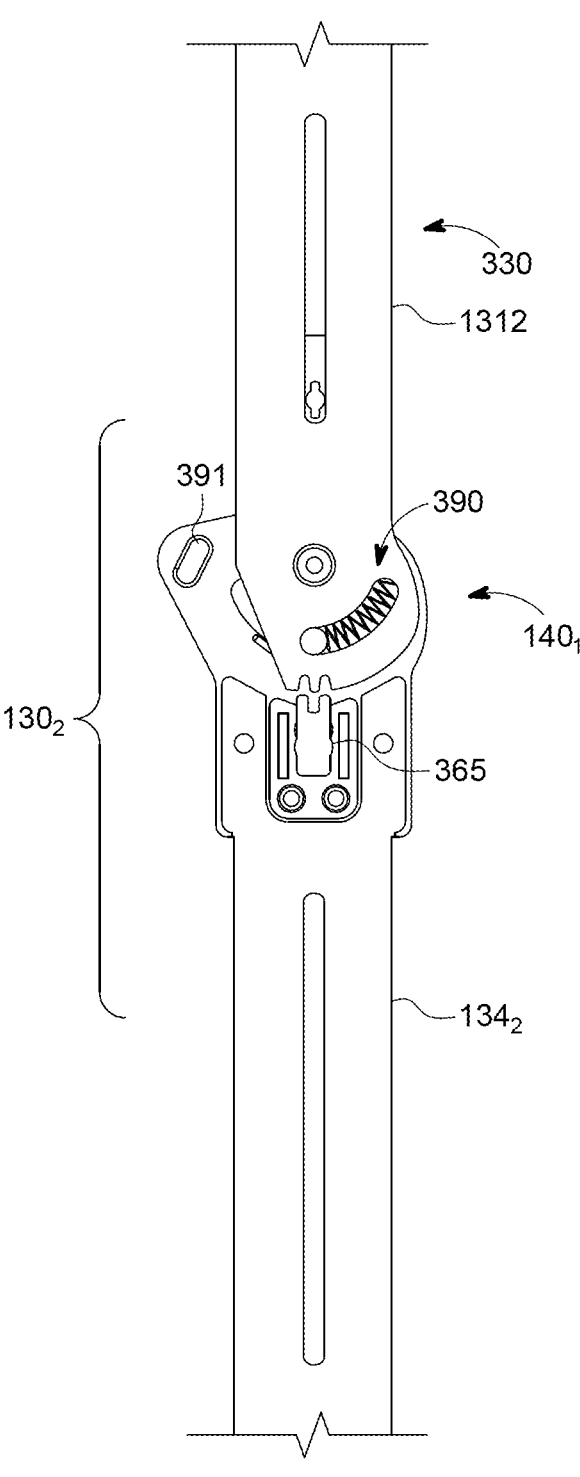
FIG. 3G is a perspective view of a second exemplary embodiment of the locking hinge with the components forming the locking hinge member of FIG. 3C along with components inclusive of a tensioning assembly.

Referring now to FIG. 3G, a second exemplary embodiment of a perspective view of a hinge 160₁ or 160₂ of FIG. 1A is shown, where the hinge (e.g., hinge 160₂) operates as a locking hinge. When placed into a locked state, the hinge 160₂ support immobility of the patient's spine by preventing flexion and extension. However, when placed into an unlocked state as shown, the hinge 160₂ allows flexion during a first movement stage by the patient while concurrently applying rearward forces to the anterior chest assembly 150 in response to extension during a second movement phase by the patient.

Figure 3H:
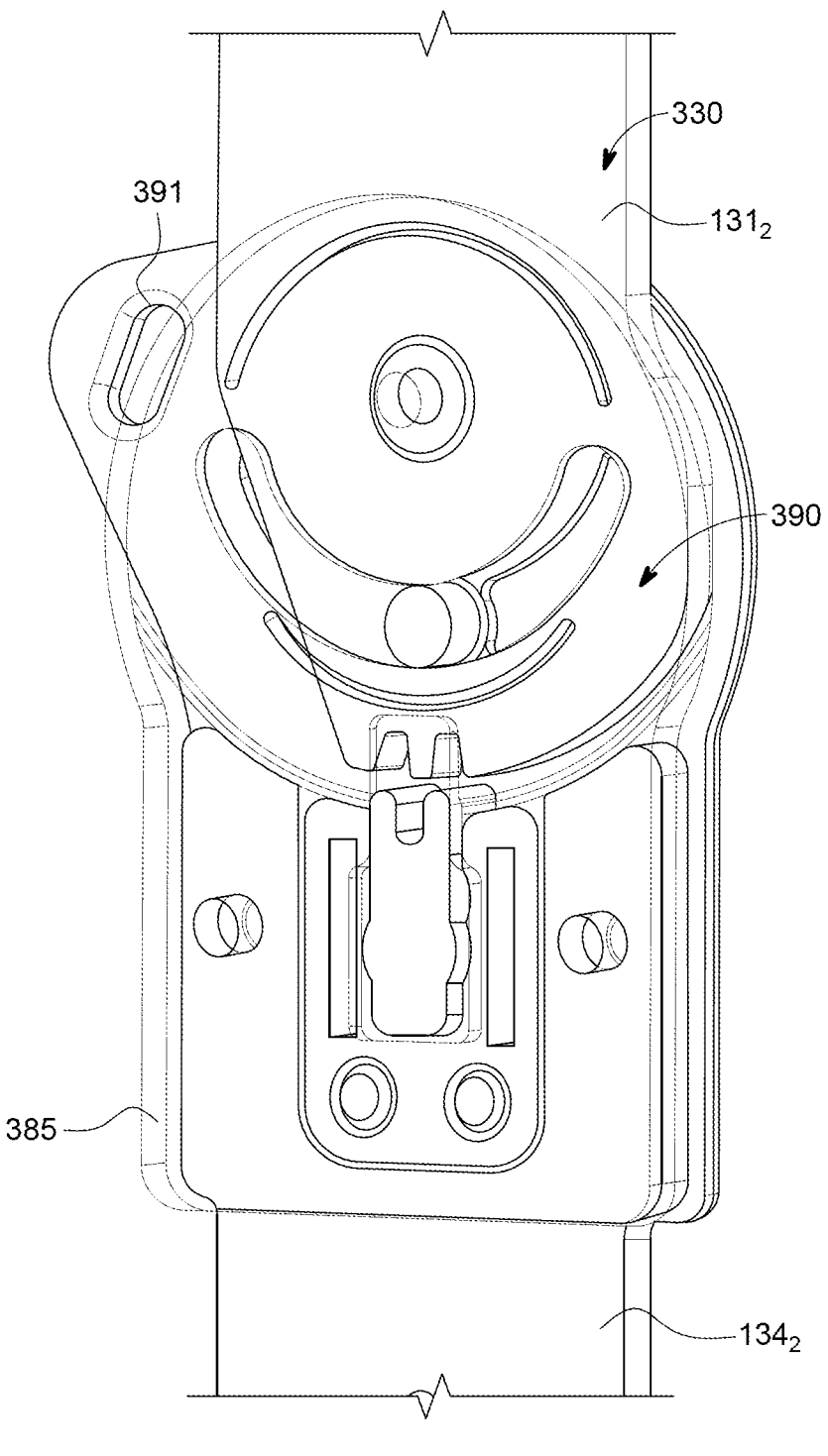
FIG. 3H is a more detailed perspective of the alignment slot of the tensioning assembly deployed as part of the locking hinge of FIG. 3G.

For this embodiment of the disclosure, as shown in FIGS. 3G-3H, the hinge 160₂ includes a casing 385, which operates as a housing that encloses components 390 that control an amount of flexion and extension, if any, permitted by the superior segment 330 (e.g., superior strut 131₂ and/or superior frame member 132₂) of the first lateral frame member 130₂. Similar to FIGS. 3A-3F, a latch controls actuation of the locking actuator 365 to allow flexion/extension movement. Additionally, the hinge 160₂ includes a tensioning assembly that controls the level of proximity (tightness) between the anterior bracing system and the posterior bracing system. For example, the tensioning assembly may include, but is not limited or restricted to an alignment slot 391, connection (anchoring) member 346, and ratchet member 393 as described below.

Figure 3I:
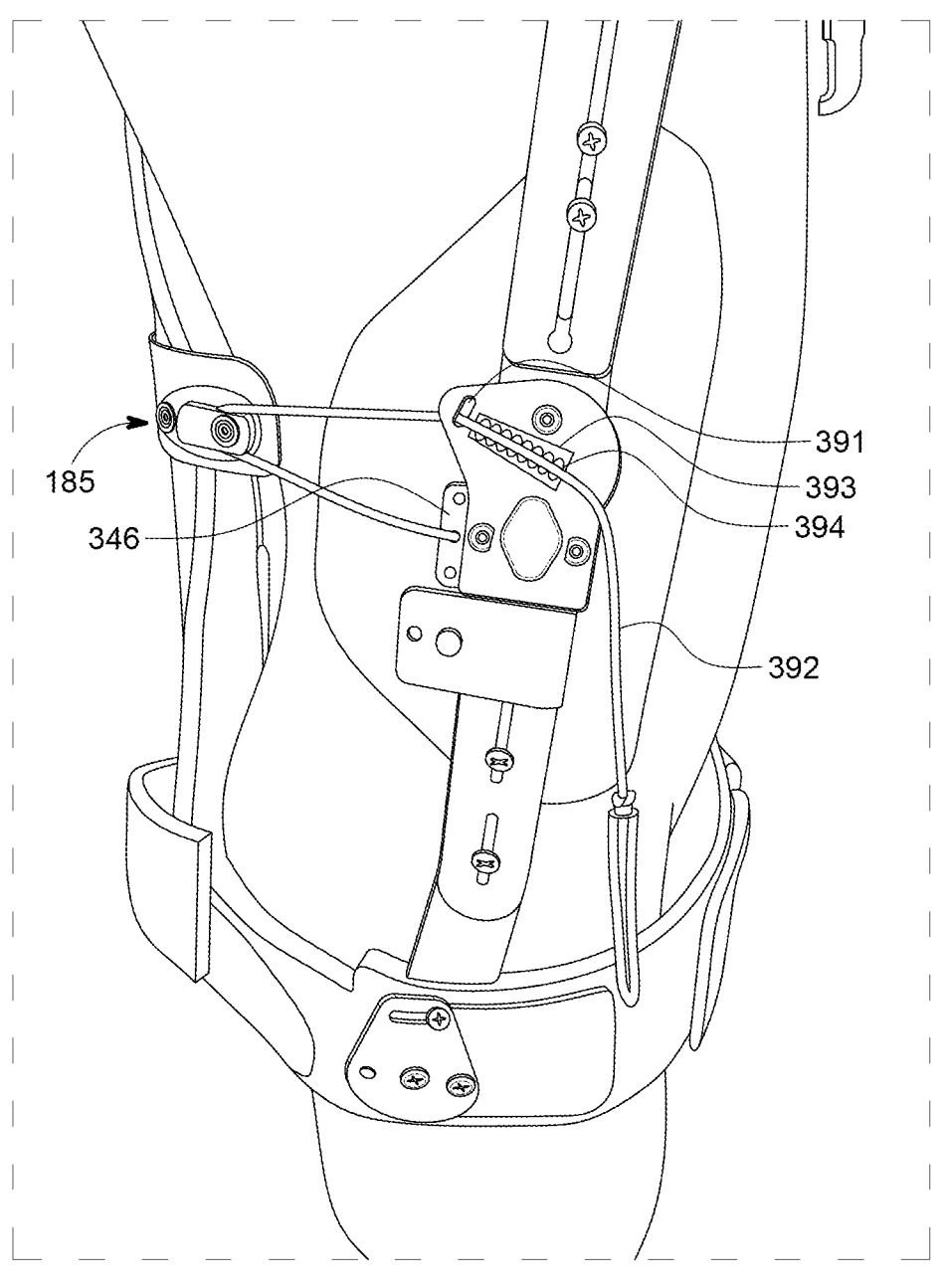
FIG. 3I is a more detailed perspective of a first embodiment of the tensioning assembly of FIGS. 3G-3H.

The hinge 160₂ further includes an alignment slot 391, which may be positioned within or outside the casing 385 (as shown), where the slot 391 operates as a guide for an interconnect 392 (e.g., cord, cable, rope, etc.) communicatively coupled to the panel reinforcement member 185 as shown in FIG. 3I. The interconnect 392 is anchored by the connection member 346 as shown in FIG. 3A.

As tension is applied to the interconnect 392 via the tensioning assembly and the interconnect 392 is moved in a forward (anterior) direction, the anterior and posterior bracing assemblies (orthopedic spine brace 100) are moved closer to reach other (and more tightly on the patient) and held in different tightening positions until released. The hinge 1602 may include a ratchet member 393, which features angled teeth that allow for pulling of the interconnect 392 in a forward (anterior) direction for tightening with relatively little resistance, but precludes the release of tension on the interconnect 392 in a backward (posterior) direct (i.e., retain its tightened position) until a release event occurs. The release event may include at least partially disengaging the interconnect 392 from the ratchet member 393 (e.g., interconnect 392 moved laterally to partially disengage from the rachet member 393). The ratchet member 393 is angled downwardly for easier (gravity assist) movement of the interconnect 392.

Figure 3J:
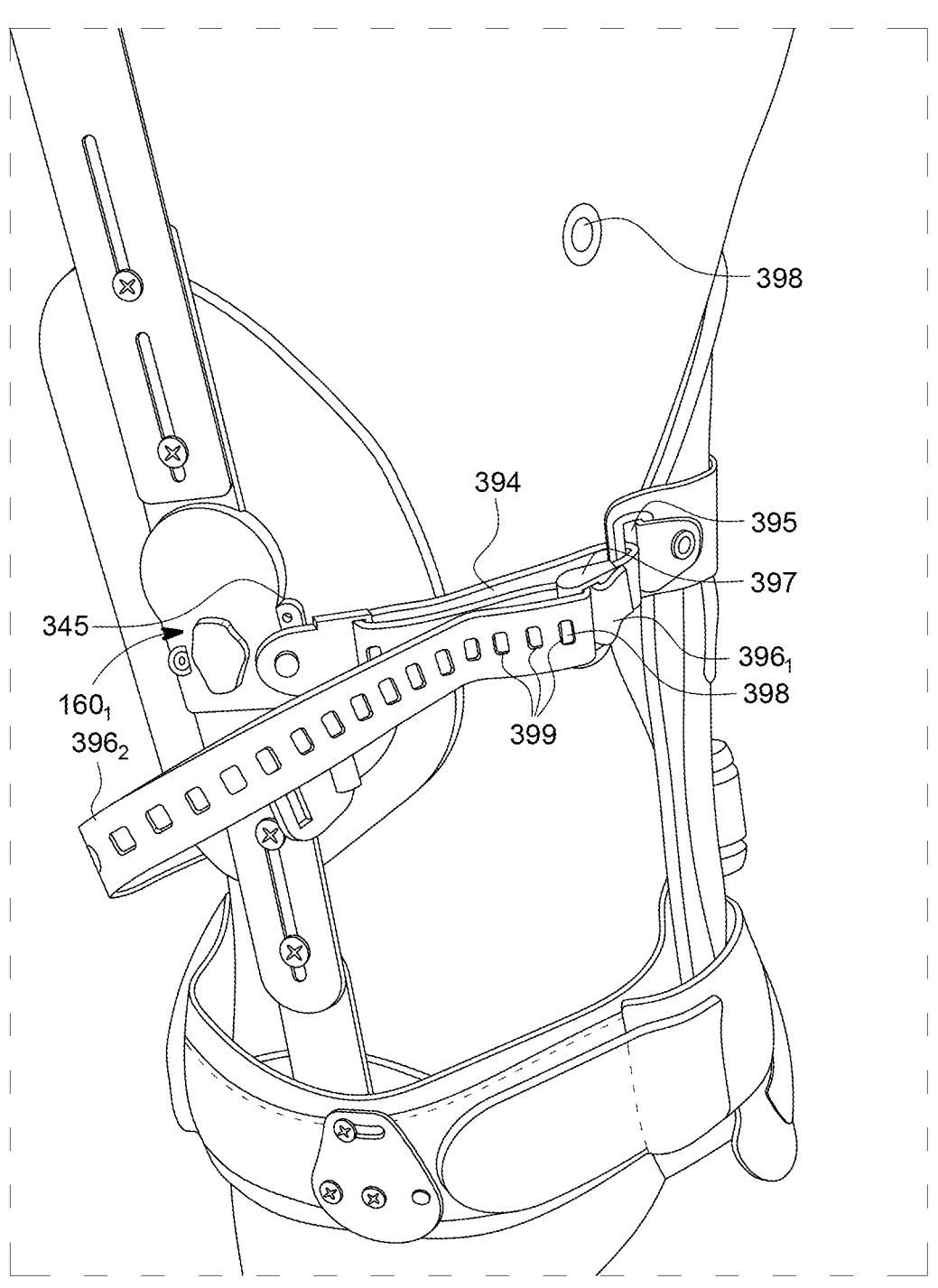
FIG. 3J is a more detailed perspective of a second embodiment of the tensioning assembly deployed with a locking hinge similar in architecture to the locking hinge of FIG. 3A or FIG. 3B.

Referring now to FIG. 3J, a third exemplary embodiment of a perspective view of a hinge 160₁ or 160₂ of FIG. 1A is shown, where the hinge (e.g., hinge 160₁) features an architecture similar to FIG. 3A as a locking hinge. In particular, for a tensioning assembly, the hinge 160₁ includes the connection member 345 (elongated strap slot), which operates as a fixed point for an interconnect 394 coupled to a second strap slot 395. The second strap slot 395 is coupled to an end of the strap 187 associated with the panel reinforcement member 185. A first end 396₁ of the interconnect 394 is coupled to a first looped fastener 397 (e.g., buckle) and a second end 396₂ of the interconnect 394 is passed through a second loop of the fastener 397 with a prong 398 inserted into a selected notch 399 on the interconnect 394. The prong 398 is shaped to retain insertion into the selected notch 399 until released.

Figure 4A:
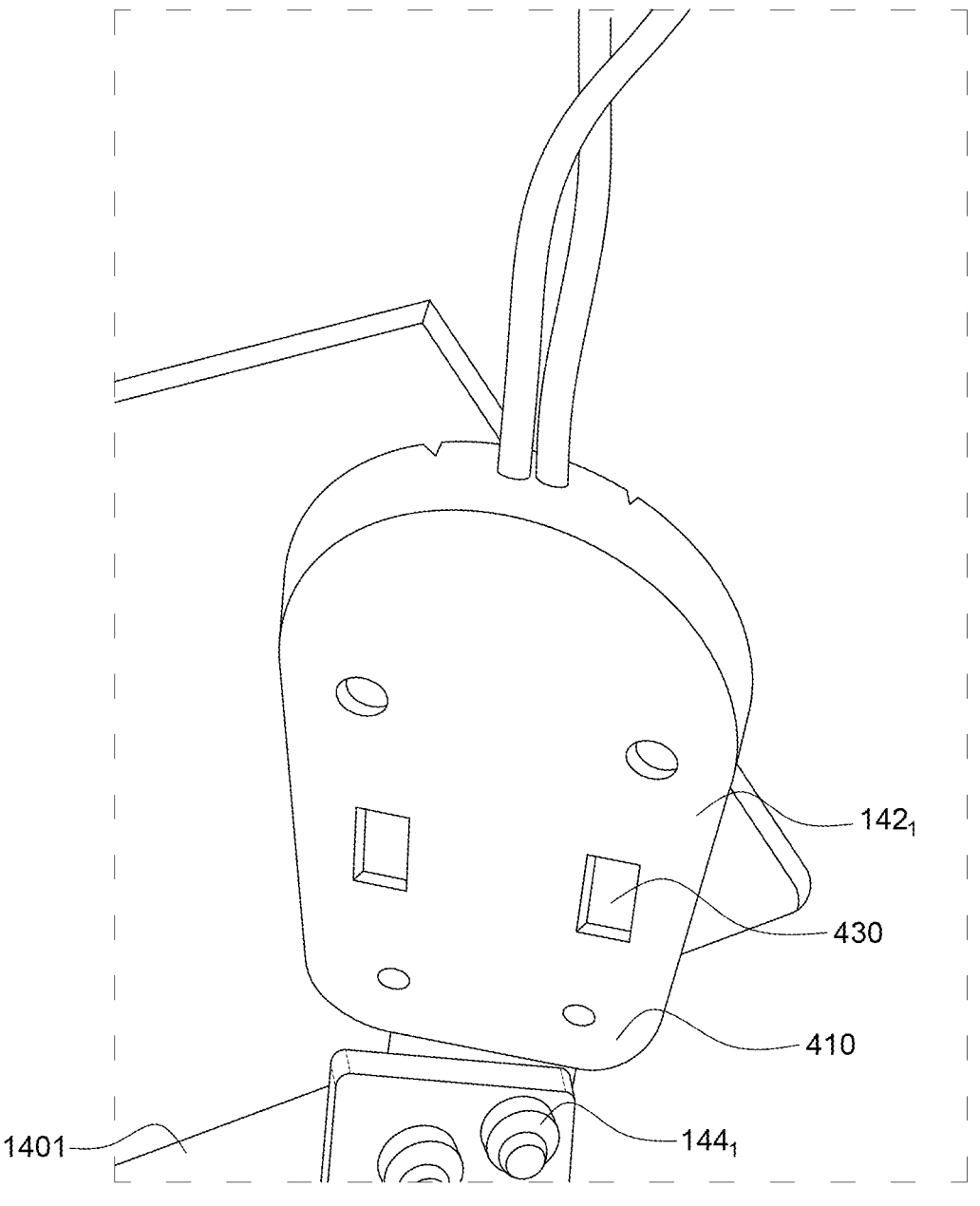
FIG. 4A is a perspective view of a swing arm positioned at a proximal curved termination area of a lateral frame member.
Figure 4B:
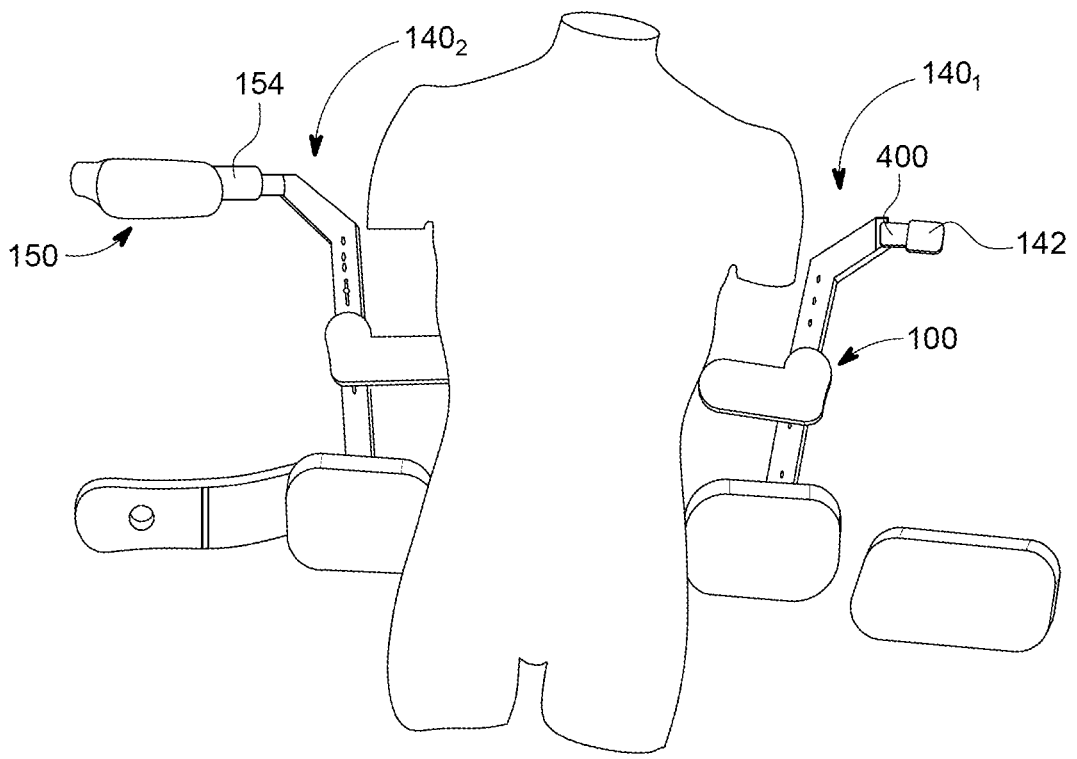
FIG. 4B is a perspective view of the orthopedic spine brace in an open position with the swing arm rotated in a direction facing laterally outward from a mid-sagittal plane.

Referring now to FIG. 4A, a perspective view of one of the swing arms 140₁ or 140₂, such as a first swing arm 140₁ coupled to the proximal (curve) termination area of the first lateral frame member 130₁, is shown. Herein, the swing arm 140₁ includes the rotatable hinge 144₁ that is coupled to a first end portion 400 of the proximal termination area (see FIG. 4B) and a first end portion 410 of the fastener 142₁. The rotating hinge 144₁ is configured with a swing range over an obtuse angle (e.g., ≥1350 such as 160-210° for example), where the rotating hinge 144₁ is placed into a plurality of positions, including a first position (e.g., zero degree position where the fastener 142₁ is attached to the anterior chest assembly 150) and placed into a second position (e.g., greater than 1200 where the fastener 142₁ is disengaged from the chest compression member 154 of the anterior chest assembly 150 and swung laterally to allow for removal of the orthopedic spine brace 100). The swing angle for the swing arm 140₁ may vary, but is normally greater than 90 degrees rotation from its connection orientation (e.g., 0-to-120°, 0-to-135°, 0-to-150°, 0-to-165°, or the like). Herein, the (quick-release) fastener 142₁ includes fastening slots 430 that are arranged to engage with protrusions within an anterior surface of the chest compression member 154 as shown in FIG. 6B below. The swing arms 140₁ and 140₂ are shown in the open (and unlocked) position in FIG. 4B.

Referring now to FIG. 5A, a perspective posterior view of the orthopedic spine brace 100 of FIGS. 1A-1C is shown. Herein, the posterior bracing system 120 features the posterior panel 180 and the panel reinforcement member 185, which is attached to both the lateral frame members 130₁ and 130₂ and the posterior panel 180. The belt 165 may be a continuous soft good threaded through slots 500 within the posterior panel 180 so that the belt 165 extends anteriorly from a backside 510 of the posterior panel 180 for attachment by the patient near the pelvic area. Alternatively, the belt 165 may feature a pair of belt members, each belt member including a first end threaded through one of the slots 500 and re-attached to a portion of the belt member to form a terminating end. A second end of the belt member extends anteriorly from the backside 510 of the posterior panel 180 for attachment to the other belt member.

Herein, according to one embodiment of the disclosure, the panel reinforcement member 185 may be attached to the posterior panel in which the strap 187 is threaded through secondary slots 520 of the panel 180 as shown in FIGS. 5B-5C. The secondary slots 520 are sized in correlation with the width of the straps 187 to provide flexibility in adjustment of the posterior panel 180 in an upward or downward manner for positioning of the posterior panel 180 relative to the lateral frame members 130₁-130₂. This allows for a more comfortable fit to the patient based on his or her anatomy.

Referring now to FIG. 5D, an exemplary embodiment of the posterior panel 180 with padding 530 positioned on the posterior panel 180 along with the panel reinforcement member 185 oriented along a traverse plane 540 and coupled to the lateral frame members $130_1$-$130_2$ of the orthopedic spine brace 100 is shown. The padding 530 includes a first pad 532 and a second pad 534, both of which are offset from the mid-sagittal plane 550 to expose a cut-out slot 560 within the posterior panel 180 and provide contact of the posterior panel 180 to the patient's back muscles so as to avoid direct contact with the spine. The cut-out slot 560 is configured to gain access to protective dressings over spinal incisions. Additionally, in lieu of the secondary slots 520 as shown in FIGS. 5B-5C, the panel reinforcement member 185 may rely on fasteners 570 for attachment to the backside 510 of the posterior panel 180.

Referring to FIG. 6A, an exemplary embodiment of the anterior chest assembly 150 of FIG. 1A is shown, where the anterior chest assembly 150 includes the removal chest plate f attached to the chest compression member 154. Herein, the chest plate 152 is removably coupled to the chest compression member 154 to allow different sizes and types of chest plates to be utilized as part of the orthopedic spine brace 100. As shown, lateral ends 600 and 610 of the chest compression member 154 are coupled to the swing arms $140_1$ and $140_2$ of the orthopedic spine brace 100. Such coupling may be accomplished by fasteners $142_1$-$142_2$ removably attached to an anterior (top) surface 620 of the chest compression member 154.

Referring now to FIG. 6B, a more detailed illustration of the anterior chest assembly 150 detached from the orthopedic spine brace of FIG. 1A is shown. Herein, one or more protrusions 630 extending from the anterior surface 620 of the chest compression member 154 are configured to engage with fastening slots 430 (see FIG. 4A) formed as part of each (quick-release) fastener (e.g., fastener $142_1$ or $142_2$). As shown in FIGS. 6C-6D, the removable chest plate 152 includes a padded posterior side 640 and a rigid anterior side 645, which includes one or more connectors 650 such as ball connectors as shown. The ball connector(s) 650 are sized for coupling with connector(s) 660 positioned on a posterior surface 625 of the chest compression member 154.

Referring now to FIG. 7A, a perspective front view of a second embodiment of the orthopedic spine brace 700 inclusive of a neck orthosis 710 is shown. Coupled to the chest compression member 154 of FIGS. 6A-6D, the neck orthosis 710 includes a torso rest 720, a front cover 730, a right cover 740, a left cover 750, and a height control knob 760 and a chin support 770. Rotation of the height control knob 760 adjusts the anterior/posterior (forward/backward) and the superior/inferior (upward/downward) movement of the chin support 770. As shown, the neck orthosis 710 is shaped with a central, radial portion 780, which resides below the high control knob 760. This allows the height control knob 760 to be rotated despite the neck orthosis 710 being coupled to the chest compression member 154.

As shown in a perspective lateral view of the neck orthosis 710 of FIG. 7A, the front cover 730 includes one or more fasteners (e.g., ball connectors similar to the ball connector(s) 650) for coupling to the connector(s) 660 of the chest compression member 154. Hence, the torso rest 720 and the front cover 730 apply a posterior directed force on the patient to retain hyperextension of the patient's spine. The orthopedic spine brace 700, operating as a cervical thoracic lumbar sacral orthosis (CTLSO) when worn, is illustrated in FIGS. 7C-7E.

Referring now to FIG. 8, a method of donning the orthopedic spine brace 100 or 700 of FIGS. 1A-7E is shown. Herein, the swing arms are positioned in a first position away from a central region of the orthopedic spine brace (operation 800). The orthopedic spine brace is positioned so that the lateral frame members are positioned in-line with the frontal plane, namely positioned along the sides of the patient (operation 810). A belt associated with the orthopedic spine brace is attached around the waist area of the patient, with the ASIS frame members contoured around the ASIS region of the patient (operation 820). Thereafter, the swing arms coupled to the superior frames of the lateral frame members are positioned in a second position toward the center region of the orthopedic spine region (operation 830).

The swing arms are coupled to an anterior chest assembly or a neck orthosis, which applies a posterior directed forward against a chest of the patient (operation 840). The belt(s) of the orthopedic spine frame is adjusted for desired tension (operation 850). As a result, removal of the orthopedic spine brace may be accomplished by decoupling at least one swing arm from the anterior chest assembly or a neck orthosis and moving of that swing arm(s) back into the first position (operation 860).

III. General Architecture—Orthopedic Spine Brace ($2^{nd}$ Embodiment)

Referring to FIGS. 9A-13E, a second embodiment of orthopedic spine brace 900 is shown. Similar to the first embodiment of the orthopedic spine brace 100 of FIGS. 1A-ID, the orthopedic spine brace 900 features the anterior chest assembly 150 maintained by a pair of lateral frame members 910 and 920. However, in contrast to the first embodiment of the orthopedic spine brace 100, the first lateral frame member 910 features the hinge 1601 positioned between a superior strut 914 and an inferior strut 916, where a first (curved) superior frame member 912 is configured to slidably engage with the superior strut 914. The first superior frame member 912 partially retains the anterior chest assembly 150. Similarly, the second lateral frame member 920 features a curved, superior frame member 922, which is configured to slidably engage with a corresponding superior strut 924. Embodiments of a superior frame member (e.g., first superior frame member 912 or 922) are illustrated in detail in FIGS. 11A-11B & 12A-12B. It is contemplated that certain features of the first embodiment of the orthopedic spine brace may be implemented within this embodiment of the orthopedic spine brace and are incorporated by reference.

Additionally, the first lateral frame member 910 is coupled to a different (second) embodiment of a first anterior superior iliac spine (ASIS) frame member 1000 (see FIGS. 10A-10D). More specifically, as shown in FIGS. 9A-10C, the inferior strut 916 of the first lateral frame member 910 is configured to slidably engage with a first inferior frame member 1010. Additionally, the first ASIS frame member 1000 is positioned within a channel 1012 formed on an exterior surface 1014 of the first inferior frame member 1010 for slidable engagement with the first ASIS frame member 1000. The first ASIS frame member 1000 and the first inferior frame member 1010 are secured together by a fastener (not shown), which is inserted through a slot 1005 within the first ASIS frame member 1000 and an aperture 1015 within the first inferior frame member 1010. Similar in structure, an inferior strut 926 of the second lateral frame member 920 is configured to slidably engage with a second inferior frame member 1020. A second ASIS frame member would be similarly engaged with the second inferior frame member 1020 (e.g., slidably engaged within a channel formed on an interior surface of the second inferior frame member 1020 and is secured by a fastener inserted through a slot within the second ASIS frame member and an aperture within the second inferior frame member 1020).

In summary, the superior frame members 912, 922 are designed to accommodate anatomical contours as well as provide improved comfort at a chest wall for the patient. In addition, beyond contouring, the lateral frame members 910 and 920 include new features including, but not limited or restricted to the following:

1) The superior frame members 912/922 transition from a flat, rectangular shape at a proximal end portion to a cylindrical shape at a distal end portion. This promotes slidable width adjustment and allows for placement of a fastener attachment plate and rotation of the fastener attachment plate to the appropriate contour of the patient's sternum.
2) Each of the proximal end portions of the superior frame members 912/922 includes a channel for slidable insertion of the first ends of the superior struts 914/924 therein. The superior struts 914/924 are attached to the superior frame members 912/922 after insertion within these channels. This attachment scheme allows for slide adjustment to proper height while maintaining strength in frame/strut coupling.
3) Ends of the inferior frame members 1010/1020, positioned on an opposite side of the (flexion) hinge 1601-1602 from the superior frame members 912/922, features a channel. These channels allow for vertical height adjustment of the ASIS frame member/lower frame coupling.
4) Each ASIS frame member (e.g., ASIS frame member 1000) is slidably coupling to the channel 1012 formed in the inferior frame member 1010. This slidable ASIS frame member 1000 coupling to the inferior frame member 1010 facilitates appropriate adjustment of anterior/posterior dimension, placing the lateral strut/hinge at midline between anterior and posterior regions.
5) Tension straps may be attached, which provide tension between upright (strut) and belt for increased anterior/posterior and mediolateral stability of the struts and the overall system. The tension straps promote stability across the sagittal, coronal, and traverse planes (or axes) as shown in FIGS. 31A-31B especially.

Referring to FIG. 9A, a front-facing perspective view of a second exemplary embodiment of the orthopedic spine brace 900 is shown. The orthopedic spine brace 900 includes an anterior bracing system 930 and a posterior bracing system 940. The anterior bracing system 930 includes a pair of lateral frame members 910 and 920, both of which extend superiorly (upwardly) from an anterior superior iliac spine (ASIS) area to a chest area. In particular, according to this second embodiment of the disclosure, the first lateral frame member 910 includes a superior strut 914 coupled to a proximal end portion 932 of the (curved) superior frame member 912. For example, as shown, the proximal end portion 932 of the first superior frame member 912 includes a channel 934 (e.g., one or more apertures) sized to receive a fastener for coupling the first superior frame member 912 to the superior strut 914 while a distal end portion 933 of the first superior frame member 912 is partially positioned over a chest area of the patient. Similarly, the second lateral frame member 920 includes a superior strut 924 slidably attached to a proximal end portion 936 of the superior frame member 922 and a distal end portion 937 to be positioned over the chest area.

As further shown in FIGS. 9A and 13A-13D, an adjustable (lateral and rotationally) chest fastening plate 950 is attached to the distal end portion 933 of the first superior frame member 912 by a tightening mechanism 952, which can be tightened or loosened by an adjustment member 953 (e.g., set screw, bolt, peg, etc.). Once loosened, the chest fastening plate 950 can be laterally adjusted (e.g., slid along the distal end portion 933) and repositioned along the distal end portion 933 of the first superior frame member 912, which allows the chest compression member 154 of the anterior chest assembly 150 to be laterally adjusted as well. Furthermore, once loosened, the chest fastening plate 950 can be rotated around the distal end portion 933 to adjust the angular orientation of the chest compression member 154 to allow for the patient's anatomy. A change in angular positioning change in the chest fastening plate 950 (and therefore the chest compression member 154) in a clockwise direction is shown in FIG. 13B. Both chest fastening plates 950 and 957 may be independently adjusted.

As shown in detail in FIGS. 13A-13D, the chest fastening plate 950 is adapted with locking protrusions 951 for attachment to fastening slots 430 (not shown, see FIG. 4A) within a fastener 954. The fastening slots may be spring-biased so that the fastener 954 is secured to the chest fastening plate 950 when the locking protrusions 951 are aligned with and inserted into the fastening slots. The fastener 954 may be released by counteracting the spring-bias upon activating a release member 956 (e.g., pulling the release member 956 laterally). Upon release, a swing hinge 955 allows the anterior chest assembly 150 to open to allow the patient to exit from the orthopedic spine brace 900.

As shown in FIG. 13A, a similar structure may be found in connection with the second superior frame member 922 featuring the same components (e.g., a rotatable chest fastening plate 957 with a tightening mechanism 958 and fastener 959. The fastener 954 may operate as quick-release fastener for attachment to the anterior chest assembly 150, where swing hinge 955 operates as allow the anterior chest assembly 150 to move laterally to create an opening between the lateral frame members 910 and 920.

As further shown in FIGS. 13A-13B & 13E, a distal end portion 933 of the first superior frame members 912 is cylindrical in form (e.g., rod-like) that is curved initially outwardly and then inwardly with a first radius of curvature while the distal end portion 937 of the second superior frame member 922 has the same form and is curved with a second radius of curvature. The first and second radii of curvature are selected to provide a comfortable fitting at the chest areas and axilla area without impeding arm swing by the patient. The orientation of the distal end portions 933/937 is generally co-planar with the patient's chest (and the removable chest plate 152 of the anterior chest assembly 150). The width (diameter) of each superior frame member 912/922, from the proximal end portion 932/936 to the distal end portion 933/937, gradually reduces as the superior frame member 912/922 transitions in structure from a generally planar structure (the proximal end portion 932/936) to a cylindrical structure (distal end portion 933/937).

Referring now to FIGS. 9B and 9D, side-facing perspective views of the orthopedic spine brace 900 of FIG. 9A is shown. Herein, based on the positioning of the rotatable chest fastening plates 950/957, the anterior chest assembly 150 is positioned to maintain the patient in an upright position and provides flexion through hinges 960/962, which separate superior struts 914/924 from the inferior struts 916/926 of the lateral frame members 910/920. Also, partial encasing the inferior frames 1010/1020 of the lateral frame members 910/920, a belt 970 is arranged to be placed around the waist of the patient and tightened through one or more hook and loop fasteners. Although not shown, the belt 970 may include one or more pads positioned on an inner (posterior) side of the belt 970 and/or one or more pads positioned along the inner (lateral) side of the belt 970.

Referring to FIG. 9C, a perspective posterior view of the orthopedic spine brace 900 of FIG. 9A is shown. Herein, the posterior bracing system 940 of the orthopedic spine brace 900 features a posterior panel 980 and a panel reinforcement member 985. The posterior panel 980 is sized for positioning adjacent to sacral and lumbar regions of a patient's back. The panel reinforcement member 985 is configured for attachment to each of the lateral frame members 910 and 920, and thereafter, a tension may be applied to straps 987 forming a portion of the panel reinforcement member 985. The tension may be applied to tighten the straps 987, and thus, provides a snug fit between the posterior panel 980 to the patient's back. Additionally, a force in a posterior direction is being applied from the anterior chest assembly 150. The adjustment in tension may be accomplished through a pull fastener (not shown), which may operate similar to a backpack buckle where tension caused by pulling of the strap 987 (or another interconnect 988) in an anterior direction causes tightening of the posterior bracing system 940.

Referring now to FIG. 9E, a perspective view of the orthopedic spine brace 900 of FIG. 9A focusing on a positioning of a plurality of tension straps 990 is shown. Herein, the tension straps 990 may include a first tension strap 991, which is positioned on a first lateral side and includes a first end with a fastener (e.g., hook fastener) 993 for extension from a first lateral pad support 998 attachment to the belt 970 or itself. Similarly, a second tension strap 994, which is positioned on a first lateral side and includes a first end with a fastener (e.g., hook fastener) 995 for attachment to the belt 970 or itself. The same tension strap layout is conducted for the second lateral side of the orthopedic spine brace 900. These tension straps 990 promote stability across the sagittal, coronal, and traverse planes (or axes).

Furthermore, as shown in FIGS. 9D & 10A-10C, maintained between the inner and outer sewn fabric forming the belt 970, an anterior superior iliac spine (ASIS) frame member 1000 is coupled to the first inferior frame member 1010. The first inferior frame member 1010 is coupled to an inferior strut 916 of the first lateral frame member 910. The first ASIS frame member 1000 is configured to fit adjacent to an ASIS of the patient. Hence, the ASIS frame member 1000 is made of a rigid material that is pliable to allow the ASIS frame member 1000 to be contoured around the (left) ASIS of the patient. A similar construction is applicable for a second ASIS frame member 1055 coupled to the second inferior frame member 1020 of the second lateral frame member 920. The second ASIS frame member 1055 would also be made of a rigid material that is pliable to allow the second ASIS frame member may be to be contoured around the (right) ASIS of the patient. As a result, the frame components of the orthopedic spine brace 900 is absent from the pelvic area.

More specifically, as shown in FIGS. 9D & 10A, the first ASIS frame member 1000 is adapted for coupling to the first inferior frame member 1010 of the first lateral frame member 910 of the orthopedic spine brace 900. The first ASIS frame member 1000 is slidably engaged within the channel 1012 formed on the exterior surface 1014 of the first inferior frame member 1010 and is secured by a fastener (not shown) inserted through the slot 1005 within the first ASIS frame member 1000 and an aperture 1015 within the first inferior frame member 1010 and secured accordingly. As shown in FIG. 9D, the first inferior strut 916 is configured to slidably engage with a superior end 1030 of the first inferior frame member 1010 and a fastener (not shown) may be inserted through a preformed aperture 1040 for coupled to the first inferior strut 916.

As illustrated in FIG. 10B, a perspective view of the ASIS frame member 1000 of FIG. 10A positioned in a minimal extended width state is shown. In this state, the aperture 1015 aligned with a right-edge area 1050 of the slot 1005 within the first ASIS frame member 1000. Furthermore, as illustrated in FIG. 10C is a perspective view of the ASIS frame member 1000 of FIG. 10A positioned in a maximum extended state is shown. In this state, the aperture 1015 is aligned with a left-edge area 1060 of the slot 1005 within the first ASIS frame member 1000. A side view of the ASIS frame member 1000 illustrating its curvature and gradual angular rotation from a first end portion 1070 to a second end portion 1080 is illustrated in FIG. 10D.

Referring to FIG. 11A, a side view of an interior surface 1100 of the first superior frame member 912 coupled to the superior strut 914 of the orthopedic brace 900 of FIGS. 9A-9D is shown. Extending above the lateral pad support 998, the distal end 1110 of the superior strut 914 is positioned within the channel 934 formed at a proximal end portion 932 of the first superior frame member 912. Confined by rails 1120 and 1122 of the channel 934, the distal end 1110 of the superior strut 914 may be slid upward or downward to adjust the height of the lateral support member 910 (and the height of the orthopedic spine brace 900). The position of the superior strut 914 in relation to the first superior frame member 912 placed at a minimum height is shown in FIG. 11B.

Referring to FIG. 12A, a side view of a superior frame member 912 or 922, such as the first superior frame member 912 of FIG. 11A, is shown. Herein, the proximal end portion 932 includes an aperture 1200 for receipt of a fastener for attachment to the superior strut 914. The front view of the superior frame member 912, as shown in FIG. 12B, illustrates the channel 934 along with both a curvature of the superior frame member 912 and the transition in shape from a generally linear form to a cylindrical form. The transition is chosen to provide a more comfortable fit as the superior frame members 912/922 are structured to avoid impinging on the axilla and breast tissue.

IV. General Architecture—Orthopedic Spine Brace
($3^{rd}$ Embodiment)

Referring now to FIG. 14A, a perspective anterior view of a third embodiment of an orthopedic spine brace including a chest plate attachment coupled thereto is illustrated. The orthopedic spine brace (spine brace) 1400 numerous posterior members including a back panel 1402, lower wing panels 1404, 1406, and a spinal process opening 1408 that runs a majority of the length of the back panel to alleviate pressure on the spinal process of a wearer. A connection piece may span the width of the spinal process opening 1408 to provide stability, support, and rigidity to the back panel 1402. It is contemplated that certain features of the first and second embodiments of the orthopedic spine brace may be implemented within this embodiment of the orthopedic spine brace and are incorporated by reference herein.

The spine brace 1400 also includes lateral frame assemblies 1410, 1412 that include mirroring components. For example, the lateral frame assembly 1410 includes an inferior strut 1412, a medial strut 1414, a superior frame member 1416, a strap adjustment member 1418, an anterior superior iliac spine (ASIS) frame member 1432, and a base frame member 1430. The lateral frame assembly 1420 includes mirroring components: an inferior strut 1422, a medial strut 1424, a superior frame member 1426, a strap adjustment member 1428, an ASIS frame member 1442, and a base frame member 1440. As each of the lateral frame members operate to provide the same functionality and are configured in the same manner, the following discussion of the lateral frame assembly 1410 applies equally to the lateral frame assembly 1420.

Referring to the components comprising the lateral frame assembly 1410, the ASIS frame member 1432 couples with the base frame member 1430 via a connection mechanism such as a screw and nut assembly, where the screw passes through a slit that runs horizontally along a portion of the length of the ASIS frame member 1432. As is seen, the ASIS frame member 1432 includes a curved portion that is configured to hug the side of a wearer, with the coupling to the base frame member 1430 determining the placement of the curved portion relative to the back panel 1402 and thus to the anterior of the wearer. In some embodiments, the ASIS frame member 1432 and the base frame member 1430 are coupled to the back panel 1402 via a belt, which may be seen in numerous figures within the set of FIGS. 1A-13E as well as FIG. 18A.

In some embodiments, the base frame member 1430 is integrally (or unitarily) formed as a portion of the inferior strut 1412. The inferior strut 1412 is positioned as the lowest strut in the lateral frame assembly 1410, with the term lowest referring to furthest strut from the chest plate attachment 1450. The inferior strut 1412 includes to side protrusions that form a channel that receives the medial strut 1414. The protrusions are best seen in FIGS. 14B and 19A-19B. The medial strut 1414 is configured to be slidably adjustable in a vertical direction within the channel of the inferior strut 1412, which operates to adjust the height of the spine brace 1400 (e.g., the vertical positioning of the chest plate attachment 1450). The positioning of the medial strut 1414 within the channel of the inferior strut 1412 (e.g., the height of the medial strut 1414) is maintained through pressure applied by an anti-rotation cap ("cap") 1606 (as labeled in at least FIG. 16C). The cap 1606 has a channel formed therethrough that receives as the medial strut 1414. The cap 1606 includes two opposing lumens 1608 that align with a vertical slit running a majority of the length of the medial strut 1414. The cap 1606 is configured to maintain the positioning of the medial strut 1414 through placement of a screw through the lumens 1608 and the slit of the medial strut 1414. A nut is placed in a cavity on the interior side surrounding the interior lumen 1608 and as the screw is tightened, pressure is applied to the medial strut 1414, which prevents movement thereof. In some embodiments as shown, the cavity that receives the nut may have a hexagonal shape, however, other shapes should be considered within the scope of the disclosure. An upper end of the medial strut 1414 couples with a lower end of a superior frame member 1416, where the coupling may be accomplished through the formation of a hinge 1500 (as discussed in detail with respect to FIGS. 15A-15F).

As will be discussed, the hinge 1500 enables rotation of the superior frame member 1416 relative to the medial strut 1414, which results in the adjustment of the positioning of the chest plate attachment 1450. In other embodiments, alternative attachments may be utilized in place of the chest plate attachment 1450, such as the neck orthosis 710 of FIGS. 7A-7E. The chest plate attachment 1450 will also be discussed in detail below with respect to FIGS. 20A-20D.

Referring to FIG. 14B, a perspective lateral view of the third embodiment of an orthopedic spine brace is shown. The spine brace 1400 is shown from an alternative perspective in FIG. 14B and without the chest plate attachment 1450 coupled thereto. Additionally, an extension strut is shown in FIG. 14B on the lateral frame assembly 1420, which will be detailed below.

1. Superior Frame Member Angle Adjustment

Referring now to FIGS. 15A-15B, the superior frame member of the orthopedic spine brace of FIG. 14A is illustrated at first and second angles relative to the medial strut. As noted above, the medial strut 1414 couples with the superior frame member 1416 to form a hinge 1500 that allows the superior frame member 1416 to rotate relative to the medial strut 1414. FIG. 15A illustrates the superior frame member 1416 at a first angle $\theta_1$ relative to the medial strut 1414 and FIG. 15B illustrates the superior frame member 1416 at a second angle $\theta_2$ relative to the medial strut 1414, where the varying angles result in adjustment of the positioning of the chest plate attachment 1450 relative to the chest of a wearer. For instance, the positioning of the superior frame member 1416 in FIG. 15A may be utilized for a wearer with a larger, broader chest while the positioning of the superior frame member 1416 in FIG. 15B may be utilized for a wearer with a flatter chest.

The hinge 1500 may be comprised of a plurality of components including the lower end 1502 of the superior frame member 1416 and the upper end 1504 of the medial strut 1414. Openings in each component may be configured to align thereby creating a lumen 1506.

Referring to FIG. 15C, a back perspective view of the hinge enabling rotation of the superior frame member relative to the medial strut is shown. The hinge 1500 operates through the use of a face gear mechanism created by teeth 1510, 1512 formed on the interior sides of each of the lower end of the superior frame member 1416 and the upper end of the medial strut 1414, respectively. When engaged, the teeth 1510, 1512 prevent rotation of the superior frame member 1416 relative to the medial strut 1414. A screw passed through the lumen 1506 and tightened with a nut on one side causes the medial and superior frame members 1414, 1416 to compress and the teeth 1510, 1512 to engage.

Additionally, the hinge 1500 includes an internal coil spring 1508 that is positioned between the superior frame member 1416 and medial strut 1414. As the screw and nut combination is loosened, the spring 1508 acts to naturally expand causing separation of the superior frame member 1416 and the medial strut 1414. The separation causes the teeth 1510, 1512 to disengage, which allows rotation of the superior frame member 1416 relative to the medial strut 1414.

Referring to FIG. 15D, a detailed view of the components comprising the hinge of FIGS. 15A-15C is illustrated. FIG. 15D illustrates that in some embodiments, the spring 1508 is positioned to surround the lumen 1506; however, other placements have been considered. Additionally, multiple springs may be utilized such as springs on opposing sides of the lumen 1506.

Referring now to FIG. 15E, a back left perspective view of the hinge of FIGS. 15A-15D is shown. FIG. 15E provides an illustration of a cavity in the interior side of the hinge 1500 and specifically of the upper end of the medial strut 1414. The cavity is seen to surround the lumen 1506 and receive the nut (not shown) of the screw and nut combination that operates to compress the spring 1508 when tightened. The hexagonal shape of the cavity is merely one embodiment of the possible shapes for the cavity. However, the hexagonal shape acts to prevent rotation of the nut, which would possibly cause inadvertent loosening of the screw and nut combination (resulting in disengagement of the teeth 1510, 1512 and an unintended adjustment of the superior frame member 1416 and chest plate attachment 1450). FIG. 15F provides an illustration of a patient (P) wearing the orthopedic spine brace of FIG. 14B with the superior frame members rotated to an angle 'A' ($\theta_A$) relative to the medial strut is shown.

2. Medial Strut Height Adjustment

Referring now to FIGS. 16A-16B, the figures illustrate the medial strut adjusted to first and second heights. As discussed briefly above, the medial strut 1414 is slidably engaged with the inferior strut 1412 allowing the medial strut 1414 to be raised or lowered to varying heights, which will be dependent on the body dimensions of each wearer. FIG. 16A illustrates the medial strut 1414 in a first adjustment position such that the medial strut 1414 extends above the cap 1606 a first height $H_1$ and FIG. 16B illustrates the medial strut 1414 in a second (raised) adjustment position such that the medial strut 1414 extends above the cap 1606 a second height Hz.

As discussed above, the cap 1606 includes a lumen 1608 that extends through the cap 1606 at holes on opposing sides, where the lumen 1608 is aligned with a vertical slit in the medial strut 1414. To fix the medial strut 1414 as a particular position (e.g., extended above the cap 1606 at a desired height), a screw (not shown) is inserted through the lumen 1608 and through the vertical slit of the medial strut 1414. A nut (not shown) is placed within a cavity surrounding the lumen 1608 on the interior side of the cap 1606 and receives the screw. As the screw and nut combination is tightened, the medial strut 1414 is fixed in place relative to the cap 1606 and the inferior strut 1412.

FIGS. 16A-16B also provide an illustration of a channel 1604 formed on the exterior side of the inferior strut 1412 ("exterior channel"). Further, FIGS. 16A-16B illustrate that the front-facing side of the inferior strut 1412 includes teeth 1600 along its length. Additionally, the back-facing side of the inferior strut 1412 includes teeth 1602 along its length (as seen in FIGS. 17A-17B). The exterior channel 1604 and the teeth 1600, 1602 are utilized in the positioning of the strap adjustment member 1418, which is discussed below with respect to FIGS. 17A-17G.

Referring now to FIG. 16C, a front interior perspective view of first lateral components of the orthopedic spine brace of FIGS. 14A-14B is shown. FIG. 16C provides a detail perspective of the cap 1606 including illustrating the inclusion of a front-facing side 1610 and a back-facing side 1612. As seen in FIG. 16C, the cap 1606 does not include teeth and thus, cannot engage with the strap adjustment member 1418. As seen in at least FIGS. 17C-17D, without including an exterior channel that aligns with the exterior channel 1604 of the inferior strut 1412, the cap 1606 acts as a stopper to the strap adjustment member 1418 and prevents vertical movement beyond the length of the inferior strut 1412.

3. Strap Adjustment Member—Height Adjustment

Referring now to FIGS. 17A-17B, the strap adjustment member is shown fixed at first and second positions along the inferior strut in accordance with the medial strut being extended or retracted to either a first height or a second height. FIGS. 17A-17B illustrate the medial strut 1414 in first and second adjustment positions with the medial strut 1414 extending above the cap 1606 at a first height $H_1$ and a second height Hz, respectively. Further, the strap adjustment member 1418 is shown at a first position in FIG. 17A with the medial strut 1414 extending a height Hz above the cap 1606 and at a first position in FIG. 17B with the medial strut 1414 extending a height $H_1$ above the cap 1606. A buckle 1705 extends from the strap adjustment member 1418

As will be discussed further below, the strap adjustment member 1418 is fixed in a desired position along the length of the inferior strut 1412 through engagement with the teeth 1600, 1602 of the inferior strut 1412.

Referring to FIG. 17C, a back perspective view of the strap adjustment member fixed at a particular position along the inferior strut is shown. The strap adjustment member 1418 is fixed in a desired position through the use of a screw 1700, which, when tightened, locks the strap adjustment member 1418 in its current position. Specifically, as the screw 1700 is tightened, the screw 1700 contacts the back-facing side of the inferior strut 1412 (e.g., the teeth 1602) and causes the opposite side of the strap adjustment member 1418 to contact the front-facing side of the inferior strut 1412 (e.g., the teeth 1600). As illustrated in FIG. 17E, strap adjustment member 1418 includes internal teeth 1704 that engage the teeth 1600. The force applied by tightening the screw 1700 maintains engagement of the teeth 1600, 1704 thereby fixing the strap adjustment member 1418 in its current position. In some embodiments, the teeth 1602 need not be present such that the screw may contact a flat surface; however, the teeth 1602 provide additionally stability.

As noted above, the inferior strut 1412 includes an exterior channel 1604. The strap adjustment member 1418 includes a protrusion 1702 configured to be received by the exterior channel 1604 and slide within the channel 1604 as the strap adjustment member 1418 is slid along the inferior strut 1412. The interaction between the channel 1604 and the protrusion 1702 prevents any rotation (or other side-to-side movement) of the strap adjustment member 1418. It is noted that preventing rotation or side-to-side movement of the strap adjustment member is important as, although not shown, the ring portion of the strap adjustment member 1418 is configured to receive a strap (e.g., the strap loops through the ring portion) and attaches to the belt (see FIG. 18A).

Referring to FIG. 17D, an exterior side perspective view of the steering ring fixed along the inferior strut as seen in FIG. 17C is illustrated. FIG. 17D provides an alternative angle of the protrusion 1702 of the strap adjustment member 1418 positioned within the exterior channel 1604 of the inferior strut 1412. FIG. 17D also provides an illustration of the teeth 1600. As stated above, as the screw 1700 is tightened, the screw contacts the back-facing side of the inferior strut 1412, which causes the strap adjustment member 1418 to shift in a backward direction such that the teeth 1704 of the strap adjustment member 1418 engage with the teeth 1600.

Referring to FIG. 17E, a bottom perspective view of the steering ring is provided. The strap adjustment member 1418 includes a first opening 1701 to receive a first screw (the screw 1700), the internal teeth 1704, a second openings 1706 and 1708 to receive a screw (not shown) for coupling the strap adjustment member 1418 with additional attachments such as buckles 1710, 1712 (FIG. 17G). In some embodiments, the hexagonal shaped opening opposite the opening 1706 may be an artifact of the manufacturing process.

Referring to FIG. 17F, a top exterior side perspective of the steering ring positioned along the inferior strut as seen in FIGS. 17C-17D is shown. FIG. 17F provides a view of the exterior channel 1604 having a first width W₁ and the protrusion 1702 having a second (smaller) width W₂. Thus, as the screw 1700 is tightened, the strap adjustment member 1418 is pushed in a backward direction relative to the inferior strut 1412 with the protrusion 1702 moving toward a backside of the exterior channel 1604, which causes engagement of the internal teeth 1704 of the strap adjustment member 1418 with the teeth 1600.

FIG. 17F also illustrates a top side 1620 of the strap adjustment member 1418. The top side 1620 of the protrusion 1602 contacts the underside of the cap 1606, which prevents the strap adjustment member 1418 from moving any further in an upward direction.

Referring to FIG. 17G, a detailed front perspective view of the orthopedic spine brace of FIGS. 14A-14B including the steering ring coupled with buckle accessories is shown. The opening 1706 of the strap adjustment member 1418 is configured to receive a screw for attaching accessories, such as additional buckles 1710 and 1720 in addition to the buckle 1705, to the strap adjustment member 1418. The additional buckles 1710, 1720 allow additional straps to be coupled to the strap adjustment member 1418 and, indirectly, the inferior strut 1412. These additional straps may loop through corresponding buckles on the opposite lateral frame assembly and/or couple with the belt 1808, 1818, which may provide additional rigidity and further restrict movement of the wearer.

4. Back Panel Pulley System

Referring now to FIG. 18A, a back perspective of a back panel pulley system coupled to the back panel of the orthopedic spine brace is shown. The back panel pulley system is comprised of cord attachment plates 1800, 1810 that are slidably coupled with the lower wing panels 1404, 1406 via tracks 1802, 1812. A belt is comprised of portions 1808, 1818, which are attached to the cord attachment plates 1800, 1810. Additionally, a pulley cord system 1820 including two cords that wrap around posts of the cord attachment plates 1800, 1810. The ends of each cord may include an attachment component that couples with the belt portions 1808, 1818 via hook and loop fasteners.

The cord attachment plates 1800, 1810 slide along the tracks 1802, 1812 based on the tightening of the cords and the dimensions of the body of the wearer. Additional detail of the operability of the back panel pulley system may be found in at least U.S. Pat. No. 8,142,377, titled "Double Pull Body Brace," which issued on Mar. 27, 2012, the contents of which are incorporated herein in their entirety.

FIG. 18A also illustrates that the back panel 1402 includes two diagonal slits 1804, 1814 at the upper side of the lower wing panels 1404, 1406 and two diagonal slits 1806, 1816 at the lower side of the lower wing panels 1404, 1406. The diagonal slits 1804, 1814, 1806, and 1816 each assist the back panel 1402, and specifically, the lower wing panels 1404, 1406 to conform to the body of the wearer. As the cords and/or the belt are tightened around the wear, the lower wing panels 1404, 1406 maintain some rigidity due to the material of the back panel 1402 but also curve slightly around the wearer's body in part because of the diagonal slits 1804, 1814, 1806, and 1816.

Referring to FIG. 18B, a back perspective of the orthopedic spine brace of FIGS. 14A-14B is shown illustrating a first cord attachment plate of the back panel pulley system slidably coupled with a lower wing of the back panel of the orthopedic spine brace. FIG. 18B illustrates detail as to the first cord attachment plate 1800 including detail of the posts around which the cords wrap. The first cord attachment plate 1800 is shown at a far-right position along the track 1802. The track 1802 stabilizes the first cord attachment plate 1800 preventing movement along the vertical direction and enables the first cord attachment plate 1800 to movement along the horizontal direction when the belt and/or pulley cord system is tightened or loosened.

5. Extension Strut Attachment

Referring now to FIG. 19A, a perspective view of the orthopedic spine brace of FIGS. 14A-14B having extension struts installed thereon is provided. FIG. 19A shows the spine brace 1400 including extension struts 1900, 1901 included in each of the lateral frame assemblies 1410, 1420. The extension struts 1900, 1901 are configured to provide additional height for the chest plate attachment 1450 by extending the length that the medial struts 1414, 1424 may extend in the vertical direction.

As should be understood from the discussion above and, for example, FIGS. 16A-16C, when the lateral frame assemblies 1410, 1420 do not include the extension struts 1900, 1901, the medial struts 1414, 1424, may only extend to a particular height depending on the length of the inferior struts 1412, 1422 and the medial struts 1414, 1424.

However, in the event that it is desired that the spine brace 1400 be adjusted beyond the height constraints of the inferior struts 1412, 1422 and the medial struts 1414, 1424, extension struts 1900, 1901 may be coupled to an upper end of the inferior struts 1412, 1422. The caps (e.g., cap 1606) are then positioned at the upper end of the extension struts 1900, 1901 such that the medial struts 1414, 1424 are disposed through the opening of each cap and into an interior channel of each of the extension struts 1900, 1901 that are similar to the interior channel of the inferior struts 1412, 1422 discussed above. As the functionality of the extension struts 1900, 1901 mirror each other, the following discussion of coupling the extension strut 1900 to the inferior strut 1412 applies equally to extension strut 1901 and the inferior strut 1422.

Referring to now FIG. 19B, a detailed interior perspective view of an extension strut of FIG. 19A coupled with an inferior strut of the orthopedic spine brace is shown. The point at which the inferior strut 1412 couples with the extension strut 1900 is shown in FIG. 19B. Specifically, the lower end of the extension strut 1900 is mated with the upper end of the inferior strut 1412 with lower protrusions 1902, 1904 of the extension strut 1900 extending over the upper end of the inferior strut 1412. The inferior strut 1412 includes a plurality of lumens forming the set of lumens 1910 that are configured to align with lumens of the extension strut 1900 (lumens 1912, see FIG. 19C). As shown in FIG. 19B, the set of lumens 1910 is comprised of three lumens (with the extension strut 1900 including two but may optionally include three). In some embodiments, coupling of the inferior strut 1412 with the extension strut 1900 using two lumens and screw/nut combinations may provide sufficient coupling stability when the screw/nut combinations are tightened. As discussed above in various embodiments, a nut of the screw/nut combinations may be disposed in the hexagonal cavities surrounding the set of lumens 1910.

The extension strut 1900 is shown to include teeth 1906 on the front-facing side that align with the teeth 1600. The extension strut 1900 also includes teeth 1908 on the back-facing side (not shown due to the perspective view) that are aligned with the teeth 1602 of the inferior strut 1412. FIG. 19B also illustrates that, following configuration of the lateral frame assembly 1410 to incorporate the extension strut 1900, the strap adjustment member 1418 may slide along the length of the inferior strut 1412, pass over the coupling point, and slide along the length of the extension strut 1900 (and may also slide in the reverse direction).

Referring to FIG. 19C, a detailed exterior perspective view of the extension strut of FIG. 19A coupled with an inferior strut of the orthopedic spine brace is shown. FIG. 19C illustrates a detailed view of the alignment of the teeth 1906 with the teeth 1600. In particular, a gap having the width of a single tooth is located at the coupling point. As such, the strap adjustment member 1418 will pass over the gap without being derailed in its movement in the vertical direction.

FIG. 19C also illustrates the lumens 1912 that align with the set of lumens 1910 of the inferior strut 1412. Additionally, an exterior channel 1914 of the extension strut 1900 is shown that operates to extend the channel 1604 of the inferior strut 1412. Thus, the protrusion 1702 of the strap adjustment member 1418 may continue between the channel 1604 and the channel 1914 as the strap adjustment member 1418 sides back and forth between the inferior strut 1412 and the extension strut 1900.

6. Chest Plate Configuration

Referring now to FIG. 20A, a perspective view of the chest plate attachment coupled to the orthopedic spine brace of FIGS. 14A-14B is shown. The chest plate attachment 1450 is shown to couple to the upper ends of the superior frame members 1416, 1426 and are configured to rest against the chest of the wearer. An example of a similar chest plate attachment may be seen in FIGS. 1A-1C.

The chest plate attachment 1450 of FIG. 20A is comprised of a plurality of components including a locking attachment member 2000, a retainer plate 2012, and a hinged attachment member 2014. The locking attachment member 2000 is formed of a housing that includes openings 2006 on each of a top and bottom face and includes an internal locking mechanism comprised of a first protrusion 2002 extending from a first spring component 2003 and a second protrusion 2004 extending from a second spring component 2005 (see FIG. 20.B). The locking attachment member 2000 operates in accordance with pressure being applied to the protrusions 2002, 2004 to compress the internal spring components 2003, 2005, which releases the locking attachment member 2000 from a coupling component 2040. Specifically, pressure applied to the protrusions 2002, 2004 operates to release the locking attachment member 2000 from a ball 2042 and a post 2054, which are components of the coupling component 2040 (see FIG. 20D). Thus, the chest plate attachment 1450 is coupled to the superior frame members 1416, 1426 via coupling components, with detail pertaining to the coupling components provided below.

The locking attachment member 2000 further includes a chest retention strut member 2008, which includes a groove (or slit)2010 running along a majority of the length of the chest retention strut member 2008. The chest retention strut member 2008 extends laterally from the locking attachment member 2000 into a channel of the retainer plate 2012 and toward the hinged attachment member 2014. The hinged attachment member 2014 is attached to the superior frame member 1426 via the coupling component 2015, which may be comprised of a ring portion that includes an opening to receive a screw, which when tightened, serves to fix the coupling component 2015 to the superior frame member 1426. The ring portion of the coupling component 2015 may have a similar form as the ring portion 2044 (FIG. 20C). In some embodiments, the ring portion may be integrally formed with the housing of the 2014.

The hinged attachment member 2014 includes a housing (illustrated as square in FIG. 20A), which may be empty (or may include a weighted component to balance the weight of the locking attachment member 2000 and the coupling component 2004). A hinge 2016 extends laterally from the housing of the hinged attachment member 2014 with a chest retention strut member 2018 extending further laterally therefrom. The hinge 2016 enables the retainer plate 2012 and the locking attachment member 2000 to rotate relative to the hinged attachment member 2014 when the locking attachment member 2000 is released from the coupling component 2040. This acts to "open" the chest plate attachment 1450. It is noted that the locking attachment member 2000 and the hinged attachment member 2014 may attach to either side of the spine brace. For instance, a wearer may prefer to reverse the opening of the chest plate attachment 1450 such that the hinged attachment member 2014 may couple with the superior frame member 1416 while the locking attachment member 2000 couples with the superior frame member 1426 via the coupling component 2040.

The retainer plate 2012 is configured to form a channel that receives the chest retention strut members 2008, 2018. The retainer plate 2012 may be formed of a back plate (chest-facing side) and two lips that extend outwardly from the back plate thereby forming the channel. The chest retention strut members 2008, 2018 are coupled to the back plate of the retainer plate 2012 via a screw or a screw/nut combination. The chest plate attachment 1450 may also include a rotating chest plate 2026 that couples to the back plate of the retainer plate 2012 via posts 2028, 2030 that connect to receptacles 2022, 2024, respectively. See FIGS. 6A-6D for representative structure.

Referring to FIG. 20B, the figure illustrates a perspective detailed view of internal components of the lock connector of the chest plate attachment coupled to the ball and post assembly of an attachment ring that couples the chest plate attachment to the orthopedic spine brace. FIG. 20B illustrates the internal components of the locking attachment member 2000 discussed above in a locked state where the spring components 2003, 2005 are engaged with the post 2054 and prevent from sliding upwardly (away from the wearer's chest) by a lip of the ball 2042 (FIG. 20D). FIG. 20C provides a perspective view of the orthopedic spine brace of FIGS. 14A-14B coupled with the attachment ring without the chest plate attachment 1450.

Referring to FIG. 20D, a detailed perspective view of the attachment ring is provided. The coupling component 2040 is shown exploded from the upper-most end of the superior frame member 1416 and including detail that illustrates the configuration of the ball 2042 and the post 2054. Further, the coupling component includes a lumen 2046 through which the superior frame member 1416 passes and an opening 2048 to receive a screw 2050, which when tightened, causes the coupling component to be fixed to the superior frame member 1416. The lumen 2046 is formed through the ring portion 2044 and a base portion 2025, from which the post 2054 extends.

IV. General Architecture—Orthopedic Spine Brace
(4$^{th}$ Embodiment)

Referring now to FIG. 21A, a perspective anterior view of a fourth embodiment of an orthopedic spine brace 2100 including a chest plate attachment 2150 coupled thereto is illustrated. The orthopedic spine brace (spine brace) 2100 features numerous posterior members including a back panel 2102, lower wing panels 2104, 2106, and a spinal process opening (hereinafter, "spinal relief") 2108 that runs a majority of the length of the back panel 2102 to alleviate pressure on the spine of a wearer. A connection piece may span the width of the spinal relief 2108 to provide stability, support, and rigidity to the back panel 2102. It is contemplated that certain components included as part of the first, second and third embodiments of the orthopedic spine brace 100/900/1400 may be implemented within the orthopedic spine brace 2100 and these features are incorporated by reference herein.

The spine brace 2100 also includes lateral frame assemblies 2110, 2120, which include mirroring components. For example, the lateral frame assembly 2110 includes an inferior strut 2112, a medial strut 2114, a superior frame member 2116, a strap adjustment member 2118, an anterior superior iliac spine (ASIS) frame member 2132, and a base frame member 2130. The lateral frame assembly 2120 includes mirroring components: an inferior strut 2122, a medial strut 2124, a superior frame member 2126, a strap adjustment member 2128, an ASIS frame member 2142, and a base frame member 2140. As each of the lateral frame assemblies 2110 and 2120 operate to provide the same functionality and are configured in the same manner, the following discussion of the lateral frame assembly 2110 would applies equally to the lateral frame assembly 2120 and vice versa.

In reference to the components comprising the lateral frame assembly 2110, the ASIS frame member 2132 couples with the base frame member 2130 via a connection mechanism such as a screw and nut assembly, where the screw passes through a slit that runs horizontally along a portion of the length of the ASIS frame member 2132. As shown in FIG. 21C, the ASIS frame member 2132 includes a curved portion that is configured to hug the side of a wearer, with the coupling to the base frame member 2130 determining the placement of the curved portion relative to the back panel 2102 and thus to the anterior of the wearer. In some embodiments, the ASIS frame member 2132 and the base frame member 2130 are coupled to the back panel 2102 via a belt 2144, which may be seen in FIG. 21B in which padding 2146 positioned on the back panel 2102, padding 2147 positioned on an interior surface of the inferior struts 2112/2122, and padding 2148 positioned on an interior surface of hinges 2200/2202.

In some embodiments, as shown in FIG. 21A, the base frame member 2130 is integrally (or unitarily) formed as a portion of the inferior strut 2112. Operating to partially house the medial strut 2114, the inferior strut 2112 is positioned as the lowest strut in the lateral frame assembly 2110, with the term lowest referring to furthest strut from the chest plate attachment 2150.

More specifically, referring now to FIG. 21C, a perspective lateral view of the orthopedic spine brace 2100 of FIG. 21A is shown. According to this embodiment of the disclosure, the inferior strut 2112 includes one or more channels 2105 that receives the medial strut 2114. The medial strut 2114 is configured to be slidably adjustable in a vertical direction within the channel(s) 2105 of the inferior strut 2112, which operates to adjust the height of the orthopedic spine brace 2100 (e.g., the vertical positioning of the chest plate attachment 2150). The positioning of the medial strut 2114 within the channel(s) 2105 of the inferior strut 2112 (e.g., the height of the medial strut 2114) is maintained through pressure applied by an anti-rotation cap 2206. The anti-rotation cap ("cap") 2206 features the one or more channels 2105 formed therethrough that receives as the medial strut 2114 and allows the medial strut 2114 to pass therethrough. However, the strap adjustment member 2118 is sized to preclude passing below the anti-rotation cap 2206.

The cap 2206 includes two opposing lumens 2208 that align with a vertical slit 2207 running a majority of the length of the medial strut 2114. The cap 2206 is configured to maintain the positioning of the medial strut 2114 through placement of a fastener (e.g., screw, bolt, dowel, etc.) through the lumens 2208 and the slit of the medial strut 2114. A complementary fastener (e.g., nut, boss, etc.) may be placed in a cavity on the interior side surrounding the interior lumen 2208. Hence, as the fasteners are tightened together, pressure is applied to the medial strut 2114 to prevent movement thereof. In some embodiments as shown, the cavity that receives the complementary fastener may have a hexagonal shape, however, other shapes should be considered within the scope of the disclosure.

As further shown in FIG. 21C, an upper end of the medial strut 2114 couples with a lower end of a superior frame member 2116, where the coupling may be accomplished through the formation of the hinge 2200. Herein, the hinge 2200 enables angular rotation of the superior frame member 2116 relative to the medial strut 2114, which results in the adjustment of the positioning of the chest plate attachment 2150. The superior frame member 2116 transitions from a flat, rectangular shape at a proximal end attached to the hinge 2200 to a cylindrical shape at a distal end portion. This promotes slidable width adjustment and allows for placement of the chest plate attachment 2150 and rotation of the chest plate attachment 2150 to the appropriate contour of the patient's sternum. Also, the upward curvature of the superior frame member 2116 allows for comfortable placement until the axilla of the patient while retention of the chest plate attachment 2150 on the chest area of the patient.

In other embodiments, alternative attachments may be utilized in place of the chest plate attachment 2150, such as the neck orthosis support member 3000 of FIGS. 30A-30D. The chest plate attachment 2150 will also be discussed in detail below with respect to FIGS. 24A-26H.

Referring to FIG. 21D, a perspective lateral view of the fourth embodiment of the orthopedic spine brace 2100 is shown. Herein, the orthopedic spine brace 2100 is shown with the belt 2144 along with the padding 2146-2148.

Referring now to FIGS. 22A-22C, illustrative embodiments of the components forming the orthopedic spine brace 2100 of FIG. 21A are shown. These components are responsible for supporting angular and linear adjustments of the superior frame member 2116, the medial strut 2114, and the strap adjustment member 2118.

1. Superior Frame Member Angle Adjustment

Herein, the superior frame member 2116 of the orthopedic spine brace 2100 of FIG. 21A is illustrated at first and second angles relative to the medial strut 2114. As noted above, the medial strut 2114 is configured for coupling with the superior frame member 2116 to form a hinge 2200 that allows the superior frame member 2116 to rotate relative to the orientation of the medial strut 2114. FIG. 22A illustrates the superior frame member 2116 at a first angle $\theta$ relative to the medial strut 2114, where the superior frame member 2116 may be rotated to a second (greater or lesser) angle than the first angle $\theta$ relative to the medial strut 2114. The varying angles allow for adjustment of the positioning of the chest plate attachment 2150 relative to the chest of a wearer. For instance, the positioning of the superior frame member 2116 in FIG. 22A may be utilized for a wearer with a larger, broader chest while the positioning of the superior frame member 2116 with a larger angle $\theta$ may be utilized for a wearer with a flatter chest. The hinge 2200 may be comprised of a plurality of components, as shown in FIGS. 15A-15C.

2. Medial Strut Height Adjustment

Referring now to FIGS. 22A-22C, the medial strut 2114 may be adjusted to multiple, different heights. As discussed briefly above, the medial strut 2114 is slidably engaged with the inferior strut 2112 allowing the medial strut 2114 to be raised or lowered to varying heights, which will be dependent on the body dimensions of each wearer. FIG. 22A illustrates the medial strut 2114 in a first adjustment position such that the medial strut 2114 (and the strap adjustment member 2118) extends above the cap 2206 by a first height $H_1$. The medial strut 2114 (and strap adjustment member 2118) may be adjusted to extend further from the cap 2206 up to a second height Hz.

As discussed above, the cap 2206 operates as a stopper to the strap adjustment member 2118 and prevents vertical movement beyond the top surface of the cap 2206. The cap 2206 includes the lumen 2208, which extends through the cap 2206 at holes on opposing sides, where the lumen 2208 is aligned with a vertical slit 2207 in the medial strut 2114. To fix the medial strut 2114 to a particular position (e.g., extended above the cap 2206 at a desired height), as shown in FIG. 22B, a first fastening member 2220 (e.g., a screw, bolt, etc.) is inserted through the lumen 2208 and through the vertical slit of the medial strut 2114. A second fastening member 2225 (e.g., a nut, etc.) is placed within a cavity surrounding the lumen 2208 on the interior side of the cap 2206 and receives the first fastening member 2220. As the fastening member combination 2220 and 2225 is tightened, a cantilever member 2230 of the cap 2206 is tightened by reducing a spacing between an interior surface 2232 of the cantilever member 2230 and an interior surface 2115 of the medial strut 2114. Once tightened, the medial strut 2114 is fixed in place relative to the cap 2206 and the inferior strut 2112.

3. Steering Ring Height Adjustment

Referring now to FIGS. 22A-22C, an illustrative embodiment of the strap adjustment member 2118 is shown, which features a steering ring 2240 fixed at first position with the medial strut 2114 being extended or retracted to a desired height. As shown in FIGS. 22A-22B, the steering ring 2240 may be angularly adjusted by approximately 270°, based on a fastener 2245 inserted through both lumen 2252 within a pair of protruding members 2250 of the strap adjustment member 2118 and a lumen (not shown) that is formed within a neck portion 2242 of the steering ring 2240 and aligned with the lumen 2252. The steering ring 2240 is interposed between the protruding members 2250 and may be secured through a fastener such as a rivet or other fastening mechanism that may include a male fastener 2245 and a complementary female fastener 2246. The female fastener 2246 could be a separate component (as shown in FIG. 22C) or may be integrated as threads formed within the lumen 2252.

Referring to FIG. 22C, a detailed view of the components forming the strap adjustment member 2118 of FIGS. 22A-22B is shown. The strap adjustment member 2118 is fixed at a particular position along the medial strut 2114 through a cantilever member 2260, similar in design to the tightening mechanism utilized for the cap 2206. Herein, the strap adjustment member 2118 includes a housing 2264, which features a lumen 2262 that extends through the housing 2264 at holes on opposing sides, where the lumen 2262 is aligned with the vertical slit 2207 in the medial strut 2114. To fix the strap adjustment member 2118 at the particular position (e.g., extended above the cap 2206 at a desired height), although not shown, a first fastening member (e.g., a screw, bolt, dowel, etc.) may be inserted through the lumen 2262 and through the vertical slit of the medial strut 2114. A second fastening member (e.g., a nut, boss, etc.) would be placed within a cavity surrounding the lumen 2262 on the interior side of the strap adjustment member 2118 to receive the first fastening member. As described above, this fastening member combination would tighten, causing an interior surface of the cantilever member 2260 to approach and come into forced contact with the interior surface 2115 of the medial strut 2114. Once tightened, the strap adjustment member 2118 is fixed in place relative to the cap 2206 and along a selected portion of the medial strut 2214.

Herein, the positioning of the chest plate attachment 2150 may be controlled by the extended length of the medial strut 2114 in relation to the cap 2206 and the positioning of a support strap 2270 may be controlled by a selected height of the steering ring 2240 attached to the strap adjustment member 2118. The adjusted positioning of the support strap 2270 allows repositioning of posterior force against the back panel 2102 to assist in a comfortable fitting of the orthopedic spine brace 2100.

Referring now to FIGS. 22D-22E, exemplary embodiments of the orthopedic spine brace 2100, featuring with a different type of chest plate attachment 2280 than illustrated in FIG. 21A, is shown. Herein, the chest plate attachment 2280 features a plurality of straps 2282 and 2284, which may be rigid, semi-rigid or non-rigid in form. One end of each of these straps 2282 and 2284 is coupled to a respective superior frame member and 2126. The other end of each of these straps 2282 and 2284 may include a buckle 2286 and 2288 (or any other fastening means) that enables the buckles to be connected together (see FIG. 22D) and both of these straps 2282 and 2284 further adjusted to provide appropriately fitting for the chest area of the wearer. The buckles 2286 and 2288 may be disconnected to allow for the donning process, allow for the wearer to remove the orthopedic spine brace 2100, or even adjust the brace 2100.

Referring now to FIG. 23A, a third embodiment of the strap adjustment member 2300 featuring multiple steering rings 2310 for strap retention is shown. The strap adjustment member 2300 features the same architecture as the strap adjustment member 2118 of FIGS. 21A and 22A-22C; however, in lieu of a single steering ring, the strap adjustment member 2300 features multiple (two or more) steering rings 2310. The steering rings 2310 are rotationally attached protruding members 2320 extending from a housing portion 2330 of the strap adjustment member 2300.

As shown in FIGS. 23A-23B, each of the steering rings 2310, namely a first steering ring 2312, a second steering ring 2314 and a third steering ring 2316, may be oriented in different angular positions and fixed at that position. As shown, the first steering ring 2312 is arranged between a spacing formed between the protruding members 2320 while the second steering ring 2314 is positioned against an outer surface 2322 of a first member of the protruding members 2320 and the third steering ring 2314 is positioned against an inner surface (not shown) of a second member of the protruding members 2320. Each of these steering rings 2312, 2314 and 2316 may be attached to the protruding members 2320 via a first fastening member 2340 and a complementary fastening member (not shown) positioned against an inner surface of the third steering ring 2316.

As an illustrative embodiment, the first steering ring 2312 may be positioned to extend substantially orthogonal to a posterior edge 2332 of the housing portion 2330 (e.g., a 9 o'clock orientation when facing an outer surface 2334 of the housing portion). Both the second steering ring 2314 and the third steering ring 2316 may be oriented at an angular offset from the first steering ring 2312. For example, the second steering ring 2314 may be oriented at an offset angle $\Delta_1$ from an angle of orientation $\Phi$ for the first steering ring 2312. Similarly, the third steering ring 2316 may be oriented at an offset angle $\Delta_2$ from an angle of orientation for the second steering ring 2314.

As shown in FIGS. 23A-23B, the steering rings 2310 may be angularly adjusted from each other and fixed to remain to the selected angular orientation by tightening the first fastening member 2340 to its complementary fastening member positioned against an inner surface of the third steering ring 2316. Hence, the steering rings 2310 are organized in a stacked arrangement with the first steering ring 2312 separated from each of the second and third steering rings 2314 and 2316 by one of the protruding members 2320 of the strap adjustment member 2300.

Referring now to FIG. 23C, an illustrative embodiment of the strap adjustment member 2300 of FIG. 23B with rotational steering rings rotated at different angular orientations is shown. Herein, the first steering ring 2312 is coupled to a first support strap 2350 that may extend around a posterior side of the back panel 2102 for attachment to a steering ring of the mirrored strap adjustment member (e.g., 2328 of FIG. 21A). The second steering ring 2314 is coupled to a second support strap 2360 that may be attached to a posterior region of the belt 2144 of FIG. 21B while the third steering ring 2316 is coupled to a third support strap 2370 that may be attached to an anterior region of the belt 2144 of FIG. 21. The second and third support straps 2360 and 2370 may be positioned in any manner to provide additional tension needed to address PJK or other spinal conditions.

It is contemplated that multiple steering rings may be deployed relying on their placement in association with components other than the strap adjustment member 2118 or 2300. For example, as shown in FIG. 23D, the second and third steering rings 2314 and 2316 may be coupled by a fastener to the hinge 2200. Additionally, or in the alternative, as shown in FIG. 23E, the second and third steering rings 2314 and 2316 may be coupled by the fastener 2220 to the cap 2206.

4. Chest Plate Attachment

Referring now to FIGS. 24A-24B, perspective views of a second embodiment of the chest plate attachment (e.g., chest plate attachment 2150 of FIG. 21A-21D) is shown. The chest plate attachment 2150 is shown as being coupled to upper ends of the superior frame members 2116, 2126 and are configured to rotatably connected to the removable (U-shaped) chest plate 152 of FIG. 1A that rests against the chest of the wearer. An example of a similar chest plate attachment may be seen in FIGS. 1A-1C or FIGS. 20A-20D.

The chest plate attachment 2150 of FIGS. 24A-24B is comprised of a plurality of components including a lock attachment member 2400, a first chest retention strut member 2410 attached at one end to the lock attachment member 2400, a hinged attachment member 2420, a second chest retention strut member 2430 attached at one end to the hinged attachment member 2420, a retainer plate 2440 to support the chest retention strut members 2410 and 2430 in a stacked orientation, and a cover 2450 coupled to the retainer plate 2440 to form a sleeve-like configuration. As shown, a lumen 2455 extends through the cover 2450 and is aligned with slots formed in the chest retention strut members 2410 and 2430. Formed on a bottom side of the retainer plate 2440, a female fastening member is sized to receive and securely retain a fastening member (e.g., a screw, bolt, dowel, etc.) inserted through the lumen 2455 and aligned slots of the chest retention strut members 2410 and 2430. Although not shown, strap adjustment members may be attached to the chest plate attachment 2150 to retain one or more shoulder strap, such as at the lock attachment member 240 and/or hinged attachment member 2420 for example.

The lock attachment member 2400 is formed of a housing 2402 that includes openings 2404 on each of a top and bottom face and includes an internal locking mechanism comprised of a first protrusion 2500 extending from a first spring component 2510 and a second protrusion 2520 extending from a second spring component 2530 (see FIGS. 25A-25B). The lock attachment member 2400 operates in accordance with pressure being applied to the protrusions 2500, 2520 to compress the internal spring components 2510, 2530, which releases the lock attachment member 2400 from a first coupling assembly 2540. Specifically, pressure applied to the protrusions 2500, 2520 operates to release the locking attachment member 2000 from a ball 2542 with an embedded fastener 2543 and a post 2544, which are components of the first coupling assembly 2540 (see FIG. 25C). Thus, the chest plate attachment 2150 is coupled to the superior frame members 2116, 2126 via coupling assemblies 2540, 2640 (see FIGS. 25C-25D) as described below.

As described above, the lock attachment member 2400 securely maintains the first chest retention strut member 2410, which includes a groove (or slit) 2412 running along a majority of the length of the first chest retention strut member 2410. The first chest retention strut member 2410 extends laterally from the lock attachment member 2400 into a channel of the retainer plate 2440 and toward the hinged attachment member 2420. The hinged attachment member 2420 is attached to the superior frame member 2126 via the second coupling assembly 2640, which may be comprised of a strut joining member 2641 (see FIG. 26A) that includes an opening to receive a fastener, which when tightened, serves to fix the second coupling assembly 2640 to the superior frame member 2126. The strut joining member 2641 of the second coupling assembly 2640 may have similar operability as the first coupling assembly 2540 for attachment to the superior frame member (FIG. 21A).

The hinged attachment member 2420 includes a cantilever hinge 2600, which includes fasteners that are rotationally attached to components of the second coupling assembly 2640, namely lateral arm members 2645 extending from a post 2644 of the second coupling assembly 2640 (see FIGS. 26A-26D). The hinged attachment member 2420 further retains an end of the second chest retention strut member 2430 positioned below the lateral arm members 2645 (see FIG. 26B). Upon disengaging the lock attachment member 2400 from the first coupling assembly 2540, the hinged attachment member 2420 enables other portions of the chest plate attachment 2150, namely a combination of the locking attachment member 2400, chest retention strut members 2410 and 2430, the retainer plate 2440 and the cover 2450, to rotate to create a spacing between the superior frame members and 2126. This acts to "open" the orthopedic spine brace 2100 for easier donning and/or adjustment. It is noted that the locking attachment member 2400 and the hinged attachment member 2420 may attach to either side of the orthopedic spine brace 2100. For instance, a wearer may prefer to reverse the opening of the chest plate attachment 2150 such that the hinged attachment member 2420 may be coupled with the superior frame member while the locking attachment member 2400 may be coupled with the superior frame member 2126.

The retainer plate 2440 is configured to form a channel that receives the chest retention strut members 2410 and 2430. The retainer plate 2440 may be formed of a back plate (chest-facing side) and two flanges (lips) that extend outwardly from longitudinal edges of the back plate thereby forming the channel. The chest retention strut members 2410 and 2430 are coupled to the back plate of the retainer plate 2440 via a screw or a screw/nut combination. The chest plate attachment 2150 is further coupled to the removable (and rotational) chest plate 152, which is couples to the back plate of the retainer plate 2440 via posts 2028, 2030 that connect to receptacles 2022, 2024, respectively. See FIGS. 20A-20D for a representative structure.

Referring now to FIG. 25A, a perspective view of the lock attachment member 2400 for the chest plate attachment 2150 of FIGS. 24A-24B is shown. Herein, the lock attachment member 2400 features the housing 2402, including the openings 2404 located on a top face 2406 of the housing 2402 and a bottom face (not shown) of the housing 2402. An internal locking mechanism 2505, shown in more detail in FIG. 25B, is comprised of the first protrusion 2500 extending from a first side surface 2408 of the housing 2402 and the second protrusion 2520 extending from a second side surface 2409 of the housing 2402. The first protrusion 2500 is coupled to the first spring component 2510 while the second protrusion 2520 is coupled to the second spring component 2530 as shown in FIG. 25B.

Referring to FIG. 25B, a detailed perspective of the lock attachment member 2400 of FIG. 25A featuring the first and second spring components 2510, 2530 is shown. Herein, both the first and second spring components 2510 and 2530 are illustrated in a locked state, where each of the spring components 2510, 2530 are engaged with the post 2544 and prevent from sliding upwardly (away from the wearer's chest) by a lip of the ball 2542. The spring components 2510, 2530 are placed into an unlocked state by applying pressure to the protrusions 2500, 2520. This pressures compress the internal spring components 2510, 2530, which allows for the release of the first coupling assembly 2540, notably the ball and post 2542 and 2544, from the locking attachment member 2000.

Referring now to FIG. 25C, a detailed perspective of the first coupling assembly 2540 operating in concert with the lock attachment member 2400 of FIG. 25A is shown. Herein, the first coupling assembly 2540 includes a strut joining member 2541 with the post 2542 featuring a lumen 2546 through which a fastener 2547 may be inserted. The fastener 2547 may be secured by a complementary press-fit fastener positioned within the lumen 2546, although alternative fastening mechanisms are available such as the use of preformed threads within the lumen 2546 or the diameter of the fastener 2547 may fit snugly within the lumen 2546 (no threading needed). An end 2548 of the fastener 2547, inserted through the lumen 2546 formed within the ball and post combination 2542 and 2544, contacts the superior frame member (or 2126) within the strut joining member 2541. This contact may be sufficient to secure the superior frame member within the strut joining member 2541.

Referring now to FIG. 26A, a perspective view of the hinged attachment member 2420 for the chest plate attachment 2150 of FIGS. 24A-24B is shown. As shown, the hinged attachment member 2420 includes the cantilever hinge 2600 and the second coupling assembly 2640, where the cantilever hinge 2600 is rotationally coupled to the second coupling assembly 2640. The cantilever hinge 2600 is constructed to secure the second chest retention strut member 2430 to the hinged attachment member 2420 and secure the superior frame member 2126 to the second coupling assembly 2640 through an optional fastener 2610. As an alternative embodiment, as shown in FIGS. 26G-26J, the hinge 2600 may be configured without the fastener 2610 from the second coupling assembly 2640. For this alternative embodiment, upon disengaging of the first coupling assembly 2540 from the housing 2402 of the lock attachment member 2400, the chest plate attachment 2150 rotates about the cantilever hinge 2600 in accordance with two planes (e.g., pivots out away from the chest and pivots downward away from the face of the patient).

Referring to FIGS. 26A-26B, an illustrative embodiment of the second coupling assembly 2640 configured to support the second chest retention strut member 2430 (tongue) in a cantilever arrangement is shown. The second coupling assembly 2640 features the strut joining member 2641, which is a cylindrical segment sized with a diameter to receive an end portion 2642 of the superior frame member 2126 (up to a raised segment 2643 operating as a stop). The post 2644 formed into a first surface 2646 of the strut joining member 2641 and feature a lumen 2615 to optionally receive the fastener 2610. The post 2644 includes lateral arm members 2645 extending from an outer surface of the post 2644 and are positioned above end portions 2620 of the second chest retention strut member 2430. The lateral arm members 2645 are constructed to receive fasteners (e.g., integrated C-clamps) formed in an underside of the cantilever hinge 2600 to allow for rotation of the second chest retention strut member 2430 and the cantilever hinge 2600 upward from the first surface 2646 of the strut joining member 2641.

Referring to FIG. 26C, an illustrative embodiment of an underside 2630 of the cantilever hinge 2600 of FIG. 26A is shown. Herein, as shown, the cantilever hinge 2600 features fasteners 2650 (e.g., C-clamps) for retention to the lateral arm members 2645 of the post 2644 as shown in FIG. 26B. Furthermore, the cantilever hinge 2600 features bosses 2660 for insertion into complementary apertures 2622 formed within the end portions 2620 of the second chest retention strut member 2430 shown in FIG. 26B. Based on the rotational coupling between the fasteners 2650 and the lateral arm members 2645, the cantilever hinge 2600 (along with the second chest retention strut member 2430) may be rotated until a stop wall 2670 of the cantilever hinge 2600, as shown in FIG. 26D, comes into contact with the post 2644.

Referring to FIG. 26E, a detailed perspective of the hinged attachment member 2420 of FIG. 26A featuring the cantilever hinge 2600 that includes a first fastener 2652 and a second fastener 2653 of the fasteners 2650. According to one embodiment of the disclosure, the fasteners 2652 and 2653 are constructed as C-clamp molded as part of the cantilever hinge 2600. The fasteners 2652-2653 are positioned on diametrically opposite sides of the post 2644 for coupling to the lateral arm members 2645 extending from the post 2644. The cantilever hinge 2600 is formed to overlay the end portions 2620 of the second chest retention strut member 2430. The relationship between the cantilever hinge 2600, an optional fastener 2612 complementary to the fastener 2610, the lumen 2615, and the superior frame member 2126 is shown in FIG. 26F.

Referring now to FIGS. 26G-26H, perspective views of an alternative embodiment of the hinged attachment member 2420 for the chest plate attachment 2150 of FIGS. 24A-24B are shown. As shown, the hinged attachment member 2420 includes the cantilever hinge 2680 and the second coupling assembly 2640, where the cantilever hinge 2680 is rotationally coupled to the second coupling assembly 2640. The cantilever hinge 2680 is constructed to secure the second chest retention strut member 2430 to the hinged attachment member 2420 and secure the superior frame member 2126 to the second coupling assembly 2640. Herein, the cantilever hinge 2680 features fasteners 2682 (e.g., C-clamps) for retention to the lateral arm members 2645 of the post 2644. Upon release of the lock attachment member 2400 of FIGS. 24A-24B, the cantilever hinge 2680 may rotate along a first axis of rotation 2684, where the fasteners 2682 integrated as part of a lower housing 2686 of the cantilever hinge 2680 rotate about the lateral arm members 2645 as illustrated in FIG. 26H.

As shown in FIG. 26I the cantilever hinge 2680 further features a hinge rotating joint 2690. The hinge rotating joint 2690 freely rotates on the end portion 2642 of the superior frame member 2126 in accordance with a second axis of rotation 2692, which is substantially orthogonal to the first axis of rotation 2684. The combination of these two rotational components allows the chest plate attachment 2150 to drop away from a face of the patient where the cantilever hinge 2680 is configured to concurrently rotate or pivot along two different directional planes (e.g., pivots out away from the chest and pivots downward away from the face of the patient) as illustrated in FIG. 26J.

5. Orthopedic Spine Brace with Chest Plate Attachment

Referring to FIGS. 27A-27B, perspective anterior and posterior views of the orthopedic spine brace 2100 of FIGS. 21A-21D is shown. Herein, the lock attachment member 2400 is detached from the first coupling assembly 2540, which is attached to the superior frame member. As a result, the chest plate attachment 2150 along with the removable chest plate 152 (and padding as shown) remains coupled to the other superior frame member 2126. The chest plate attachment 2150 features the lock attachment member 2400, the first chest retention strut member 2410, the hinged attachment member 2420, the second chest retention strut member 2430, the retainer plate 2440 and the cover 2450. The hinged attachment member 2420 allows the chest plate attachment 2150 to be pivoted (rotated) in order to provide a spacing between the superior struts to allow the wearer to remove or readjust the orthopedic spine brace 2100 as shown in FIG. 27B.

Referring to FIG. 28A, a perspective view of the first hinge 2200 interconnecting the superior frame member with the medial strut 2114 and a second hinge 2202 interconnecting the superior frame member 2126 with the medial strut 2124 of FIGS. 21A-21D is shown. Herein, as shown in FIG. 28B, each of the hinges (e.g., hinge 2200) is configured with a concave recess 2800 formed by mirrored, concave recess portions 2810 and 2820. These concave recess portions 2810 and 2820 are located on different sides of a diameter 2830 visible at the joining of these recessed portions 2810 and 2820. The diameter 2830 provides a visual for rotational adjustment of the hinge 2200 based on visual indicia 2840 formed on a perimeter of a casing of the hinge 2200 or the upper end of the medial strut 2114.

Referring now to FIG. 28C, a perspective view of an exemplary embodiment of optional hip support members 2850 and 2855 coupled to the inferior struts 2112 and 2122 of the orthopedic spine brace of FIGS. 21A-21D is shown. Herein, according to one embodiment of the disclosure, the hip support member 2850 may be coupled to both an anterior superior iliac spine (ASIS) frame member 2860 and base frame member 2865 extending from the inferior strut 2112. The ASIS frame member 2860 (and its counterpart member extending from inferior strut 2122) provides rigidity for provide support for the orthopedic spine brace 2100 of FIG. 28A, while also provides flexibility (lateral bending) around contours of the patient to increase comfort when worn. Also, the flexibility allows for adjustment of the depth of the orthopedic spine brace 2100 (e.g., deeper, or shallower from a midline of the patient). Similarly, the hip support member 2855 may be coupled to both an ASIS frame member 2870 and a base frame member 2875 extending from the inferior strut 2122. When deployed, the hip support members 2850 and 2855 provide the orthopedic spine brace 2100 with additional lateral stability.

Referring now to FIG. 29A, a posterior view of the back panel 2102 of the orthopedic spine brace 2100 of FIGS. 21A-21D is shown. For this illustrative embodiment, the back panel 2102 includes a plurality of locking slots 2910 and a strap retention (center) slot 2920. Positioned between the locking slots 2910, the center slot 2920 is sized to receive a strap (not shown) that is looped generally along a sagittal plane and rests against a posterior surface 2930 of the support strap 2270, which is attached to the steering rings of the strap adjustment members 2118 and 2128 as partially shown in FIG. 22A. Hence, one end of the strap would be attached to the center slot 2920 while the other end of the strap may be attached to a posterior pad 2975 placed within the spinal relief section 2108 of the back panel 2102. The strap is intended to mitigate unwanted movement of the support strap 2270.

As shown in FIG. 29B, a perspective view of an extension panel 2950 coupled to the back panel 2102 of the orthopedic spine brace 2100 of FIGS. 21A-21D is shown. For this illustrative embodiment, the extension panel 2950 includes a plurality of locking protrusions 2960 for insertion into and secured with the locking slots 2910. A clip 2970 is formed toward a bottom of the extension panel 2950 to provide additional stability by attachment to the strap retention slot 2920 of the back panel 2102. Positioned toward a top of the extension panel 2950, a secondary center slot 2980 is sized for receive a strap (not shown) that is looped generally along a sagittal plane and rests against the posterior surface 2930 of the support strap 2270, which is attached to the steering rings of the strap adjustment member 2118 and 2128 as partially shown in FIG. 22A. Similar to above, one end of the strap would be attached to the secondary center slot 2920 while the other end of the strap may be attached to the posterior pad 2975 placed within the spinal relief section 2108 of the back panel 2102. The strap is intended to mitigate unwanted movement of the support strap 2270.

6. Neck Orthosis

Referring to FIG. 30A, a perspective view of a neck orthosis support member 3000 adapted for coupling to the chest plate attachment 2150 of FIGS. 24A-24B is shown. According to this illustrative embodiment, the neck orthosis support member 3000 includes a front panel 3010 with a lumen 3015 aligned with the lumen 2455 placed within the cover 2450 of the chest plate attachment 2150 of FIG. 24A. The front panel 3010 is configured with an underside that conforms with the cover 2450 and not extend beyond the parameter formed by the chest plate 152. The neck orthosis support member 3000 further includes a collar attachment member 3020 and an angular adjustment assembly 3030.

Herein, the collar attachment member 3020 includes a first collar attachment portion 3022 and a second collar attachment portion 3024, which are separated distally to allow for a neck orthosis to be held between the collar attachment portions 3022 and 3024. For example, for a neck orthosis, a front-facing adjustment dial would be positioned between the first collar attachment portion 3022 and the second collar attachment portion 3024. Fasteners 3026 and 3028 are positioned on the first and second collar attachment portions 3022 and 3024 for attachment to complementary slots within the neck orthosis. An axial rod (not shown) spans between the first collar attachment portion 3022 and the second collar attachment portion 3024 for attachment to the angular adjustment assembly 3030.

According to one embodiment of the disclosure, the angular adjustment assembly 303 features a pair of arms that support rotation along a first axis of rotation 3040 supported by the front panel 3010 and a second axis of rotation 3050 supported by the collar attachment member 3020. The first axis of rotation 3040 allows the chest plate attachment 2150 to be pivoted relative to the collar attachment member 3020, and the second axis of rotation 3050 allows the collar attachment member 3020 to be pivoted relative to the chest plate attachment 2150. This multi-pivotable neck orthosis support member 3000 provides greater degrees of freedom in adjustment of the neck orthosis in relation to the chest area of the wearer to provide better comfort and more precise donning.

Herein, as shown in FIGS. 30B-30C, the lateral views of the collar attachment member 3000 of FIG. 30A are shown, where the collar attachment member 3000 is positioned with a first orientation (FIG. 30B) or a second orientation (FIG. 30C). In the second orientation, the collar adjustment member 3020 is positioned substantially vertical to the chest plate 152 instead of the angled placement behind the chest plate 152. A perspective view of the neck orthosis support member 3000 positioned in the second orientation is further shown in FIG. 30D.

Referring now to FIGS. 31A-31B, perspective views of the orthopedic spine brace 2100 of FIG. 21A including a chest plate attachment 2150 coupled thereto are illustrated. The orthopedic spine brace 2100 features lateral frame assemblies 2110, 2120, which include mirroring components. For example, the lateral frame assembly 2110 includes the inferior strut 2112, the medial strut 2114, the superior frame member, the strap adjustment member 2118, the ASIS frame member 2122, and the base frame member 2130. Similar in construction as the lateral frame assembly 2110, the lateral frame assembly 2120 includes the inferior strut 2122, the medial strut 2124, the superior frame member 2126, the strap adjustment member 2128, the anterior superior iliac spine (ASIS) frame member 2142, and the base frame member 2140. As each of the lateral frame assemblies 2110 and 2120 operate to provide the same functionality and are configured in the same manner, the following discussion of the lateral frame assembly 2120 would applies equally to the lateral frame assembly 2120 and vice versa.

As generally shown in FIGS. 23E & 31A, the anti-rotation cap 2206 may be configured to retain at least the second steering ring 2314, which is coupled to a first tension strap 3100. With a similar construction, the anti-rotation cap 3110 of the second lateral frame assembly 2120 may be configured to retain at least one steering ring 3120, which is coupled to a second tension strap 3130. As shown in FIG. 31B, from a posterior viewpoint, the tension straps 3100 and 3130 are secured to the wing panels 2104 and 2106 within an area protected by a secure cover 3140 that is positioned between the lower wing panels 2104 and 2106 of the back panel 2102. Although not shown, for each anti-rotation cap 2206/3110 (e.g., cap 2206), a third steering ring may be deployed and arranged extending anteriorly to receive tension straps connected to an anterior panel (bracing system) 3150. Oriented to rest against the abdomen and/or chest area of the patient, an anterior bracing system 3150 is overlapped by the belt 2144. The anterior bracing system 3150 of FIG. 31A may include lateral panels 3152-3154 for attachment to interior padding of the belt 2144 by hook-loop connection scheme or steering rings/tension straps connection schemes as used for the posterior panel shown in FIG. 31B. Alternatively, the anterior bracing system 3150 may include a central anterior panel, extendable lateral panels, and an extension rod coupled to the anterior panel and extending in a superior direction as illustrated in U.S. application Ser. No. 18/162,367 filed Jan. 31, 2023, the contents of which are incorporated by reference herein.

IV. General Architecture—Orthopedic Spine Brace (5$^{th}$ Embodiment)

Referring now to FIG. 32A, a perspective view of another exemplary embodiment of an orthopedic spine brace 3200 is shown. The orthopedic spine brace 3200 includes an anterior bracing system 3210, a posterior bracing system 3250 (see FIG. 32B) and a superior bracing system 3300 (see FIGS. 33A-33D). The superior bracing system 3300 may be coupled to the anterior bracing system 3210 through an extension rod 3220 and extension coupler 3230 combination. The superior bracing system 3300 may be further coupled to the posterior bracing system 3250 through a back panel 3255.

More specifically, the anterior bracing system 3210 features an anterior panel 3215, the extension rod 3220, a pair of lateral panels 3225 and 3227, and the extension coupler 3230. As shown in FIG. 32A, the extension rod 3220 is coupled to the anterior panel 3215 that extends in a superior direction therefrom. Additionally, extending laterally from the anterior panel 3215, the pair of lateral panels 3225 and 3227 may be made of a rigid or semi-rigid material such as any type of hardened, flexible plastic (e.g., sheet of polyethylene, polycarbonate, etc.). As a result, as shown, the lateral panels 3225 and 3227 may be angularly bent into a concave form to provide lateral support for the orthopedic spine brace 3200 and form around a hip area of the patient as shown.

The extension coupler 3230 is coupled to a distal end of the extension rod 3220. The extension coupler 3230 is further shown as being coupled to the chest plate attachment 2150. In particular, the chest plate attachment 2150 may be configured with connectors 3235a and 3235b (collectively, connectors 3235), which are adapted to receive one or more complementary posts 3237a and 3237b (collectively, posts 3237). This provides and supports pivotal movement of the chest plate attachment 2150 despite being coupled to the extension coupler 3230 of the anterior bracing system 3210.

Herein, the superior bracing system 3300 includes the pair of superior frame member and 2126 (see FIG. 27B) and the chest plate attachment 2150 coupled to each of the superior frame members and 2126. More specifically, the first superior frame member is coupled to the lock attachment member 2400 (see FIGS. 25A-25C) of the chest plate attachment 2150 while the second frame member 2126 is coupled to the hinged attachment member 2420 (see FIGS. 26G-25J) of the chest plate attachment 2150. This construction allows the lock attachment member 2400 to disengage from the chest plate attachment 2150, causing the chest plate attachment 2150 to rotate downward in accordance with two planes (e.g., pivots out away from the chest and pivots downward away from the face of the patient) as illustrated in FIG. 26J. As a result, the patient is able to remove or don the orthopedic spine brace 3200 by slipping on/off the shoulder straps 3240.

Referring now to FIG. 32B, a rear-facing view of the posterior bracing system 3250 is shown. The posterior bracing system 3250 includes the back panel 3255, an extension panel 3260, and a pair of connection strap guides 3265 and 3267, and locking slots 3270. The pair of connection strap guides 3265 and 3267 are coupled to extend from a posterior surface 3275 of the back panel 3255. As shown, a center slot 3280 is positioned between the plurality of locking slots 3270 and provides a clinician with access to a patient's back without removal of the back panel 3255. The connection strap guides 3265 and 3267 allow for vertical (superior/inferior) adjustment of connection straps 3290 of the superior bracing system 3300 along with preventing unwanted rotation (tilting) of the superior bracing system 3300.

As further shown in FIG. 32B, the extension panel 3260 is coupled to the back panel 3255 of the orthopedic spine brace 3200. For this illustrative embodiment, the extension panel 3260 includes a plurality of locking protrusions 3262 for insertion into and secured with the locking slots 3270. A clip 3272 is formed toward a bottom of the extension panel 3260 to provide additional stability in its attachment to the back panel 3255.

Referring to FIGS. 33A-33D, an exemplary embodiment of the superior bracing system 3300 of FIG. 32A is shown. Herein, as shown in FIG. 33A, the superior bracing system 3300 features the chest plate attachment 2150 coupled to the pair of superior frame member and 2126 (see FIG. 27B). In lieu of being supported by lateral frame assemblies 2110 and 2120 as shown in FIG. 21A, the superior frame members and 2126 is supported by overlapping, semi-rigid connection straps 3310 and 3320 illustrated as connection straps 3290 in FIG. 32B. In particular, a first end 3312 of a first connection strap 3310 is coupled to the first angularly adjustable hinge 2200 while a first end 3322 of a second connection strap 3320 is coupled to the second angularly adjustable hinge 2202. Both of the connection straps 3310 and 3320 include sleeves 3314 and 3324, respectively. The outer surfaces of these sleeves 3314 and 3324 include unbroken loop (i.e., hook & hoop such as Velcro®) material, while at least one of the sleeves (e.g., sleeve 3314 for the first connection strap 3310) includes a pocket 3316 to receive a portion of the second connection strap 3320 and corresponding sleeve 3324.

More specifically, a first sleeve 3314 (containing the first connection strap 3310) include the pocket 3316 and a fastening tab 3318. The fastening tab 3318 includes hook material for coupling to the UBL outer surface of a second sleeve 3324 (containing the second connection strap 3320) after insertion of at least a second end/sleeve 3326/3324 of the second connection strap 3320 within the pocket 3316 as shown in FIGS. 33C and 33D. The sleeved, first connection strap 3310/3314 and the sleeved, second connection strap 3320/3324 are secured by the superior bracing strap guides 3265 and 3267 as shown in FIG. 33D. A second end of the sleeved, second connection strap 3320 is inserted into the pocket 3316 of the sleeved, first connection strap 3310 and laterally moved until the overlapping straps provide support for the superior bracing system 3300 and the insertion is secured by the fastening tab 3318.

In the foregoing description, the invention is described with reference to specific exemplary embodiments thereof. However, it will be evident that various modifications and changes may be made thereto without departing from the broader spirit and scope of the invention as set forth in the claims to follow.

What is claimed is:

1. An orthopedic spine brace, comprising: a back panel; a plurality of superior frame members including a first superior frame member and a second superior frame member; and a chest plate attachment coupled to each of the plurality of superior frame members, the chest plate attachment comprises (i) a first attachment member coupled to the first superior frame member, (ii) a first chest retention strut member coupled to the first attachment member, (iii) a second attachment member coupled to the second superior frame member, and (iv) a second chest retention strut member coupled to the second attachment member and overlaying the first chest retention strut member, wherein the first attachment member comprises a housing and an internal locking mechanism, the internal locking mechanism includes a first protrusion coupled to a first spring component and extending from the housing and a second protrusion coupled to a second spring component and extending from the housing, and in response to pressure being applied to the first protrusion and the second protrusion, the first spring component and the second spring component are compressed to generate an opening from which a first post of a first coupling assembly is released from the first attachment member, and wherein the second attachment member is rotationally coupled to a second coupling assembly.

2. The orthopedic spine brace of claim 1, wherein the first coupling assembly is coupled to the first superior frame member, the first coupling assembly comprises at least the first post.

3. The orthopedic spine brace of claim 2, wherein the second coupling assembly is coupled to the second superior frame member, the second coupling assembly comprises the second post and lateral arm members extending from the second post.

4. The orthopedic spine brace of claim 3, wherein the second attachment member corresponds to a cantilever hinge.

5. The orthopedic spine brace of claim 4, wherein the cantilever hinge includes one or more fasteners sized for receipt of the lateral arm members extending from the second post and adapted to enable rotation of the chest plate attachment in accordance with a first axis of rotation upon release of the first attachment member from the first coupling assembly.

6. The orthopedic spine brace of claim 5, wherein the cantilever hinge further includes a hinge rotating joint that allows the cantilever hinge to freely rotate in accordance with a second axis of rotation orthogonal to the first axis of rotation thereby concurrently rotating the chest plate attachment in two different planes of rotation.

7. The orthopedic spine brace of claim 1 wherein the second attachment member corresponds to a hinged attachment member including a cantilever hinge configured to rotate along a first axis of rotation and a second axis of rotation orthogonal to the first axis of rotation in response to removal of the first attachment member from the first superior frame member.

8. The orthopedic spine brace of claim 7, wherein the cantilever hinge comprises fasteners configured for coupling to lateral arm members of a second post extending from the second coupling assembly positioned on the second superior frame member.

9. The orthopedic spine brace of claim 1, wherein:
   the first superior frame member includes (i) a first end formed with a planar shape for coupling to a first hinge and (ii) a second end formed with a cylindrical shape; and
   the second superior frame member includes (i) a first end formed with a planar shape and (ii) a second end formed with a cylindrical shape.

10. The orthopedic spine brace of claim 1, wherein a first end of the first chest 26, retention strut member is configured for attachment to the first coupling assembly, the first coupling assembly includes the first post attached to a strut joining member positioned below the first chest retention strut member and oriented to extend through the first chest retention strut member.

11. The orthopedic spine brace of claim 1 further comprising:
an extension rod; and
an extension coupler coupled to a distal end of the extension rod and to a cover of the chest plate attachment, the cover positioned to overlay the first chest retention strut member and the second chest retention strut member.

12. The orthopedic spine brace of claim 1 further comprising:
one or more connection straps coupled to the plurality of superior frame members and the back panel.

13. An orthopedic spine brace comprising: a back panel; a plurality of superior frame members including a first superior frame member and a second superior frame member; and a chest plate attachment coupled to each of the plurality of superior frame members, the chest plate attachment including (i) a first attachment member for coupling to a second end of the first superior frame member, (ii) a second attachment member for coupling to a second end of the second superior frame member, (iii) a first chest retention strut member coupled to the first attachment member, and (iv) a second chest retention strut member coupled to the second attachment member and overlaying the first chest retention strut member, wherein the first attachment member comprises a housing and an internal locking mechanism, the internal locking mechanism includes a first protrusion coupled to a first spring component and extending from the housing and a second protrusion coupled to a second spring component and extending from the housing, and in response to pressure being applied to the first protrusion and the second protrusion, the first spring component and the second spring component are compressed to generate an opening from which a first post of a first coupling assembly is released from the first attachment member, and wherein the second attachment member comprises a cantilever hinge.

14. The orthopedic spine brace of claim 13, wherein:
the first superior frame member includes (i) the first end formed with a planar shape for coupling to the first attachment member and (ii) the second end formed with a cylindrical shape; and
the second superior frame member includes (i) the first end formed with a planar shape for coupling to the second attachment member and (ii) the second end formed with a cylindrical shape.

15. The orthopedic spine brace of claim 14 further comprising: a second coupling assembly coupled to the second end of the second superior frame member, the second coupling assembly comprises a second post and lateral arm members extending from the second post secured by components within the second attachment member, wherein the first coupling assembly is coupled to the second end of the first superior frame member, the first coupling assembly comprises at least the first post secured by the first attachment member.

16. The orthopedic spine brace of claim 15, wherein the cantilever hinge of the first attachment member is rotationally coupled to the second coupling assembly.

17. The orthopedic spine brace of claim 16, wherein the cantilever hinge includes one or more fasteners sized for receipt of the lateral arm members extending from the second post and adapted to enable rotation of the chest plate member in accordance with a two orthogonal axes of rotation upon release of the first attachment member from the first coupling assembly thereby concurrently rotating the chest plate member in two different planes of rotation.

18. A chest plate attachment comprising: a first attachment member configured for coupling to a first superior frame member; a first chest retention strut member coupled to the first attachment member; a second attachment member configured for coupling to a second superior frame member; and a second chest retention strut member coupled to the second attachment member and overlaying the first chest retention strut member, wherein the first attachment member comprises a housing and an internal locking mechanism, the internal locking mechanism includes (i) a first protrusion coupled to a first spring component and extending from the housing and (ii) a second protrusion coupled to a second spring component and extending from the housing, and in response to pressure being applied to the first protrusion and the second protrusion, the first spring component and the second spring component are compressed to generate an opening from which a first post used to couple the first attachment member to the first superior frame member is released from the first attachment member, and wherein the second attachment member is rotationally coupled to a second coupling assembly that is used for coupling the second attachment member to the second superior frame member.

19. The chest plate attachment of claim 18, wherein the second attachment member corresponds to a cantilever hinge.

20. The chest plate attachment of claim 19, wherein the cantilever hinge includes one or more fasteners sized for receipt of the lateral arm members extending from the second post and adapted to enable rotation of the chest plate attachment in accordance with a first axis of rotation upon release of the first attachment member from a first coupling assembly.

21. The chest plate attachment of claim 20, wherein the cantilever hinge further includes a hinge rotating joint that allows the cantilever hinge to freely rotate in accordance with a second axis of rotation orthogonal to the first axis of rotation thereby concurrently rotating the chest plate attachment in two different planes of rotation.

22. The chest plate attachment of claim 18, wherein the second attachment member corresponds to a hinged attachment member including a cantilever hinge configured to rotate along a first axis of rotation and a second axis of rotation orthogonal to the first axis of rotation in response to removal of the first attachment member from the first superior frame member when attached.

23. The chest plate attachment of claim 22, wherein the cantilever hinge comprises fasteners configured for coupling to lateral arm members of a post extending from the second coupling assembly positioned on the second superior frame member.

24. The chest plate attachment of claim 18 being a component of an orthopedic spine brace including the first superior frame member, the second superior frame member, a first coupling assembly coupled to the first superior frame member, and the second coupling assembly coupled to the second superior frame member.

* * * * *